(12) United States Patent
Liu et al.

(10) Patent No.: US 7,442,160 B2
(45) Date of Patent: *Oct. 28, 2008

(54) EVOLVING NEW MOLECULAR FUNCTION

(75) Inventors: David R. Liu, Lexington, MA (US); Zev J. Gartner, Somerville, MA (US); Matthew W. Kanan, Cambridge, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/141,542

(22) Filed: May 31, 2005

(65) Prior Publication Data

US 2005/0227281 A1 Oct. 13, 2005

Related U.S. Application Data

(63) Continuation of application No. 10/101,030, filed on Mar. 19, 2002, now Pat. No. 7,070,928.

(60) Provisional application No. 60/306,691, filed on Jul. 20, 2001, provisional application No. 60/277,094, filed on Mar. 19, 2001, provisional application No. 60/277,081, filed on Mar. 19, 2001.

(51) Int. Cl.
*C40B 30/04* (2006.01)
*C40B 10/00* (2006.01)
*C40B 30/08* (2006.01)
*C40B 40/00* (2006.01)
*C40B 50/10* (2006.01)
*C40B 70/00* (2006.01)
*C12Q 1/68* (2006.01)
*C07H 21/02* (2006.01)

(52) U.S. Cl. .................. 506/9; 506/1; 506/11; 506/13; 506/28; 506/41; 435/6; 435/91.2; 536/23.1

(58) Field of Classification Search ...................... None
See application file for complete search history.

(56) References Cited

U.S. PATENT DOCUMENTS 4,683,202 A 7/1987 Mullis (Continued)

FOREIGN PATENT DOCUMENTS

DE 196 46 372 6/1997

(Continued)

OTHER PUBLICATIONS

Brenner et al. Encoded combinatorial chemistry. Proc Natl Acad Sci U S A. Jun. 15, 1992;89(12):5381-3.*

(Continued)

*Primary Examiner*—Young J. Kim
*Assistant Examiner*—Samuel Woolwine
(74) *Attorney, Agent, or Firm*—Goodwin Procter LLP

(57) ABSTRACT

Nature evolves biological molecules such as proteins through iterated rounds of diversification, selection, and amplification. The present invention provides methods, compositions, and systems for synthesizing, selecting, amplifying, and evolving non-natural molecules based on nucleic acid templates. The sequence of a nucleic acid template is used to direct the synthesis of non-natural molecules such as unnatural polymers and small molecules. Using this method combinatorial libraries of these molecules can be prepared and screened. Upon selection of a molecule, its encoding nucleic acid template may be amplified and/or evolved to yield the same molecule or related molecules for re-screening. The inventive methods and compositions of the present invention allow for the amplification and evolution of non-natural molecules in a manner analogous to the amplification of natural biopolymer such as polynucleotides and protein.

33 Claims, 68 Drawing Sheets

U.S. PATENT DOCUMENTS

| | | | |
|---|---|---|---|
| 4,863,857 A | 9/1989 | Blalock et al. | |
| 5,162,218 A | 11/1992 | Schultz | |
| 5,270,170 A | 12/1993 | Schatz et al. | |
| 5,449,602 A | 9/1995 | Royer et al. | |
| 5,539,082 A | 7/1996 | Nielsen et al. | |
| 5,547,835 A | 8/1996 | Koster | |
| 5,559,000 A | 9/1996 | Janda et al. | |
| 5,573,905 A | 11/1996 | Lerner et al. | |
| 5,574,141 A | 11/1996 | Seliger et al. | |
| 5,597,697 A | 1/1997 | Diamond | |
| 5,605,798 A | 2/1997 | Koster | |
| 5,622,824 A | 4/1997 | Koster | |
| 5,637,682 A * | 6/1997 | Nieuwlandt et al. | 536/22.1 |
| 5,639,603 A | 6/1997 | Dower et al. | |
| 5,660,988 A | 8/1997 | Duck et al. | |
| 5,677,195 A | 10/1997 | Winkler et al. | |
| 5,691,141 A | 11/1997 | Koster | |
| 5,698,685 A | 12/1997 | Summerton et al. | |
| 5,708,153 A | 1/1998 | Dower et al. | |
| 5,719,262 A | 2/1998 | Buchardt et al. | |
| 5,721,099 A | 2/1998 | Still et al. | |
| 5,723,289 A | 3/1998 | Eaton et al. | |
| 5,723,598 A | 3/1998 | Lerner et al. | |
| 5,770,358 A | 6/1998 | Dower et al. | |
| 5,770,367 A | 6/1998 | Southern et al. | |
| 5,786,461 A | 7/1998 | Buchardt et al. | |
| 5,789,160 A | 8/1998 | Eaton et al. | |
| 5,789,162 A | 8/1998 | Dower et al. | |
| 5,811,238 A | 9/1998 | Stemmer et al. | |
| 5,840,485 A | 11/1998 | Lebl et al. | |
| 5,843,701 A | 12/1998 | Gold et al. | |
| 5,846,839 A | 12/1998 | Gallop et al. | |
| 5,851,765 A | 12/1998 | Koster | |
| 5,858,660 A | 1/1999 | Eaton et al. | |
| 5,872,003 A | 2/1999 | Koster | |
| 5,922,545 A | 7/1999 | Mattheakis et al. | |
| 5,925,517 A | 7/1999 | Tyagi et al. | |
| 5,945,325 A * | 8/1999 | Arnold et al. | 435/197 |
| 5,958,691 A | 9/1999 | Pieken et al. | |
| 5,958,703 A | 9/1999 | Dower et al. | |
| 5,986,053 A | 11/1999 | Ecker et al. | |
| 5,998,140 A | 12/1999 | Dervan et al. | |
| 6,037,120 A | 3/2000 | Benner | |
| 6,043,031 A | 3/2000 | Koster et al. | |
| 6,048,698 A | 4/2000 | Eaton et al. | |
| 6,060,596 A | 5/2000 | Lerner et al. | |
| 6,074,823 A | 6/2000 | Koster | |
| 6,080,826 A | 6/2000 | Grubbs et al. | |
| 6,103,476 A | 8/2000 | Tyagi et al. | |
| 6,127,154 A | 10/2000 | Mosbach et al. | |
| 6,140,053 A | 10/2000 | Koster | |
| 6,140,493 A | 10/2000 | Dower et al. | |
| 6,140,496 A | 10/2000 | Benner | |
| 6,143,497 A | 11/2000 | Dower et al. | |
| 6,150,097 A | 11/2000 | Tyagi et al. | |
| 6,165,717 A | 12/2000 | Dower et al. | |
| 6,175,001 B1 | 1/2001 | Barbas et al. | |
| 6,194,144 B1 | 2/2001 | Koster | |
| 6,194,550 B1 | 2/2001 | Gold et al. | |
| 6,207,446 B1 | 3/2001 | Szostak et al. | |
| 6,214,553 B1 | 4/2001 | Szostak et al. | |
| 6,225,450 B1 | 5/2001 | Koster | |
| 6,238,871 B1 | 5/2001 | Koster | |
| 6,287,765 B1 | 9/2001 | Cubicciotti | |
| 6,291,160 B1 | 9/2001 | Lerner et al. | |
| 6,291,161 B1 | 9/2001 | Lerner et al. | |
| 6,368,874 B1 | 4/2002 | Gallop et al. | |
| 6,391,593 B1 | 5/2002 | Weston et al. | |
| 6,436,635 B1 | 8/2002 | Fu et al. | |
| 6,511,809 B2 | 1/2003 | Baez et al. | |
| 6,607,878 B2 | 8/2003 | Sorge | |
| 6,680,192 B1 | 1/2004 | Lerner et al. | |
| 7,070,928 B2 | 7/2006 | Liu et al. | |
| 7,223,545 B2 | 5/2007 | Liu et al. | |
| 7,306,904 B2 | 12/2007 | Landegren et al. | |
| 2001/0036638 A1 | 11/2001 | Nolan et al. | |
| 2002/0034757 A1 | 3/2002 | Cubicciotti | |
| 2002/0038000 A1 | 3/2002 | Gold et al. | |
| 2002/0064798 A1 | 5/2002 | Nolan et al. | |
| 2003/0099945 A1 | 5/2003 | Eaton et al. | |
| 2003/0104389 A1 | 6/2003 | Sergeev | |
| 2003/0113738 A1 | 6/2003 | Liu et al. | |
| 2003/0143561 A1 | 7/2003 | Pedersen et al. | |
| 2004/0014090 A1 | 1/2004 | Neri et al. | |
| 2004/0049008 A1 | 3/2004 | Pedersen et al. | |
| 2004/0180412 A1 | 9/2004 | Liu et al. | |
| 2005/0025766 A1 | 2/2005 | Liu et al. | |
| 2005/0042669 A1 | 2/2005 | Liu et al. | |
| 2005/0142583 A1 | 6/2005 | Liu et al. | |
| 2005/0170376 A1 | 8/2005 | Liu et al. | |
| 2005/0221316 A1 | 10/2005 | Pedersen et al. | |
| 2005/0233381 A1 | 10/2005 | Liu et al. | |
| 2005/0281819 A9 | 12/2005 | Liu et al. | |
| 2006/0223086 A1 | 10/2006 | Liu et al. | |

FOREIGN PATENT DOCUMENTS

| | | |
|---|---|---|
| EP | 0 324 616 | 7/1989 |
| EP | 0 604 552 | 8/1993 |
| EP | 0 643 778 | 3/1995 |
| EP | 0 773 227 | 5/1997 |
| WO | WO-91/05058 | 4/1991 |
| WO | WO-92/02536 | 2/1992 |
| WO | WO-93/06121 | 4/1993 |
| WO | WO-93/20242 | 10/1993 |
| WO | WO-96/09316 | 3/1996 |
| WO | WO-00/23458 | 4/2000 |
| WO | WO-00/32823 | 6/2000 |
| WO | WO-00/47775 | 8/2000 |
| WO | WO-00/61775 | 10/2000 |
| WO | WO-01/16352 | 3/2001 |
| WO | WO-02/074929 | 9/2002 |
| WO | WO-02/102820 | 12/2002 |
| WO | WO-02/103008 | 12/2002 |
| WO | WO-03/031591 | 4/2003 |
| WO | WO-03/078050 | 9/2003 |
| WO | WO-03/078445 | 9/2003 |
| WO | WO-03/078446 | 9/2003 |
| WO | WO-03/078625 | 9/2003 |
| WO | WO-03/078626 | 9/2003 |
| WO | WO-03/078627 | 9/2003 |
| WO | WO-03/082901 | 10/2003 |
| WO | WO-2004/001042 | 12/2003 |
| WO | WO-2004/013070 | 2/2004 |
| WO | WO-2004/016767 | 2/2004 |
| WO | WO-2004/024929 | 3/2004 |
| WO | WO-2004/039825 | 5/2004 |
| WO | WO-2004/056994 | 7/2004 |
| WO | WO-2004/074429 | 9/2004 |
| WO | WO-2004/074501 | 9/2004 |
| WO | WO-2004/083427 | 9/2004 |
| WO | WO-2004/110964 | 12/2004 |
| WO | WO-2005/003778 | 1/2005 |

OTHER PUBLICATIONS

Acevedo et al., "Non-Enzymatic Transcription of an Oligodeoxynucleotide 14 Residues Long" J. Mol. Biol. 197: 187-193 (1987).

Alvarez et al., "Photocleavable Protecting Groups as Nucleobase Protections Allowed the Solid-Phase Synthesis of Base-Sensitive SATE-Prooligonucleotides" J. Org. Chem. 64: 6319-6328 (1999).

Anderson et al. "A Comparison of Selected mRNA and Protein Abundances in Human Liver" Electrophiresis 18: 533-537 (1997).

Arap et al., "Steps Toward Mapping the Human Vasculature by Phage Display" Nat. Med. 8(2) 121-127 (2002).
Arnold et al., "Directed Evolution of Biocatalysts" Curr. Opin. Chem. Biol. 3: 54-59 (1999).
Arnold, "Design by Directed Evolution" Acc. Chem. Res. 31: 125-131 (1998).
Bain et al. "Ribosome-Mediated Incorporation of a Non-Standard Amino Acid into a Peptide Through Expansion of the Genetic Code" Nature 356: 537-539 (1992).
Baldwin et al. "Enzymes in Synthetic Organic Chemistry" Tetrahedron Organic Chemistry Series 12: 1-40.
Ban et al., "The Complete Atomic Structure of the Large Ribosomal Subunit at 2.4 Å Resolution" Science 289: 905-920 (2000).
Bannwarth et al., "A Simple and Effective Chemical Phosphyorylation Procedure for Biomolecules" Helv. Chim. Acta 70: 175-186 (1987).
Barbas et al., "Phage Display: A Laboratory Manual" Cold Spring Harbor Laboratory Press New York 736 pages (2001).
Barbas et al., Chem. Int. Ed. vol. 37, 1998. 2872-2875 Benner Reviews.
Becker et al., "Synthesis, Sar and In Vivo Activity of Novel Thienopyridine Sulfonamide Pyrrolidinones as Factor Za Inhibitors" Bioorg. Med. Chem. Lett. 9: 2753-2758 (1999).
Berger et al., "Universal Bases for Hybridization, Replication and Chain Termination" Nucleic Acids Research 28(15): 2911-2914 (2000).
Blanco et al., "A Method for Detecting Protein-DNA Interactions of Sites of Chromatin Replication" Analytical Biochemistry 163: 537-545 (1987).
Bogarad et al., "A Hierarchical Approach to Protein Molecular Evolution" Proc. Natl. Acad. Sci. USA 96: 2591-2595 (1999).
Böhler et al. "Template Switching Between PNA and RNA Oligonucleotides" Nature 376: 578-581 (1995).
Bolli et al., "Pyranosyl-RNA: Chiroselective Self-Assembly of Base Sequences by Ligative Oligomerization of Tetranucleotide-2'3'-Cyclophosphates (with a Commentary Concerning the Origin of Biomolecular Homochirality)" Chem. Biol. 4: 309-320 (1997).
Boschelli et al., "Synthesis of Amphotericin B. 2. Fragment C-D of the Aglycone" Tetrahedron Lett. 26: 5239-5242 (1985).
Bostwick et al., "RPR120844, A Novel, Specific Inhibitor of Coagulation Factor Xa Inhibits Venous Thrombosis in the Rabbit" Thromb Haemost 81: 157-160 (1999).
Brenner et al., "Encoded Combinatorial Chemistry" Proc. Natl. Acad. Sci. 89: 5381-5383 (1992).
Brenner et al., "In Vitro Cloning of Complex Mixtures of DNA on Microbeads: Physical Separation of Differentially Expressed cDNAs" Proc. Natl. Acad. Sci. USA 97(4): 1665-1670 (2000).
Bresler et al., "Stability of Peptidyl-tRNA—The Intermediate of Protein Synthesis" Biochimica et Biophysica Acta 155: 465-475 (1968).
Brooks et al., "Antiintegrin αvβ3 Blocks Human Breast Cancer Growth and Angiogenesis in Human Skin" J. Clin. Invest. 96: 1815-1822 (1995).
Brooks et al., "Disruption of Angiogenesis by PEX, a Noncatalytic Metalloproteinase Fragment with Integrin Binding Activity" Cell 92: 391-400 (1998).
Brooks et al., Integrin αvβ3 Antagonists Promote Tumor Regression by Inducing Apoptosis of Angiogenic Blood Vessels Cell 79: 1157-1164 (1994).
Bruick et al., "Template-Directed Ligation of Peptides to Oligonucleotides" Chem. Biol. 3: 49-56 (1996).
Cadwell et al., "Randomization of Genes by PCR Mutagenesis" PCR Methods Appl. 2: 28-33 (1992).
Celewicz et al., "Mass Spectrometry of Some Derivatives of 5-(Indol-2-yl) Pyrimidine" Pol. J. Chem. 72: 725-734 (1998).
Chan et al., "Intra-tRNA distance measurements for nucleocapsid protein-dependent tRNA unwinding during priming of HIV reverse transcription" Proc. Natl. Acad. Sci. USA 96: 459-464 (1999).
Chen et al., "Template-Directed Synthesis on Oligodeoxycytidylate and Polydeoxycytidylate Templates" J. Mol. Biol. 181: 271-279 (1985).
Cho et al., "An Unnatural Biopolymer" Science 261: 1303-1305 (1993).
Choi et al., "Inhibition of Neointimal Hyperplasia by Blocking αvβ3 Integrin with a Small Peptide Antagonist Gpen GRGDSPCA" J. Vasc. Surg. 19: 125-134 (1994).
Choi-Sledeski et al., "Sulfonamidopyrrolidinone Factor Xa Inhibitors: Potency and Selectivity Enhancements via P-1 and P-4 Optimization" J. Med. Chem. 42: 3572-3587 (1999).
Collado et al., "Diastereoselective Functionalization of 5-Hydroxy Prolinates by Tandem Horner-Emmons-Michael Reaction" Tetrahedron Lett. 35: 8037 (1994).
Compton, "Nucleic Acid Sequence-Based Amplification" Nature 350: 91-92 (1991).
Czlapinski et al., "Nucleic Acid Template-Directed Assembly of Metallosalen-DNA Conjugates" J. Am. Chem. Soc. 123: 8618-8619 (2001).
Davis, "Intermediates in Amino Acid Biosynthesis" Adv. Enzymol. 16: 287-295 (1955).
Dechantsreiter et al., "N-Methylated Cyclic RGD Peptides as Highly Active and Selective αvβ3 Integrin Antogaonists" J. Med. Chem. 42: 3033-3040 (1999).
Dewey et al., "New Uridine Derivatives for Systematic Evolution of RNA Ligands b Exponential Enrichment" J. Am. Chem. Soc. 117: 8474-8475 (1995).
Dietz et al., Photochemical Reduction of 5-Bromouracil by Cystine Derivatives and Coupling of 5-Bromouracil to Cystine Derivatives: Photochemistry and Photobiology 49(2): 121-129 (1989).
Drews, "Drug Discovery: A Historical Perspective" Science 287: 1960-1964 (2000).
Eaton, "The Joys of In Vitro Selection: Chemically Dressing Oligonucleotides to Satiate Protein Targets" Current Opinion in Chemical Biology 1: 10-16 (1997).
El-Dorry, "Purification of mRNA Coding for Rat-Liver Fructose-1,6-bisphosphatase by polysome immunoabsorption" Biochimica et Biophysica Acta 867: 252-255 (1986).
Eliseev et al., "Dynamic Combinatorial Chemistry: Evolutionary Formation and Screening of Molecular Libraries" Combinatorial Chemistry in Biology 243: 159-172 (1999).
Ellis et al., "Functional Analysis of the T-Cell Restricted Protein Tyrosine Kinase TxK" Biochem. J. 335: 277-284 (1998).
Ewing et al., "Design and Structure—Activity Relationships of Potent and Selective Inhibitors of Blood Coagulation Factor Xa" J. Med. Chem. 42: 3557-3571 (1999).
Famulok et al., "Oligonucleotide Libraries-Variatio Delectat" Curr. Opin. Chem. Biol. 2: 320-327 (1998).
Fenn et al., "Direct Quantitation of Biotin-Labeled Nucleotide Analogs in RNA Transcripts" Analytical Chemistry 190: 78-83 (1990).
Fleet et al., "Enantiospecific Synthesis of Shikimic Acid from D-Mannose: Formation of a Chiral Cyclohexene by Intramolecular Olefination of a Carbohydrate-Derived Intermediate" J. Chem. Soc. Perkins, Trans. I: 905-908 (1984).
Fleischer et al., "Conversion of Aliphatic and Alicyclic Polyalcohols to the Corresponding Primary Polyamines" J. Org. Chem. 36(20): 3042-3044 (1971).
Francis et al., "Combinatorial Libraries of Transition-Metal Complexes, Catalysts and Materials" Curr. Opin. Chem. Biol. 2: 422-428 (1998).
Francis et al., "Discovery of Novel Catalysts for Alkene Epoxidation from Metal-Binding Combinatorial Libraries" Angew. Chem. Int. Ed. Engl. 38: 937-941 (1999).
Frankel et al., "Encodamers: Unnatural Peptide Oligomers Encoded in RNA" Chemistry and Biology 10: 1043-1050 (2003).
Friedlander et al., "Definition of Two Angiogenic Pathways by Distinct αv Integrins" Science 270: 1500-1502 (1995).
Fruchart et al., "A New Linker for the Synthesis of C-Terminal Peptide α-oxo-Aldehydes" Tetrahedron Lett. 40: 6225 (1999).
Fruchtel et al., "Organic Chemistry on Solid Supports" Angew. Chem. Int. Ed. Engl. 35: 17-42 (1996).
Gad, "Synaptic Vesicle endocytosis studied in a living synapse" Nobel Institute for Neurophysiology, Karolinska Institutet, Sweden 1-48 (2000).
Gallop et al., "Applications Combinatorial Technologies to Drug Discovery, 1. Background and Peptide Combinatorial Libraries" J. Med. Chem. 37: 1233-1251 (1994).

Gartner et al., "The Generality of DNA-Templated Synthesis as a Basis for Evolving Non-Natural Small Molecules" J. Am. Chem. Soc. 123: 6961-6963 (2001).

Gat et al., "Reading DNA Differently" Biopolymers 48: 19-28 (1998).

Gevorkian et al. "Rapid Communication Identification of Autoimmune Thrombocytopenic Purpura-Related Epitopes using Phage-Display Peptide Library" Clin. Immunol. Immunopathol 86: 305-309 (1998).

Geyer et al., "Conformational Analysis of a Cyclic RGD Peptide Containing a ψ [CH2-NH] Bond: A Positional Shift in Backbone Structure Caused by a Single Dipeptide Mimetic" J. Am. Chem. Soc. 116: 7735-7743 (1994).

Gilbertson et al., "Asymmetric Catalysis with Libraries of Palladium β-Turn Phosphine Complexes" J. Am. Chem. Soc. 122: 6522-6523 (2000).

Gocke, "Mechanism of Quinolone Mutagenicity in Bacteria" Mutation Research 248: 135-143 (1991).

Gordon et al., Applications of Combinatorial Technologies to Drug Discovery. 2. Combinatorial Organic Synthesis, Library Screening Strategies, and Future Directions, J. Med. Chem. 37(10): 1385-1401 (1994).

Gourtain et al., "Enhancing the Catalytic Repertoire of Nucleic Acids. II. Simultaneous Incorporation of Amino and Imidazolyl Functionalities by Two Modified Triphosphates During PCR" Nucleic Acids Res. 29: 1898-1905 (2001).

Greene et al., "Protective Groups in Organic Synthesis 3rd ed.", 780 pages Wiley & Sons (1999).

Grubina et al., "Summer Research Report: DNA-Templated Synthesis of a Synthetic Small Molecule Library" The Nucleus 10-14, Jan. 2004.

Gryaznov et al., "Chemical Ligation of Oligonucleotides in the Presence and Absence of a Template" J. Am. Chem. Soc. 115: 3808-3809 (1993).

Gryaznov et al., "Template Controlled Coupling and Recombination of Oligonucleotide Blocks Containing Thiophosphoryl Groups" Nucleic Acids Research 21(6): 1403-1408 (1993).

Guatelli et al., "Isothermal, In Vitro Amplification of Nucleic Acids by a Multienzyme Reaction Modeled After Retroviral Replication" Proc. Natl. Acad. Sci. 87: 1874-1878 (1990).

Gyllensten et al., "Generation of Single-Stranded DNA by the Polymerase Chain Reaction and its Application to Direct Sequencing of the HLA-DQA locus", PNAS 85: 7652-7656 (1988).

Haaima et al., "Peptide Nucleic Acids (PNAs) Containing Thymine Monomers Derived from Chiral Amino Acids: Hybridization and Solubility Properties of D-Lysine PNA" Angew. Chem. Int. Ed. Engl. 35: 1939-1942 (1996).

Haeuptle et al., "Translation Arrest by Oligodeoxynucleotides Complementary to mRNA Coding Sequences Yields Polypeptides of Predetermined Length" Nucleic Acids Research 14(3): 1427-1448 (1986).

Hamburger et al., "Peptidyl-tRNA XI. The Chemical Synthesis of Phenylalanine-Containing Oligopeptidyl-tRNA" Biochimica et Biophysica Acta, 213: 115-123 (1970).

Haubner et al. "Structural and Functional Aspects of RGD-Containing Cyclic Pentapeptides as Highly Potent and Selective Integrin αvβ3 Antagonists" J. Am. Chem. Soc. 118: 7461-7472 (1996).

Herrera-Estrella et al., "VirD Proteins of Agrobacterium Tumefaciens are Required for the Formation of a Covalent DNA—Protein Complex at the 5' Terminus of T-Strand Molecules" The EMBO Journal 7(13): 4055-4062 (1988).

Herrlein et al., "A Covalent Lock for Self-Assembled oligonucleotide Conjugates" J. Am. Chem. Soc. 117: 10151-10152 (1995).

Heywood et al., "A Study of Muscle Polyribosomes and the Coprecipitation of Polynbosomes with Myosin" J. Biol. Chem. 7: 3289-3296 (1968).

Heywood et al., "The Identification of Polyribosomes Synthesizing Myosin" PNAS 57: 1002-1009 (1967).

Hirama et al., "Asymmetric Induction in the Intramolecular Conjugate Addition of-or σ-Carbamoyloxy -, β-Unsaturated Esters. A New Method for Diastereoselective Amination and Divergent Synthesis of 3-Amino-2,3,6-Trideoxyhexoses" Heterocycles 28: 1229-1247 (1989).

Hirama et al., "Intramolecular Michael Addition of O-Carbamates to αβ Unsaturated Esters: A New Diastereoselective Amination in an Acyclic System" J. Am. Chem. Soc. 107: 1797-1798 (1985).

Hooper et al., "Mode of Action of the New Quinolones: New Data" Eur. J. Clin. Microbiol. Infect. Dis. 10(4): 223-231 (1991).

Houdebine et al., "Purification of the mRNAs for Ewe αs -Casein and β-Casein by Immunoprecipitation of of Polysomes" Eur. J. Biochem. 63: 9-14 (1976).

House et al., "The Chemistry of Carbanions. XVII. The Addition of Methyl Organometallic Reagents to Cyclohexenone Derivatives" J. Org. Chem. 33: 949 (1968).

Hughes, "Application of Polymer-Bound Phosphonium Salts as Traceless Supports for Solid" Tetrahedron Lett. 37: 7595-7598 (1996).

Hyrup et al., "Peptide Nucleic Acids (PNA): Synthesis, Properties and Potential Applications" Bioorganic & Medical Chemistry 4(1): 5-23 (1996).

Illuminati et al., "Ring Closure Reactions of Bifunctional Chain Molecules" Acc. Chem. Res. 14: 95-102 (1981).

Inoue et al., "Oligomerization of (Guanosine 5'-Phosphor)-2-Methylimidazolide on Poly(C): An RNA Polymerase Model" J.Mol. Biol. 162: 201-217 (1982).

Inoue et al., "Substituent Control of the Poly(C)—Directed Oligomerization of Guanosine 5'-Phosphoroimidazolide" J. Am. Chem. Soc. 103: 7666-7667 (1981).

Inoue et al., "Template-Directed Synthesis on the Pentanucleotide CpCpGpCpC" J. Mol. Biol. 178: 669-676 (1984).

International Search Report for Application No. PCT/US02/08546 dated Dec. 17, 2002.

International Search Report for Application No. PCT/US03/25984 dated Jan. 18, 2005.

Ito et al., "Acetone-Sensitized Photocoupling of 5-Bromouridine to Trytophan Derivatives via Electron-Transfer Process" J. Amer. Chem. Soc. 102: 7535-7541 (1980).

Jemth et al., "Kinetic Characterization of Recombinant Human Glutathione Transferase T1-1, A Polymorphic Detoxication Enzyme" Arch. Biochem. Biophys. 348(2): 247-54 (1997).

Johanson et al., "Regioselective Reductive Ring-Opening of 4-Methoxybenzylidene Acetals of Hexopyranosides. Access to a Novel Protecting-Group Strategy. Part 1" J. Chem. Soc. Perkins Trans. I: 2371-2374 (1984).

Johnson et al. "Evidence for Posttranslational O-Glycosylation of Fetuin" Biochemistry 25: 5518-5525 (1986).

Johnston et al., "RNA-Catalyzed RNA Polymerization: Accurate and General RNA-Templated Primer Extension" Science 292: 1319-1325 (2001).

Jost et al., "Quantitative Precipitation of Short Oligonucleotides with Low Concentrations of Cetyltrimethylammonium Bromide" Nucleic Acids Res. 17: 2143 (1989).

Kahl et al., "Introducing Structural Diversity in Oligonucleotides via Photolabile, Convertible C5-Substituted Nucleotides" J.Am. Chem. Soc. 121(4): 597-604 (1999).

Keiler et al., "Role of a Peptide Tagging System in Degradation of Proteins Synthesized from Damaged Messenger RNA" Science 271: 990-993 (1996).

King et al., Bis (Dialkylamino) Phosphines J. Org. Chem. 49: 1784-1789 (1984).

Kinoshita et al., "Enzymatic Synthesis of Code Regions for Encoded combinatorial Chemistry (ECC)" Nucleic Acids Symposium Series 34: 201-202 (1995).

Kuntz et al., "Combinatorial Catalyst Discovery" Current Opinion in Chemical Biology 3: 313-319 (1999).

Kupsch et al., "Isolation of Human Tumor-Specific Antibodies by Selection of an Antibody Phage Library on Melanoma Cells" Clin Cancer Res. 5: 925-931 (1999).

Latham et al. "The Application of a Modified Nucleotide in Aptamer Selection: Novel Thrombin Aptamers Containing 5-(Pentynyl)-2'-Deoxyuridine" Nucleic Acids Res. 22: 2817-2822 (1994).

Leadley et al., "Pharmacodynamic Activity and Antithrombotic Efficacy of RPR120844, a Novel Inhibitor of Coagulation Factor Xa" J. Cardiovasc. Pharmacol. 34: 791-799 (1999).

Lee et al., "Enhancing the Catalytic Repertoire of Nucleic Acids: a Systematic Study of Linker Length and Rigidity" Nucleic Acids Res. 29: 1565-1573 (2001).

Leon et al., "Covalent Coupling of 4-Thiouridine in the Initiator Methionine tRNA to Specific Lysine Residues in *Escherichia coli* Methionyl-tRNA Synthetase" Biochemistry 26: 7113-7121 (1987).

Li et al. "DNA-Catalyzed Polymerization" J. Am. Chem. Soc. 124: 746-747 (2002).

Li et al., "A Catalytic DNA for Porphyrin Metallation" Nat. Struct. Biol. 3: 743-747 (1996).

Li et al., "Capping DNA with DNA" Biochemistry 39: 3106-3114 (2000).

Li et al., "Chemical Self-Replication of Palindromic Duplex DNA" Nature 369: 218-221 (1994).

Li et al., "Phosphorylating DNA with DNA" Proc. Natl. Acad. Sci. USA 96: 2746-2751 (1999).

Li et al., "Toward an Efficient DNAzyme" Biochemistry 36: 5589-5599 (1997).

Lin et al. "Formation of an Amino-Acid-Binding Pocket Through Adaptive Zippering-Up of a Large DNA Hairpin Loop" Chem. Biol. 5: 555-572 (1998).

Lin et al., "Structural Basis of DNA Folding and Recognition in an AMP-DNA Aptamer Complex: Distinct Architectures But Common Recognition Motifs for DNA and RNA Aptamers Complexed to AMP" Chem. Biol. 4: 817-832 (1997).

Liu et al. "Generating New Molecular Function: A Lesson from Nature" Angew. Chem. Intl. Ed. Eng. 38: 37-54 (1999).

Loss, "Spin-based Quantum Information Processing in Nanostructures" Dept. of Phys., Univ. of Basel, Switzerland.

Luo et al., "Analysis of the Structure and Stability of a Backbone-Modified Oligonucleotide: Implications for Avoiding Product Inhibition in Catalytic Template-Directed Synthesis" J. Am. Chem. Soc. vol. 120, No. 13: 3019-3031 (1998), see entire document, especially pp. 3019-3020.

Luther et al., "Surface-Promoted Replication and Exponential Amplification of DNA Analogues" Nature 396: 245-248 (1998).

Lynn et al., "Water-Soluble Ruthenium Alkylidenes: Synthesis, Characterization, and Application to Olefin Metathesis in Protic Solvents" J. Am. Chem. Soc. 122: 6601-6609 (2000).

Lynn et al., "Living Ring-Opening Metathesis Polymerization in Water J. Am. Chem. Soc. 12: 1627-1628 (1998).

MacLean et al., "Encoded Combinatorial Chemistry Synthesis and Screening of a Library of Highly Functionalized Pyrrolidines" Proc. Natl. Acad. Sci. USA 94: 2805-2810 (1997).

Magid, "Nucleophilic and Organometallic Displacement Reactions of Allylic Compounds: Stereo- and Regiochemistry" Tetrahedron 36: 1901-1930 (1980).

Mahal et al., "Engineering Chemical Reactivity on Cell Surfaces Through Oligosaccharid Biosynthesis" Science 276: 1125-1128 (1997).

Maignan et al., "Crystal Structures of Human FactorXa Complexed with Potent Inhibitors" J. Med. Chem. 43: 3226-3232 (2000).

Marks et al., "Molecular Evolution of Proteins on Filamentous Phage" J. Biol. Chem. 267(23): 16007-16010 (1992).

Marlowe et al., "Design, Synthesis and Structure-Activity Relationship of a Series of Arginine Aldehyde Factor Xa Inhibitors. Part 1: Structures Based on the (D)-Arg-Gly-Arg Tripeptide Squence" Bioorg. Med. Chem. Lett. 10: 13-16 (2000).

Mattheakis et al., "An In Vitro Polysome Display System for Identifying Ligands from Very Large Peptide Libraries" Proc. Natl. Acad. Sci. USA 91: 9022-9026 (1994).

Mel'nikov et al., "Solubilization of DNA-Cationic Lipid Complexes in Hydrophobic Solvents. A Single-Molecule Visualization by Fluorescence Microscopy" Langmuir 15: 1923-1928 (1999).

Minshull et al., "Protein Evolution by Molecular Breeding" Curr. Opin. Chem. Biol. 3: 284-290 (1999).

Mirza et al., "Synthesis of Shikimic Acid And Its Phosphonate Analogue Via Knoevenagel Condensation" Tetrahedron Lett. 32: No. 33, 4111-4114 (1991).

Miyamoto-Sato et al., "Highly stable and efficient mRNA templates for mRNA-protein fusions and C-terminally labeled proteins" Nucleic Acids Research vol. 31 No. 15 e78 (2003).

Mohr et al., "Synthesis of Water-Soluble, Aliphatic Phoshines and Their Application to Well-Defined Ruthenium Olefin Metathesis Catalysts" Organometallics 15: 4317-4325 (1996).

Muth et al., "A Single Adenosine with a Neutral pKa in the Ribosomal Peptidyl Transferase Center" Science 289: 947-950 (2000).

Nagasaka et al., "Witlig Reactions of 1-Alkoxycarbonyl-2-Hydroxypyrrolidines and—Piperidines: Synthesis of ($\pm$)—Hygrine and (($\pm$)-2-Epilasubine II" Heterocycles 29: 155-164 (1989).

Nakano et al., "General Acid-Base Catalysis in the Mechanism of a Hepatitis Delta Virus Ribozyme" Science 287: 1493-1497 (2000).

Nazarenko et al., "A closed tube format for amplification and detection of DNA based on energy transfer" Nucleic Acid Research25(12): 2516-2521 (1997).

Nemoto et al., "In vitro virus: Bonding of mRNA bearing puromycin at the 3'-terminal end to the C-terminal end of its encoded protein on the ribosome in vitro" European Biochemical Societies Letters 414: 405-408 (1997).

Nissen et al., "The Structural Basis of Ribosome Activity in Peptide Bond Synthesis" Science 289: 920-930 (2000).

Nolte et al., "Mirror-Design of L-Oligonucleotide Ligands Binding to L-Arginine" Nature Biotechnology 14: 1116-1121 (1996).

Norris et al., "Mechanistic Studies of the 5-lodouracil Chromophore Relevant to Its Use in Nucleoprotein Photo-Cross-Linking" J. Amer. Chem. Soc. 118: 5796-5803 (1996).

Olofson et al., "Selective N-Dealkylation of Teritiary Amines with Vinyl Chloroformate: An Improved Synthesis of Naloxone" Tetrahedron Lett. 18: 1567-1570 (1977).

Olofson et al, "Use of the Vinyloxycarbonyl Group for Amino Protection in Peptide Synthesis" Tetrahedron Lett. 18: 1563-1566 (1977).

Olofson et al., "Value of Vinyloxycarbonyl Unit in Hydroxyl Protection: Application to the Synthesis of Nalorphine" Tetrahedron Lett. 18: 1571-1574 (1977).

Orgel et al., "Unnatural Selection in Chemical Systems" Acc. Chem. Res. 28: 109-118 (1995).

Pagratis et al., "Potent 2'-Amino-, and 2'-Fluoro-2'-Deoxyribonucleotide RNA Inhibitors of Keratinocyte Growth Factor" Nature Biotechnology 15: 68-72 (1997).

Pasqualini et al., "Aminopeptidase N Is a Receptor for Tumor-homing Peptides and a Target for Inhibiting Angiogenesis" Cancer Res. 60: 722-727 (2000).

Pasqualini et al., "Organ Targeting In Vivo Using Phage Display Peptide Libraries" Nature 380: 364-366 (1996).

Pedersen et al., "A Method for Directed Evolution and Functional Cloning of Enzymes" Proc. Natl. Acad. Sci. USA 95: 10523-10528 (1998).

Perrin et al., "Bridging the Gap Between Protein and Nucleic Acids: A Metal-Independent RNAseA Mimic with Two Protein-Like Functionalities" J. Am. Chem. Soc. 123: 1556-1563 (2001).

Perrin et al., "Expanding the Catalytic Repertoire of Nucleic Acid Catalysts: Simultaneous Incorporatio of Two Modified Deoxyribonucleoside Triphosphates Bearing Ammonium and Imidazolyl Functionalities" Nucleosides & Nucleotides 18: 377-391 (1999).

Pfaff et al., "Selective Recognition of Cyclis RGD Peptides of NMR Defined Conformation of $\alpha IIb\beta 3$, $\alpha 5\beta 1$ Integrins" J. Biol. Chem. 269: 20233-20238 (1994).

Polacek et al., "Ribosomal Peptidyl Transferase can Withstand Mutations at the Putative Catalytic Nucleotide" Nature 411: 498-501 (2001).

Püschl et al., "Peptide Nucleic Acids (PNAs) with a Functional Backbone" Tetrahedron Lett. 39: 4707-4710 (1998).

Rai et al., "Development of Potent and Selective Factor Xa Inhibitors" Bioorg. Med. Chem. Lett. 11: 1797-1800 (2001).

Rembold et al., "Single-Strand Regions of Poly(G) Act as Templates for oligo(C) Synthesis" J. Mol. Evol. 38: 205-210 (1994).

Roberts et al., "RNA-Peptide Fusions for the In Vitro Selection of Peptides and Proteins" Proc. Natl. Acad. Sci. USA 94: 12297-12302 (1997).

Rodriguez et al., "Template-Directed Extension of a Guanosine 5'-Phosphate Covalently Attached to an Oligodeoxycytidylate Template" J. Mol. Evol. 33: 477-482 (1991).

Saiki et al., "Enzymatic Amplification of β-Globin Genomic Sequences and Restriction Site Analysis for Diagnosis of Sickle Cell Anemia" Science 230: 1350-1354 (1985).

Sakthivel et al., "Expanding the Potential of DNA for Binding and Catalysis: Highly Functionalized dUTP Derivatives That Are Substrates for Thermostable DNA Polymerases" Angew. Chem. Int. Ed. 37: 2872-2875 (1998).

Salas et al., "Biosynthetic Polydeoxynucleotides as Direct Templates for Polypeptide Synthesis" Journal of Biological Chemistry 243(5): 1012-1015 (1968).

Santoro et al., "A General Purpose RNA-Cleaving DNA Enzyme" Proc. Natl. Acad. Sci. USA 94: 4262-4266 (1997).

Saxon et al., "A 'Traceless' Staudinger Ligation for the Chemoselective Synthesis of Amide Bonds" Organic Letters 2(14): 2141-2143 (2000).

Scharf et al., "Direct Cloning and Sequence Analysis of Enzymatically Amplified Genomic Sequences" Science 233: 1076-1078 (1986).

Scheffer et al., "Selection and Characterisation of a Phage-Displayed Human Antibody (Fab) Reactive to the Lung Resistance-Related Major Vault Protein" Br. J. Cancer 86: 954-962 (2002).

Schmidt et al., "Information Transfer from DNA to Peptide Nucleic Acids by Template-Directed Syntheses" Nucleic Acids Res. 25: 4792-4796 (1997).

Schmidt-Dannert et al., "Directed Evolution of Industrial Enzymes" Trends Biotechnol. 17: 135-136 (1999).

Scholl et al., "Synthesis and Activity of a New Generation of Ruthenium-Based Olefin Metathesis Catalysts Coordinated with 1,3-Dimesityl-4,5-Dihydroimidazol-2-Ylidene Ligands" Org. Lett. 1(6): 953-956 (1999).

Schultze et al., Three-Dimensional Solution Structure of the Thrombin-Binding DNA Aptamer d(GGTTGGTGTGGTTGG) J. Mol. Biol. 235: 1532-1547 (1994).

Schwartz et al., "Template-Directed Synthesis of Novel, Nucleic Acid-Like Structures" Science 228: 585-587 (1985).

Scott, "How Were Porphyrins and Lipids Synthesized in the RNA World?" Tetrahedron Lett. 38: 4961-4964 (1997).

Seeberger et al., "Solid-Phase Oligosaccharide Synthesis and Combinatorial Carbohydrate Libraries" Chem. Rev. 100: 4349-4393 (2000).

Seeberger, P.H., Ed., "Solid Support Oligosaccharide Synthesis and Combinatorial Carbohydrate Libraries" Wiley-Interscience: New York 2001.

Seela et al., "Oligonucleotides Containing 7-Deazaadenines: The Influence of the 7-Substituent Chain Length and Charge on the Duplex Stability" Helv. Chem. Acta. 82: 1878-1898 (1999).

Seela et al., "Palladium-Catalyzed Cross Coupling of 7-Iodo-2' Deoxytubercidin with Terminal Alkynes" Synthesis: 726-730 (1996).

Shao et al., "Random-Priming in Vitro Recombination: An Effective Tool for Directed Evolution" Nucleic Acids Research 26(2): 681-83 (1998).

Sheppard et al., "A DNA Enzyme with N-Glycosylase Activity" Proc. Natl. Acad. Sci. USA 97: 7802-7807 (2000).

Shimizu et al., "Search for Chiral Catalysts Through Ligand Diversity: Substrate-Specific Catalysts and Ligand Screening on Solid Phase" Angew. Chem. Int. Ed. 36(16): 1704-1707 (1997).

Shishido et al., "1,2-Asymmetric Induction in Intramolecular Michael Reaction. A Novel and Enantioselective Route to (+) Geissman Lactone" J. Chem. Soc. Perkins Trans. 1: 993-1004 (1987).

Siegel et al., "Isolation of Cell Surface-Specific Human Monoclonal Antibodies Using Phage Display and Magnetically-Activated Cell Sorting: Applications in Immunohematology" J. Immunol. Methods 206: 73-85 (1997).

Smith, G., "Filamentous Fusion Phage: Novel Expression Vectors That Display Cloned Antigens on the Virion Surface" Science 228: 1315-1317 (1985).

Smith, G., "The Progeny of Sexual PCR" Nature 370: 324-325 (1995).

Soumillion et al., "Selection of β-Lactamase on Filamentous Bacteriophage by Catalytic Activity" J. Mol. Biol. 237: 415-22 (1994).

Stemmer et al., "DNA Shuffling by Random Fragmentation and Reassembly: In Vitro Recombination for Molecular Evolution" Proc. Natl. Acad. Sci. USA 91: 10747-10751 (1994).

Stemmer, "Rapid Evolution of a Protein In Vitro by DNA Shuffling" Nature 370: 389-391 (1994).

Still et al., "Chemical Consequences of Conformation in Macrocyclic Compounds," Tetrahedron 37: 3981-3996 (1981).

Summerer D. et al., "DNA-Templated Synthesis: More Versatile Than Expected" Angewandte Chemie. Int'l Edit., Verlag Chemie. Weinheim, DE, vol. 41, No. 1: 89-90 (2002).

Supplementary European Search Report for Application No. EP 02 75 3671 dated Sep. 21, 2004.

Sutherlin et al., "Stereoselective Synthesis of Dipyranyl C-Disaccharides" Tetrahedron Lett. 34(31): 4897-4900 (1993).

Tamura et al., "Oligonucleotide-Directed Peptide Synthesis in a Ribosome- and Ribozyme-Free System" Proc. Natl. Acad. Sci. USA 98: 1393-1397 (2001).

Tarasow et al., "Dressed for Success: Realizing the Catalytic Potential of RNA" Biopolymers 48: 29-37 (1998).

Tseng-Law et al., "Identification of a Peptide Directed Against the Anti-CD34 Antibody, 9C5, by Phage Display and Its Use in Hematopoietic Stem Cell Selection" Exp. Hematol 27: 936-945 (1999).

Uhlmann et al., "Synthesis and Properties of PNA/DNA Chimeras" Angew. Chem. Int. Ed. Engl. 35: 2632-2635 (1996).

Vacca et al., "New Advances in the Discovery of Thrombin and Factor Xa Inhibitors" Curr. Opin. Chem. Biol. 4: 394-400 (2000).

Van Gelder et al., PNAS, 85: 77652-77656 (1988).

Varner et al., "Review: αvβ3: The Integrin Angiogenesis and Apoptosis" Cell Adhes Commun 3: 367-374 (1995).

Visscher et al., "Template-Directed Synthesis of Acyclic Oligonucleotide Analogs" Journal of Molecular Evolution 28: 3-6 (1988).

Walder et al., "Complementary Carrier Peptide Synthesis: General Strategy and Implications for Prebiotic Origin of Peptide Synthesis" Proc. Nat. Acad. Sci. USA 76(1): 51-55 (1979).

Wells et al., "Rapid Evolution of Peptide and Protein Binding Properties in Vitro" Curr. Opin. Struct. Biol. 2: 597-604 (1992).

Wermuth et al., "Stereoisomerism and Biological Activity of the Selective and Superactive αvβ3 Integrin Inhibitor Cyclo (-RGDfV-) and Its Retro-Inverso Peptide" J. Am. Chem. Soc. 119: 1328-1335 (1997).

Wiegand et al., "Selection of RNA Amide Synthases" Chemistry and Biology 4: 675-683 (1997).

Wilson et al., "In Vitro Selection of Functional Nucleic Acids" Annu. Rev. Biochem. 68: 611-647 (1999).

Winter et al., "Making Antibodies by Phage Display Technology" Annu. Rev. Immunol. 12: 433-455 (1994).

Wong et al., "Enzymes in Synthetic Organic Chemistry" 388 pages Pergamon: Tetrahedron Organic Chemistry Series 12: 1994 (Index only enclosed).

Woodward et al., "Asymmetric Total Synthesis of Erythromycin. 1. Synthesis of an Erythronolide A Seco Acid Derivative via Asymmetric Induction" J. Am. Chem. Soc. 103: 3210-3213 (1981).

Xu et al., "Nonenzymatic Autoligation in Direct Three-Color Detection of RNA and DNA Point Mutations" Nature Biotechnology 19: 148-152 (2001).

Xu et al., "Rapid and Selective Selenium-Mediated Autoligation of DNA Strands" J. Am. Chem. Soc. 122: 9040-9041 (2000).

Zarling et al., "Mapping of Lymphocyte Surface Polypeptide Antigens by Chemical Cross-Linking with Bsocoes" J. Immunology 124: 913-920 (1980).

Zhan et al. "Chemical Amplification through Template-Directed Synthesis" J. Am. Chem. Soc. vol. 119, No. 50: 12420-12421 (1997), see entire document.

Zhang et al., "Lactone and Lactam Library Synthesis by Silver Ion-Assisted Orthogonal Cyclization of Unprotected Peptides" J. Am. Chem. Soc. 121: 3311-3320 (1999).

Zhao et al., "A Methodological Comparison: The Advantage of Phosphorimidates in Expanding the Sugar Nucleotide Repertoire" J. Org. Chem. 63: 7568-7572 (1998).

Zhao et al., "Molecular Evolution by Staggered Extension Process (StEP) in Vitro Recombination" Nature Biotechnology 16(3): 258-61 (1998).

Zhao et al., "Optimization of DNA Shuffling for High Fidelity Recombination" Nucleic Acids Research 25(6): 1307-1308 (1997).

Schmidt et al., "Information Transfer from Peptide Nucleic Acids to RNA by Template-Directed Syntheses" Nucleic Acids Research 25(23): 4797-4802 (1997).

Dewey et al., "Integrated drug discovery technology in a test tube," www.currentdrugdiscovery.com (Jul. 2002).

Kanavarioti et al., Journal of Organic Chemistry vol. 64, pp. 8323-8333 (Oct. 1999).

Letter from Mr. Iver P. Cooper to the Office of Naval Research, dated May 25, 2004.

Letter from the Office of Naval Research to Mr. Iver P. Cooper, dated Feb. 1, 2005.

Appeal letter and memorandum to the General Counsel of the Navy on behalf of Mr. Iver P. Cooper, dated Apr. 1, 2005.

Letter from the Office of the General Counsel of the Navy to Mr. Iver P. Cooper, dated Aug. 5, 2005.

Slides 1, 2, 3, and 30 of Professor David Liu's slide presentation entitled "Unnatural Molecule Evolution."

Plaintiff's Complaint, filed Nov. 18, 2005, *Iver P. Cooper v. U.S. Department of Navy*, Case 1:05-cv-02252-EGS.

Defendant's Answer to Plaintiff's Complaint, filed Feb. 10, 2006, *Iver P. Cooper v. U.S. Department of Navy*, Case 1:05-cv-02252-EGS.

Motion of Plaintiff Iver Cooper for Summary Judgement, filed May 15, 2006, *Iver P. Cooper v. U.S. Department of Navy*, Case 1:05-cv-02252-EGS.

Plaintiff's Memorandum of Points & Authorities of Plaintiff Iver Cooper in Support of his Motion for Summary Judgment, filed May 15, 2006, *Iver P. Cooper v. U.S. Department of Navy*, Case 1:05-cv-02252-EGS.

Defendant's Motion for Summary Judgment, filed May 15, 2006, *Iver P. Cooper v. U.S. Department of Navy*, Case 1:05-cv-02252-EGS.

Defendent's Memorandum of Law in Support of Defendant's Motion for Summary Judgment, filed May 15, 2006, *Iver P. Cooper v. U.S. Department of Navy*, Case 1:05-cv-02252-EGS.

Defendant's Opposition to Plaintiff's Cross Motion for Summary Judgment, filed Jun. 21, 2006, *Iver P. Cooper v. U.S. Department of Navy*, Case 1:05-cv-02252-EGS.

Plaintiff's Memorandum of Points & Authorities of Plaintiff Iver Cooper in Opposition to Defendant's Motion for Summary Judgment, filed Jun. 21, 2006, *Iver P. Cooper v. U.S. Department of Navy*, Case 1:05-cv-02252-EGS.

Defendant's Reply to Plaintiff's Opposition to Defendant's Motion for Summary Judgment, filed Jul. 20, 2006, *Iver P. Cooper v. U.S. Department of Navy*, Case 1:05-cv-02252-EGS.

Plaintiff's Reply in Support of His Motion for Summary Judgment, filed Jul. 20, 2006, *Iver P. Cooper v. U.S. Department of Navy*, Case 1:05-cv-02252-EGS.

Kang and Rokita, "Site Specific and photo-induced alkylation of DNA by a dimethylanthraquinone-oligodeoxynucleotide conjugate," Nucleic Acid Res. (Oct. 15, 1996) 24(20): 3896-902.

Supplementary European Partial Search Report for EP03788662, dated Feb. 22, 2006 (2 pages).

Landegren et al. (1988) Science 241(4869): 1077-1080.

Li et al. (2004) "DNA-templated organic synthesis: nature's strategy for controlling chemical reactivity applied to synthetic molecules," Angewandte Chemie (Intl. Ed. In English) 43(37): 4848-70.

New England Biolabs 1998/1999 Catalog. Cover and p. 284.

Podyminogin et al., "Sequence-specific covalent modification of DNA by cross-linking oligonucleotides. Catalysis by RecA and implication for the mechanism of synaptic joint formation," Biochemistry (Oct. 10, 1995) 34(40): 13098-108.

International Search Report for Application No. PCT/US06/02420 dated Jul. 28, 2006 (3 pages).

Dorner et al. (1984) Journal of Virology 50(3): 507-514.

Brooker, Genetics Analysis and Principles ed. 1, 1999, Nenlo Park, CA, pp. 326, 368, 372, 373, and 379.

Gartner et al. (2001) Supporting Materials for "The Generality of DNA-Templated Synthesis as a Basis for Evolving Non-Natural Small Molecules" J. Am. Chem. Soc. 123: 6961-6963 (2001).

Stryer (1995) Biochemistry, 4th Edition, Chapter 37.

Rohatgi et al. (1996) J. Am. Chem. Soc. 118: 3332-39.

Rohatgi et al. (1996) J. Am. Chem. Soc. 118: 3340-44.

Suga et al. (1998) J. Am. Chem. Soc. 120: 1151-1156.

Suga et al. (1998) Biochem. 37: 10118-25.

Lee et al. (2000) Nature Struct. Biol. 7: 28-33.

Bartel et al. (1993) Science 261 1411-18.

Xu et al. (1999) Nucl. Acids Res. 27: 875-81.

Ekland et al. (1995) Science 269: 364-70.

Jenne et al. (1998) Chem. Biol. 5: 23-24.

Goodwin et al. (1992) J. Am. Chem. Soc. 114: 9197-98.

Xu et al. (1998) Nucl. Acids Res. 26(13): 3159-64.

Homepage of David R. Liu (http://evolve.harvard.edu) available at Mar. 11, 2000 according to the Wayback Machine (http://web.archive.org).

Homepage of David R. Liu (http://evolve.harvard.edu) available at Oct. 15, 2000 according to the Wayback Machine (http://web.archive.org).

Homepage of David R. Liu (http://evolve.harvard.edu) available at Mar. 11, 2000 according to the Wayback Machine (http://web.archive.org).

Opposition to European Patent No. EP1423400, filed May 9, 2007 (Communication issued from EPO on May 15, 2007).

Harris et al. (1999) "Directed Molecular Evolution," Origins of Life and Evolution of the Biosphere 29: 425-435.

Arnold et al. (1989) "Assay Formats Involving Acridinium-Ester-Labeled DNA Probes" Clin. Chem. 35(8): 1588-94.

Balachander et al. (1990) "Monolayer Transformation by Nucleophilic Substitution: Applications to the Creation of New Monolayer Assemblies," Langmuir 6(11): 1621-1627.

Knight et al. (1999) "Accuracy of Genotyping of Single-Nucleotide Polymorphisms by PCR-ELISA Allele-Specific Oligonucleotide Hybridization Typing and by Amplification Refractory Mutation System," Clinical Chemistry 45(10): 1860-1863.

Kuimelis et al. (1995) "Cleavage Properties of an Oligonucleotide Containing a Bridged Internucleotide 5'-Phosphothioate RNA Linkage," Nucl. Acids Res. 23(23): 4753-60.

Ma et al. (2000) "Nucleic acid-triggered catalytic drug release," PNAS USA: 97(21): 11159-63.

Mag et al. (1991) "Synthesis and Selective Cleavage of an Oligodeoxynucleotide Containing a Bridged Internucleotide 5'-Phosphorothioate Linkage," Nucl. Acids Res. 19(7):1437-1441.

Metelev et al. (2001) "New Chemically Reactive dsDNAs Containing Single Internucleotide Monophosphoryldithio links: reactivity of 5'-mercapto-oligodeoxyribonucleotides," Nucl. Acids Res. 29(19): 4062-69.

Sando et al. (2002) "Quencher as leaving group: Efficient detection of DNA-joining reactions," JACS 124(10): 2096-97.

Tyagi et al. (1996) "Molecular Beacons: Probes that Fluoresce Upon Hybridization," Nature Biotechnology 14(1): 303-08.

Gartner et al. (2002) "Expanding the Reaction and Scope of DNA-Templated Synthesis," Angewandte Chemie 41(10): 1796-1800.

Gartner et al. (2002) "Multistep small-molecule synthesis programmed by DNA templates," J. Amer. Chem. Society 124(35): 10304-06.

European Patent Office (EPO) Examination Report; European Application No. EP 03788662.9, mailed Nov. 21, 2007 (15 pages).

\* cited by examiner

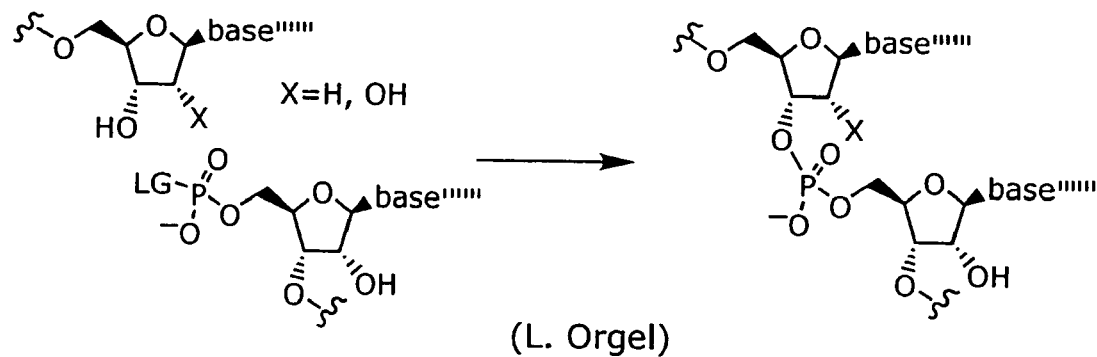
(L. Orgel)
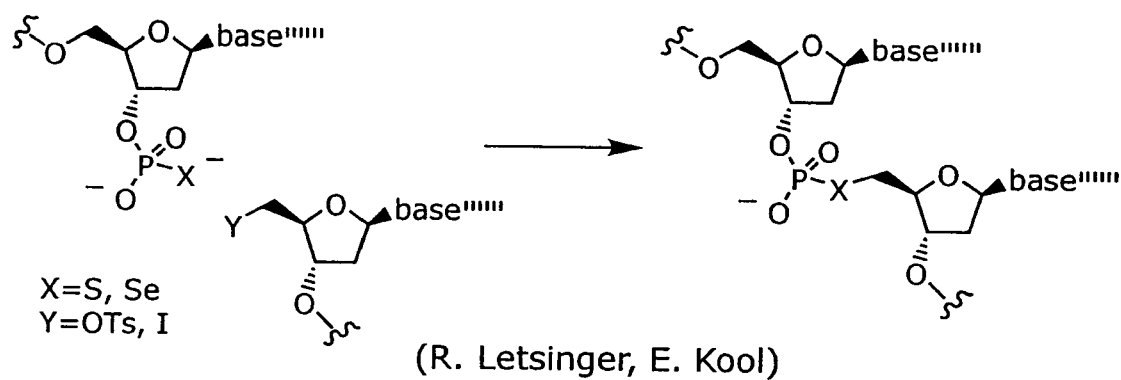
(R. Letsinger, E. Kool)
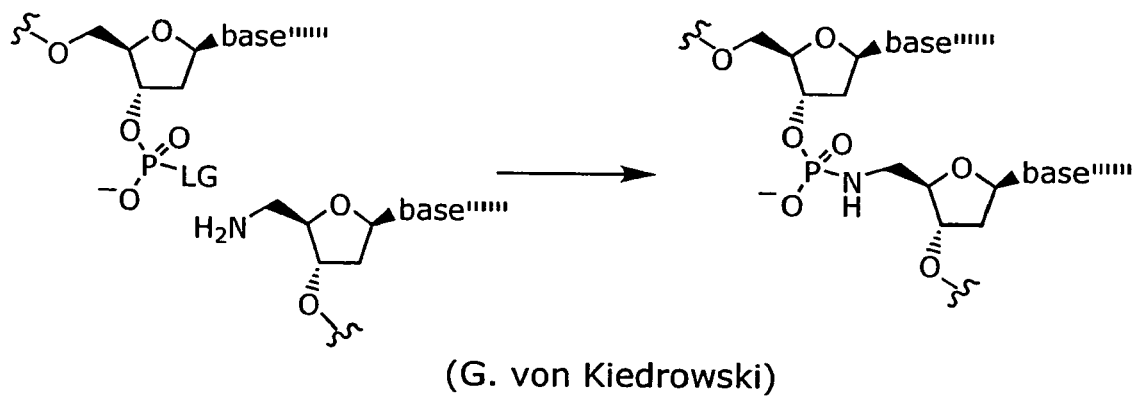
(G. von Kiedrowski)
FIG. 2A

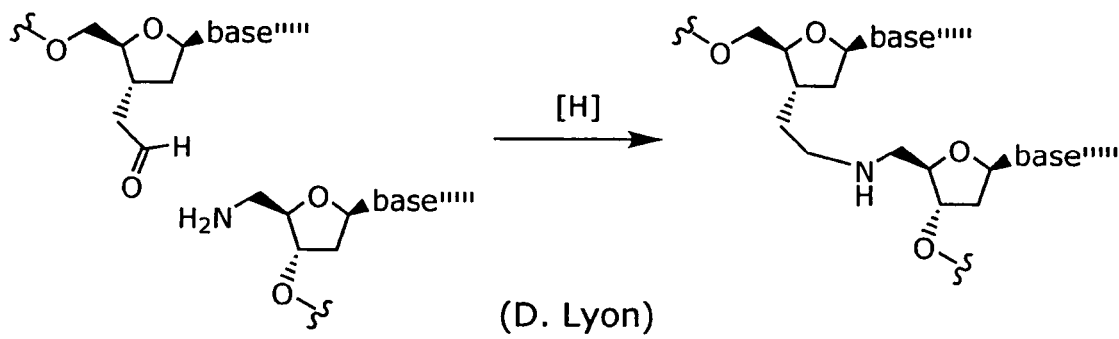
(D. Lyon)
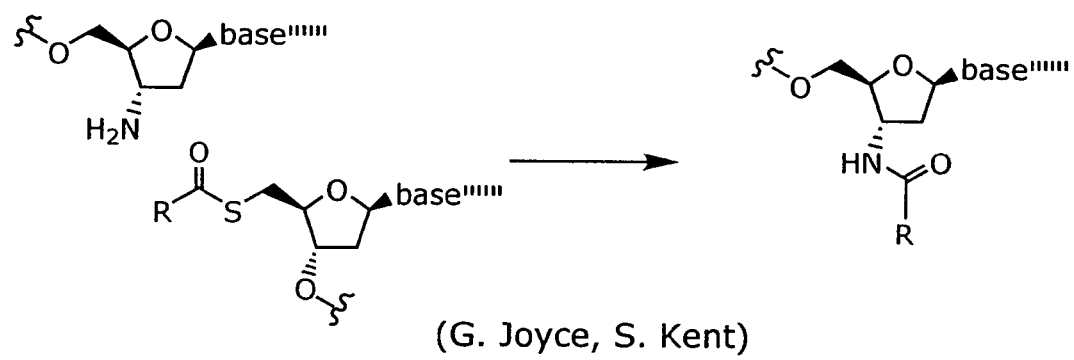
(G. Joyce, S. Kent)
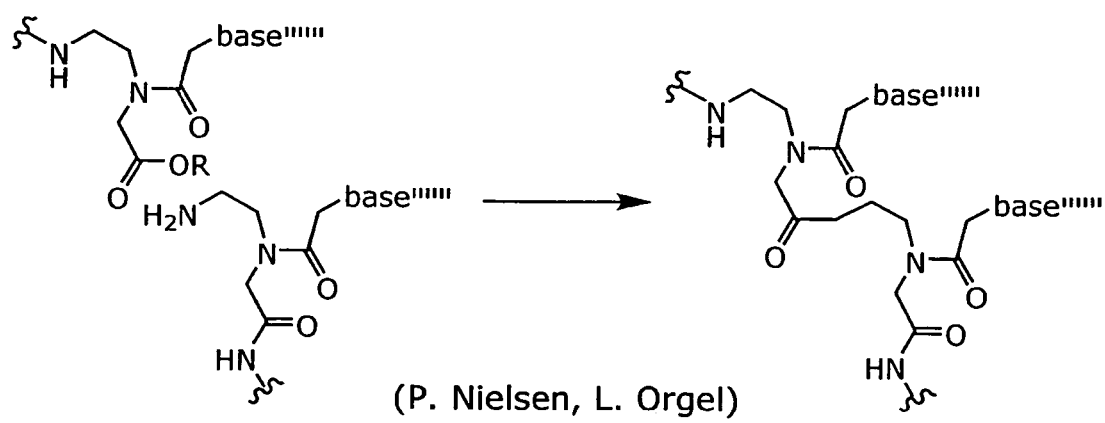
(P. Nielsen, L. Orgel)
FIG. 2B

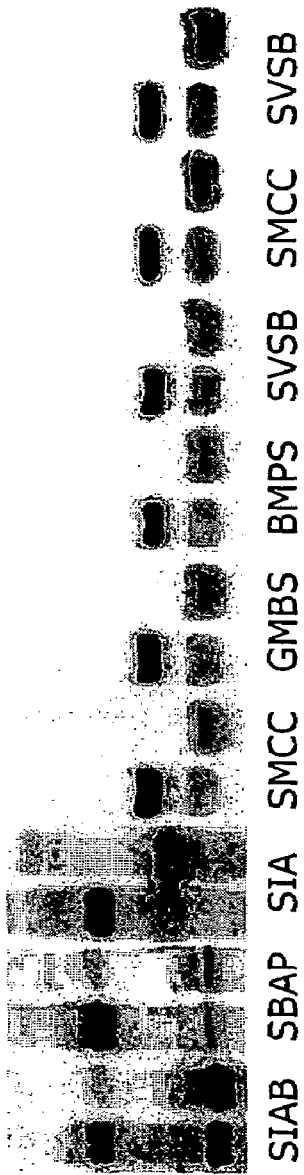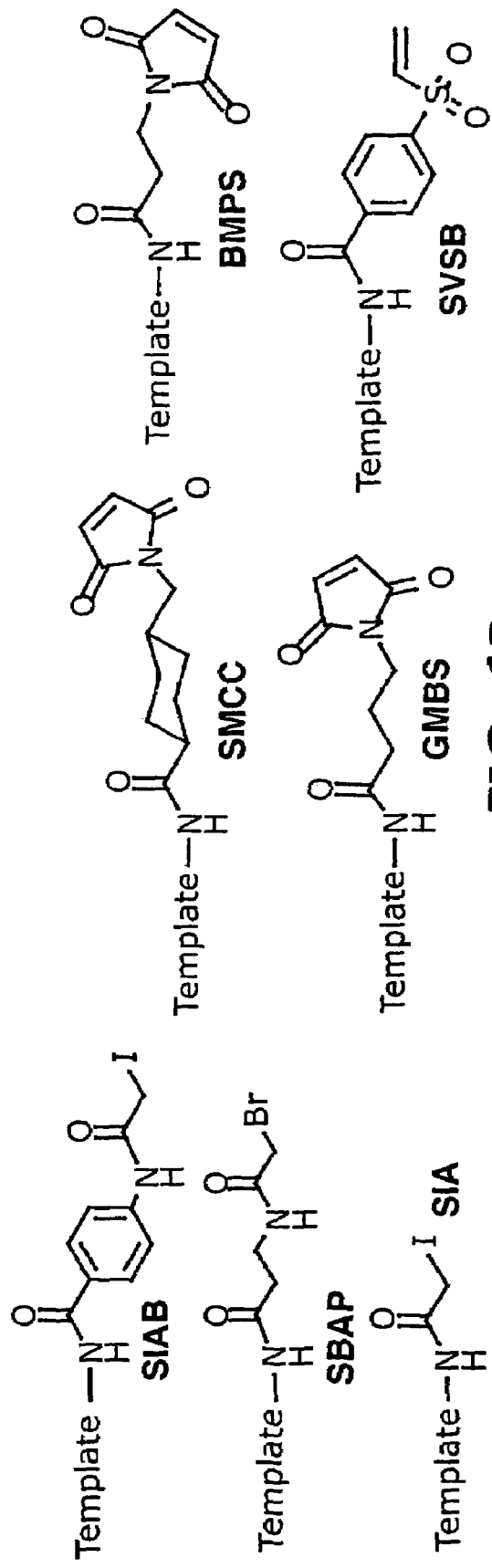
FIG. 6B

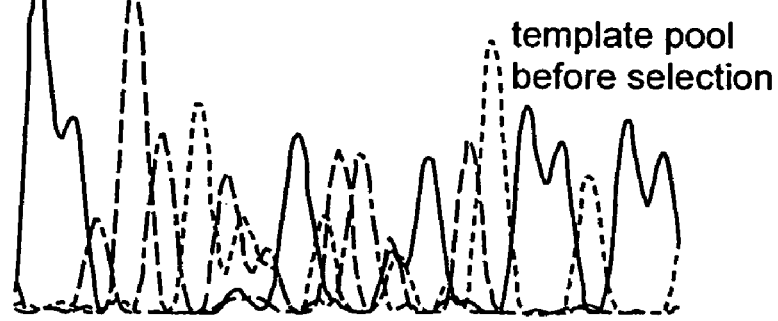
(SEQ ID NO: 35)
3'---GGT AT C<u>NN G NT NGN</u> C GGC G G--- non-biotin encoding
template pool before selection
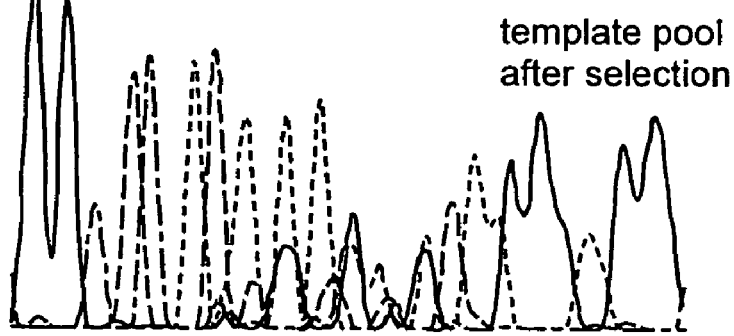
(SEQ ID NO: 36)
3'--- G GT AT C<u>AC C CGT CAC</u> GG C GG--- biotin encoding
template pool after selection
FIG. 12A

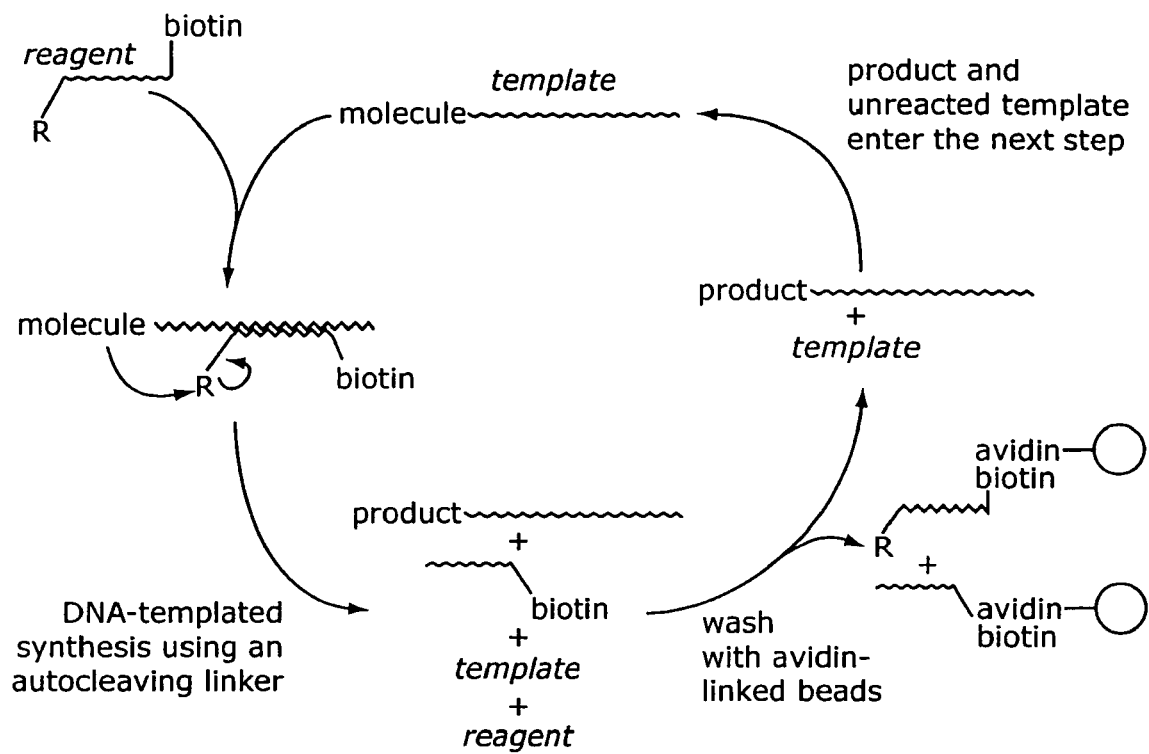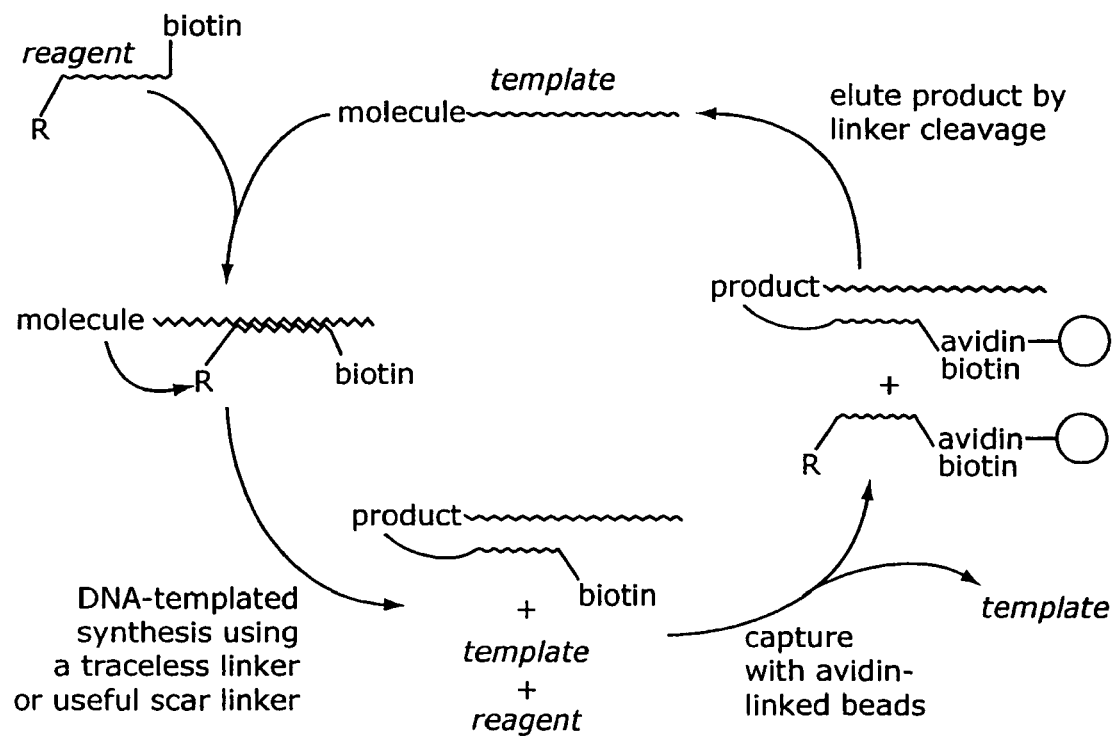
FIG. 34

Structures of reagent libraries:
5'-GCCXXXXCGC-linker-amino acid$_2$ (SEQ ID NO: 44)
5'-CCGXXXXGCC-linker-amino acid$_3$ (SEQ ID NO: 45)
5'-GCGXXXXCCG-linker-amino acid$_4$ (SEQ ID NO: 46)

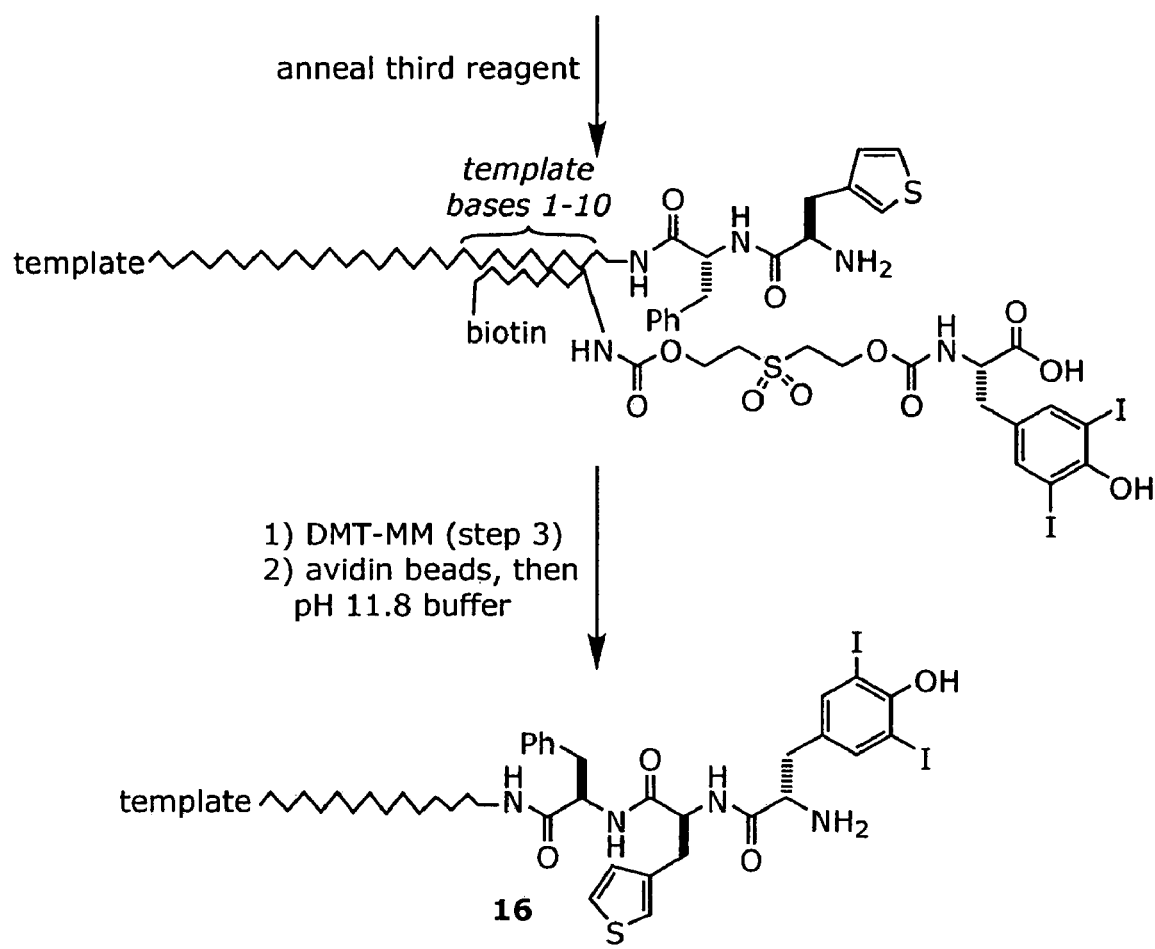
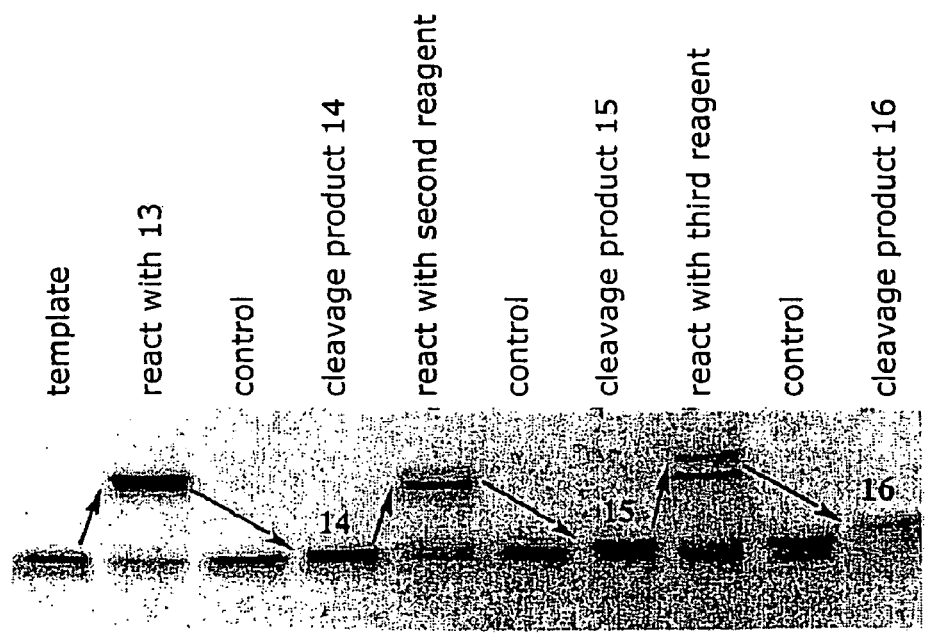
FIG. 39B

FIG. 53

(SEQ ID NO: 74) 5'-ACGTAGCGGGCGTCGCNNNNNNNNNNNNNNNNNNNNCCGTCATCGAGCCCT-3'

20 or 40 random bases
synthetic template library

3'-GGCAGTAGCTCGGGAT⌇NH₂-5 (SEQ ID NO: 75)
5'-TACGTAGCGGGCGTCGC-3' (SEQ ID NO: 76)
    |
  biotin DNA polymerase
dCTP, dGTP
dA*TP or dATP
dU*TP or dTTP

*=non-natural nucleotide

3'-ATGCATCGCCCGCAGCGNNNNNNNNNNNNNNNNNNNNGGCAGTAGCTCGGGAT⌇NH₂-5 (SEQ ID NO: 77)
5'-TACGTAGCGGGCGTCGCNNNNNNNNNNNNNNNNNNNNCCGTCATCGAGCCCTA-3' (SEQ ID NO: 78)
    |
  biotin denature strands, remove
undesired strand with
avidin magnetic beads

3'-ATGCATCGCCCGCAGCGNNNNNNNNNNNNNNNNNNNNGGCAGTAGCTCGGGAT⌇NH₂-5' (SEQ ID NO: 79)

FIG. 54

EVOLVING NEW MOLECULAR FUNCTION

PRIORITY INFORMATION

This application is a continuation of U.S. patent application Ser. No. 10/101,030, filed Mar. 19, 2002, which claims the benefit of and priority under 35 U.S.C §119(e) to U.S. provisional patent application 60/277,081, filed Mar. 19, 2001, entitled "Nucleic Acid Directed Synthesis of Chemical Compounds"; 60/277,094, filed Mar. 19, 2001, entitled "Approaches to Generating New Molecular Function"; and 60/306,691, filed Jul. 20, 2001, entitled "Approaches to Generating New Molecular Function"; the entire contents of each of these applications are hereby incorporated by reference.

STATEMENT REGARDING FEDERALLY SPONSORED RESEARCH

This invention was sponsored by the Office of Naval Research, grant number N00014-00-1-0596, and the government has certain rights to this invention.

BACKGROUND OF THE INVENTION

The classic "chemical approach" to generating molecules with new functions has been used extensively over the last century in applications ranging from drug discovery to synthetic methodology to materials science. In this approach (FIG. 1, black), researchers synthesize or isolate candidate molecules, assay these candidates for desired properties, determine the structures of active compounds if unknown, formulate structure-activity relationships based on the assay and structural data, and then synthesize a new generation of molecules designed to possess improved properties. While combinatorial chemistry methods (see, for example, A. V. Eliseev and J. M. Lehn. *Combinatorial Chemistry In Biology* 1999, 243, 159-172; K. W. Kuntz, M. L. Snapper and A. H. Hoveyda. *Current Opinion in Chemical Biology* 1999, 3, 313-319; D. R. Liu and P. G. Schultz. *Angew. Chem. Intl. Ed. Eng.* 1999, 38, 36) have increased the throughput of this approach, its fundamental limitations remain unchanged. Several factors limit the effectiveness of the chemical approach to generating molecular function. First, our ability to accurately predict the structural changes that will lead to new function is often inadequate due to subtle conformational rearrangements of molecules, unforeseen solvent interactions, or unknown stereochemical requirements of binding or reaction events. The resulting complexity of structure-activity relationships frequently limits the success of rational ligand or catalyst design, including those efforts conducted in a high-throughput manner. Second, the need to assay or screen, rather than select, each member of a collection of candidates limits the number of molecules that can be searched in each experiment. Finally, the lack of a way to amplify synthetic molecules places requirements on the minimum amount of material that must be produced for characterization, screening, and structure elucidation. As a result, it can be difficult to generate libraries of more than roughly $10^6$ different synthetic compounds.

In contrast, Nature generates proteins with new functions using a fundamentally different method that overcomes many of these limitations. In this approach (FIG. 1, gray), a protein with desired properties induces the survival and amplification of the information encoding that protein. This information is diversified through spontaneous mutation and DNA recombination, and then translated into a new generation of candidate proteins using the ribosome. The power of this process is well appreciated (see, F. Arnold *Acc. Chem. Res.* 1998, 31, 125; F. H. Arnold et al. *Curr. Opin. Chem. Biol.* 1999, 3, 54-59; J. Minshull et al. *Curr. Opin. Chem. Biol.* 1999, 3, 284-90) and is evidenced by the fact that proteins and nucleic acids dominate the solutions to many complex chemical problems despite their limited chemical functionality. Clearly, unlike the linear chemical approach described above, the steps used by Nature form a cycle of molecular evolution. Proteins emerging from this process have been directly selected, rather than simply screened, for desired activities. Because the information encoding evolving proteins (DNA) can be amplified, a single protein molecule with desired activity can in theory lead to the survival and propagation of the DNA encoding its structure. The vanishingly small amounts of material needed to participate in a cycle of molecular evolution allow libraries much larger in diversity than those synthesized by chemical approaches to be generated and selected for desired function in small volumes.

Acknowledging the power and efficiency of Nature's approach, researchers have used molecular evolution to generate many proteins and nucleic acids with novel binding or catalytic properties (see, for example, J. Minshull et al. *Curr. Opin. Chem. Biol.* 1999, 3, 284-90; C. Schmidt-Dannert et al. *Trends Biotechnol.* 1999, 17, 135-6; D. S. Wilson et al. *Annu. Rev. Biochem.* 1999, 68, 611-47). Proteins and nucleic acids evolved by researchers have demonstrated value as research tools, diagnostics, industrial reagents, and therapeutics and have greatly expanded our understanding of the molecular interactions that endow proteins and nucleic acids with binding or catalytic properties (see, M. Famulok et al. *Curr. Opin. Chem. Biol.* 1998, 2, 320-7).

Despite nature's efficient approach to generating function, nature's molecular evolution is limited to two types of "natural" molecules—proteins and nucleic acids—because thus far the information in DNA can only be translated into proteins or into other nucleic acids. However, many synthetic molecules of interest do not in general represent nucleic acid backbones, and the use of DNA-templated synthesis to translate DNA sequences into synthetic small molecules would be broadly useful only if synthetic molecules other than nucleic acids and nucleic acid analogs could be synthesized in a DNA-templated fashion. An ideal approach to generating functional molecules would merge the most powerful aspects of molecular evolution with the flexibility of synthetic chemistry. Clearly, enabling the evolution of non-natural synthetic small molecules and polymers, similarly to the way nature evolves biomolecules, would lead to much more effective methods of discovering new synthetic ligands, receptors, and catalysts difficult or impossible to generate using rational design.

SUMMARY OF THE INVENTION

The recognition of the need to be able to amplify and evolve classes of molecules besides nucleic acids and proteins led to the present invention providing methods and compositions for the template-directed synthesis, amplification, and evolution of molecules. In general, these methods use an evolvable template to direct the synthesis of a chemical compound or library of chemical compounds (i.e., the template actually encodes the synthesis of a chemical compound). Based on a library encoded and synthesized using a template such as a nucleic acid, methods are provided for amplifying, evolving, and screening the library. In certain embodiments of special interest, the chemical compounds are compounds that are not, or do not resemble, nucleic acids or analogs thereof. In certain embodiments, the chemical compounds of these template-encoded combinatorial libraries are polymers and more preferably are unnatural polymers (i.e., excluding natural peptides, proteins, and polynucleotides). In other embodiments, the chemical compounds are small molecules.

In certain embodiments, the method of synthesizing a compound or library of compounds comprises first providing one or more nucleic acid templates, which one or more nucleic acid templates optionally have a reactive unit associated therewith. The nucleic acid template is then contacted with one or more transfer units designed to have a first moiety, an anti-codon, which hybridizes to a sequence of the nucleic acid, and is associated with a second moiety, a reactive unit, which includes a building block of the compound to be synthesized. Once these transfer units have hybridized to the nucleic acid template in a sequence-specific manner, the synthesis of the chemical compound can take place due to the interaction of reactive moieties present on the transfer units and/or the nucleic acid template. Signficantly, the sequence of the nucleic acid can later be determined to decode the synthetic history of the attached compound and thereby its structure. It will be appreciated that the method described herein may be used to synthesize one molecule at a time or may be used to synthesize thousands to millions of compounds using combinatorial methods.

It will be appreciated that libraries synthesized in this manner (i.e., having been encoded by a nucleic acid) have the advantage of being amplifiable and evolvable. Once a molecule is identified, its nucleic acid template besides acting as a tag used to identify the attached compound can also be amplified using standard DNA techniques such as the polymerase chain reaction (PCR). The amplified nucleic acid can then be used to synthesize more of the desired compound. In certain embodiments, during the amplification step mutations are introduced into the nucleic acid in order to generate a population of chemical compounds that are related to the parent compound but are modified at one or more sites. The mutated nucleic acids can then be used to synthesize a new library of related compounds. In this way, the library being screened can be evolved to contain more compounds with the desired activity or to contain compounds with a higher degree of activity.

The methods of the present invention may be used to synthesize a wide variety of chemical compounds. In certain embodiments, the methods are used to synthesize and evolve unnatural polymers (i.e., excluding polynucleotides and peptides), which cannot be amplified and evolved using standard techniques currently available. In certain other embodiments, the inventive methods and compositions are utilized for the synthesis of small molecules that are not typically polymeric. In still other embodiments, the method is utilized for the generateion of non-natural nucleic acid polymers.

The present invention also provides the transfer molecules (e.g., nucleic acid templates and/or transfer units) useful in the practice of the inventive methods. These transfer molecules typically include a portion capable of hybridizing to a sequence of nucleic acid and a second portion with monomers, other building blocks, or reactants to be incorporated into the final compound being synthesized. It will be appreciated that the two portions of the transfer molecule are preferably associated with each other either directly or through a linker moiety. It will also be appreciated that the reactive unit and the anti-codon may be present in the same molecule (e.g., a non-natural nucleotide having functionality incorporated therein).

The present invention also provides kits and compositions useful in the practice of the inventive methods. These kits may include nucleic acid templates, transfer molecules, monomers, solvents, buffers, enzymes, reagents for PCR, nucleotides, small molecule scaffolds, etc. The kit may be used in the synthesis of a particular type of unnatural polymer or small molecule.

DEFINITIONS

The term antibody refers to an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

The term, associated with, is used to describe the interaction between or among two or more groups, moieties, compounds, monomers, etc. When two or more entities are "associated with" one another as described herein, they are linked by a direct or indirect covalent or non-covalent interaction. Preferably, the association is covalent. The covalent association may be through an amide, ester, carbon-carbon, disulfide, carbamate, ether, or carbonate linkage. The covalent association may also include a linker moiety such as a photocleavable linker. Desirable non-covalent interactions include hydrogen bonding, van der Waals interactions, hydrophobic interactions, magnetic interactions, electrostatic interactions, etc. Also, two or more entities or agents may be "associated" with one another by being present together in the same composition.

A biological macromolecule is a polynucleotide (e.g., RNA, DNA, RNA/DNA hybrid), protein, peptide, lipid, natural product, or polysaccharide. The biological macromolecule may be naturally occurring or non-naturally occurring. In a preferred embodiment, a biological macromolecule has a molecular weight greater than 500 g/mol.

Polynucleotide, nucleic acid, or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

A protein comprises a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. A protein may refer to a full-length protein or a fragment of a protein. Inventive proteins preferably contain only natural amino acids, although non-natural amino acids (i.e., compounds that do not occur in nature but that can be incorporated into a polypeptide chain; see, for example, http://www.cco.caltech.edu/~dadgrp/Unnatstruct-.gif, which displays structures of non-natural amino acids that have been successfully incorporated into functional ion channels) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term small molecule, as used herein, refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it possesses one or more of the following characteristics including having several carbon-carbon bonds, having multiple stereocenters, having multiple functional groups, having at least two different types of functional groups, and having a molecular weight of less than 1500, although this characterization is not intended to be limiting for the purposes of the present invention.

The term small molecule scaffold, as used herein, refers to a chemical compound having at least one site for functionalization. In a preferred embodiment, the small molecule scaffold may have a multitude of sites for functionalization. These functionalization sites may be protected or masked as would be appreciated by one of skill in this art. The sites may also be found on an underlying ring structure or backbone.

The term transfer unit, as used herein, refers to a molecule comprising an anti-codon moiety associated with a reactive unit, including, but not limited to a building block, monomer, monomer unit, or reactant used in synthesizing the nucleic acid-encoded molecules.

DESCRIPTION OF THE FIGURES

FIGS. 2A and 2B depict certain DNA-templated reactions for nucleic acids and analogs thereof.

FIG. 6B depicts matched (M) or mismatched (X) reagents linked to thiols (S) or primary amines (N) were mixed with 1 equiv of template functionalized with the variety of electrophiles shown. Reactions with thiol reagents were conducted at pH 7.5 under the following conditions: SIAB and SBAP: 37° C., 16 h; SIA: 25° C., 16 h, SMCC, GMBS, BMPS, SVSB: 25° C., 10 min. Reactions with amine reagents were conducted at 25° C., pH 8.5 for 75 minutes.

FIG. 12A depicts Lanes 1 and 5: PCT: amplified library before streptavidin binding selection. Lanes 2 and 6: PCR amplified library after selection. Lanes 3 and 7: PCR amplified authentic biotin-encoding template. Lane 4: 20 bp ladder. Lanes 5-7 were digested with Tsp45I. DNA sequencing traces of the amplified templates before and after selection are also shown, together with the sequences of the non-biotin encoding and biotin-encoding templates.

FIGS. 13A-D depict exemplary DNA-templated reactions. For all reactions under the specified conditions, product yields of reactions with matched template and reagent sequences were greater than 20-fold higher than that of control reactions with scrambled reagent sequences. Reactions were conducted at 25° C. with one equivalent each of template and reagent at 60 nM final concentration unless otherwise specified. Conditions: a) 3 mM $NaBH_3CN$, 0.1 M MES buffer pH 6.0, 0.5 M NaCl, 1.5 h; b) 0.1 M TAPS buffer pH 8.5, 300 mM NaCl, 12 h; c) 0.1 M pH 8.0 TAPS buffer, 1 M NaCl, 5° C., 1.5 h; d) 50 mM MOPS buffer pH 7.5, 2.8 M NaCl, 22 h; e) 120 nM 19, 1.4 mM $Na_2PdCl_4$, 0.5 M NaOAc buffer pH 5.0, 18 h; f) Premix $Na_2PdCl_4$ with two equivalents of $P(p-SO_3C_6H_4)_3$ in water 15 min., then add to reactants in 0.5 M NaOAc buffer pH 5.0, 75 mM NaCl, 2 h (final [Pd]=0.3 mM, [19]=120 nM). The olefin geometry of products from 13 and the regiochemistries of cycloaddition products from 14 and 16 are presumed but not verified.

FIG. 34 depicts strategies for purifying products of DNA-templated synthesis. Using biotinylated reagent oligonucleotides, products arising from an autocleaving linker are partially purified by washing the crude reaction with avidin-linked beads (top). Products generated from DNA-templated reactions using the scarless or useful scar linkers can be purified by using biotinylated reagent oligonucleotides, capturing crude reaction products with avidin-linked beads, and eluting desired products by inducing linker cleavage (bottom).

FIGS. 39A and 39B depict DNA-templated multi-step tripeptide synthesis. Each DNA-templated amide formation used reagents containing the sulfone linker described in the text. Conditions: step 1: activate two equivalents 13 in 20 mM EDC, 15 mM sulfo-NHS, 0.1 M MES buffer pH 5.5, 1 M NaCl, 10 min, 25° C., then add to template in 0.1 M MOPS pH 7.5, 1M NaCl, 25° C., 1 h; steps 2 and 3: two equivalents of reagent, 50 mM DMT-MM, 0.1 M MOPS buffer pH 7.0, 1 M NaCl, 6 h, 25° C. Desired product after each step was purified by capturing on avidin-linked beads and eluting with 0.1 M CAPS buffer pH 11.8, 60 mM BME, 37° C., 2 h. The progress of each reaction and purification was followed by denaturing polyacrylamide gel electrophoresis (bottom). Lanes 3, 6, and 9: control reactions using reagents containing scrambled oligonucleotide sequences.

FIG. 53 depicts certain exemplary nucleotide triphosphates.

FIG. 54 depicts a general method for the generation of libraries of metal-binding polymers.

DESCRIPTION OF CERTAIN EMBODIMENTS OF THE INVENTION

Figure 1:
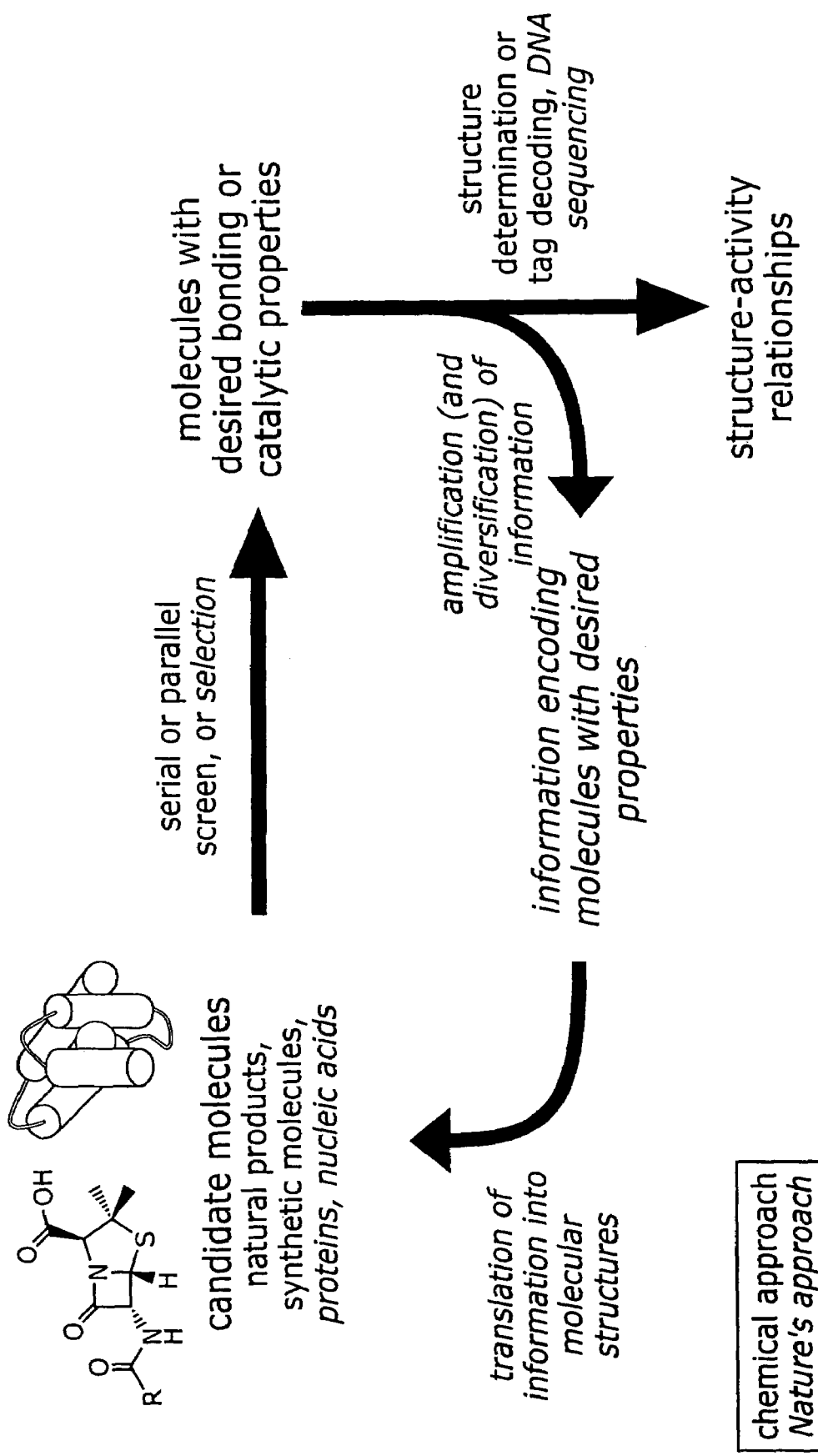
FIG. 1 depicts nature's approach (gray) and the classical chemical approach (black) to generating molecular function.

As discussed above, it would be desirable to be able to evolve and amplify chemical compounds including, but not limited to small molecules and polymers, in the same way that biopolymers such as polynucleotides and proteins can be amplified and evolved. It has been demonstrated that DNA-templated synthesis provides a possible means of translating the information in a sequence of DNA into a synthetic small molecule. In general, DNA templates linked to one reactant may be able to recruit a second reactive group linked to a complementary DNA molecule to yield a product. Since DNA hybridization is sequence-specific, the result of a DNA-templated reaction is the translation of a specific DNA sequence into a corresponding reaction product. As shown in FIG. 2, the ability of single-stranded nucleic acid templates to catalyze the sequence-specific oligomerization of complementary oligonucleotides (T. Inoue et al. *J. Am. Chem. Soc.* 1981, 103, 7666; T. Inou et al. *J. Mol. Biol.* 1984, 178, 669-76) has been demonstrated. This discovery was soon followed by findings that DNA or RNA templates could catalyze the oligomerization of complementary DNA or RNA mono-, di-, tri-, or oligonucleotides (T. Inoue et al. *J. Am. Chem. Soc.* 1981, 103, 7666; L. E. Orgel et al. *Acc. Chem. Res.* 1995, 28, 109-118; H. Rembold et al. *J. Mol. Evol.* 1994, 38, 205; L. Rodriguez et al. *J. Mol. Evol.* 1991, 33, 477; C. B. Chen et al. *J. Mol. Biol.* 1985, 181, 271). DNA or RNA templates have since been shown to accelerate the formation of a variety of non-natural nucleic acid analogs, including peptide nucleic acids (C. Bohler et al. *Nature* 1995, 376, 578), phosphorothioate—(M. K. Herrlein et al. *J. Am. Chem. Soc.* 1995, 117, 10151-10152), phosphoroselenate—(Y. Xu et al. *J. Am. Chem. Soc.* 2000, 122, 9040-9041; Y. Xu et al. *Nat. Biotechnol.* 2001, 19, 148-152) and phosphoramidate-(A. Luther et al. *Nature* 1998, 396, 245-8) containing nucleic acids, non-ribose nucleic acids (M. Bolli et al. *Chem. Biol.* 1997, 4, 309-20), and DNA analogs in which a phosphate linkage has been replaced with an aminoethyl group (Y. Gat et al. *Biopolymers* 1998, 48, 19-28). Nucleic acid templates can also catalyze amine acylation between nucleotide analogs (R. K. Bruick et al. *Chem. Biol.* 1996, 3, 49-56).

However, although the ability of nucleic acid templates to accelerate the formation of a variety of non-natural nucleic acid analogues has been demonstrated, nearly all of these reactions previously shown to be catalyzed by nucleic acid templates were designed to proceed through transition states closely resembling the structure of the natural nucleic acid backbone (FIG. 2), typically affording products that preserve the same six-bond backbone spacing between nucleotide units. The motivation behind this design was presumably the assumption that the rate enhancement provided by nucleic acid templates depends on a precise alignment of reactive groups, and the precision of this alignment is maximized when the reactants and products mimic the structure of the DNA and RNA backbones. Evidence in support of the hypothesis that DNA-templated synthesis can only generate products that resemble the nucleic acid backbone comes from the well-known difficulty of macrocyclization in organic synthesis (G. Illuminati et al. *Acc. Chem. Res.* 1981, 14, 95-102; R. B. Woodward et al. *J. Am. Chem. Soc.* 1981, 103, 3210-3213). The rate enhancement of intramolecular ring closing reactions compared with their intermolecular counterparts is known to diminish quickly as rotatable bonds are added between reactive groups, such that linking reactants with a flexible 14-carbon linker hardly affords any rate acceleration (G. Illuminati et al. *Acc. Chem. Res.* 1981, 14, 95-102).

Because synthetic molecules of interest do not in general resemble nucleic acid backbones, the use of DNA-templated synthesis to translate DNA sequences into synthetic small molecules would be broadly useful only if synthetic molecules other than nucleic acids and nucleic acid analogs could be synthesized in a DNA-templated fashion. The ability of DNA-templated synthesis to translate DNA sequences into arbitrary non-natural small molecules therefore requires demonstrating that DNA-templated synthesis is a much more general phenomenon than has been previously described.

Signficantly, for the first time it has been demonstrated herein that DNA-tempated synthesis is indeed a general phenomenon and can be used for a variety of reactions and conditions to generate a diverse range of compounds, specifically including for the first time, compounds that are not, or do not resemble, nucleic acids or analogs thereof. More specifically, the present invention extends the ability to amplify and evolve libraries of chemical compounds beyond natural biopolymers. The ability to synthesize chemical compounds of arbitrary structure allows researchers to write their own genetic codes incorporating a wide range of chemical functionality into novel backbone and side-chain structures, which enables the development of novel catalysts, drugs, and polymers, to name a few examples. For example, the ability to directly amplify and evolve these molecules by genetic selection enables the discovery of entirely new families of artificial catalysts which possess activity, bioavailability, solvent, or thermal stability, or other physical properties (such as fluorescence, spin-labeling, or photolability) which are difficult or impossible to achieve using the limited set of natural protein and nucleic acid building blocks. Similarly, developing methods to amplify and directly evolve synthetic small molecules by iterated cycles of mutation and selection enables the isolation of novel ligands or drugs with properties superior to those isolated by traditional rational design or combinatorial screening drug discovery methods. Additionally, extending the approaches described herein to polymers of significance in material science would enable the evolution of new plastics.

In general, the method of the invention involves 1) providing one or more nucleic acid templates, which one or more nucleic acid templates optionally have a reactive unit associated therewith; and 2) contacting the one or more nucleic acid templates with one or more transfer units designed to have a first moiety, an anti-codon which hybridizes to a sequence of the nucleic acid, and is associated with a second moiety, a reactive unit, which includes specific functionality, a building block, reactant, etc. for the compound to be synthesized. It will be appreciated that in certain embodiments of the invention, the transfer unit comprises one moiety incorporating the hybridization capablility of the anti-codon unit and the chemical functionality of the reaction unit. Once these transfer units have hybridized to the nucleic acid template in a sequence-specific manner, the synthesis of the chemical compound can take place due to the interaction of reactive units present on the transfer units and/or the nucleic acid template. Significantly, the sequence of the nucleic acid can later be determined to decode the synthetic history of the attached compound and thereby its structure. It will be appreciated that the method described herein may be used to synthesize one molecule at a time or may be used to synthesize thousands to millions of compounds using combinatorial methods.

Figure 3:
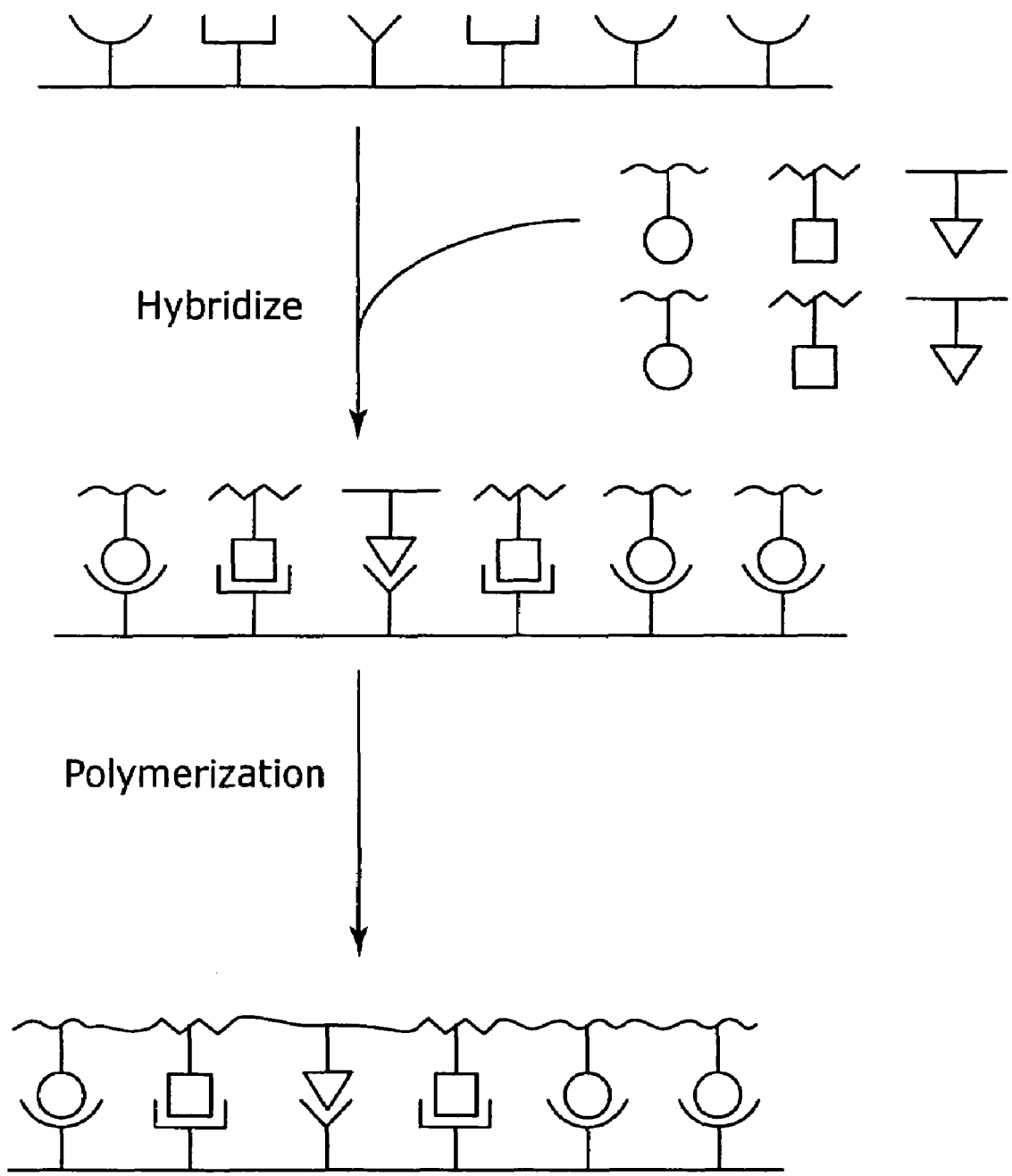
FIG. 3 depicts the general method for synthesizing a polymer using nucleic acid-templated synthesis.

It will be appreciated that a variety of chemical compounds can be prepared and evolved according to the method of the invention. In certain embodiments of the invention, however, the methods are utilized for the synthesis of chemical compounds that are not, or do not, resemble nucleic acids or nucleic acid analogs. For example, in certain embodiments of the invention, small molecule compounds can be syntheiszed by providing a template which has a reactive unit (e.g., building block or small molecule scaffold) associated therewith (attached directly or through a linker as described in more detail in Examples 5 herein), and contacting the template simultaneously or sequentially with one or more transfer units having one or more reactive units associated therewith. In certain other embodiments, non-natural polymers can be synthesized by providing a template and contacting the template simultaneously with one or more transfer units having one or more reactive units associated therewith under conditions suitable to effect reaction of the adjacent reactive units on each of the transfer units (see, for example, FIG. 3, and examples 5 and 9, as described in more detail herein).

Certain embodiments are discussed in more detail below; however, it will be appreciated that the present invention is not intended to be limited to those embodiments discussed below. Rather, the present invention is intended to encompass these embodiments and equivalents thereof.

Templates

As discussed above, one or more templates are utilized in the method of the invention and hybridize to the transfer units to direct the synthesis of the chemical compound. As would be appreciated by one of skill in this art, any template may be used in the methods and compositions of the present invention. Templates which can be mutated and thereby evolved can be used to guide the synthesis of another chemical compound or library of chemical compounds as described in the present invention. As described in more detail herein, the evolvable template encodes the synthesis of a chemical compound and can be used later to decode the synthetic history of the chemical compound, to indirectly amplify the chemical compound, and/or to evolve (i.e., diversify, select, and amplify) the chemical compound. The evolvable template is, in certain embodiments, a nucleic acid. In certain embodiment of the present invention, the template is based on a nucleic acid.

The nucleic acid templates used in the present invention are made of DNA, RNA, a hybrid of DNA and RNA, or a derivative of DNA and RNA, and may be single- or double-stranded. The sequence of the template is used in the inventive method to encode the synthesis of a chemical compound, preferably a compound that is not, or does not resemble, a nucleic acid or nucleic acid analog (e.g., an unnatural polymer or a small molecule). In the case of certain unnatural polymers, the nucleic acid template is used to align the monomer units in the sequence they will appear in the polymer and to bring them in close proximity with adjacent monomer units along the template so that they will react and become joined by a covalent bond. In the case of a small molecule, the template is used to bring particular reactants within proximity of the small molecule scaffold in order that they may modify the scaffold in a particular way. In certain other embodiments, the template can be utilized to generate non-natural polymers by PCR amplification of a synthetic DNA template library consisting of a random region of nucleotides, as describe in Example 9 herein.

As would be appreciated by one of skill in the art, the sequence of the template may be designed in a number of ways without going beyond the scope of the present invention. For example, the length of the codon must be determined and the codon sequences must be set. If a codon length of two is used, then using the four naturally occurring bases only 16 possible combinations are available to be used in encoding the library. If the length of the codon is increased to three (the number Nature uses in encoding proteins), the number of possible combinations is increased to 64. Other factors to be considered in determining the length of the codon are mismatching, frame-shifting, complexity of library, etc. As the length of the codon is increased up to a certain extent the number of mismatches is decreased; however, excessively long codons will hybridize despite mismatched base pairs. In certain embodiments of special interest, the length of the codon ranges between 2 and 10 bases.

Figure 4:
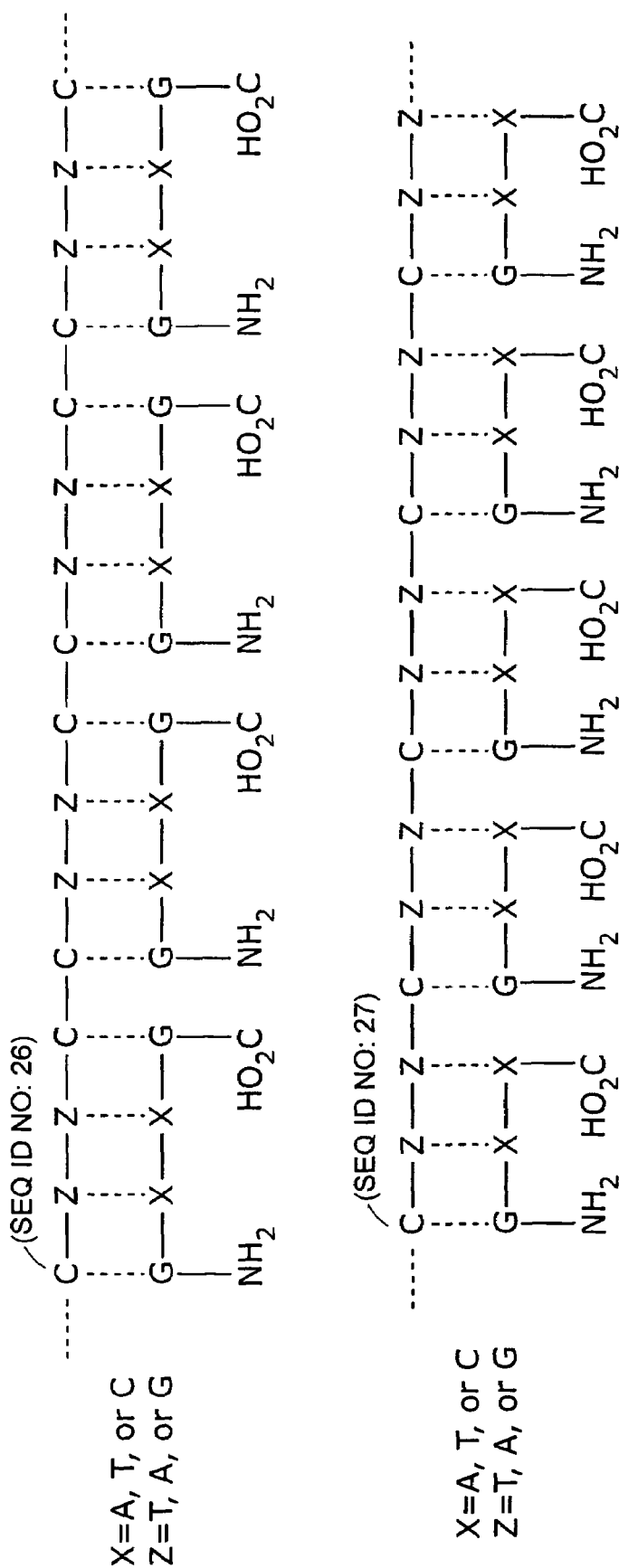
FIG. 4 shows a quadruplet and triplet non-frameshifting codon set. Each set provides nine possible codons.

Another problem associated with using a nucleic acid template is frame shifting. In Nature, the problem of frameshifting in the translation of protein from an mRNA is avoided by use of the complex machinery of the ribosome. The inventive methods, however, will not take advantage of such complex machinery. Instead, frameshifting may be remedied by lengthening each codon such that hybridization of a codon out of frame will guarantee a mismatch. For example, each codon may start with a G, and subsequent positions may be restricted to T, C, and A (FIG. 4). In another example, each codon may begin and end with a G, and subsequent positions may be restricted to T, C, and A. Another way of avoiding frame shifting is to have the codons sufficiently long so that the sequence of the codon is only found within the sequence of the template "in frame". Spacer sequences may also be placed in between the codons to prevent frame shifting.

It will be appreciated that the template can vary greatly in the number of bases. For example, in certain embodiments, the template may be 10 to 10,000 bases long, preferably between 10 and 1,000 bases long. The length of the template will of course depend on the length of the codons, complexity of the library, length of the unnatural polymer to be synthesized, complexity of the small molecule to be synthesized, use of space sequences, etc. The nucleic acid sequence may be prepared using any method known in the art to prepare nucleic acid sequences. These methods include both in vivo and in vitro methods including PCR, plasmid preparation, endonuclease digestion, solid phase synthesis, in vitro transcription, strand separation, etc. In certain embodiments, the nucleic acid template is synthesized using an automated DNA synthesizer.

As discussed above, in certain embodiments of the invention, the method is used to synthesize chemical compounds that are not, or do not resemble, nucleic acids or nucleic acid analogs. Although it has been demonstrated that DNA-templated synthesis can be utilized to direct the synthesis of nucleic acids and analogs thereof, it has not been previously demonstrated that the phenomenon of DNA-tempalted synthesis is general enough to extend to other more complex chemical compounds (e.g., small molecules, non-natural polymers). As described in detail herein, it has been demonstrated that DNA-templated synthesis is indeed a more general phenomenon and that a variety of reactions can be utilized.

Thus, in certain embodiments of the present invention, the nucleic acid template comprises sequences of bases that encode the synthesis of an unnatural polymer or small molecule. The message encoded in the nucleic acid template preferably begins with a specific codon that bring into place a chemically reactive site from which the polymerization can take place, or in the case of synthesizing a small molecule the "start" codon may encode for an anti-codon associated with a small molecule scaffold or a first reactant. The "start" codon of the present invention is analogous to the "start" codon, ATG, found in Nature, which encodes for the amino acid methionine. To give but one example for use in synthesizing an unnatural polymer library, the start codon may encode for a start monomer unit comprising a primary amine masked by a photolabile protecting group, as shown below in Example 5A.

In yet other embodiments of the invention, the nucleic acid template itself may be modified to include an initiation site for polymer synthesis (e.g., a nucleophile) or a small molecule scaffold. In certain embodiments, the nucleic acid template includes a hairpin loop on one of its ends terminating in a reactive group used to initiate polymerization of the monomer units. For example, a DNA template may comprise a hairpin loop terminating in a 5'-amino group, which may be protected or not. From the amino group polymerization of the unnatural polymer may commence. The reactive amino group can also be used to link a small molecule scaffold onto the nucleic acid template in order to synthesize a small molecule library.

To terminate the synthesis of the unnatural polymer a "stop" codon should be included in the nucleic acid template preferably at the end of the encoding sequence. The "stop" codon of the present invention is analogous to the "stop" codons (i.e., TAA, TAG, TGA) found in mRNA transcripts. In Nature, these codons lead to the termination of protein synthesis. In certain embodiments, a "stop" codon is chosen that is compatible with the artificial genetic code used to encode the unnatural polymer. For example, the "stop" codon should not conflict with any other codons used to encode the synthesis, and it should be of the same general format as the other codons used in the template. The "stop" codon may encode for a monomer unit that terminates polymerization by not providing a reactive group for further attachment. For example, a stop monomer unit may contain a blocked reactive group such as an acetamide rather than a primary amine as shown in Example 5A below. In yet other embodiments, the stop monomer unit comprises a biotinylated terminus providing a convenient way of terminating the polymerization step and purifying the resulting polymer.

Transfer Units

As described above, in the method of the invention, transfer units are also provided which comprise an anti-codon and a reactive unit. It will be appreciated that the anti-codons used in the present invention are designed to be complementary to the codons present within the nucleic acid template, and should be designed with the nucleic acid template and the codons used therein in mind. For example, the sequences used in the template as well as the length of the codons would need to be taken into account in designing the anti-codons. Any molecule which is complementary to a codon used in the template may be used in the inventive methods (e.g., nucleotides or non-natural nucleotides). In certain embodiments, the codons comprise one or more bases found in nature (i.e., thymidine, uracil, guanidine, cytosine, adenine). In certain other embodiments, the anti-codon comprises one or more nucleotides normally found in Nature with a base, a sugar, and an optional phosphate group. In yet other embodiments, the bases are strung out along a backbone that is not the sugar-phosphate backbone normally found in Nature (e.g., non-natural nucleotides).

As discussed above, the anti-codon is associated with a particular type of reactive unit to form a transfer unit. It will be appreciated that this reactive unit may represent a distinct entity or may be part of the functionality of the anti-codon unit (see, Example 9). In certain embodiments, each anti-codon sequence is associated with one monomer type. For example, the anti-codon sequence ATTAG may be associated with a carbamate residue with an iso-butyl side chain, and the anti-codon sequence CATAG may be associated with a carbamate residue with a phenyl side chain. This one-for-one mapping of anti-codon to monomer units allows one to decode any polymer of the library by sequencing the nucleic acid template used in the synthesis and allows one to synthesize the same polymer or a related polymer by knowing the sequence of the original polymer. It will be appreciated by one of skill in this art that by changing (e.g., mutating) the sequence of the template, different monomer units will be brought into place, thereby allowing the synthesis of related polymers, which can subsequently be selected and evolved.

In certain preferred embodiments, several anti-codons may code for one monomer unit as is the case in Nature.

In certain other embodiments of the present invention where a small molecule library is to be created rather than a polymer library, the anti-codon is associated with a reactant used to modify the small molecule scaffold. In certain embodiments, the reactant is associated with the anti-codon through a linker long enough to allow the reactant to come in contact with the small molecule scaffold. The linker should preferably be of such a length and composition to allow for intramolecular reactions and minimize intermolecular reactions. The reactants include a variety of reagents as demonstrated by the wide range of reactions that can be utilized in DNA-templated synthesis (see Example 2, 3 and 4 herein) and can be any chemical group, catalyst (e.g., organometallic compounds), or reactive moiety (e.g., electrophiles, nucleophiles) known in the chemical arts.

Additionally, the association between the anti-codon and the monomer unit or reactant in the transfer unit may be covalent or non-covalent. In certain embodiments of special intereste, the association is through a covalent bond, and in certain embodiments the covalent linkage is severable. The linkage may be cleaved by light, oxidation, hydrolysis, exposure to acid, exposure to base, reduction, etc. For examples of linkages used in this art, please see Fruchtel et al. *Angew. Chem. Int. Ed. Engl.* 35:17, 1996, incorporated herein by reference. The anti-codon and the monomer unit or reactant may also be associated through non-covalent interactions such as ionic, electrostatic, hydrogen bonding, van der Waals interactions, hydrophobic interactions, pi-stacking, etc. and combinations thereof. To give but one example, the anti-codon may be linked to biotin, and the monomer unit linked to streptavidin. The propensity of streptavidin to bind biotin leads to the non-covalent association between the anti-codon and the monomer unit to form the transfer unit.

Synthesis of Certain Exemplary Compounds

It will be appreciated that a variety of compounds and/or libraries can be prepared using the method of the invention. As discussed above, in certain embodiments of special interest, compounds that are not, or do not resemble, nucleic acids or analogs thereof, are synthesized according to the method of the invention.

In certain embodiments, polymers, specifically unnatural polymers, are prepared according to the method of the present invention. The unnatural polymers that can be created using the inventive method and system include any unnatural polymers. Exemplary unnatural polymers include, but are not limited to, polycarbamates, polyureas, polyesters, polyacrylate, polyalkylene (e.g., polyethylene, polypropylene), polycarbonates, polypeptides with unnatural stereochemistry, polypeptides with unnatural amino acids, and combination thereof. In certain embodiments, the polymers comprises at least 10 monomer units. In certain other embodiments, the polymers comprise at least 50 monomer units. In yet other embodiments, the polymers comprise at least 100 monomer units. The polymers synthesized using the inventive system may be used as catalysts, pharmaceuticals, metal chelators, materials, etc.

In preparing certain unnatural polymers, the monomer units attached to the anti-codons and used in the present invention may be any monomers or oligomers capable of being joined together to form a polymer. The monomer units may be carbamates, D-amino acids, unnatural amino acids, ureas, hydroxy acids, esters, carbonates, acrylates, ethers, etc. In certain embodiments, the monomer units have two reactive groups used to link the monomer unit into the growing polymer chain. Preferably, the two reactive groups are not the same so that the monomer unit may be incorporated into the polymer in a directional sense, for example, at one end may be an electrophile and at the other end a nucleophile. Reactive groups may include, but are not limited to, esters, amides, carboxylic acids, activated carbonyl groups, acid chlorides, amines, hydroxyl groups, thiols, etc. In certain embodiments, the reactive groups are masked or protected (Greene & Wuts *Protective Groups in Organic Synthesis*, 3rd Edition Wiley, 1999; incorporated herein by reference) so that polymerization may not take place until a desired time when the reactive groups are deprotected. Once the monomer units are assembled along the nucleic acid template, initiation of the polymerization sequence results in a cascade of polymerization and deprotection steps wherein the polymerization step results in deprotection of a reactive group to be used in the subsequent polymerization step (see, FIG. 3).

The monomer units to be polymerized may comprise two or more units depending on the geometry along the nucleic acid template. As would be appreciated by one of skill in this art, the monomer units to be polymerized must be able to stretch along the nucleic acid template and particularly across the distance spanned by its encoding anti-codon and optional spacer sequence. In certain embodiments, the monomer unit actually comprises two monomers, for example, a dicarbamate, a diurea, a dipeptide, etc. In yet other embodiments, the monomer unit actually comprises three or more monomers.

The monomer units may contain any chemical groups known in the art. As would be appreciated by one of skill in this art, reactive chemical groups especially those that would interfere with polymerization, hybridization, etc. are masked using known protecting groups. (Greene & Wuts *Protective Groups in Organic Synthesis*, 3rd Edition Wiley, 1999; incorporated herein by reference). In general, the protectirig groups used to mask these reactive groups are orthogonal to those used in protecting the groups used in the polymerization steps.

In synthesizing an unnatural polymer, in certain embodiments, a template is provided encoding the sequence of monomer units. Transfer units are then allow to contact the template under conditions that allow for hybridization of the anti-codons to the template. Polymerization of the monomer units along the template is then allowed to occur to form the unnatural polymer. The newly synthesized polymer may then be cleaved from the anti-codons and/or the template. The template may be used as a tag to elucidate the structure of the polymer or may be used to amplify and evolve the unnatural polymer. As will be described in more detail below, the present method may be used to prepare a library of unnatural polymers. For example, in certain embodiments, as described in more detail in Example 9 herein, a library of DNA templates can be utilized to prepare unnatural polymers. In general, the method takes advantage of the fact that certain DNA polymerases are able to accept certain modified nucleotide triphosphate substrates and that several deoxyribonucleotides and ribonucleotides bearing modified groups that do not participate in Watson-Crick bonding are known to be inserted with high sequence specificity opposite natural DNA templates. Accordingly, single stranded DNA containing modified nucleotides can serve as efficient templates for the DNA-polymerase catalyzed incorporation of natural or modified nucleotides.

It will be appreciated that the inventive methods may also be used to synthesize other classes of chemical compounds besides unnatural polymers. For example, small molecules may be prepared using the methods and compositions provided by the present invention. These small molecules may be natural product-like, non-polymeric, and/or non-oligomeric. The substantial interest in small molecules is due in part to their use as the active ingredient in many pharmaceutical preparations although they may also be used as catalysts, materials, additives, etc.

In synthesizing small molecules using the method of the present invention, an evolvable template is also provided. The template may either comprise a small molecule scaffold upon which the small molecule is to be built, or a small molecule scaffold may be added to the template. The small molecule scaffold may be any chemical compound with sites for functionalization. For example, the small molecule scaffold may comprises a ring system (e.g., the ABCD steroid ring system found in cholesterol) with functionalizable groups off the atoms making up the rings. In another example, the small molecule may be the underlying structure of a pharmaceutical agent such as morphine or a cephalosporin antibiotic (see Examples 5C and 5D below below). The sites or groups to be functionalized on the small molecule scaffold may be protected using methods and protecting groups known in the art. The protecting groups used in a small molecule scaffold may be orthogonal to one another so that protecting groups can be removed one at a time.

In this embodiment, the transfer units comprise an anti-codon similar to those described in the unnatural polymer synthesis; however, these anti-codons are associated with reactants or building blocks to be used in modifying, adding to, or taking away from the small molecule scaffold. The reactants or building blocks may be electrophiles (e.g., acetyl, amides, acid chlorides, esters, nitrites, imines), nucleophiles (e.g., amines, hydroxyl groups, thiols), catalysts (e.g., organometallic catalysts), side chains, etc. See, for example reactions in aqueous and organic media as described herein in Examples 2 and 4. The transfer units are allowed to contact the template under hydridizing conditions, and the attached reactant or building block is allowed to react with a site on the small molecule scaffold. In certain embodiments, protecting groups on the small molecule template are removed one at a time from the sites to be functionalized so that the reactant of the transfer unit will react at only the desired position on the scaffold. As will be appreciated by one of skill in the art, the anti-codon may be associated with the reactant through a linker moiety (see, Example 3). The linker facilitates contact of the reactant with the small molecule scaffold and in certain embodiments, depending on the desired reaction, positions DNA as a leaving group ("autocleavable" strategy), or may link reactive groups to the template via the "scarless" linker strategy (which yields product without leaving behind additional chemical functionality), or a "useful scar" strategy (in which the linker is left behind and can be functionalized in subsequent steps following linker cleavage). The reaction condition, linker, reactant, and site to be functionalized are chosen to avoid intermolecular reactions and accelerate intramolecular reactions. It will also be appreciated that the method of the present invention contemplates both sequential and simultaneous contacting of the template with transfer units depending on the particular compound to be synthesized. In certain embodiments of special interest, the multi-step synthesis of chemical compounds is provided in which the template is contacted sequentially with two or more transfer units to facilitate multi-step synthesis of complex chemical compounds.

After the sites on the scaffold have been modified, the newly synthesized small molecule is linked to the template that encoded is synthesis. Decoding of the template tag will allow one to elucidate the synthetic history and thereby the structure of the small molecule. The template may also be amplified in order to create more of the desired small molecule and/or the template may be evolved to create related small molecules. The small molecule may also be cleaved from the template for purification or screening.

As would be appreciated by one of skill in this art, a plurality of templates may be used to encode the synthesis of a combinatorial library of small molecules using the method described above. This would allow for the amplification and evolution of a small molecule library, a feat which has not been accomplished before the present invention.

Method of Synthesizing Libraries of Compounds

In the inventive method, a nucleic acid template, as described above, is provided to direct the synthesis of an unnatural polymer, a small molecule, or any other type of molecule of interest. In general, a plurality of nucleic acid templates is provided wherein the number of different sequences provided ranges from 2 to $10^{15}$. In one embodiment of the present invention, a plurality of nucleic acid templates is provided, preferably at least 100 different nucleic acid templates, more preferably at least 10000 different nucleic acid templates, and most preferably at least 1000000 different nucleic acid templates. Each template provided comprises a unique nucleic acid sequence used to encode the synthesis of a particular unnatural polymer or small molecule. As described above, the template may also have functionality such as a primary amine from which the polymerization is initiated or a small molecule scaffold. In certain embodiments, the nucleic acid templates are provided in one "pot". In certain other embodiments, the templates are provided in aqueous media, and subsequent reactions are performed in aqueous media.

To the template is added transfer units with anti-codons, as described above, associated with a monomer unit, as described above. In certain embodiments, a plurality of transfer units is provided so that there is an anti-codon for every codon represented in the template. In a preferred embodiment, certain anti-codons are used as start and stop sites. In general, a large enough number of transfer units is provided so that all corresponding codon sites on the template are filled after hybridization.

The anti-codons of the transfer units are allowed to hybridize to the nucleic acid template thereby bringing the monomer units together in a specific sequence as determined by the template. In the situation where a small molecule library is being synthesized, reactants are brought in proximity to a small molecule scaffold. The hybridization conditions, as would be appreciated by those of skill in the art, should preferably allow for only perfect matching between the codon and its anti-codon. Even single base pair mismatches should be avoided. Hybridization conditions may include, but are not limited to, temperature, salt concentration, pH, concentration of template, concentration of anti-codons, and solvent. The hybridization conditions used in synthesizing the library may depend on the length of the codon/anti-codon, the similarity between the codons present in the templates, the content of G/C versus A/T base pairs, etc (for further information regarding hybridization conditions, please see, *Molecular Cloning: A Laboratory Manual,* 2nd Ed., ed. by Sambrook, Fritsch, and Maniatis (Cold Spring Harbor Laboratory Press: 1989); *Nucleic Acid Hybridization* (B. D. Hames & S. J. Higgins eds. 1984); the treatise, *Methods in Enzymology* (Academic Press, Inc., N.Y.); Ausubel et al. *Current Protocols in Molecular Biology* (John Wiley & Sons, Inc., New York, 1999); each of which is incorporated herein by reference).

After hybridization of the anti-codons to the codons on the template have occurred, the monomer units are then polymerized in the case of the synthesis of unnatural polymers. The polymerization of the monomer units may occur spontaneously or may need to be initiated, for example, by the deprotection of a reactive groups such as a nucleophile or by providing light of a certain wavelength. In certain other embodiments, polymers can be catalyzed by DNA polymerization capable of effecting polymerization of non-natural nucleotides (see, Example 9). The polymerization preferably occurs in one direction along the template with adjacent monomer units becoming joined through a covalent linkage. The termination of the polymerization step occurs by the addition of a monomer unit that is not capable of being added onto. In the case of the synthesis of small molecules, the reactants are allowed to react with the small molecule scaffold. The reactant may react spontaneously, or protecting groups on the reactant and/or the small molecule scaffold may need to be removed. Other reagents (e.g., acid, base, catalyst, hydrogen gas, etc.) may also be needed to effect the reaction (see, Examples 5A-5E).

After the unnatural polymers or small molecules have been created with the aid of the nucleic acid template, they may be cleaved from the nucleic acid template and/or anti-codons used to synthesize them. In certain embodiments, the polymers or small molecules are assayed before being completely detached from the nucleic acid templates that encode them. Once the polymer or small molecule is selected, the sequence of the template or its complement may be determined to elucidate the structure of the attached polymer or small molecule. This sequence may then be amplified and/or evolved to create new libraries of related polymers or small molecules that in turn may be screened and evolved.

Uses

The methods and compositions of the present invention represent a new way to generate molecules with desired properties. This approach marries the extremely powerful genetic methods, which molecular biologists have taken advantage of for decades, with the flexibility and power of organic chemistry. The ability to prepare, amplify, and evolve unnatural polymers by genetic selection may lead to new classes of catalysts that possess activity, bioavailability, stability, fluorescence, photolability, or other properties that are difficult or impossible to achieve using the limited set of building blocks found in proteins and nucleic acids. Similarly, developing new systems for preparing, amplifying, and evolving small molecules by iterated cycles of mutation and selection may lead to the isolation of novel ligands or drugs with properties superior to those isolated by slower traditional drug discovery methods (see, Example 7).

Performing organic library synthesis on the molecular biology scale is a fundamentally different approach from traditional solid phase library synthesis and carries significant advantages. A library created using the inventive methods can be screened using any method known in this art (e.g., binding assay, catalytic assay). For example, selection based on binding to a target molecule can be carried out on the entire library by passing the library over a resin covalently linked to the target. Those biopolymers that have affinity for the resin-bound target can be eluted with free target molecules, and the selected compounds can be amplified using the methods described above. Subsequent rounds of selection and amplification can result in a pool of compounds enriched with sequences that bind the target molecule. In certain embodiments, the target molecule mimics a transition state of a chemical reaction, and the chemical compounds selected may serve as a catalyst for the chemical reaction. Because the information encoding the synthesis of each molecule is covalently attached to the molecule at one end, an entire library can be screened at once and yet each molecule is selected on an individual basis.

Such a library can also be evolved by introducing mutations at the DNA level using error-prone PCR (Cadwell et al. *PCR Methods Appl.* 2:28, 1992; incorporated herein by reference) or by subjecting the DNA to in vitro homologous recombination (Stemmer *Proc. Natl. Acad. Sci. USA* 91:10747, 1994; Stemmer *Nature* 370:389, 1994; each of which is incorporated herein by reference). Repeated cycled of selection, amplification, and mutation may afford biopolymers with greatly increased binding affinity for target molecules or with significantly improved catalytic properties. The final pool of evolved biopolymers having the desired properties can be sequenced by sequencing the nucleic acid cleaved from the polymers. The nucleic acid-free polymers can be purified using any method known in the art including HPLC, column chromatography, FLPC, etc., and its binding or catalytic properties can be verified in the absence of covalently attached nucleic acid.

Figure 5:
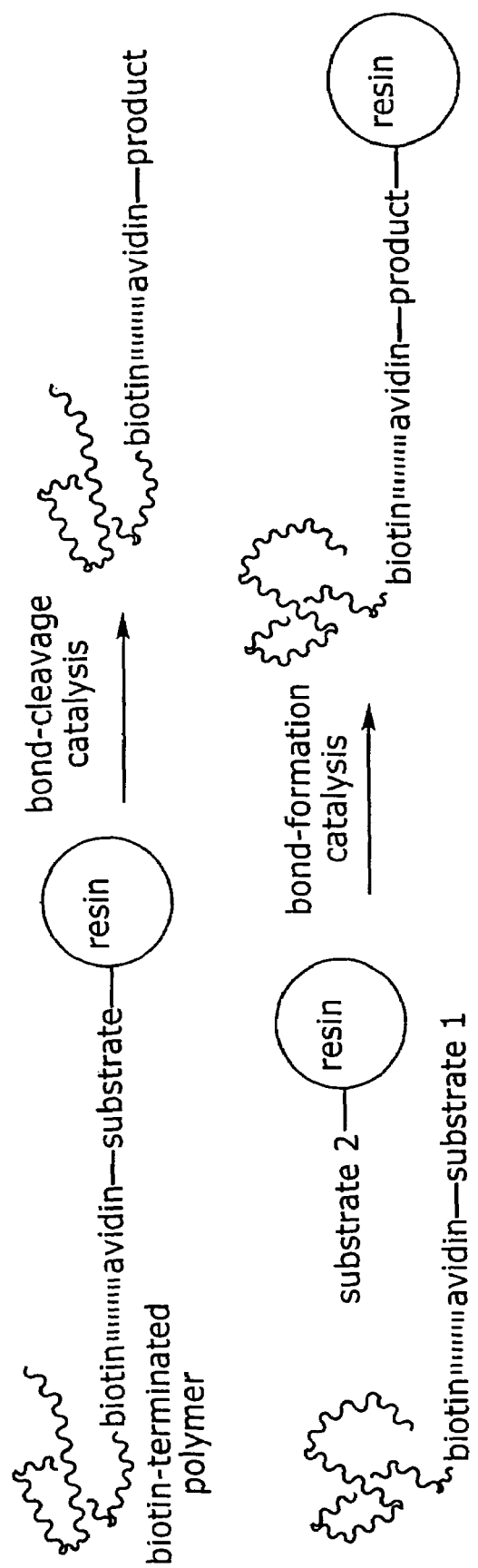
FIG. 5 shows methods of screening a library for bond-cleavage and bond-formation catalysts. These methods take advantage of streptavidin's natural affinity for biotin.

The polymerization of synthetically-generated monomer units independent of the ribosomal machinery allows the incorporation of an enormous variety of side chains with novel chemical, biophysical, or biological properties. Terminating each biopolymer with a biotin side chain, for example, allows the facile purification of only full-length biopolymers which have been completely translated by passing the library through an avidin-linked resin. Biotin-terminated biopolymers can be selected for the actual catalysis of bond-breaking reactions by passing these biopolymers over resin linked through the substrate to avidin (FIG. 5). Those biopolymers that catalyze substrate cleavage would self-elute from a column charged with this resin. Similarly, biotin-terminated biopolymers can be selected for the catalysis of bond-forming reactions (FIG. 5). One substrate is linked to resin and the second substrate is linked to avidin. Biopolymers that catalyze bond formation between the substrates are selected by their ability to ligate the substrates together, resulting in attachment of the biopolymer to the resin. Novel side chains can also be used to introduce cofactor into the biopolymers. A side chain containing a metal chelator, for example, may provide biopolymers with metal-mediated catalytic properties, while a flavin-containing side chain may equip biopolymers with the potential to catalyze redox reactions.

In this manner unnatural biopolymers may be isolated which serve as artificial receptors to selectively bind molecules or which catalyze chemical reactions. Characterization of these molecules would provide important insight into the ability of polycarbamates, polyureas, polyesters, polycarbonates, polypeptides with unnatural side chain and stereochemistries, or other unnatural polymers to form secondary or tertiary structures with binding or catalytic properties.

Kits

The present invention also provides kits and compositions for use in the inventive methods. The kits may contain any item or composition useful in practicing the present invention. The kits may include, but is not limited to, templates, anticodons, transfer units, monomer units, building blocks, reactants, small molecule scaffolds, buffers, solvents, enzymes (e.g., heat stable polymerase, reverse transcriptase, ligase, restriction endonuclease, exonuclease, Klenow fragment, polymerase, alkaline phosphatase, polynucleotide kinase), linkers, protecting groups, polynucleotides, nucleosides, nucleotides, salts, acids, bases, solid supports, or any combinations thereof.

As would be appreciated by one of skill in this art, a kit for preparing unnatural polymers would contain items needed to prepare unnatural polymers using the inventive methods described herein. Such a kit may include templates, anti-codons, transfer units, monomers units, or combinations thereof. A kit for synthesizing small molecules may include templates, anti-codons, transfer units, building blocks, small molecule scaffolds, or combinations thereof.

The inventive kit may also be equipped with items needed to amplify and/or evolve a polynucleotide template such as a heat stable polymerase for PCR, nucleotides, buffer, and primers. In certain other embodiments, the inventive kit includes items commonly used in performing DNA shuffling such as polynucleotides, ligase, and nucleotides.

In addition to the templates and transfer units described herein, the present invention also includes compositions comprising complex small molecules, scaffolds, or unnatural polymer prepared by any one or more of the methods of the invention as described herein.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

Example 1

The Generality of DNA-Templated Synthesis

Figure 6A:
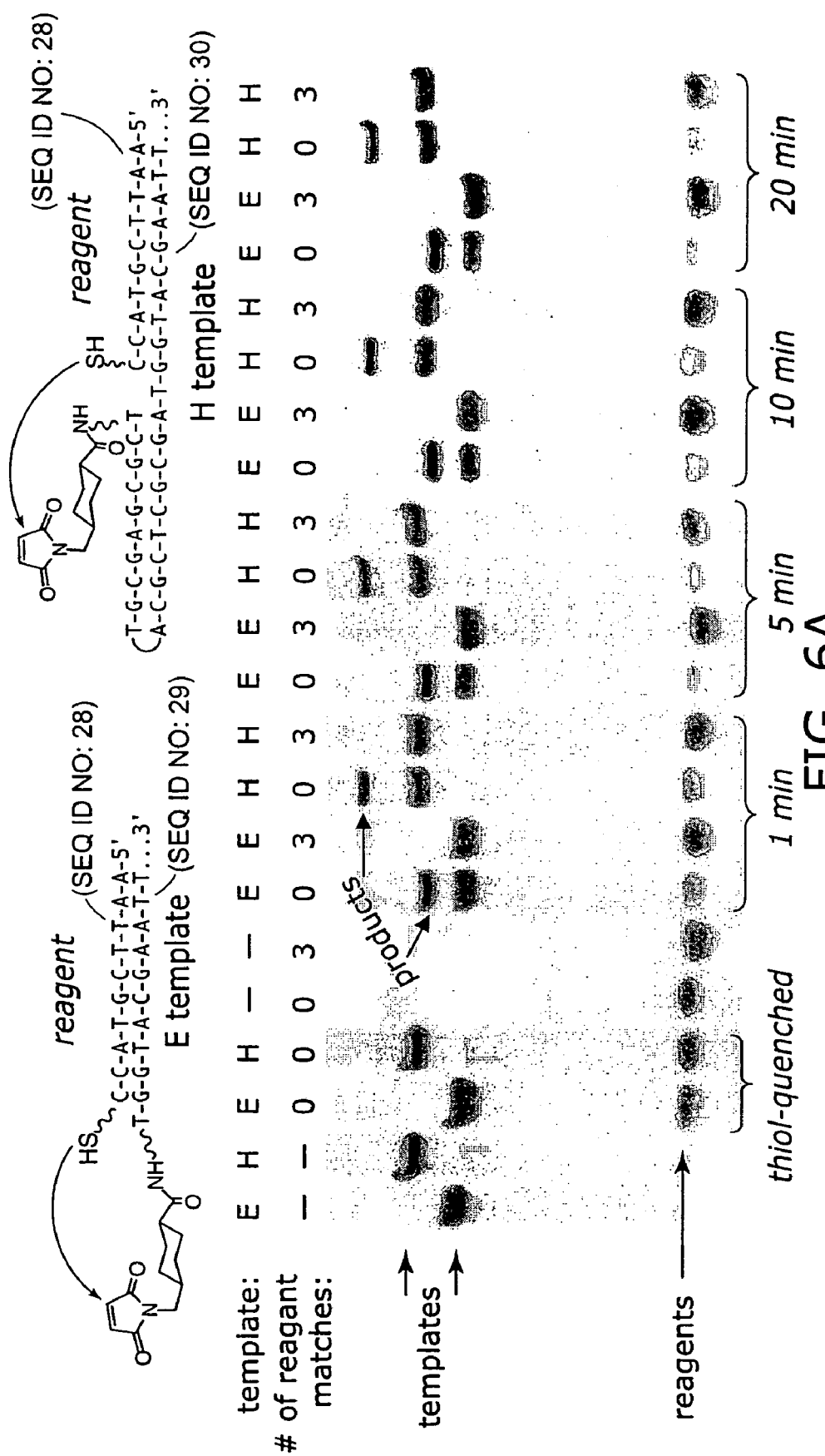
FIG. 6A depicts the synthesis directed by hairpin (H) and end-of-helix (E) DNA templates. Reactions were analyzed by denaturing PAGE after the indicated reaction times. Lanes 3 and 4 contained templates quenched with excess β-mercaptoethanol prior to reaction.

Clearly, implementing the small molecule evolution approach described above requires establishing the generality of DNA-templated synthesis. The present invention, for the first time, establishes the generality fo this approach and thus enables the syntheis of a vareity of chemical compounds using DNA-templated synthesis. As shown in FIG. 6a, the ability of two DNA architectures to support solution-phase DNA-templated synthesis was established. Both hairpin (H) and end-of-helix (E) templates bearing electrophilic maleimide groups reacted efficiently with one equivalent of thiol reagent linked to a complementary DNA oligonucleotide to yield the thioether product in minutes at 25° C. DNA-templated reaction rates ($k_{app}$=~$10^5$ $M^{-1}s^{-1}$) were similar for H and E architectures despite significant differences in the relative orientation of their reactive groups. In contrast, no product was observed when using reagents containing sequence mismatches, or when using templates pre-quenched with excess β-mercaptoethanol (FIG. 6a). Both templates therefore support the sequence-specific DNA-templated addition of a thiol to a maleimide even though the structures of the resulting products differ markedly from the structure of the natural DNA backbone. Little or no non-templated intermolecular reaction products are observed under the reaction conditions (pH 7.5, 25° C., 250 mM NaCl, 60 nM template and reagent).

Additionally, sequence-specific DNA-templated reactions spanning a variety of reaction types ($S_N2$ substitutions, additions to α,β-unsaturated carbonyl systems, and additions to vinyl sulfones), nucleophiles (thiols and amines), and reactant structures all proceeded in good yields with excellent sequence selectivity (FIG. 6b). Expected product masses were verified by mass spectrometry. In each case, matched but not mismatched reagents afforded product efficiently despite considerable variations in their transition state geometry, steric hindrance, and conformational flexibility. Collectively these findings indicate that DNA-templated synthesis is a general phenomenon capable of supporting a range of reaction types, and is not limited to the creation of structures resembling nucleic acid backbones as described previously.

Figure 7:
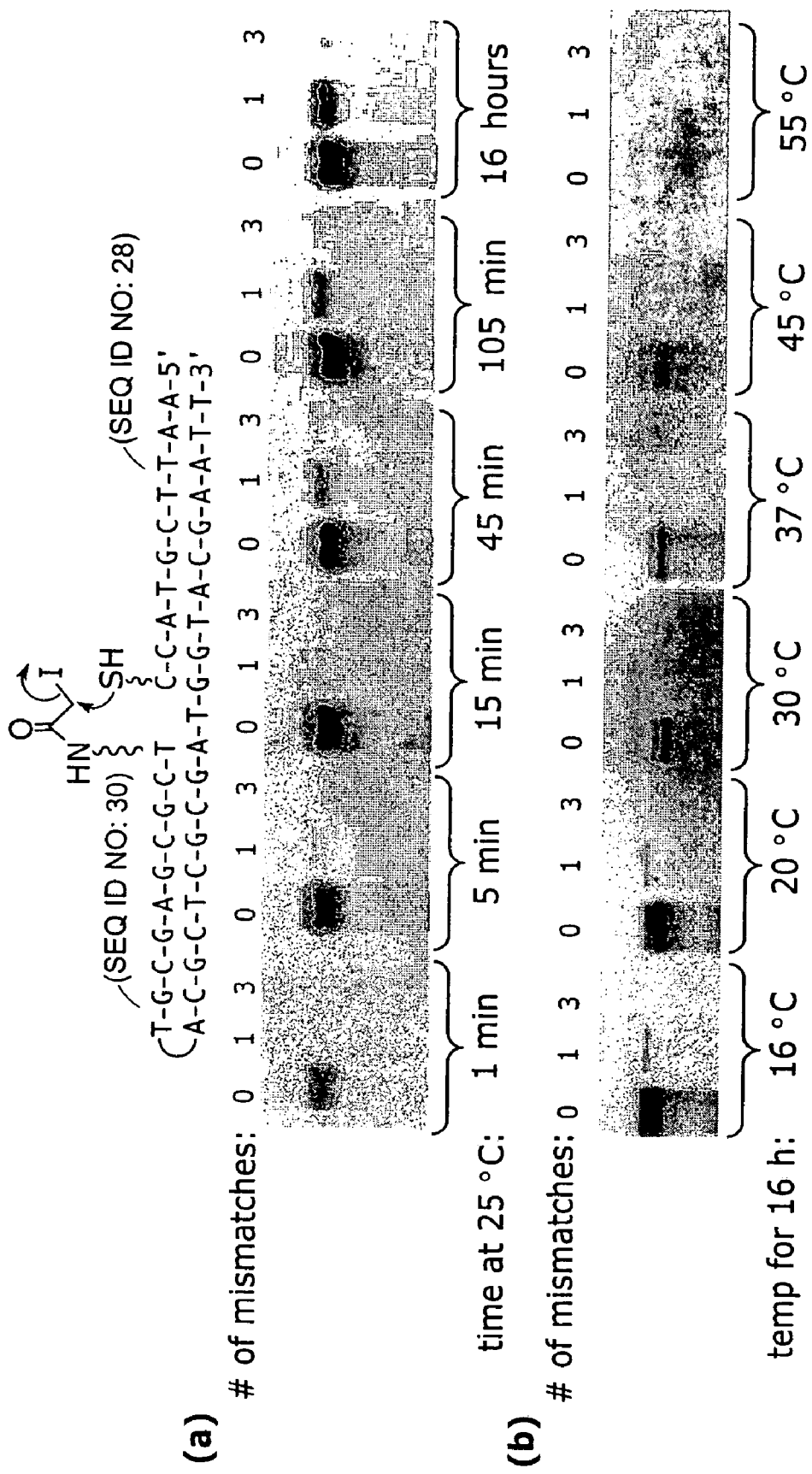
FIG. 7 depicts (a) H templates linked to a-iodoacetamide group which were reacted with thiol reagents containing 0, 1, or 3 mismatches at 25° C. (b) Reactions in (a) were repeated at the indicated temperature for 16 h. Calculated reagent Tm: 38° C. (matched), 28° C. (single mismatch).

Since sequence discrimination is important for the faithful translation of DNA into synthetic structures, the reaction rate of a matched reagent compared with that of a reagent bearing a single mismatched base near the center of its 10-base oligonucleotide was measured. At 25° C., the initial rate of reaction of matched thiol reagents with iodoacetamide-linked H templates is 200-fold faster than that of reagents bearing a single mismatch ($k_{app}$=2.4×$10^4$ $M^{-1}s^{-1}$ vs. 1.1×$10^2$ $M^{-1}s^{-1}$, FIG. 7). In addition, small amounts of products arising from the annealing of mismatched reagents can be eliminated by elevating the reaction temperature beyond the $T_m$ of the mismatched reagents (FIG. 7). The decrease in the rate of product formation as temperature is elevated further indicates that product formation proceeds by a DNA-templated mechanism rather than a simple intermolecular mechanism.

Figure 8:
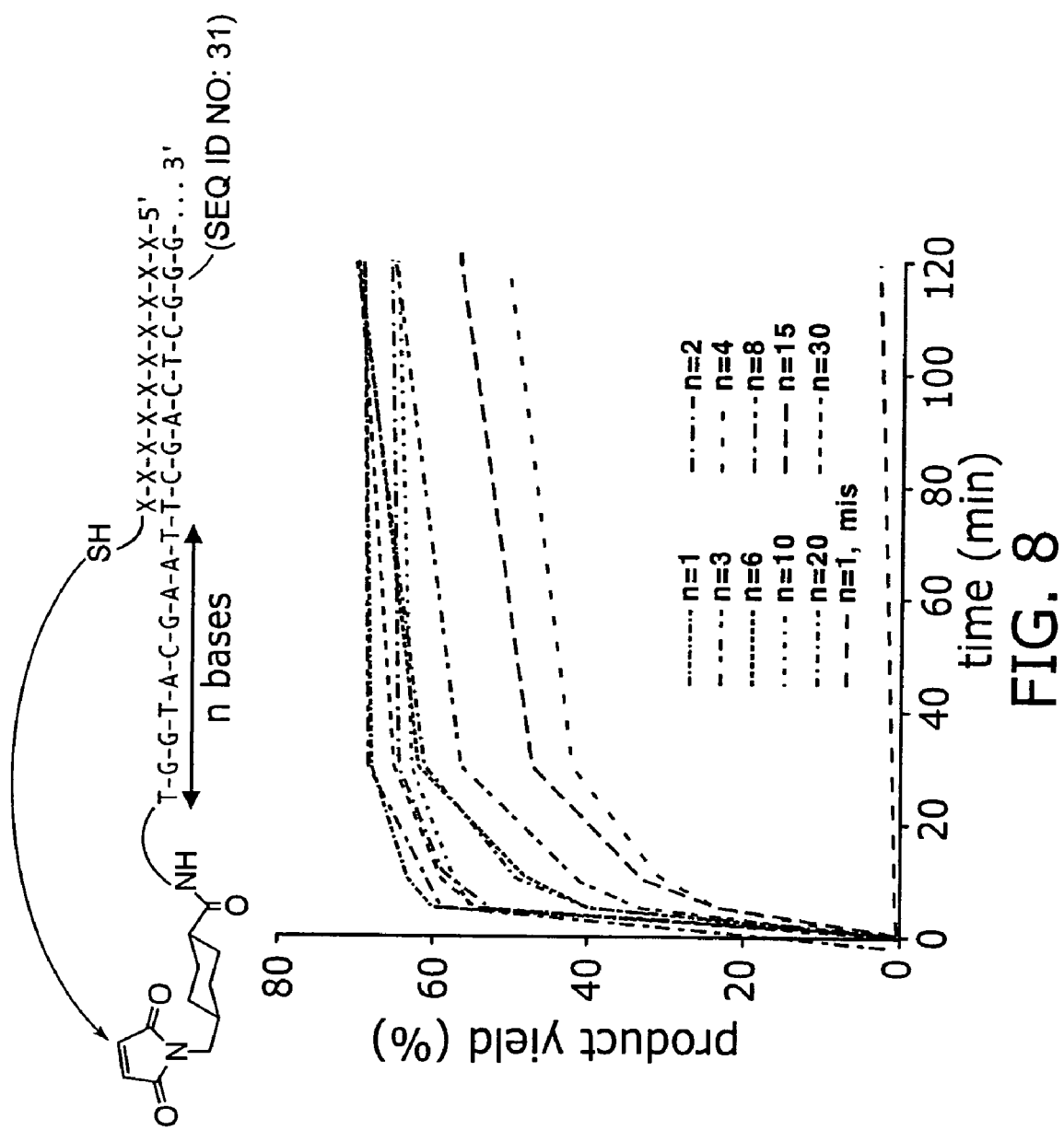
FIG. 8 depicts a reaction performed using a 41-base E template and a 10-base reagent designed to anneal 1-30 bases from the 5' end of the template. The kinetic profiles in the graph show the average of two trials (deviations <10%). The "n=1 mis" reagent contains three mismatches.

In addition to reaction generality and sequence specificity, DNA-templated synthesis also demonstrates remarkable distance independence. Both H and E templates linked to maleimide or α-iodoacetamide groups promote sequence-specific reaction with matched, but not mismatched, thiol reagents annealed anywhere on the templates examined thus far (up to 30 bases away from the reactive group on the template). Reactants annealed one base away react with similar rates as those annealed 2, 3, 4, 6, 8, 10, 15, 20, or 30 bases away (FIG. 8). In all cases, templated reaction rates are several hundred-fold higher than the rate of untemplated (mismatched) reaction ($k_{app}$=$10^4$-$10^5$ $M^{-1}s^{-1}$ vs. 5×$10^1$ $M^{-1}s^{-1}$). A internening distances of 30 bases, products are efficiently formed presumably through transition states resembling 200-membered rings. These findings contrast sharply with the well-known difficulty of macrocyclization (see, for example, G. Illuminati et al. *Acc. Chem. Res.* 1981, 14, 95-102; R. B. Woodward et al. *J. Am. Chem. Soc.* 1981, 103, 3210-3213) in organic synthesis.

Figure 9:
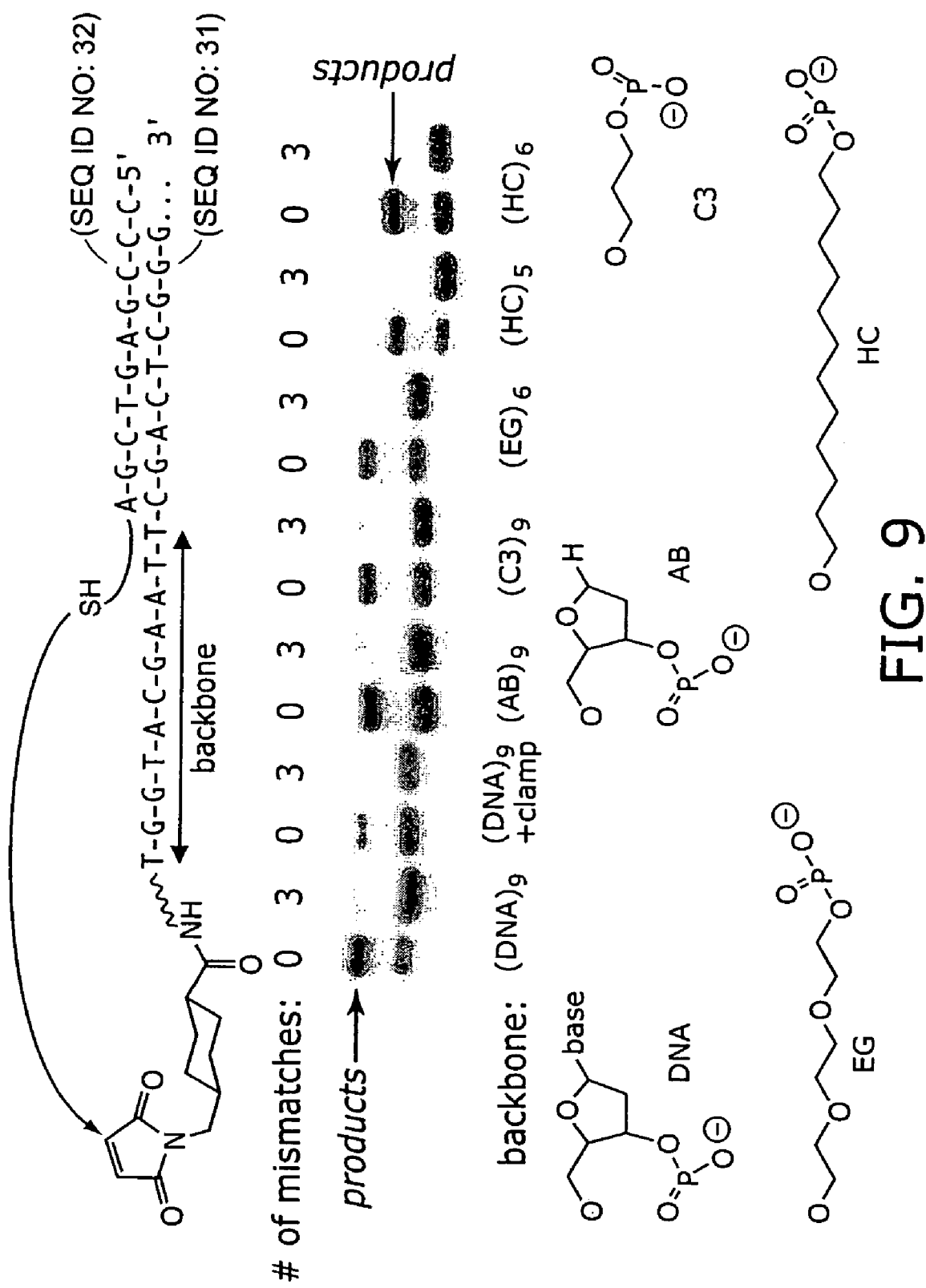
FIG. 9 depicts the repeated n=10 reaction in FIG. 8 in which the nine bases following the 5'-NH2-dT were replaced with the backbone analogues shown. Five equivalents of a DNA oligonucleotide complementary to the intervening bases were added to the "DNA+clamp" reaction. Reagents were matched (0) or contained three mismatches (3). The gel shows reactions at 25° C. after 25 min.

To determine the basis of the distance independence of DNA-templated synthesis, a series of modified E templates were first synthesized in which the intervening bases were replaced by a series of DNA analogs designed to evaluate the possible contribution of (i) interbase interactions, (ii) conformational preferences of the DNA backbone, (iii) the charged phosphate backbone, and (iv) backbone hydrophilicity. Templates in which the intervening bases were replaced with any of the analogs in FIG. 9 had little effect on the rates of product formation. These findings indicate that backbone structural elements specific to DNA are not responsible for the observed distance independence of DNA-templated synthesis. However, the addition of a 10-base DNA oligonucleotide "clamp" complementary to the single-stranded intervening region significantly reduced product formation (FIG. 9), suggesting that the flexibility of this region is critical to efficient DNA-templated synthesis.

Figure 10:
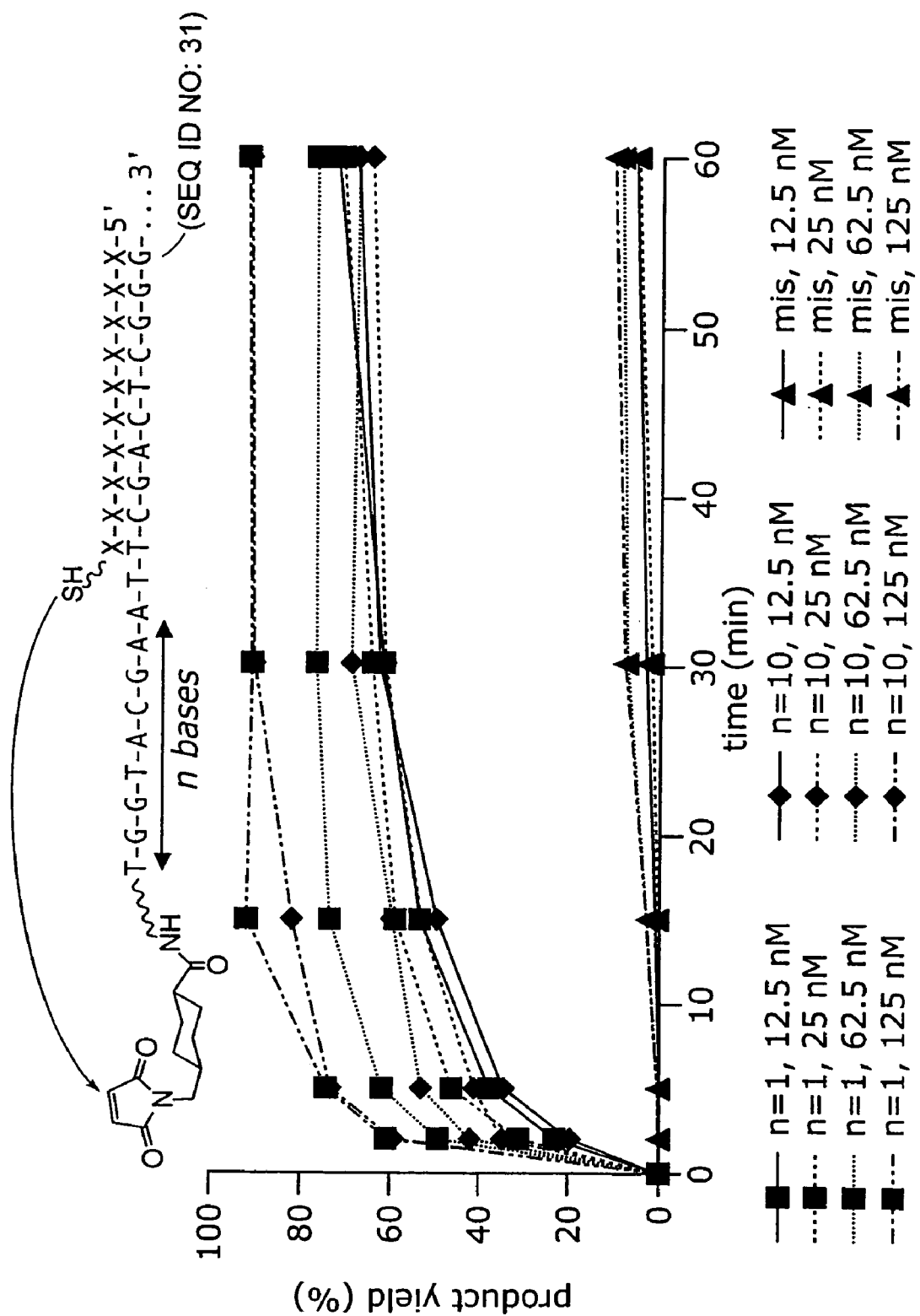
FIG. 10 depicts the n=1, n=10, and n=1 mismatched (mis) reactions described in FIG. 8 which were repeated with template and reagent concentrations of 12.5, 25, 62.5 or 125 nM.

The distance independent reaction rates may be explained if the bond-forming events in a DNA-templated format are sufficiently accelerated relative to their nontemplated counterparts such that DNA annealing, rather than bond formation, is rate-determining. If DNA annealing is at least partially rate limiting, then the rate of product formation should decrease as the concentration of reagents is lowered because annealing, unlike templated bond formation, is a bimolecular process. Decreasing the concentration of reactants in the case of the E template with one or ten intervening bases between reactive groups resulted in a marked decrease in the observed reaction rate (FIG. 10). This observation suggests that proximity effects in DNA-templated synthesis can enhance bond formation rates to the point that DNA annealing becomes rate-determining.

Figure 11A:
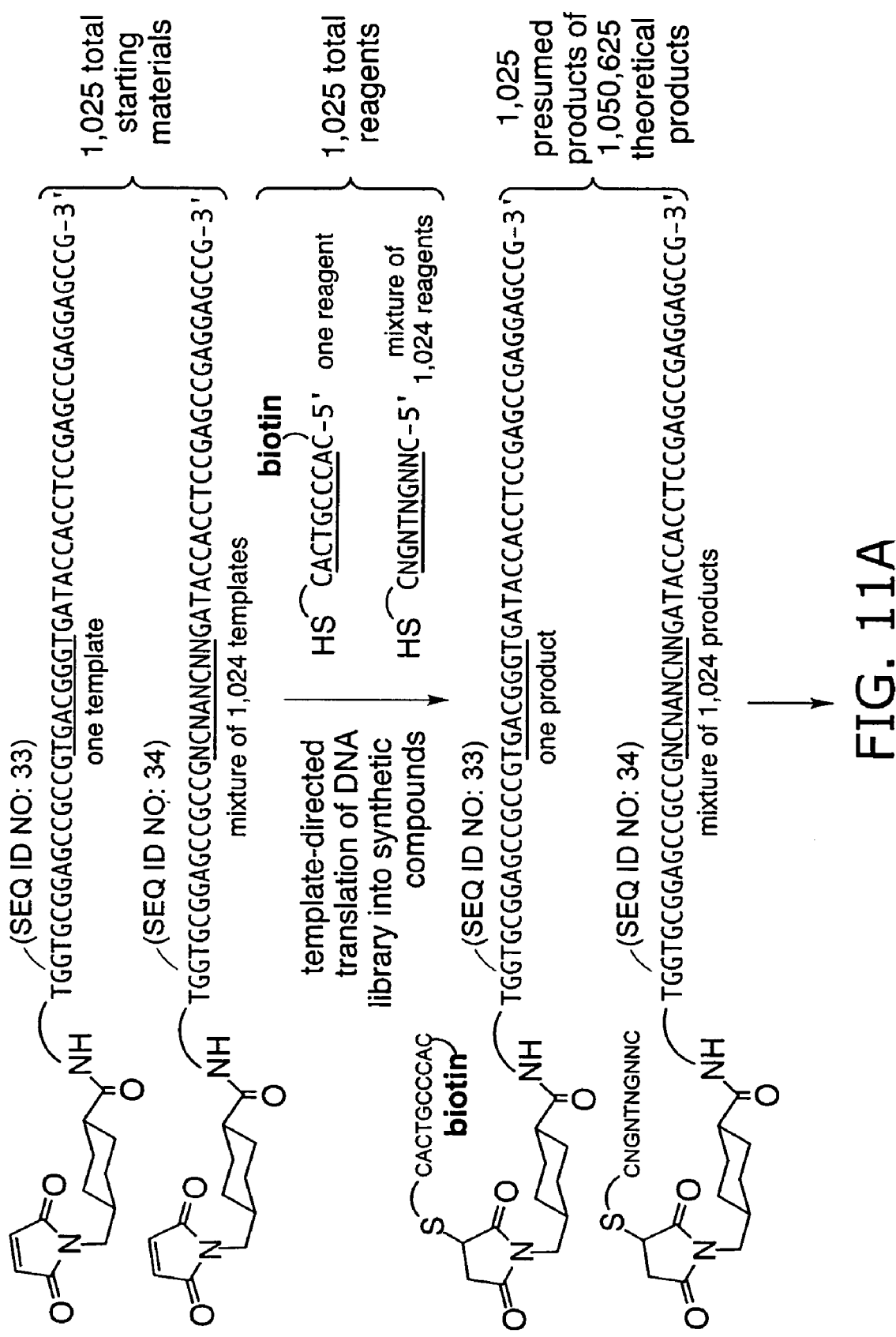
FIGS. 11A and 11B depict a model translation, selection and amplification of synthetic molecules that bind streptavidin from a DNA-encoded library.
Figure 11B:
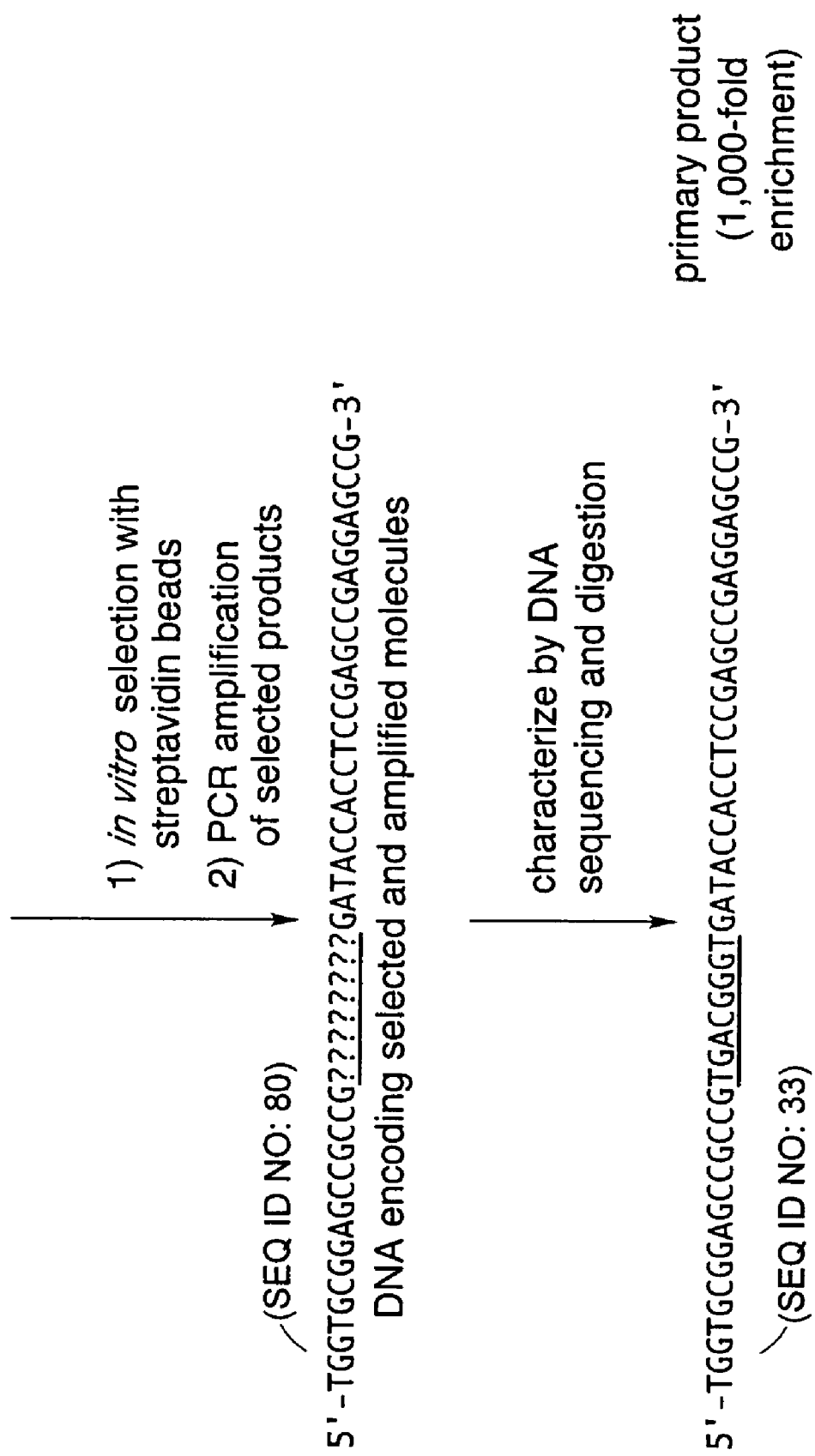

These findings raise the possibility of using DNA-templated synthesis to translate in one pot libraries of DNA into solution-phase libraries of synthetic molecules suitable for PCR amplification and selection. The ability of DNA-templated synthesis to support a variety of transition state geometries suggests its potential in directing a range of powerful water-compatible synthetic reactions (see, Li, C. J. Organic Reactions in Aqueous Media, Wiley and Sons, New York: 1997). The sequence specificity described above suggests that mixtures of reagents may be able to react predictably with complementary mixtures of templates. Finally, the observed distance independence suggests that different regions of DNA "codons" may be used to encode different groups on the same synthetic scaffold without impairing reactions rates. As a demonstration of this approach, a library of 1,025 maleimide-linked templates was syntheisized, each with a different DNA sequence in an eight-base encoding region (FIG. 11). One of these sequences, 5'-TGACGGGT-3' [SEQ ID NO: 1], was arbitrarily chosen to code for the attachment of a biotin group to the template. A library of thiol reagents linked to 1,025 different oligonucleotides was also generated. The reagent linked to 3'-ACTGCCCA-5' [SEQ ID NO: 2] contained a biotin group, while the other 1,024 reagents contained no biotin. Equimolar ratios of all 1,025 templates and 1,025 reagents were mixed in one pot for 10 minutes at 25° C. and the resulting products were selected in vitro for binding to streptavidin. Molecules surviving the selection were amplified by PCR and analyzed by restriction digestion and DNA sequencing.

Figure 12B:
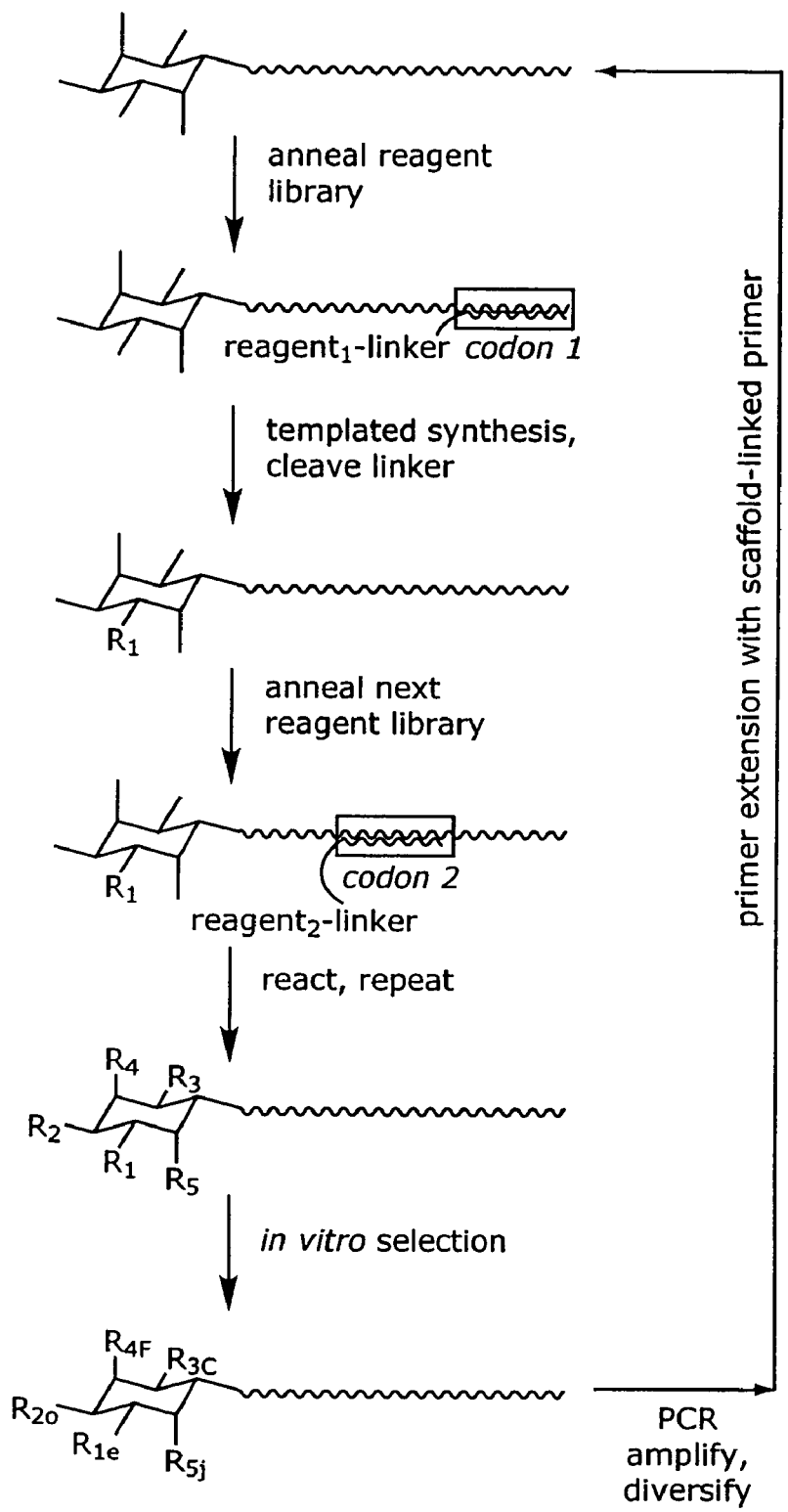
FIG. 12B depicts a general scheme for the creation and evolution of libraries of non-natural molecules using DNA-templated synthesis, where —$R_1$ represents the library of product functionality transferred from reagent library 1 and —$R_{1B}$ represents a selected product.

Digestion with the restriction endonuclease Tsp45I, which cleaves GTGAC and therefore cuts the biotin encoding template but none of the other templates, revealed a 1:1 ratio of biotin encoding to non-biotin encoding templates following selection (FIG. 12). This represents a 1,000-fold enrichment compared with the unselected library. DNA sequencing of the PCR amplified pool before and after selection suggested a similar degree of enrichment and indicated that the biotin-encoding template is the major product after selection and amplification (FIG. 12). The ability of DNA-templated synthesis to support the simultaneous sequence-specific reaction of 1,025 reagents, each of which faces a 1,024:1 ratio of non-partner to partner templates, demonstrates its potential as a method to create synthetic libraries in one pot. The above proof-of-principle translation, selection, and amplification of a synthetic library member having a specific property (avidin affinity in this example) addresses several key requirements for the evolution of non-natural small molecule libraries toward desired properties.

Taken together, these results suggest that DNA-templated synthesis is a surprisingly general phenomenon capable of directing, rather than simply encoding, a range of chemical reactions to form products unrelated in structure to nucleic acid backbones. For several reactions examined, the DNA-templated format accelerates the rate of bond formation beyond the rate of a 10-base DNA oligonucleotide annealing to its complement, resulting in surprising distance independence. The facile nature of long-distance DNA-templated reactions may also arise in part from the tendency of water to contract the volume of nonpolar reactants (see, C.-J. Li et al. Organic Reactions in Aqueous Media, Wiley and Sons: New York, 1997) and from possible compactness of the intervening single-stranded DNA between reactive groups. These findings may have implications for prebiotic evolution and for understanding the mechanisms of catalytic nucleic acids, which typically localize substrates to a strand of RNA or DNA.

Methods:

DNA synthesis. DNA oligonucleotides were synthesized on a PerSeptive Biosystems Expedite 8909 DNA synthesizer using standard protocols and purified by reverse phase HPLC. Oligonucleotides were quantitated spectrophotometrically and by denaturing polyacrylamide gel electrophoresis (PAGE) followed by staining with ethidium bromide or SYBR Green (Molecular Probes) and quantitation using a Stratagene Eagle Eye II densitometer. Phosphoramidites enabling the synthesis of 5'-$NH_2$-dT, 5' tetrachlorofluorescein, abasic backbone spacer, C3 backbone spacer, 9-bond polyethylene glycol spacer, 12-bond saturated hydrocarbon spacer, and 5' biotin groups were purchased from Glen Research. Thiol-linked oligonucleotide reagents were synthesized on C3 disulfide controlled pore glass (Glen Research).

Template functionalization. Templates bearing 5'-$NH_2$-dT groups were transformed into a variety of electrophilic functional groups by reaction with the appropriate electrophile-NHS ester (Pierce). Reactions were performed in 200 mM sodium phosphate pH 7.2 with 2 mg/mL electrophile-NHS ester, 10% DMSO, and up to 100 μg of 5'-amino template at 25° C. for 1 h. Desired products were purified by reverse-phase HPLC and characterized by gel electrophoresis and MALDI mass spectrometry.

DNA-templated synthesis reactions. Reactions were initiated by mixing equimolar quantities of reagent and template in buffer containing 50 mM MOPS pH 7.5 and 250 mM NaCl at the desired temperature (25° C. unless stated otherwise). Concentrations of reagents and templates were 60 nM unless otherwise indicated. At various time points, aliquots were removed, quenched with excess β-mercaptoethanol, and analyzed by denaturing PAGE. Reaction products were quantitated by densitometry using their intrinsic fluorescence or by staining followed by densitometry. Representative products were also verified by MALDI mass spectrometry.

In vitro selection for avidin binding. Products of the library translation reaction were isolated by ethanol precipitation and dissolved in binding buffer (10 mM Tris pH 8, 1 M NaCl, 10 mM EDTA). Products were incubated with 30 μg of streptavidin-linked magnetic beads (Roche Biosciences) for 10 min at room temperature in 100 uL total volume. Beads were washed 16 times with binding buffer and eluted by treatment with 1 μmol free biotin in 100 uL binding buffer at 70° C. for 10 minutes. Eluted molecules were isolated by ethanol precipitation and amplified by standard PCR protocols (2 mM $MgCl_2$, 55° C. annealing, 20 cycles) using the primers 5'-TG-GTGCGGAGCCGCCG [SEQ ID NO: 3] and 5'-CCACT-GTCCGTGGCGCGACCCCGGCTCC      TCGGCTCGG

[SEQ ID NO: 4].Automated DNA sequencing used the primer 5'-CCACTGTCCGTGGCGCGACCC [SEQ ID NO: 5].

DNA Sequences. Sequences not provided in the figures are as follows: matched reagent in FIG. 6b SIAB and SBAP reactions: 5'-CCCGAGTCGAAGTCGTACC-SH [SEQ ID NO: 6]; mismatched reagent in FIG. 6b SIAB and SBAP reactions: 5'-GGGCTCAGCTTCCCCATAA-SH [SEQ ID NO: 7];mismatched reagents for other reactions in FIGS. 6b, 6c, 6d, and 8a; 5'-FAAATCTTCCC-SH (F=tetrachlorofluorescein) [SEQ ID NO: 8];reagents in FIGS. 6c and 6d containing one mismatch: 5'FAATTCT-TACC-SH [SEQ ID NO: 9]; E templates in FIGS. 6a, 6b SMCC, GMBS, BMPS, and SVSB reactions, and 8a: 5'-($NH_2$dT)-CGCGAGCGTACGCTCGCGATGGTAC-GAATTCGACTCGGGAATACCACCTTCGACTCG AGG [SEQ ID NO: 10]; H template in FIG. 6b SIAB, SBAP, and SIA reactions: 5'-($NH_2$dT)-CGCGAGCGTACG CTCGCG ATGGTACGAATTC [SEQ ID NO: 11]; clamp oligonucleotide in FIG. 8b: 5'-ATTCGTACCA [SEQ ID NO: 12].

Example 2

Exemplary Reactions for Use in DNA-Templated Synthesis

As discussed above, the generality of DNA-templated synthetic chemistry was examined (see, Liu et al. *J. Am. Chem. Soc.* 2001, 123, 6961). Specifically, the ability of DNA-templated synthesis to direct a modest collection of chemical reactions without requiring the precise alignment of reactive groups into DNA-like conformations was demonstrated. Indeed, the distance independence and sequence fidelity of DNA-templated synthesis allowed the simultaneous, one-pot translation of a model library of more than 1,000 templates into the corresponding thioether products, one of which was enriched by in vitro selection for binding to the protein streptavidin and amplified by PCR.

As described in detail herein, the generality of DNA-templated synthesis has been further expanded and it has been demonstrated that a variety of chemical reactions can be utilized for the construction of small molecules and in particular, for the first time, DNA-templated organometallic couplings and carbon-carbon bond forming reactions other than pyrimidine photodimerization. These reactions clearly represent an important step towards the in vitro evolution of non-natural synthetic molecules by enabling the DNA-templated construction of a much more diverse set of structures than has previously been achieved.

Figure 13A:
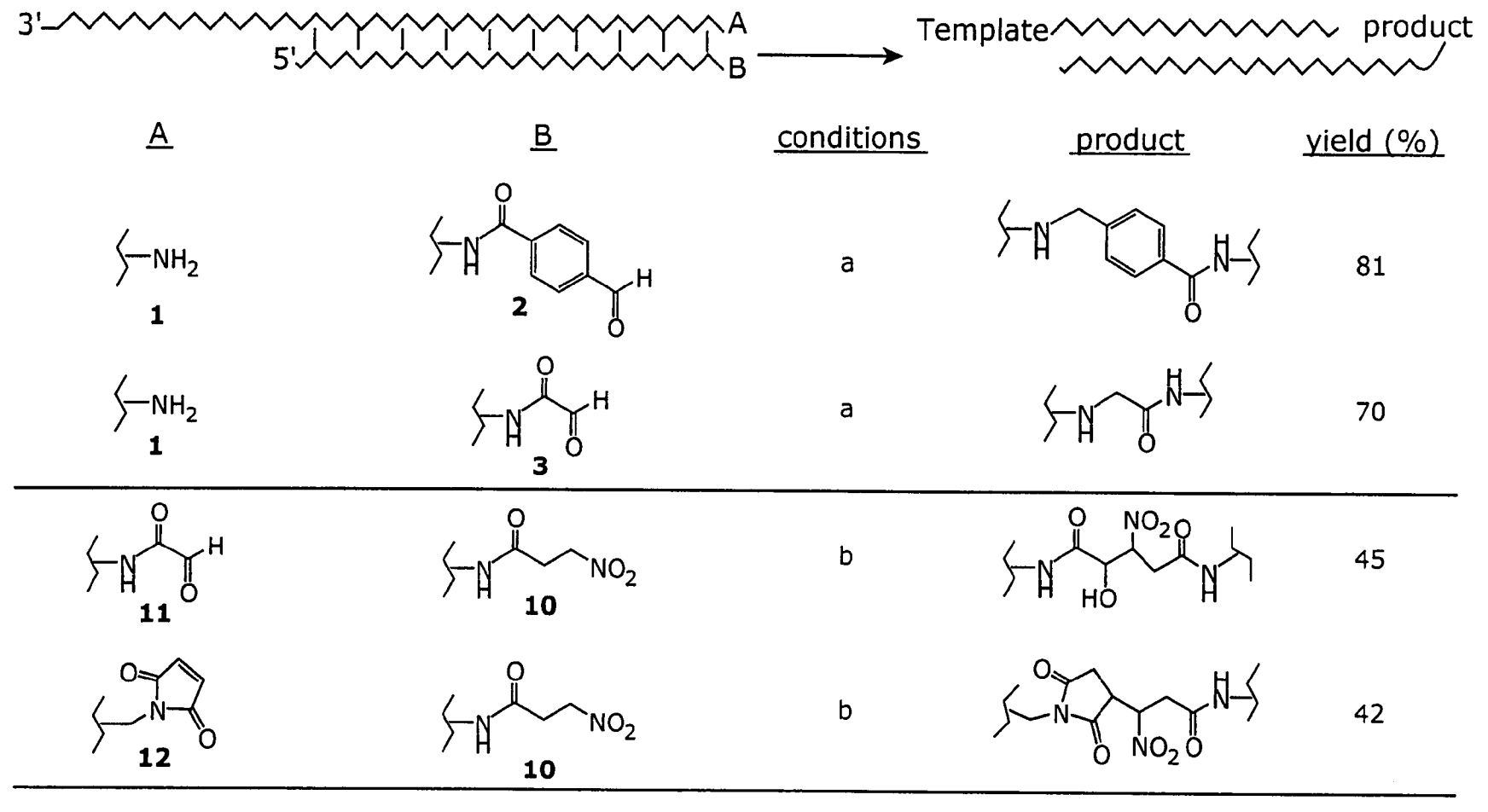
Figure 13B:
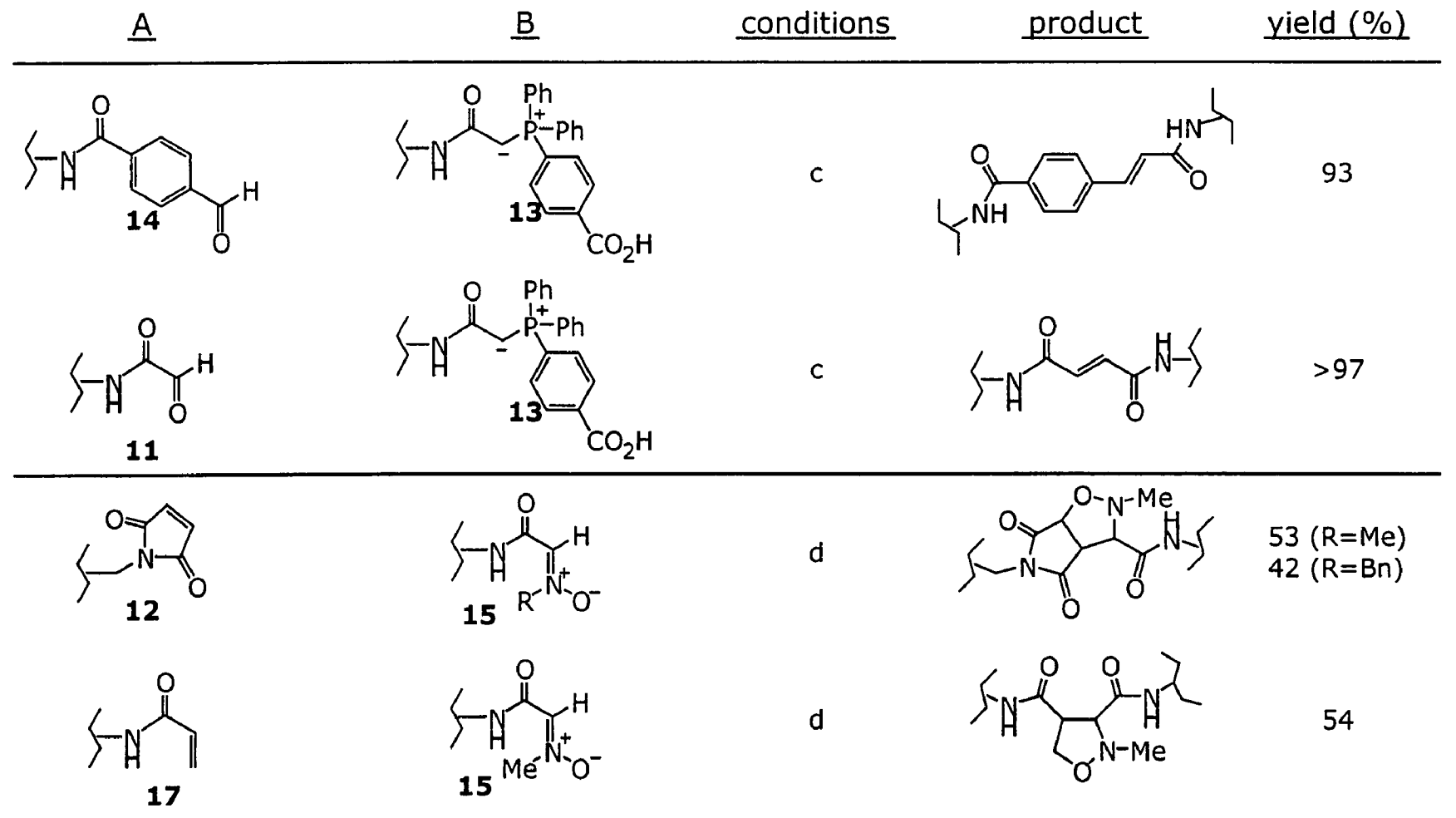
Figure 13C:
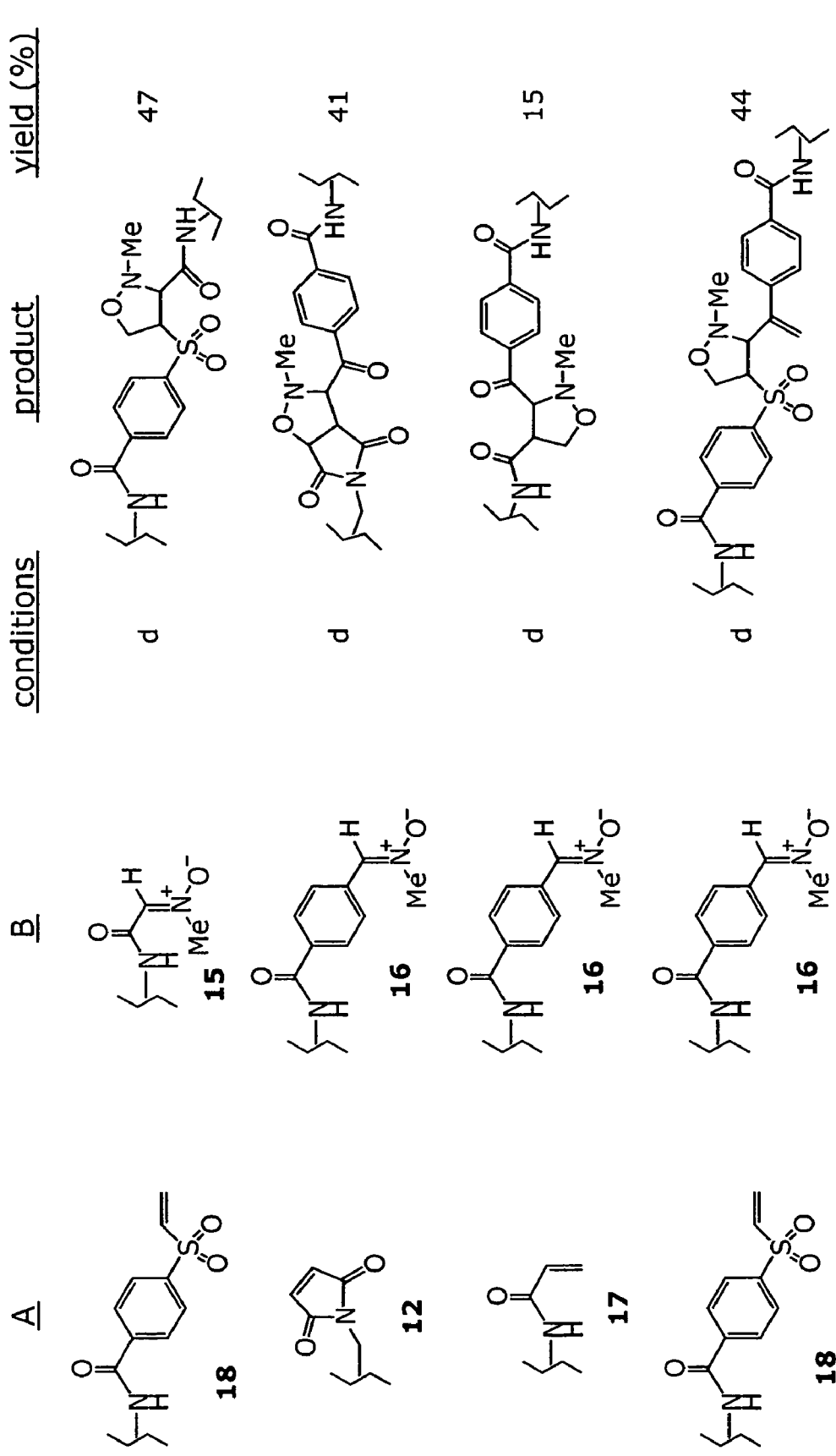
Figure 13D:
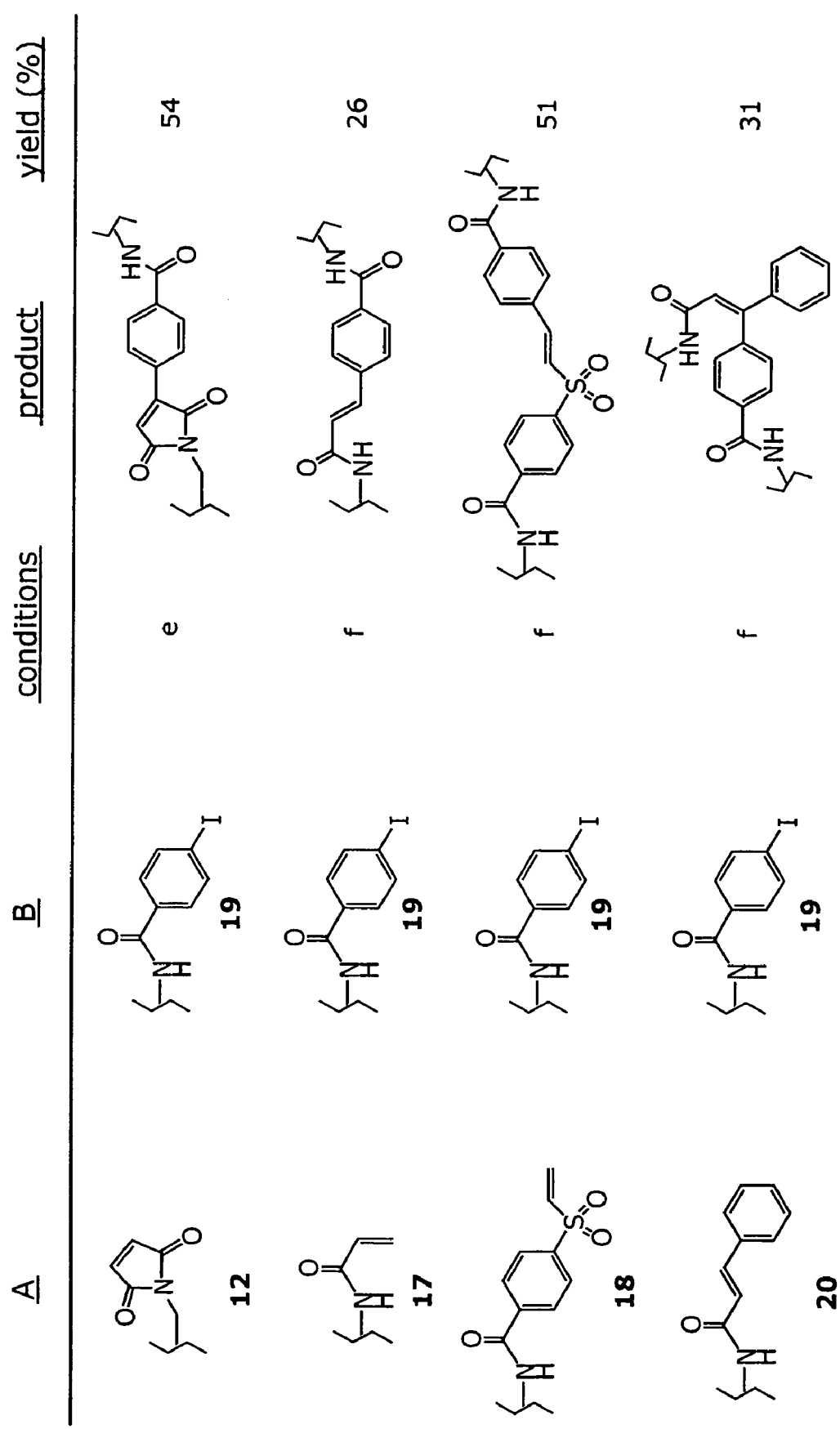
Figure 14:
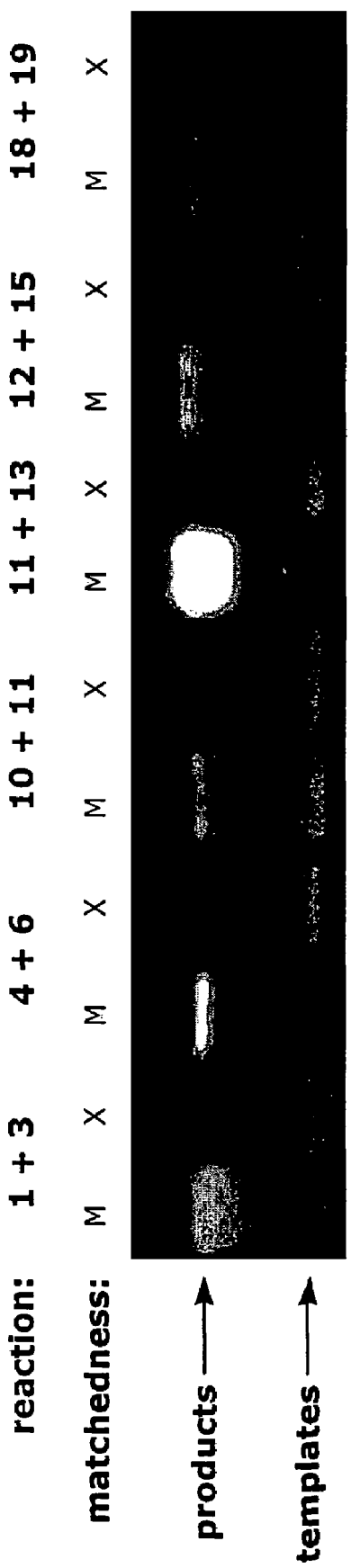
FIG. 14 depicts analysis by denaturing polyacrylamide gel electrophoresis of representative DNA-templated reactions listed in FIGS. 13 and 15. The structures of reagents and templates correspond to the numbering in FIGS. 13 and 15. Lanes 1, 3, 5, 7, 9, 11: reaction of matched (complementary) reagents and templates under conditions listed in FIGS. 13 and 15 (the reaction of 4 and 6 was mediated by DMT-MM). Lanes 2, 4, 6, 8, 10, 12: reaction of mismatched (non-complementary) reagents and templates under conditions identical to those in lanes 1, 3, 5, 7, 9 and 11, respectively.
Figure 15A:
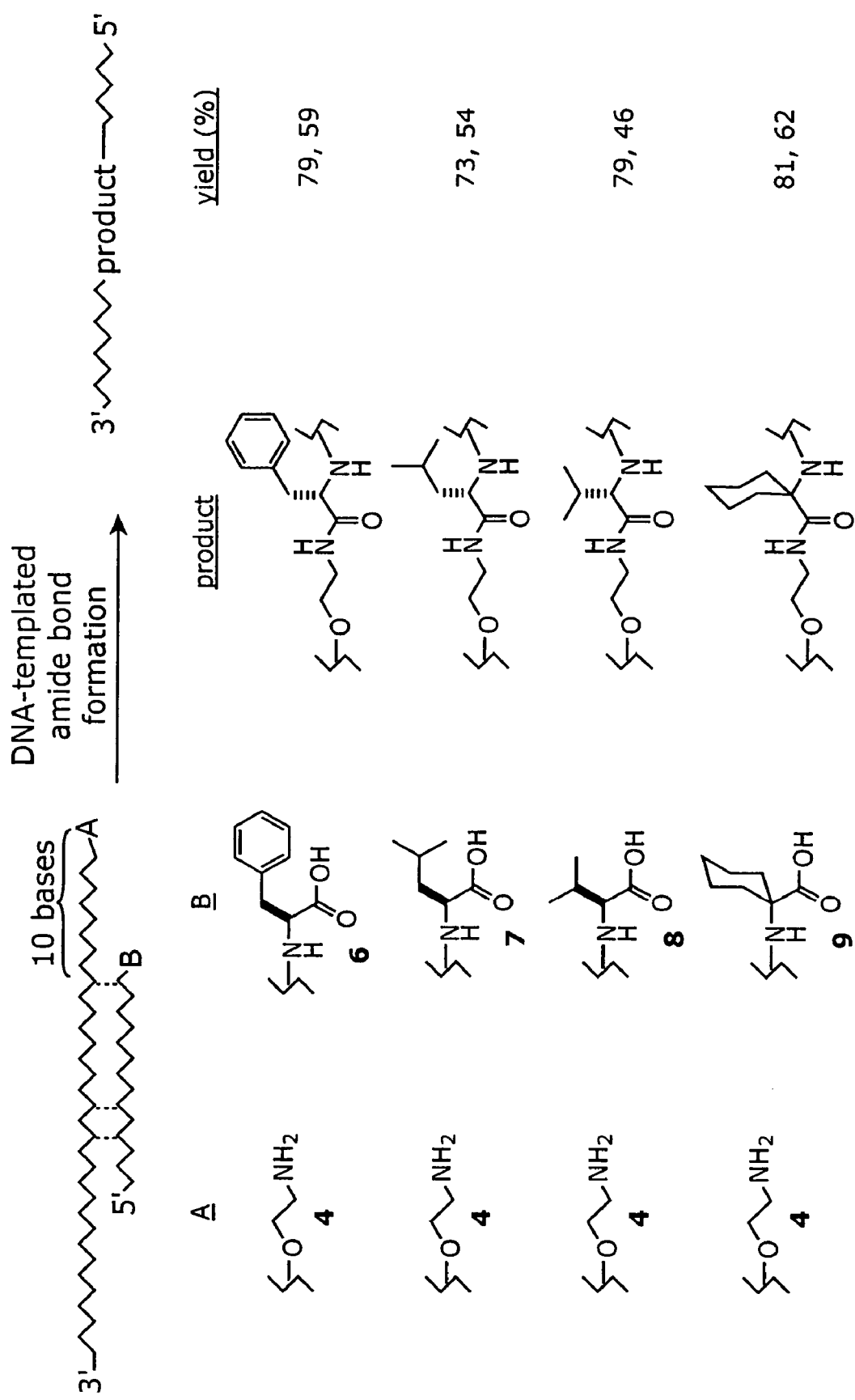
FIGS. 15A and 15B depict DNA-templated amide bond formation mediated by EDC and sulfo-NHS or by DMT-MM for a variety of substituted carboxylic acids and amines. In each row, yields of DMT-MM-mediated reactions between reagents and templates complementary in sequence are followed by yields of EDC and sulfo-NHS-mediated reactions. Conditions: 60 nM template, 120 nM reagent, 50 mM DMT-MM in 0.1 M MOPS buffer pH 7.0, 1 M NaCl, 16 h, 25° C.; or 60 nM template, 120 nM reagent, 20 mM EDC, 15 mM sulfo-NHS, 0.1 M MES buffer pH 6.0, 1 M NaCl, 16 h, 25° C. In all cases, control reactions with mismatched reagent sequences yielded little or no detectable product.
Figure 15B:
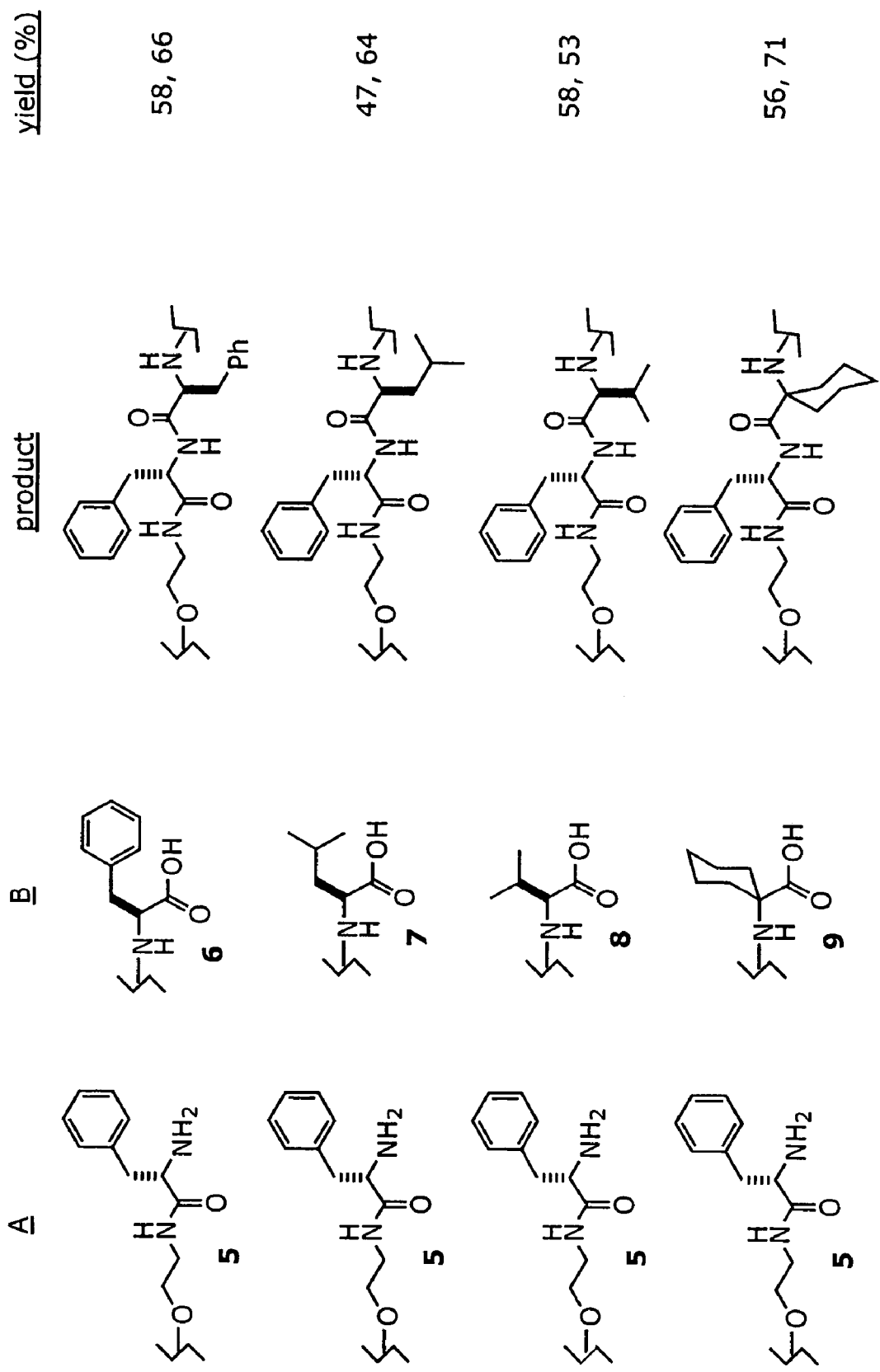

The ability of DNA-templated synthesis to direct reactions that require a non-DNA-linked activator, catalyst or other reagent in addition to the principal reactants has also been demonstrated herein. To test the ability of DNA-templated synthesis to mediate such reactions without requiring structural mimicry of the DNA-templated backbone, DNA-templated reductive aminations between an amine-linked template (1) and benzaldehyde- or glyoxal-linked reagents (3) with millimolar concentrations of $NaBH_3CN$ at room temperature in aqueous solutions can be performed. Significantly, products formed efficiently when the template and reagent sequences were complementary, while control reactions in which the sequence of the reagent did not complement that of the template, or in which $NaBH_3CN$ was omitted, yielded no significant product (see FIGS. 13 and 14). Although DNA-templated reductive aminations to generate products closely mimicking the structure of double-stranded DNA have been previously reported (see, for example, X. Li et al. *J. Am. Chem. Soc.* 2002, 124, 746 and Y. Gat et al. *Biopolymers* 1998, 48, 19), the above results demonstrate that reductive amination to generate structures unrelated to the phosphoribose backbone can take place efficiently and sequence-specifically. Referring to FIG. 15, DNA-templated aide bond formations between amine-linked templates 4 and 5 and carboxylate-linked reagents 6-9 mediated by 1-(3-dimethylaminopropyl)-3-ethylcarbodiimide (EDC) and N-hydroxylsulfosuccinimide (sulfo-NHS) to generate amide products in good yields at pH 6.0, 25° C. (FIG. 15). Product formation was sequence-specific, dependent on the presence of EDC, and suprisingly insensitive to the steric encumbrance of the amine or carboxylate. Efficient DNA-templated amide formation was also mediated by the water-stable activator 4-(4,6-dimethoxy-1,3,5-trizin-2-yl)-4-methylmorpholinium chloride (DMT-MM) instead of EDC and sulfo-NHS (FIGS. 14 and 15). The efficiency and generality of DNA-templated amide bond formation under these conditions, together with the large number of commercially available chiral amines and carboxylic acids, make this reaction an attractive candidate in future DNA-templated syntheses of structurally diverse small molecule libraries.

It will be appreciated that carbon-carbon bond forming reactions are also important in both chemical and biological syntheses and thus several such reactions are utilized in DNA-templated format. Both the reaction of nitroalkane-linked reagent (10) with aldehyde-linked template (11) (nitro-aldol or Henry reaction) and the conjugate addition of 10 to maleimide-linked template (12) (nitro-Michael addition) proceeded efficiently and with high sequence specificity at pH 7.5-8.5, 25° C. (FIGS. 13 and 14). In addition, the sequence-specific DNA-templated Wittig reaction between stabilized phosphorus ylide reagent 13 and aldehyde-linked templates 14 or 11 provided the corresponding olefin products in excellent yields at pH 6.0-8.0, 25° C. (FIGS. 13 and 14). Similarly, the DNA templated 1,3-dipolar cycloaddition between nitrone-linked reagents 15 and 16 and olefin-linked templates 12, 17 or 18 also afforded products sequence specifically at pH 7.5, 25° C. (FIGS. 13 and 14).

In addition to the reactions described above, organometallic coupling reactions can also be utilized in the present invention. For example, DNA-templated Heck reactions were performed in the presence of water-soluble Pd precatalysts. In the presence of 170 mM $Na_2PdCl4$, aryl iodide-linked reagent 19 and a variety of olefin-linked templates including maleimide 12, acrylamide 17, vinyl sulfone 18 or cinnamamide 20 yielded Heck coupling products in modest yields at pH 5.0, 25° C. (FIGS. 13 and 14). For couplings with olefins 17, 18 and 20, adding two equivalents of $P(p-SO_3C_6H_4)_3$ per equivalent of Pd prior to template and reagent addition typically increased overall yields by 2-fold. Control reactions containing sequence mismatches or lacking Pd precatalyst yielded no product. To our knowledge, the above DNA-templated nitro aldol addition, nitro Michael addition, Wittig olefination, dipolar cycloaddition, and Heck coupling represent the first reported nucleic-acid templated organometallic reactions and carbon-carbon bond forming reactions other than pyrimidine photodimerization.

It was previously discovered that the same DNA-templated reactions demonstrate distance independence, the ability to form product at a rate independent of the number of intervening bases between annealed reactants. It was hypothesized (FIG. 16a) that distance independence arises when the rate of bond formation in the DNA-templated reaction is greater than the rate of template-reagent annealing. Although only a subset of chemistries fall into this category, any DNA-templated reaction that affords comparable product yields when the reagent is annealed at various distances from the reactive end of the template is of special interest because it can be encoded at a variety of template positions. To evaluate the ability of the DNA-templated reactions developed above to take place efficiently when reactants are separated by distances relevant to library encoding, the yields of reductive amination, amide formation, nitro-aldol addition, nitro-Michael addition, Wittig olefination, dipolar cycloaddition, and Heck coupling when zero or ten bases separated annealed reactive groups (FIG. 16a, n=0 versus n=10) were compared. Among the reactions described above or in previous work, amide bond formation, nitro-aldol addition, Wittig olefination, Heck coupling, conjugate addition of thiols to maleimides and $S_N2$ reaction between thiols and α-iodo amides demonstrate comparable product formation when reactive groups are separated by zero or ten bases (FIG. 16b). These findings indicate that these reactions can be encoded during synthesis by nucleotides that are distal from the reactive end of the template without significantly impairing product formation.

Figure 17:
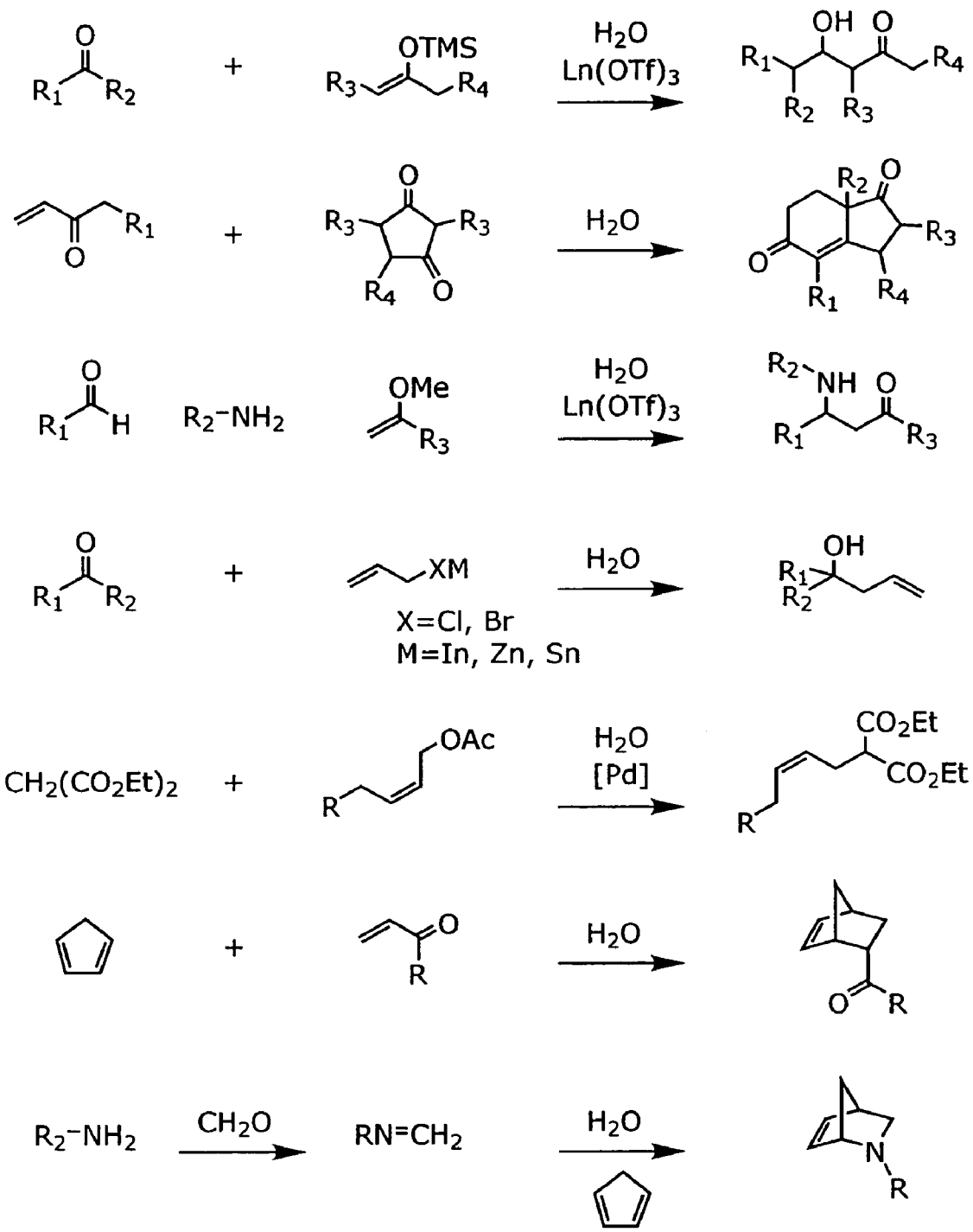
FIG. 17 depicts certain exemplary DNA-templated complexity building reactions.

In addition to the DNA-templated $S_N2$ reaction, conjugate addition, vinyl sulfone addition, amide bond formation, reductive amination, nitro-aldol (Henry reaction), nitro Michael, Wittig olefination, 1,3-dipolar cycloaddition and Heck coupling reactions described directly above, a variety of additional reagents can also be utilized in the method of the present invention. For example, as depicted in FIG. 17, powerful aqueous DNA-templated synthetic reactions including, but not limited to, the Lewis acid-catalyzed aldol addition, Mannich reaction, Robinson annulation reactions, additions of allyl indium, zinc and tin to ketones and aldehydes, Pd-assisted allylic substitution, Diels-Alder cycloadditions, and hetero-Diels-Alder reactions can be utilized efficiently in aqueous solvent and are important complexity-building reactions.

Taken together, these results expand considerably the reaction scope of DNA-templated synthesis. A wide variety of reactions proceeded efficiently and selectively only when the corresponding reactants are programmed with complementary sequences. By augmenting the repertoire of known DNA-templated reactions to now include carbon-carbon bond forming and organometallic reactions (nitro-aldol additions, nitro-Michael additions, Wittig olefinations, dipolar cycloadditions, and Heck couplings) in addition to previously reported amide bond formation (see, Schmidt et al. *Nucleic Acids Res.* 1997, 25, 4792; Bruick et al. *Chem. Biol.* 1996, 3, 49), imine formation (Czlapinski et al. *J. Am. Chem. Soc.* 2001, 123, 8618), reductive amination (Li et al. *J. Am. Chem. Soc.* 2002, 124, 746; Gat et al. *Biopolymers,* 1998, 48, 19), $S_N2$ reactions (Gartner et al. *J. Am. Chem. Soc.* 2001, 123, 6961; Xu et al. *Nat. Biotechnol.* 2001, 19, 148; Herrlein et al. *J. Am. Chem. Soc.* 1995, 117, 10151) conjugate addition of thiols (Gartner et al. *J. Am. Chem. Soc.* 2001, 123, 6961), and phosphoester or phosphonamide formation (Orgel et al. *Acc. Chem. Res.* 1995, 28, 109; Luther et al. *Nature,* 1998, 396, 245), these results may enable the sequence-specific translation of libraries of DNA into libraries of structurally and functionally diverse synthetic products. Since minute quantities of templates encoding desired molecules can be amplified by PCR, the yields of DNA-templated reactions are arguably less critical than the yields of traditional synthetic transformations. Nevertheless, many of the reactions developed above proceed efficiently. In addition, by demonstrating that DNA-templated synthesis in the absence of proteins can direct a large diversity of chemical reactions, these findings support previously proposed hypotheses that nucleic acid-templated synthesis may have translated replicable information into some of the earliest functional molecules such as polyketides, terpenes and polypeptides prior to the evolution of protein-based enzymes. The diversity of chemistry shown here to be controllable simply by bringing reactants into proximity by DNA hybridization without obvious structural requirements provides an experimental basis for these possibilities. The translation of amplifiable information into a wide range of structures is a key requirement for applying nature's molecular evolution approach to the discovery of non-natural molecules with new functions.

Methods for Exemplary Reactions for Use in DNA-Templated Synthesis:

Functionalized templates and reagents were typically prepared by reacting 5'-$NH_2$ terminated oligonucleotides (for template 1), 5'-$NH_2$—$(CH_2O)_2$ terminated oligonucleotides (for all other templates) or 3'-$OPO_3$—$CH_2CH(CH_2OH)$ $(CH_2)_4NH_2$ terminated nuclotides (for all reagents) with the appropriate NHS esters (0.1 volumes of a 20 mg/mL solution in DMF) in 0.2 M sodium phosphate buffer, pH 7.2, 25° C., 1 h to provide the template and reagent structures shown in FIGS. 13 and 15. For amino acid linked reagents 6-9,3'-$OPO_3CH_2CH(CH_2OH)(CH_2)_4NH_2$ terminated oligonucleotides in 0.2 M sodium phosphate buffer, pH 7.2 were reacted with 0.1 volumes of a 100 mM bis[2-(succinimidyloxycarbonyloxy)ethyl]sulfone (BSOCOES, Pierce) solution in DMF for 10 min at 25° C., followed by 0.3 volumes of a 300 mM amino acid in 300 mM NaOH for 30 min at 25° C.

Functionalized templates and reagents were purified by gel filtration using Sephadex G-25 followed by reverse-phase HPLC (0.1 triethylammonium acetate-acetonitrile gradient) and characterized by MALDI mass spectrometry. DNA templated reactions were conducted under the conditions described in FIGS. 13 and 15 and products were characterized by denaturing polyacrylamide gel electrophoresis and MALDI mass spectrometry.

Figure 16:
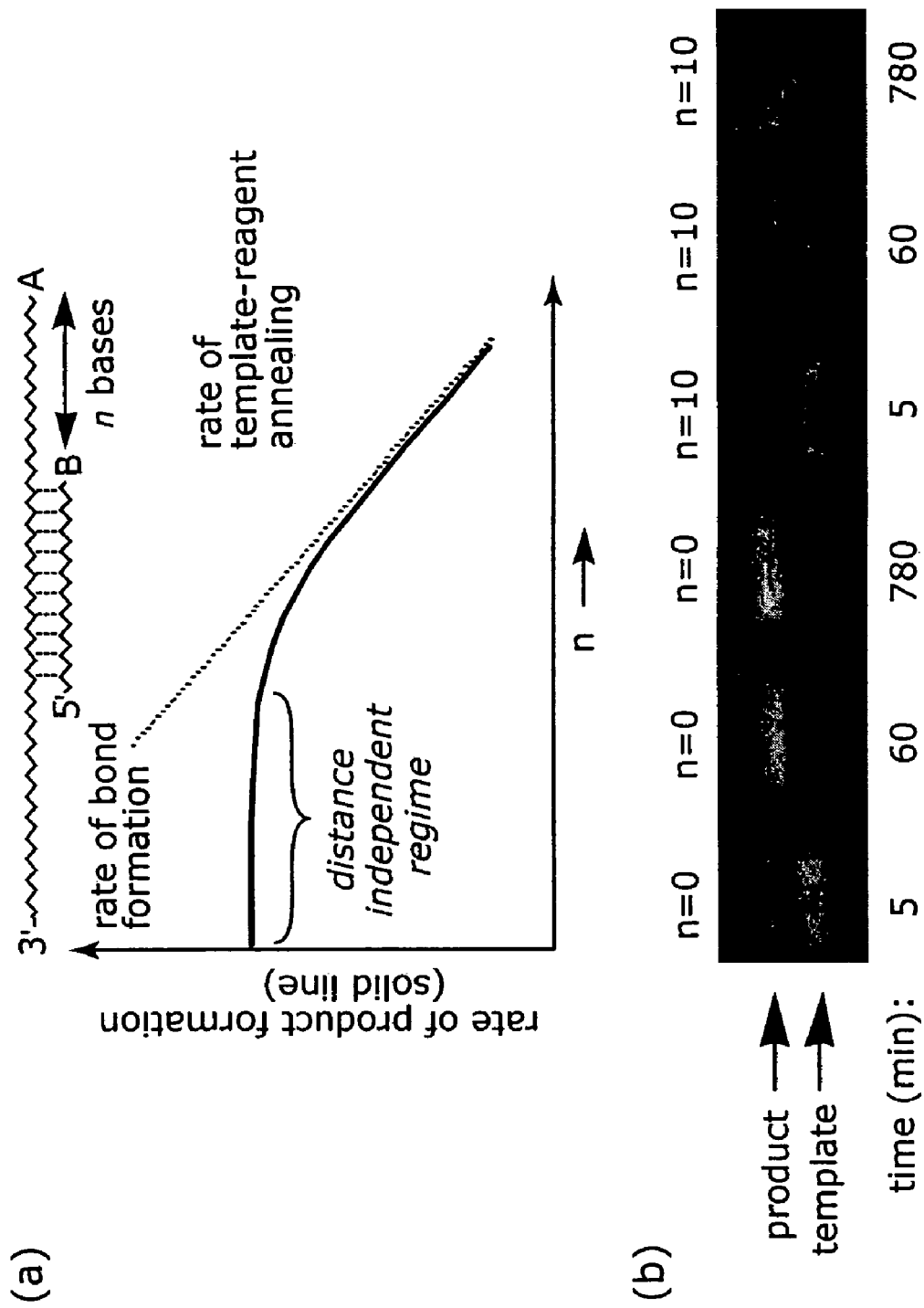
FIG. 16 depicts (a) Conceptual model for distance-independent DNA-templated synthesis. As the distance between the reactive groups of an annealed reagent and template (n) is increased, the rate of bond formation is presumed to decrease. For those values of n in which the rate of bond formation is significantly higher than the rate of template-reagent annealing, the rate of product formation remains constant. In this regime, the DNA-templated reaction shows distance independence. (b) Denaturing polyacrylamide gel electrophoresis of a DNA-templated Wittig olefination between complementary 11 and 13 with either zero bases (lanes 1-3) or ten bases (lanes 4-6) separating annealed reactants. Although the apparent second order rate constants for the n=0 and n=10 reactions differ by three-fold (kapp (n=0)=9.9×10$_3$ M$^{-1}$s$^{-1}$ while kapp (n=10)=3.5×10$^3$ M$^{-1}$s$^{-1}$), product yields after 13 h at both distances are nearly quantitative. Control reactions containing sequence mismatches yielded no detectable product (not shown).

The sequences of oligonucleotide templates and reagents are as follows (5' to 3' direction, n refers to the number of bases between reactive groups when template and reagent are annealed as shown in FIG. 16). 1: TGGTACGAATTC-GACTCGGG [SEQ ID NO: 13]; 2 and 3 matched: GAGTC-GAATTCGTACC [SEQ ID NO: 14]; 2 and 3 mismatched: GGGCTCAGCTTCCCCA [SEQ ID NO: 15]; 4 and 5: GGTACGAATTCGACTCGGGAATACCACCTT [SEQ ID NO: 16]; 6-9 matched (n=10): TCCCGAGTCG [SEQ ID NO: 17]; 6 matched (n=0): AATTCGTACC [SEQ ID NO: 18]; 6-9 mismatched: TCACCTAGCA [SEQ ID NO: 19]; 11, 12, 14, 17, 18, 20: GGTACGAATTCGACTCGGGA [SEQ ID NO: 20]; 10, 13, 16, 19 matched: TCCCGAGTCGAATTCG-TACC [SEQ ID NO: 21]; 10, 13 16,19 mismatched: GGGCT-CAGCTTCCCCATAAT [SEQ ID NO: 22]; 15 matched: AATTCGTACC [SEQ ID NO: 23]; 15 mismatched: TCG-TATTCCA [SEQ ID NO: 24]; template for n=10 vs. n 0 comparison: TAGCGATTACGGTACGAATTC-GACTCGGGA [SEQ ID NO: 25].

Reaction yields quantitated by denaturing polyacrylamide gel electrophoresis followed by ehidium bromide staining, UV visualization, and CCD-based densitometry of product and template starting material bands. Yield calculations assumed that templates and products stained with equal intensity per base; for those cases in which produces are partially double-stranded during quantitation, changes in staining intensity may result in higher apparent yields.

Example 3

Development of Exemplary Linkers

Figure 18:
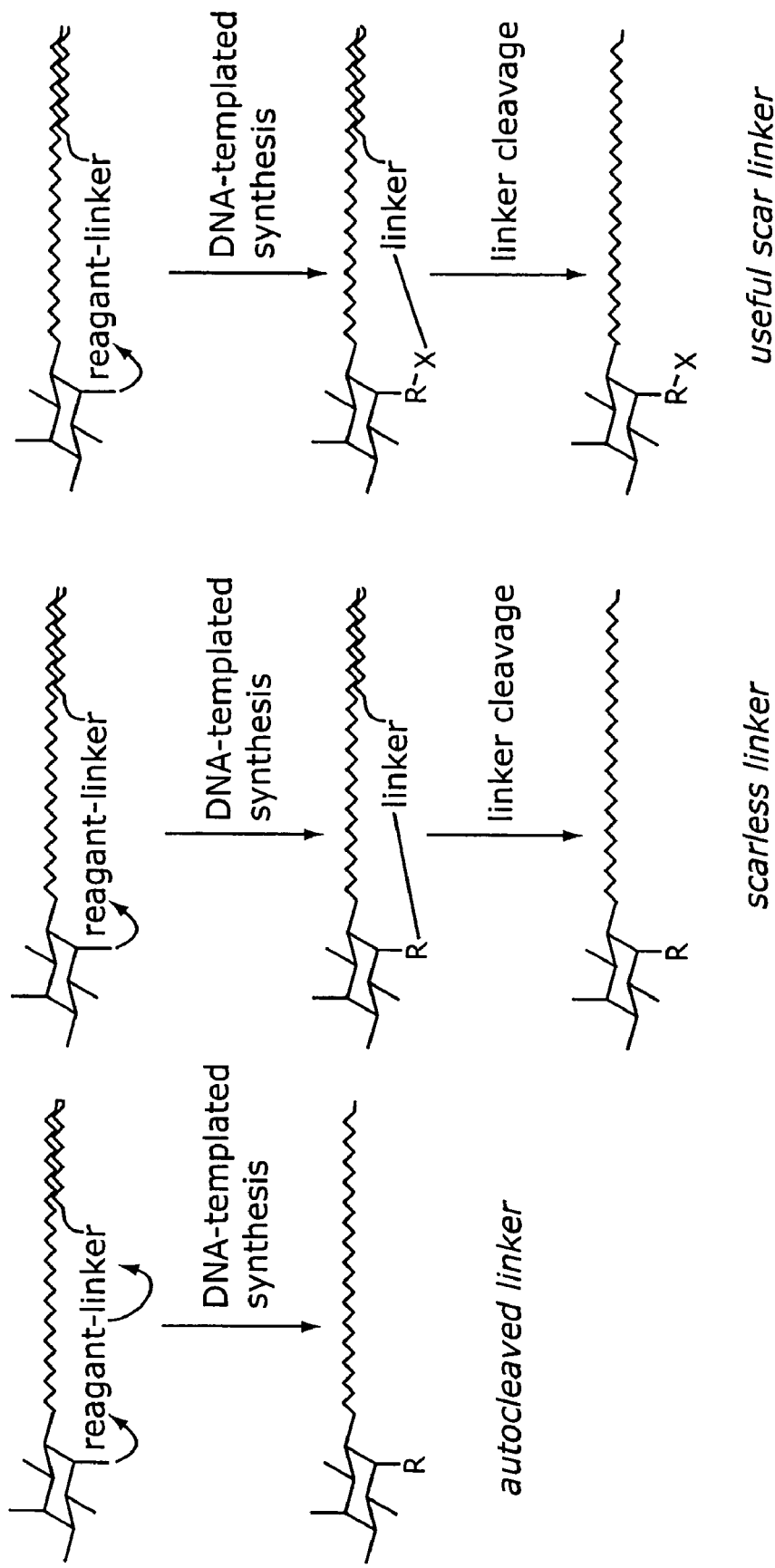
FIG. 18 depicts certain exemplary linkers for use in the method of the invention.
Figure 19:
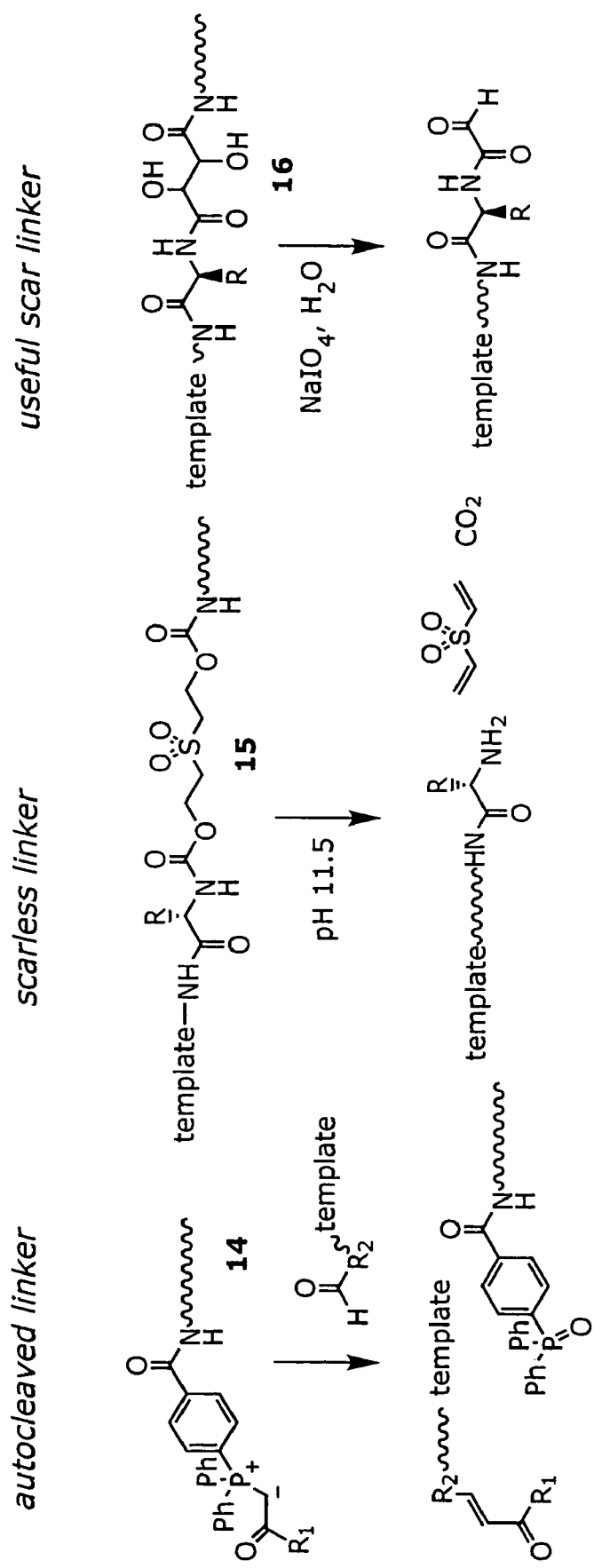
FIG. 19 depicts certain additional exemplary linkers for use in the method of the invention.
Figure 20:
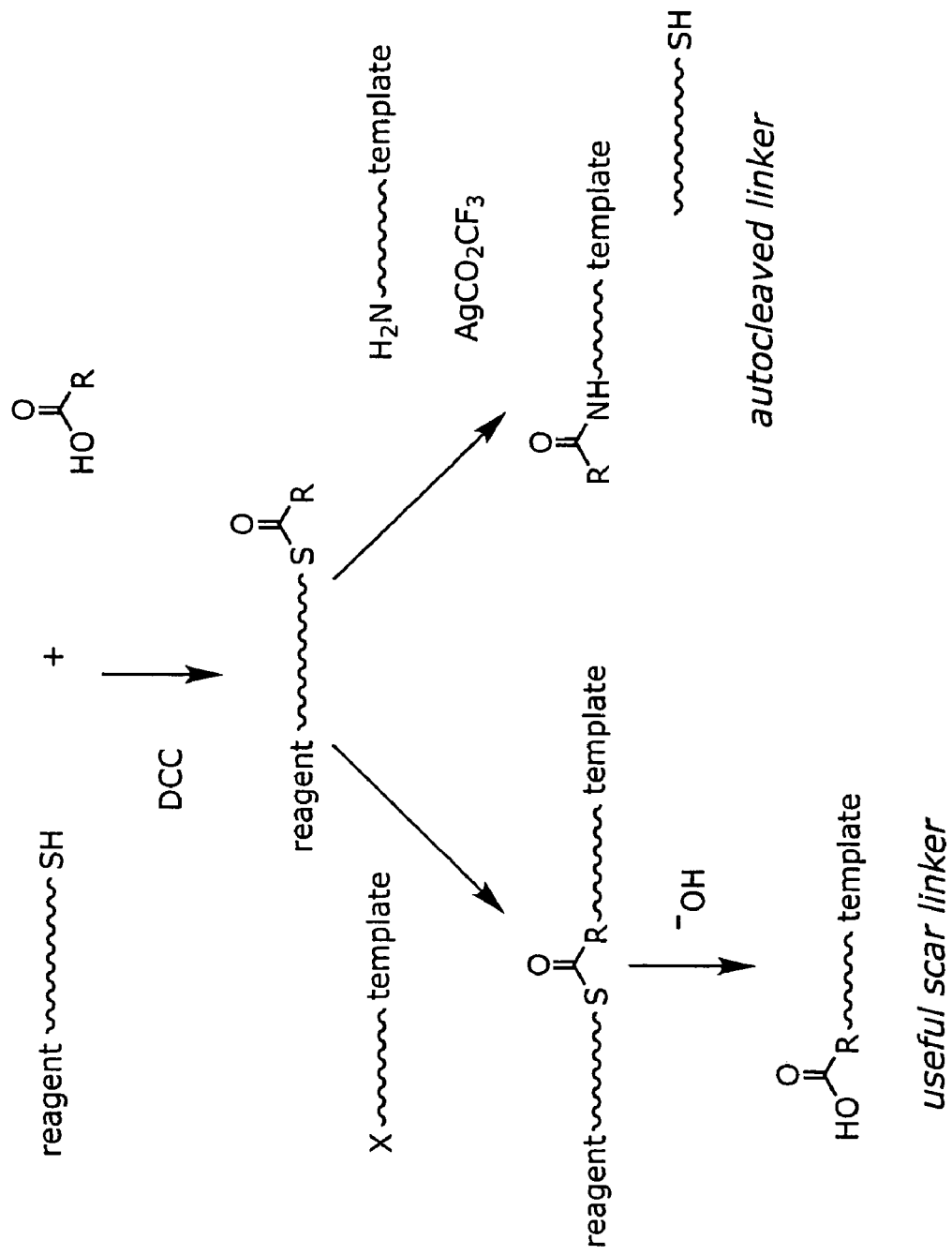
FIG. 20 depicts an exemplary thioester linker for use in the method of the invention.

As will be appreciated by one of ordinary skill in the art, it is frequently useful to leave the DNA moiety of the reagents linked to products during reaction development to facilitate analysis by gel electrophoresis. The use of DNA-templated synthesis to translate libraries of DNA into corresponding libraries of synthetic small molecules suitable for in vitro selection, however, requires the development of cleavable linkers connecting reactive groups of reagents with their decoding DNA oligonucleotides. As described below and herein, three exemplary types of linkers have been developed (see, FIG. 18). For reagents with one reactive group, it would be desirable to position DNA as a leaving group to the reactive moiety. Under this "autocleavable" linker strategy, the DNA-reactive group bond is cleaved as a natural consequence of the reaction. As but one example of this approach, a fluorescent Wittig phosphorane reagent (14, referring to FIG. 19) was synthesized in which the decoding DNA oligonucleotide was attached to one of the aryl phosphine groups (see, FIG. 19, left). DNA-templated Wittig reaction with aldehyde-linked templates resulted in the nearly quantitative transfer of the fluorescent group from the Wittig reagent to the template and the concomitant liberation of the alkene product from the DNA moiety of the reagent. Additionally, reagents bearing more than one reactive group can be linked to their decoding DNA oligonucleotides through one of two additional linker strategies. In the "scarless" linker strategy, DNA-templated reaction of one reactive group is followed by cleavage of the linker attached through a second reactive group to yield products without leaving behind additional chemical functionality. For example, a series of amino acid reagents were syntheisized which were connected through a carbamoylethylsulfone linker to their decoding DNA oligonucleotides (FIG. 19, center). Products of DNA-templated amide bond formation using these amino acid reagents were treated with aqueous alkaline buffer to effect the quantitative elimination and spontaneous decarboxylation of the carbamoyl group. The product of leaving this scarless linker is therefore the cleanly transferred amino acid moiety. In yet other embodiment of the invention, a third linker strategy, a "useful scar" may be utilized on the theory that it may be advantageous to introduce useful chemical groups as a consequence of linker cleavage. In particular, a "useful scar" can be functionalized in subsequent steps and is left behind following linker cleavage. For example, amino acid reagents linked through 1,2-diols to their decoding DNA oligonucleotides were generated. Following amide bond formation, this linker was quantitatively cleaved by oxidation with $NaIO_4$ to afford products bearing useful aldehyde groups (see, FIG. 19, right). In addition to the linkers described directly above, a variety of additional linkers can be utilized. For example, as shown in FIG. 20, a thioester linker can be generated by carbodiimide-mediated coupling of thiol-terminated DNA with carboxylate-containing reagents and can be cleaved with aqueous base. As the carboxylate group provides entry into the DNA-templated amide bond formation reactions described above, this linker would liberate a "useful scar" when cleaved (see, FIG. 20). Alternatively, the thioester linker can be used as an autocleavable linker during an amine acylation reaction in the presence of Ag(I) cations (see, Zhang et al. *J. Am. Chem. Soc.* 1999, 121, 3311-3320) since the thiol-DNA moiety of the reagent is liberated as a natural consequence of the reaction. It will be appreciated that a thioether linker that can be oxidized and eliminated at pH 11 to liberate a vinyl sulfone can be utilized as a "useful scar" linker. As demonstrated herein, the vinyl sulfone group serves as the substrate in a number of subsequent DNA-templated reactions.

Example 4

Exemplary Reactions in Organic Solvents

Figure 21:
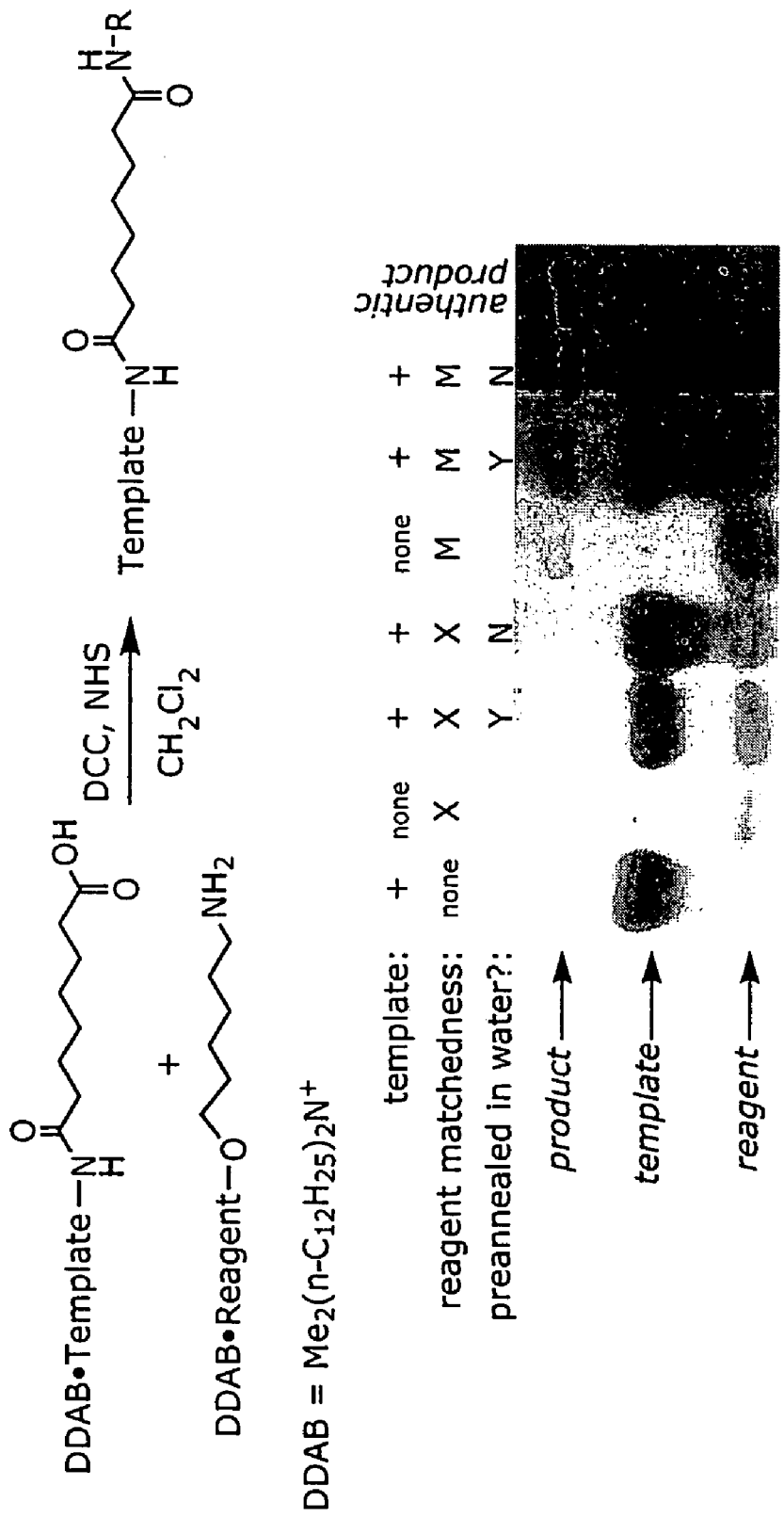
FIG. 21 depicts DNA-templated amide bond formation reactions in which reagents and templates are complexed with dimethyldidodecylammonium cations.

As demonstrated herein, a variety of DNA-templated reactions can occur in aqueous media. It has also been demonstrated, as discussed below, that DNA-templated reactions can occur in organic solvents, thus greatly expanding the scope of DNA-templated synthesis. Specifically, DNA templates and reagents have been complexed with long chain tetraalkylammonium cations (see, Jost et al. *Nucleic Acids Res.* 1989, 17, 2143; Mel'nikov et al. *Langmuir,* 1999, 15, 1923-1928) to enable quantitative dissolution of reaction components in anhydrous organic solvents including $CH_2Cl_2$, $CHCl_3$, DMF and MeOH. Surprisingly, it was found that DNA-templated synthesis can indeed occur in anhydrous organic solvents with high sequence selectivity. Depicted in FIG. 21 are DNA-templated amide bond formation reacations in which reagents and templates are complexed with dimethyldidodecylammonium cations either in separate vessels or after preannealing in water, lyophilized to dryness, dissolved in $CH_2Cl_2$, and mixed together. Matched, but not mismatched, reactions provided products both when reactants were preannealed in aqueous solution and when they were mixed for the first time in $CH_2Cl^2$ (see, FIG. 21). DNA-templated amide formation and Pd-mediated Heck coupling in anhydrous DMF also proceeded sequence-specifically. Clearly, these observations of sequence-specific DNA-templated synthesis in organic solvents implies the presence of at least some secondary structure within tetraalkylammonium-complexed DNA in organic media, and should enable DNA receptors and catalysts to be evolved towards stereoselective binding or catalytic properties in organic solvents. Specifically, DNA-templated reactions that are known to occur in aqueous media, including conjugate additions, cycloadditions, displacement reactions, and Pd-mediated couplings can also be performed in organic solvents. In certain other embodiments, reactions in organic solvents may be utilized that are inefficient or impossible to perform in water. For example, while Ru-catalyzed olefin metathesis in water has been reported by Grubbs and co-workers (see, Lynn et al. *J. Am. Chem. Soc.* 1998, 120, 1627-1628; Lynn et al. *J. Am. Chem. Soc.* 2000, 122, 6601-6609; Mohr et al. *Organometallics* 1996, 15, 4317-4325), the aqueous metathesis system is extremely functional group sensitive. The functional group tolerance of Ru-catalyzed olefin metathesis in organic solvents, however, is significantly more robust. Some exemplary reactions to utilize in organic solvents include, but are not limited to 1,3-dipolar cycloaddition between nitrones and olefins which can proceed through transition states that are less polar than ground state starting materials.

As detailed above, the generality of DNA-templated synthesis has been established by performing several distinct DNA-templated reaction types, none of which are limited to producing structures that resemble the natural nucleic acid backbone, and many of which are highly useful carbon-carbon bond forming or complexity-building synthetic reactions. It has been shown that the distance independence of DNA-templated synthesis allows different regions of a DNA template to each encode different synthetic reactions. DNA-templated synthesis can maintain sequence fidelity even in a library format in which more than 1,000 templates and 1,000 reagents react simultaneously in one pot. As described above and below, linker strategies have been developed, which together with the reactions developed as described above, have enabled the first multi-step DNA-templated synthesis of simple synthetic small molecules. Additionally, the sequence-specific DNA-templated synthesis in organic solvents has been demonstrated, further expanding the scope of this approach.

Example 5

Synthesis of Exemplary Compounds and Libraries of Compounds

A) Synthesis of a Polycarbamate Library: One embodiment of the strategy described above is the creation of an amplifiable polycarbamate library. Of the sixteen possible dinucleotides used to encode the library, one is assigned a start codon function, and one is assigned to serve as a stop codon. An artificial genetic code is then created assigning each of the up to 14 remaining dinucleotides to a different monomer. For geometric reasons one monomer actually contains a dicarbamate containing two side chains. Within each monomer, the dicarbamate is attached to the corresponding dinucleotide (analogous to a tRNA anticodon) through a silyl enol ether linker which liberates the native DNA and the free carbamate upon treatment with fluoride. The dinucleotide moiety exists as the activated 5'-2-methylimidazole phosphate, that has been demonstrated (Inoue et al. *J. Mol. Biol.* 162:201, 1982; Rembold et al. *J. Mol. Evol.* 38:205, 1994; Chen et al. *J. Mol. Biol.* 181:271, 1985; Acevedo et al. *J. Mol. Biol.* 197:187, 1987; Inoue et al. *J. Am. Chem. Soc.* 103:7666, 1981; each of which is incorporated herein by reference) to serve as an excellent leaving group for template-directed oligomerization of nucleotides yet is relatively stable under neutral or basic aqueous conditions (Schwartz et al. *Science* 228:585, 1985; incorporated herein by reference): The dicarbamate moiety exists in a cyclic form linked through a vinyloxycarbonate linker. The vinylcarbonate group has been demonstrated to be stable in neutral or basic aqueous conditions (Olofson et al. *Tetrahedron Lett.* 18:1563, 1977; Olofson et al. *Tetrahedron Lett.* 18:1567, 1977; Olofson et al. *Tetrahedron Lett.* 18:1571, 1977; each of which is incorporated herein by reference) and further has been shown to provide carbamates in very high yields upon the addition of amines (Olofson et al. *Tetrahedron Lett.* 18:1563, 1977; incorporated herein by reference).

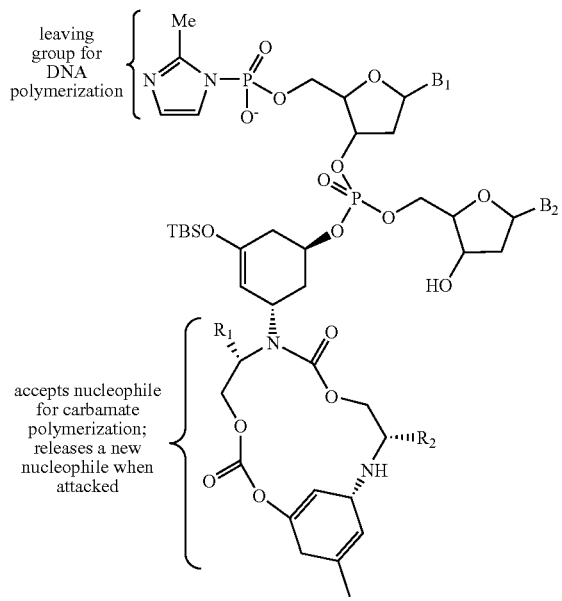

When attacked by an amine from a nascent polycarbamate chain, the vinyl carbonate linker, driven by the aromatizatibn of m-cresol, liberates a free amine. This free amine subsequently serves as the nucleophile to attack the next vinyloxycarbonate, propagating the polymerization of the growing carbamate chain. Such a strategy minimizes the potential for cross-reactivity and bi-directional polymerization by ensuring that only one nucleophile is present at any time during polymerization.

Figure 22:
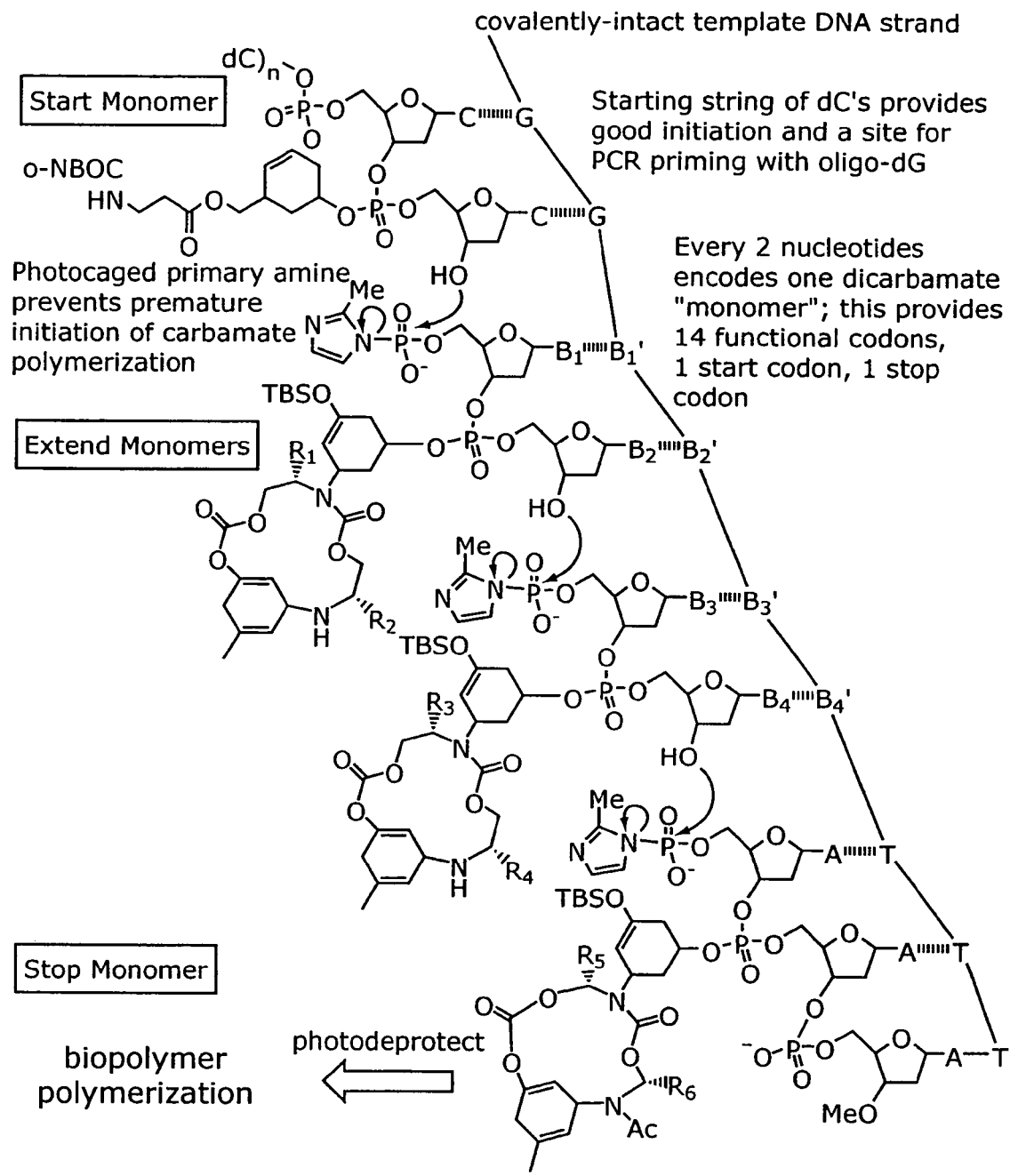
FIG. 22 depicts the assembly of transfer units along the nucleic acid template and polymerization of the nucleotide anti-codon moieties.

Using the monomer described above, artificial translation of DNA into a polycarbamate can be viewed as a three-stage process. In the first stage, single stranded DNA templates encoding the library are used to guide the assembly and polymerization of the dinucleotide moieties of the monomers, terminating with the "stop" monomer which possesses a 3'methyl ether instead of a 3'hydroxyl group (FIG. 22).

Figure 23:
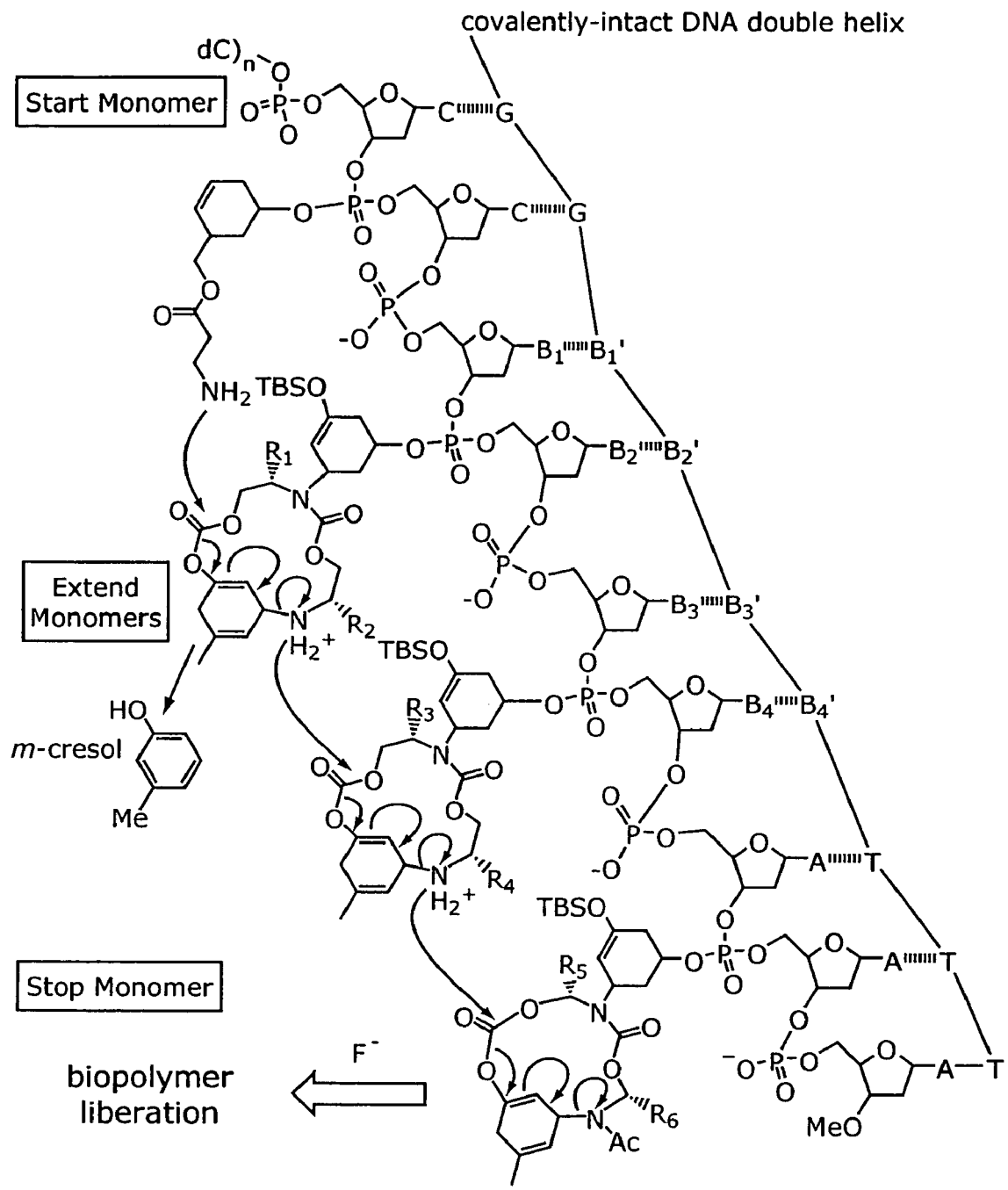
FIG. 23 depicts the polymerization of the dicarbamate units along the nucleic acid template to form a polycarbamate. To initiate polymerization the "start" monomer ending in a o-nitrobenzylcarbamate is photodeprotected to reveal the primary amine that initiates carbamate polymerization. Polymerization then proceeds in the 5' to 3' direction along the DNA backbone, with each nucleophilic attack resulting in the subsequent unmasking of a new amine nucleophile. Attack of the "stop" monomer liberates an acetamide rather than an amine, thereby terminating polymerization.

Once the nucleotides have assembled and polymerized into double-stranded DNA, the "start" monomer ending in a o-nitrobenzylcarbamates is photodeprotected to reveal the primary amine that initiates carbamate polymerization. Polymerization proceeds in the 5' to 3' direction along the DNA backbone, with each nucleophilic attack resulting in the subsequent unmasking of a new amine nucleophile. Attack of the "stop" monomer liberates an acetamide rather than an amine, thereby, termination polymerization (FIG. 23). Because the DNA at this stage exists in a stable double-stranded form, variables such as temperature and pH may be explored to optimize polymerization efficiency.

Figure 24:
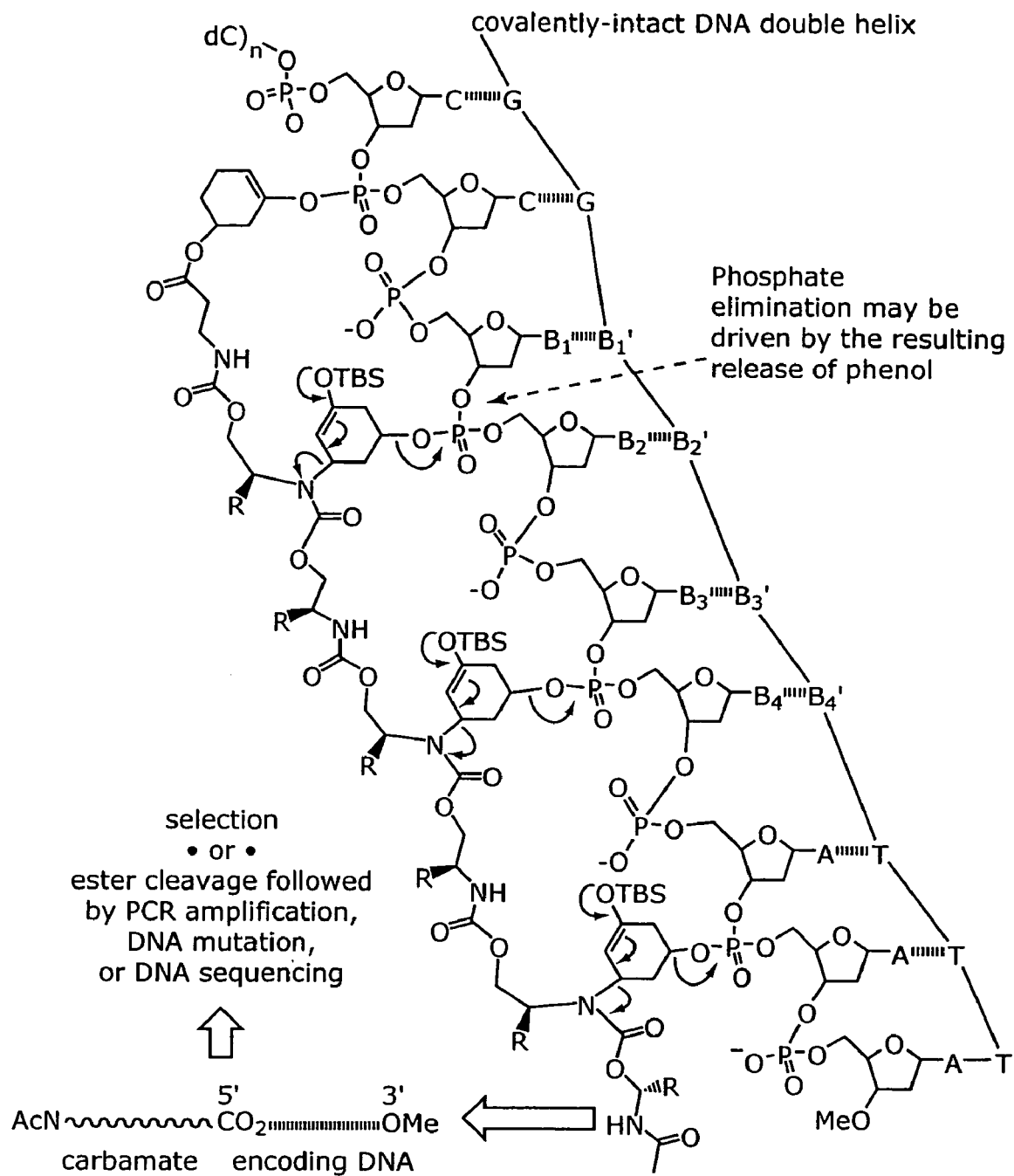
FIG. 24 depicts cleavage of the polycarbamate from the nucleotide backbone. Desilylation of the enol ether linker attaching the anti-codon moiety to the monomer unit and the elimination of phosphate driven by the resulting release of phenol provides the provides the polycarbamate covalently linked at its carboxy terminus to its encoding single-stranded DNA.
Figure 25:
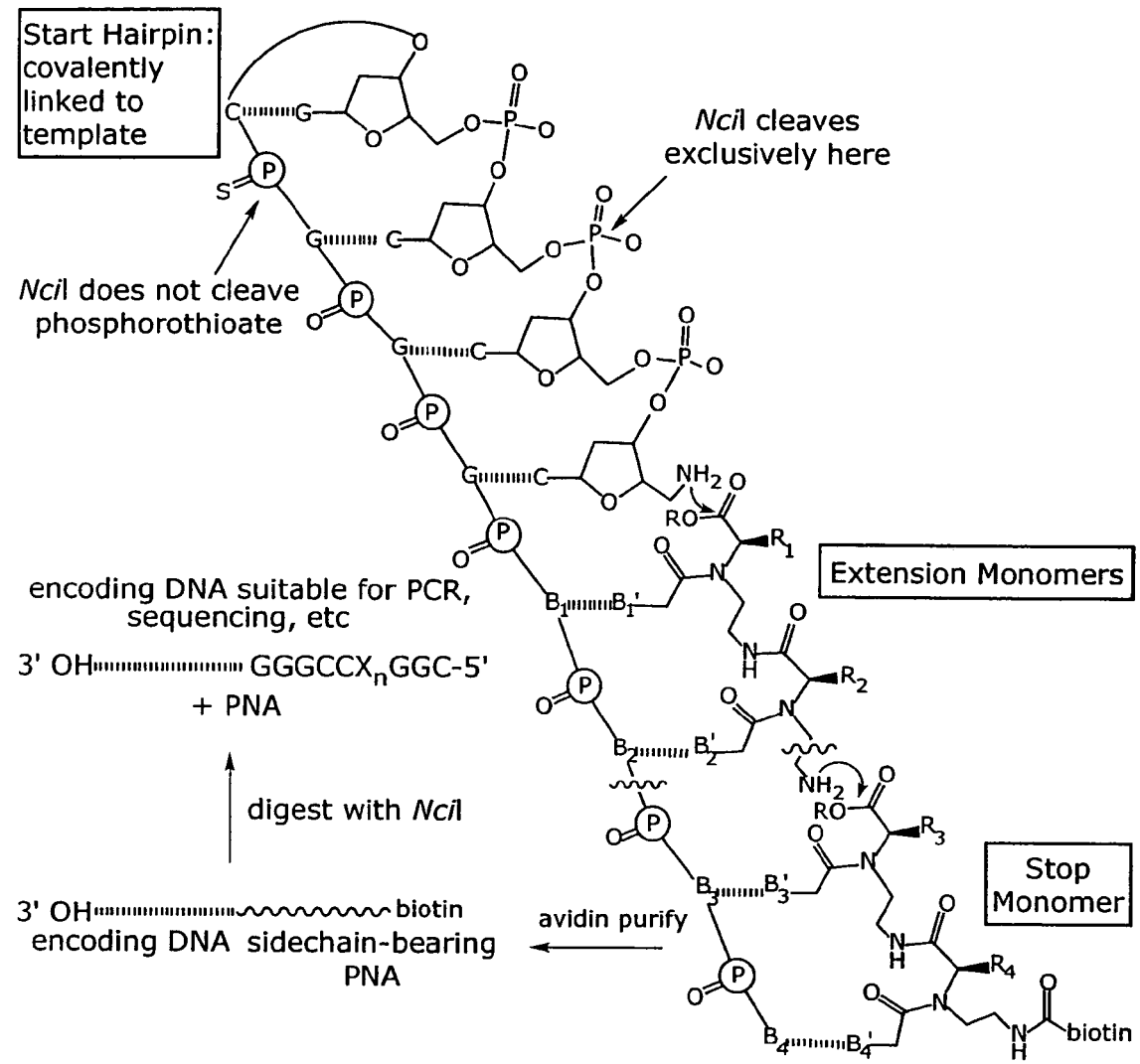
FIG. 25 depicts components of an amplifiable, evolvable functionalized peptide nucleic acid library.

Following polymerization the polycarbamate is cleaved from the phosphate backbone of the DNA upon treatment with fluoride. Desilylation of the enol ether linker and the elimination of the phosphate driven by the resulting release of phenol provides the polycarbamate covalently linked at its carboxy terminus to its encoding single-stranded DNA (FIG. 24).

At this stage the polycarbamate may be completely liberated from the DNA by base hydrolysis of the ester linkage. The liberated poLycarbamate can be purified by HPLC and retested to verify that its desired properties are intact. The free DNA can be amplified using PCR, mutated with error-prone PCR (Cadwell et al. *PCR Methods Appl.* 2:28, 1992; incorporated herein by reference) or DNA shuffling (Stemmer *Proc. Natl. Acad. Sci. USA* 91:10747, 1994; Stemmer *Nature* 370:389, 1994; U.S. Pat. No. 5,811,238, issued Sep. 22, 1998; each of which is incorporated herein by reference), and/or sequenced to reveal the primary structure of the polycarbamate.

Synthesis of monomer units. After the monomers are synthesized, the assembly and polymerization of the monomers on the DNA scaffold should occur spontaneously. Shikimic acid 1, available commercially, biosynthetically (Davis *Adv. Enzymol.* 16:287, 1955; incorporated herein by reference), or by short syntheses from D-mannose (Fleet et al. *J. Chem. Soc., Perkins Trans.* 1905, 1984; Harvey et al. *Tetrahedron Lett.* 32:4111, 1991; each of which is incorporated herein by reference), serves as a convenient starting point for the monomer synthesis. The syn hydroxyl groups are protected as the p-methoxybenzylidene, and remaining hydroxyl group as the tert-butyldimethylsilyl ether to afford 2. The carboxylate moiety of the protected shikimic acid is then reduced completely by LAH reduction, tosylation of the resulting alcohol, and further reduction with LAH to provide 3.

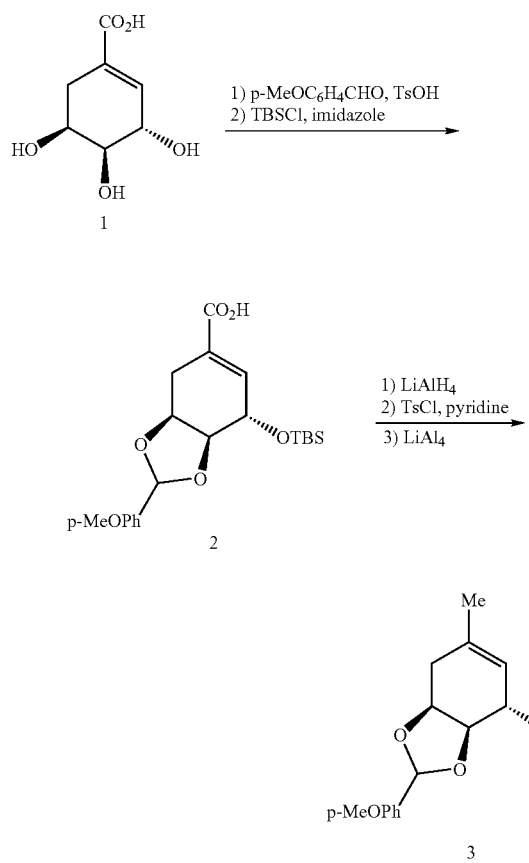

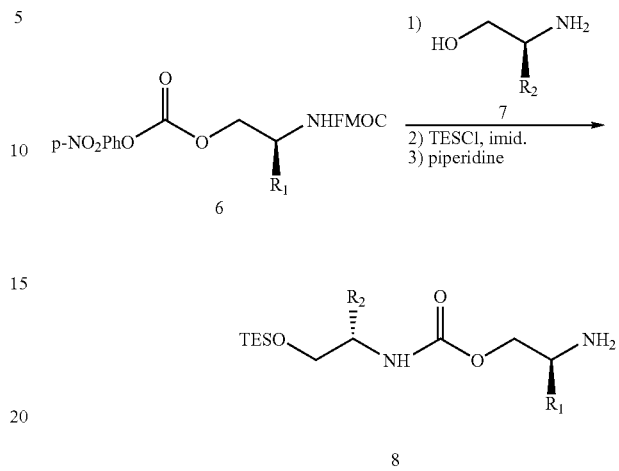

Commercially available and synthetically accessible N-protected amino acids serve as the starting materials for the dicarbamate moiety of each monomer. Reactive side chains are protected as photolabile ethers, esters, acetals, carbamates, or thioethers. Following chemistry previously developed (Cho et al. *Science* 261:1303, 1993; incorporated herein by reference), a desired amino acid 4 is converted to the corresponding amino alcohol 5 by mixed anhydride formation with isobutylchloroformate followed by reduction with sodium borohydride. The amino alcohol is then converted to the activated carbonate by treatment with p-nitrophenylchloroformate to afford 6, which is then coupled to a second amino alcohol 7 to provide, following hydroxyl group silylation and FMOC deprotection, carbamate 8.

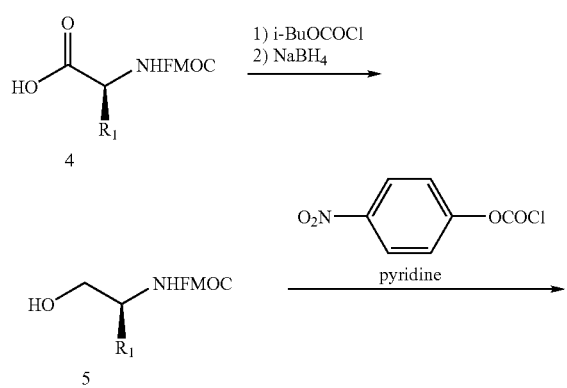

Coupling of carbamate 8 onto the shikimic acid-derived linker proceeds as follows. The allylic hydroxyl group of 3 is deprotected with TBAF, treated with triflic anhydride to form the secondary triflate, then displaced with aminocarbamate 8 to afford 9. Presence of the vinylic methyl group in 3 should assist in minimizing the amount of undesired product resulting from $S_N2'$ addition (Magid *Tetrahedron* 36:1901, 1980; incorporated herein by reference). Michael additions of deprotonated carbamates to α,β-unsaturated esters have been well documented (Collado et al. *Tetrahedron Lett.* 35:8037, 1994; Hirama et al. *J. Am. Chem. Soc.* 107:1797, 1985; Nagasaka et al. *Heterocycles* 29:155, 1989; Shishido et al. *J. Chem. Soc. Perkins Trans. I* 993, 1987; Hirama et al. *Heterocycles* 28:1229, 1989; each of which is incorporated herein by reference). By analogy, the secondary amine is protected as the o-nitrobenzyl carbamate (NBOC), and the resulting compound is deprotonated at the carbamate nitrogen. This deprotonation can typically be performed with either sodium hydride or potassium tert-butyloxide (Collado et al. *Tetrahedron Lett.* 35:8037, 1994; Hirama et al. *J. Am. Chem. Soc.* 107:1797, 1985; Nagasaka et al. *Heterocycles* 29:155, 1989; Shishido et al. *J. Chem. Soc. Perkins Trans.* 1993, 1987; Hirama et al. *Heterocycles* 28:1229, 1989; each of which is incorporated herein by reference), although other bases may be utilized to minimize deprotonation of the nitrobenzylic protons. Additions of the deprotonated carbamate to α,β-unsaturated ketone 10, followed by trapping of the resulting enolate with TBSCI, should afford silyl enol ether 11. The previously found stereoselectivity of conjugate additions to 5-substituted enones such as 10 (House et al. *J. Org. Chem.* 33:949, 1968; Still et al. *Tetrahedron* 37:3981, 1981; each of which is incorporated herein by reference) suggests that preferential formation of 11 over its diastereomer. Ketone 10, the precursor to the fluoride-cleavable carbamate-phosphate linker, may be synthesized from 2 by one pot decarboxylation (Barton et al. *Tetrahedron* 41:3901, 1985; incorporated herein by reference) followed by treatment with TBAF, Swem oxidation of the resulting alcohol to afford 12, deprotection with DDQ, selective nitrobenzyl ether formation of the less-hindered alcohol, and reduction of the α-hydroxyl group with samarium iodide (Molander In *Organic Reactions*, Paquette, Ed. 46:211, 1994; incorporated herein by reference).

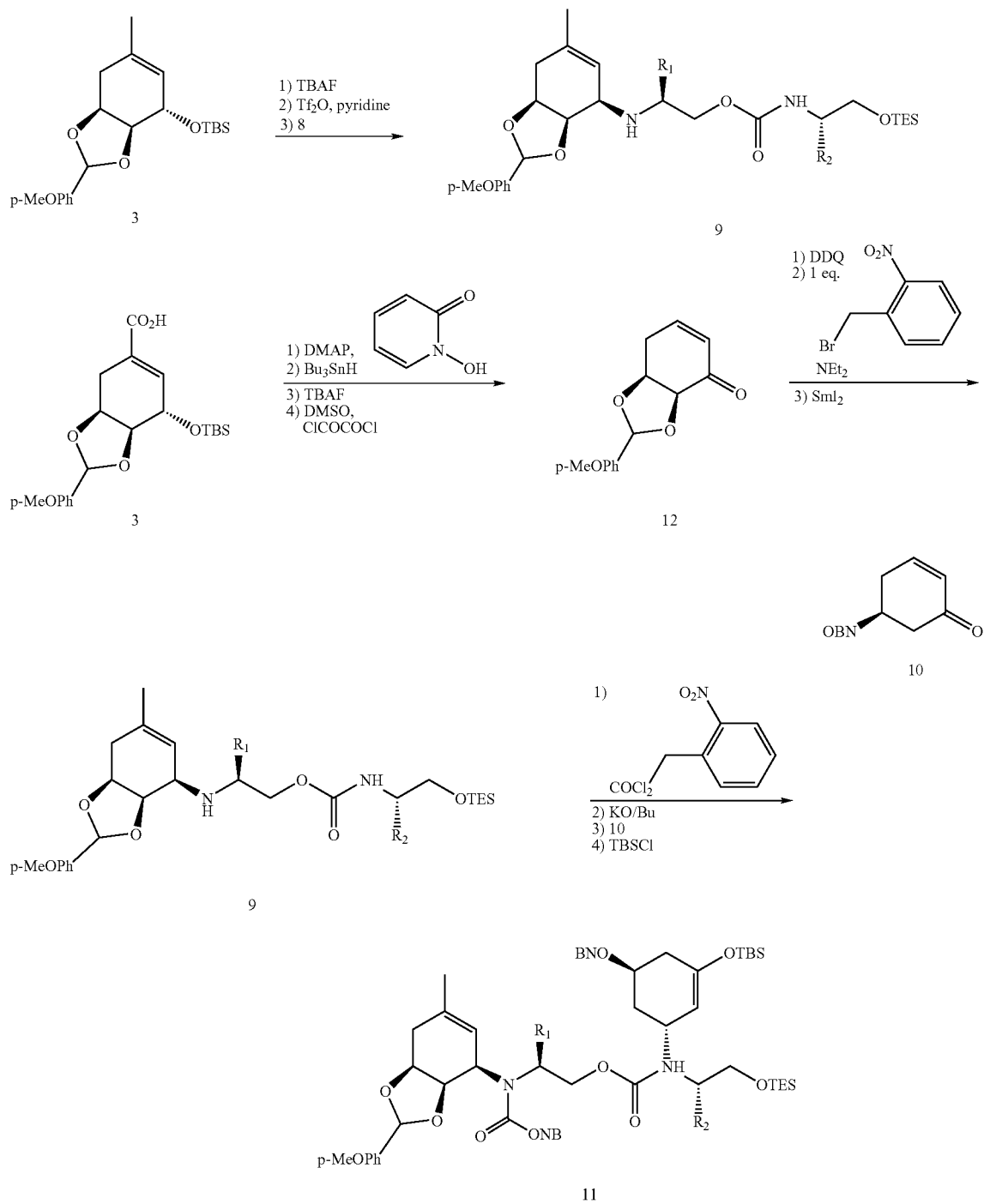

The p-methoxybenzylidiene group of 11 is transformed into the α-hydroxy PMB ether using sodium cyanoborohydride and TMS chloride (Johansson et al. *J. Chem. Soc. Perkin Trans.* 12371, 1984; incorporated herein by reference) and the TES group deprotected with 2% HF (conditions that should not affect the TBS ether (Boschelli et al. *Tetrahedron Lett.* 26:5239, 1985; incorporated herein by reference)) to provide 13. The PMB group, following precedent (Johansson et al. *J. Chem. Soc. Perkin Trans.* 12371, 1984; Sutherlin et al. *Tetrahedron Lett.* 34:4897, 1993; each of which is incorporated herein by reference), should remain on the more hindered secondary alcohol. The two free hydroxyl groups may be macrocyclized by very slow addition of 13 to a solution of p-nitrophenyl chloroformate (or another phosgene analog), providing 14. The PMB ether is deprotected, and the resulting alcohol is converted into a triflate and eliminated under kinetic conditions with a sterically hindered base to afford vinyloxycarbonate 15. Photodeprotection of the nitrobenzyl ether and nitrobenzyl carbamate yields alcohol 16.

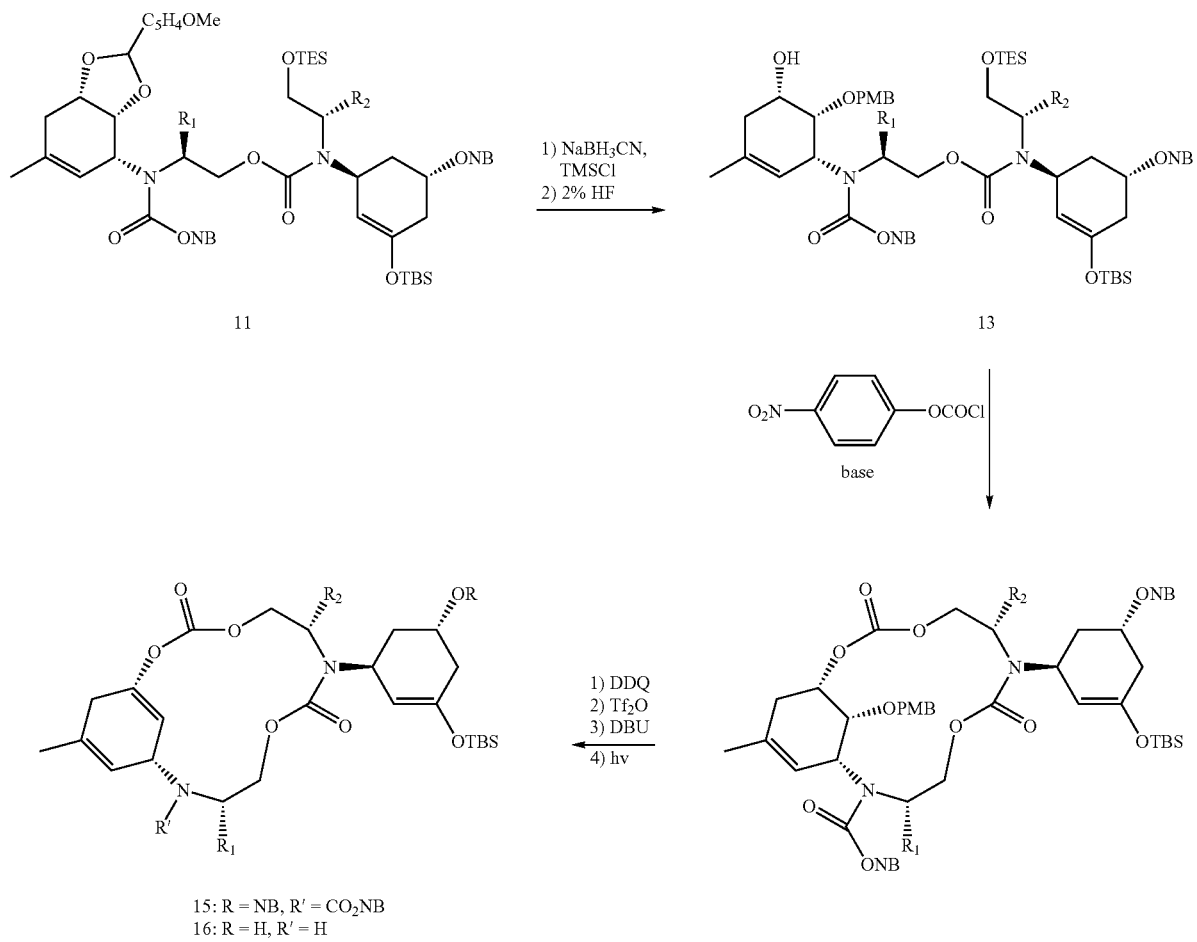

The monomer synthesis is completed by the sequential coupling of three components. Chlorodiisopropylaminophosphine 17 is synthesized by the reaction of PCl₃ with diisopropylamine (King et al. *J. Org. Chem.* 49:1784, 1984; incorporated herein by reference). Resin-bound (or 3'-o-nitrobenzylether protected) nucleoside 18 is coupled to 17 to afford phosphoramidite 19. Subsequent coupling of 19 with the nucleoside 20 (Inoue et al. *J. Am. Chem. Soc.* 103:7666, 1981; incorporated herein by reference) provides 21. Alcohol 16 is then reacted with 21 to yield, after careful oxidation using MCPBA or I₂ followed by cleavage from the resin (or photodeprotection), the completed monomer 22. This strategy of sequential coupling of 17 with alcohols has been successfully used to generate phosphates bearing three different alkoxy substituents in excellent yields (Bannwarth et al. *Helv. Chim. Acta* 70:175, 1987; incorporated herein by reference).

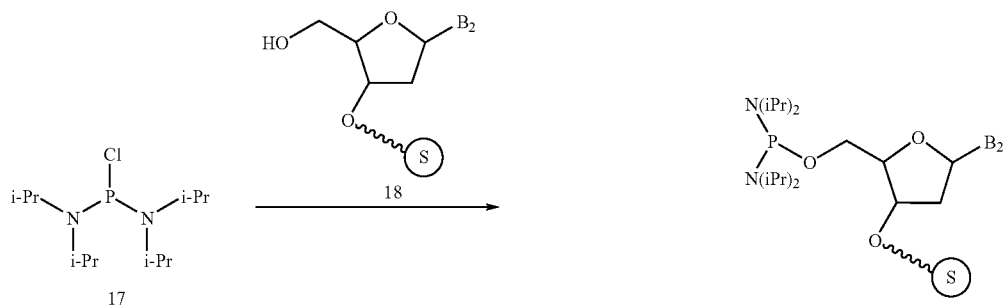

-continued

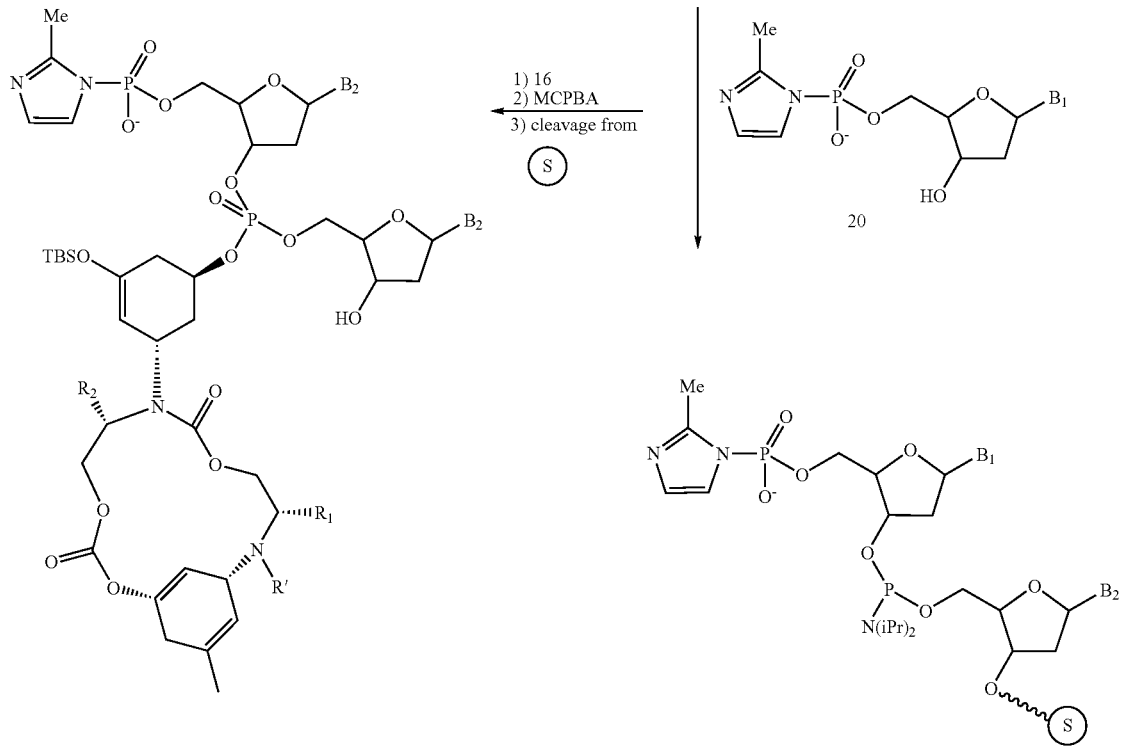

22

21

The unique start and stop monomers used to initiate and terminate carbamate polymerization may be synthesized by simple modification of the above scheme.

B) Evolvable Functionalized Peptide-Nucleic Acids (PNAs): In another embodiment an amplifiable peptide-nucleic acid library is created. Orgel and co-workers have demonstrated that peptide-nucleic acid (PNAs) oligomers are capable of efficient polymerization on complementary DNA or RNA templates (Böhler et al. *Nature* 376:578, 1995; Schmidt et al. *Nucl. Acids Res.* 25:4792, 1997; each of which is incorporated herein by reference). This finding, together with the recent synthesis and characterization of chiral peptide nucleic acids bearing amino acid side chains (Haaima et al. *Angew. Chem. Int. Ed. Engl.* 35:1939-1942, 1996; Püschl et al. *Tetrahedron Lett.* 39:4707, 1998; each of which is incorporated herein by reference), allows the union of the polymer backbone and the growing nucleic acid strand into a single structure. In this example, each template consists of a DNA hairpin terminating in a 5' amino group; the solid-phase and solution syntheses of such molecules have been previously described (Uhlmann et al. *Angew. Chem. Int. Ed. Engl.* 35:2632, 1996; incorporated herein by reference). Each extension monomer consists of a PNA trimer (or longer) bearing side chains containing functionality of interest. An artificial genetic code is written to assign each trinucleotide to a different set of side chains. Assembly, activation (with a carbodiimide and appropriate leaving group, for example), and polymerization of the PNA dimers along the complementary DNA template in the carboxy- to amino-terminal direction affords the unnatural polymer (FIG. 20). Choosing a "stop" monomer with a biotinylated N-terminus provides a convenient way of terminating the extension and purifying full-length polymers. The resulting polymers, covalently linked to their encoding DNA, are ready for selection, sequencing, or mutation.

The experimental approach towards implementing an evolvable functionalized peptide nucleic acid library comprises (i) improving and adapting known chemistry for the high efficiency template-directed polymerization of PNAs; (ii) defining a codon format (length and composition) suitable for PNA coupling of a number of diverse monomers on a complementary strand of encoding DNA free from significant infidelity, framshifting, or spurious initiation of polymerization; (iii) choosing an initial set of side chains defining our new genetic code and synthesizing corresponding monomers; and (iv) subjecting a library of functionalized PNAs to cycles of selection, amplification, and mutation and characterizing the resulting evolved molecules to understand the basis of their novel activities.

Figure 26:
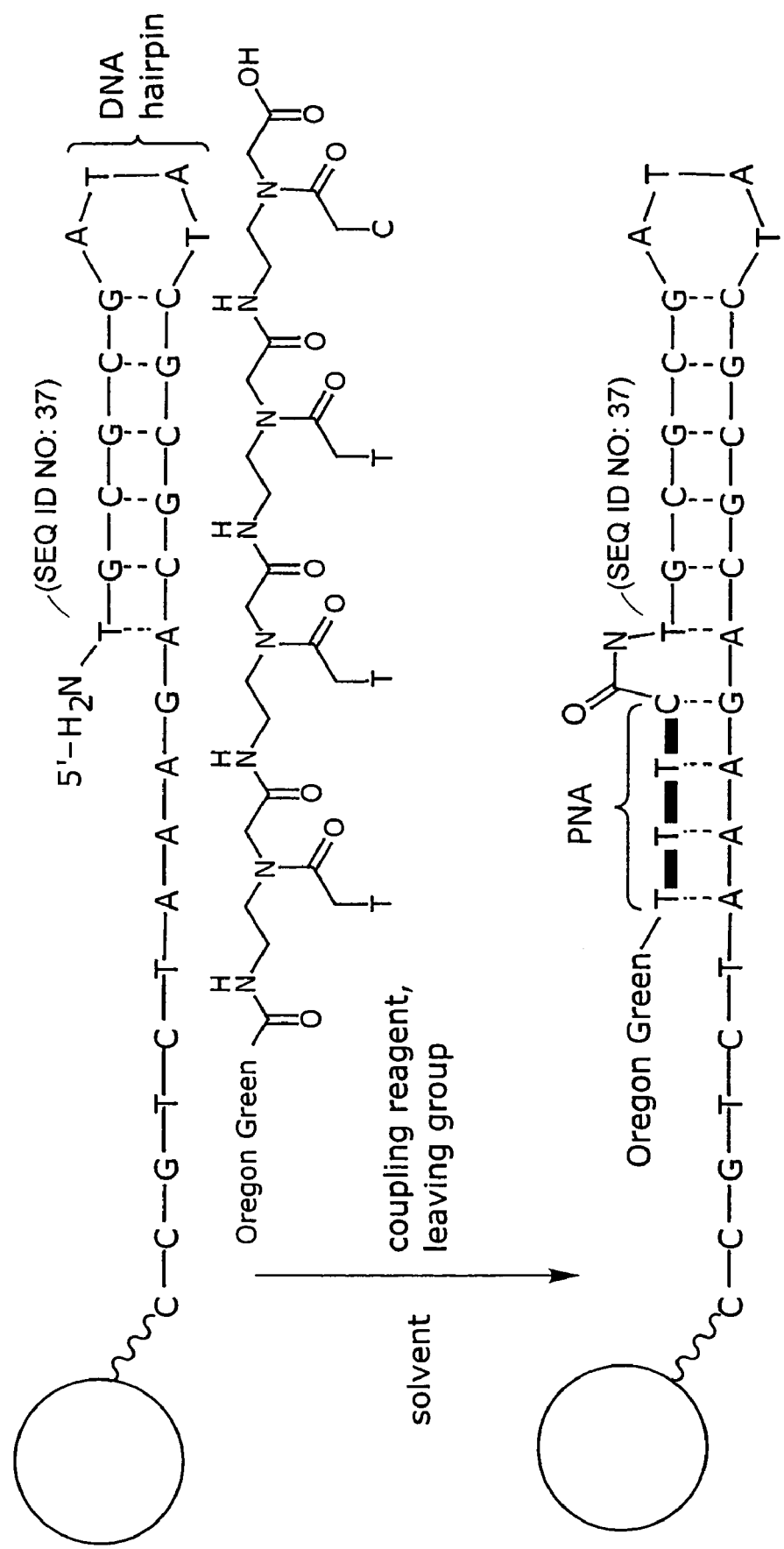
FIG. 26 depicts test reagents used to optimize reagents and conditions for DNA-templated PNA coupling.

(i) Improving coupling chemistry: While Orgel and coworkers have reported template-directed PNA polymerization, reported yields and number of successful couplings are significantly lower than would be desired. A promising route towards improving this key coupling process is exploring new coupling reagents, temperatures, and solvents which were not previously investigated (presumably because previous efforts focused on conditions which could have existed on prebiotic earth). The development of evolvable functionalized PNA polymers involves employing activators (DCC, DIC, EDC, HATU/DIEA, HBTU/DIEA, ByBOP/DIEA, chloroacetonitrile), leaving groups (2-methylimidazole, imidazole, pentafluorophenol, phenol, thiophenol, trifluoroacetate, acetate, toluenesulfonic acids, coenzyme A, DMAP, ribose), solvents (aqueous at several pH values, DMF, DMSO, chloroform, TFE), and temperature (0° C., 4° C., 25° C., 37° C., 55° C.) in a large combinatorial screen to isolate new coupling conditions. Each well of a 384-well plate is assigned a specific combination of one activator, leaving group, solvent, and temperature. Solid-phase synthesis beads covalently linked to DNA hairpin templates are placed in each well, together with a fluorescently labeled PNA monomer complementary to the template. A successful coupling event results in the covalent linking of the fluorophore to the beads (FIG. 26); undesired non-templated coupling can be distinguished by control reactions with mismatched monomers. Following bead washing and cleavage of the product from solid support, each well is assayed with a fluorescence plate reader.

(ii) Defining a codon format: While Nature has successfully employed a triplet codon in protein biosynthesis, a new polymer assembled under very different conditions without the assistance of enzymes may require an entirely novel codon format. Frameshifting may be remedied by lengthening each codon such that hybridizing a codon out of frame guarantees a mismatch (for example, by starting each codon with a G and by restricting subsequent positions in the codon to T, C, and A). Thermodynamically, one would also expect fidelity to improve as codon length increases to a certain point. Codons that are excessively long, however, will be able to hybridize despite mismatched bases and moreover complicate monomer synthesis. An optimal codon length for high fidelity artificial translation can be defined using an optimized plate-based combinatorial screen developed above. The length and composition of each codon in the template is varied by solid-phase synthesis of the appropriate DNA hairpin. These template hairpins are then allowed to couple with fluorescently labeled PNA monomers of varying sequence. The ideal codon format allows only monomers bearing exactly complementary sequences to couple with templates, even in the presence of mismatched PNA monomers (which are labeled differently to facilitate assaying of matched versus mismatched coupling). Triplet and quadruplet codons in which two bases are varied among A, T, and C while the remaining base or bases are fixed as G to ensure proper registration during polymerization are first studied.

Figure 27:
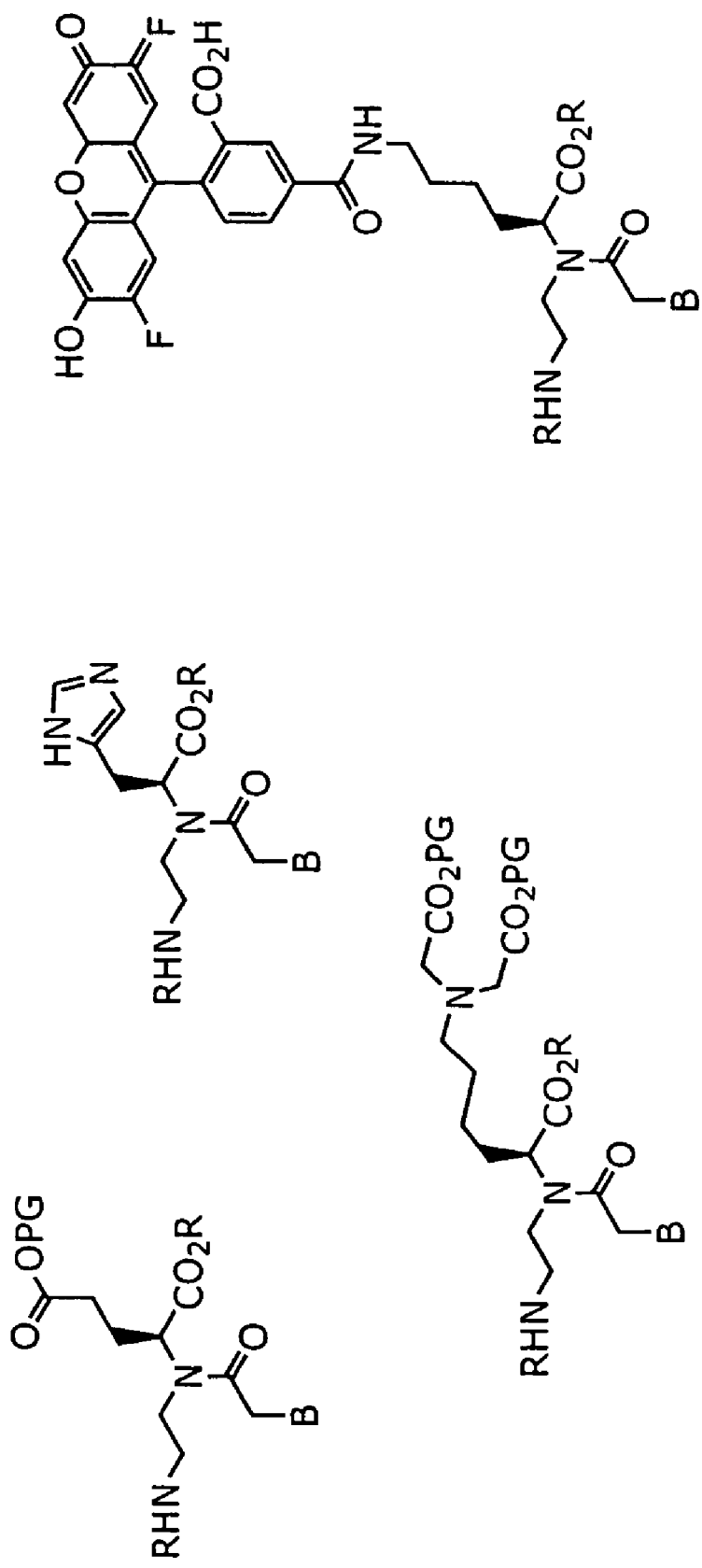
FIG. 27 depicts a simple set of PNA monomers derived from commercially available building blocks useful for evolving a PNA-based fluorescent Ni$^{2+}$ sensor.

(iii) Writing a new genetic code: Side chains are chosen which provide interesting functionality not necessarily present in natural biopolymers, which are synthetically accessible, and which are compatible with coupling conditions. For example, a simple genetic code which might be used to evolve a $Ni^{+2}$ chelating PNA consists of a variety of protected carboxylate-bearing side chains as well as a set of small side chains to equip polymers with conformational flexibility and structural diversity (FIG. 27). Successful selection of PNAs capable of binding $Ni^{+2}$ with high affinity could be followed by an expansion of this genetic code to include a fluorophore as well as a fluorescent quencher. The resulting polymers could then be evolved towards a fluorescent $Ni^{+2}$ sensor which possesses different fluorescent properties in the absence or presence of nickel. Replacing the fluorescent side chain with a photocaged one may allow the evolution of polymers that chelate $Ni^{+2}$ in the presence of certain wavelengths of light or which release $Ni^{+2}$ upon photolysis. These simple examples demonstrate the tremendous flexibility in potential chemical properties of evolvable unnatural molecules conferred by the freedom to incorporate synthetic building blocks no longer limited to those compatible with the ribosomal machinery.

Figure 28:
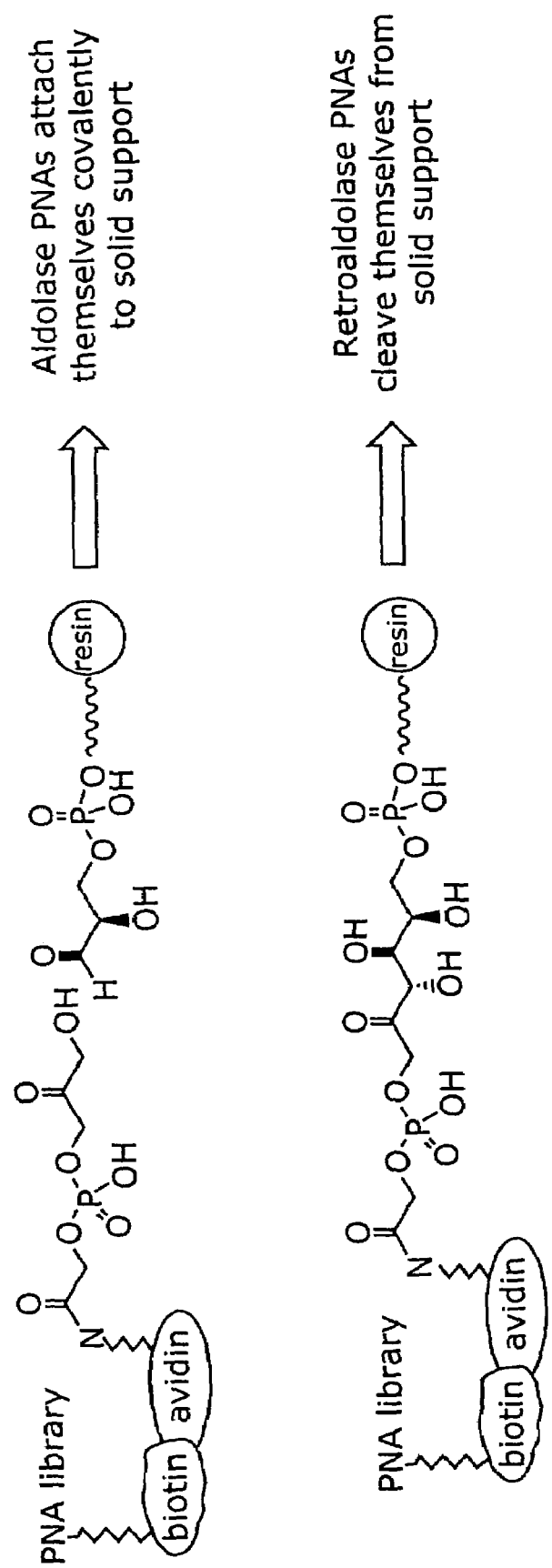
FIG. 28 depicts two schemes for the selection of a biotin-terminated functionalized PNA capable of catalyzing an aldol or retroaldol reaction.

(iv) Selecting for desired unnatural polymers: Many of the methods developed for the selection of biological molecules can be applied to selections for evolved PNAs with desired properties. Like nucleic acid or phage-display selections, libraries of unnatural polymers generated by the DNA-templated polymerization methods described above are self-tagged and therefore do not need to be spatially separated or synthesized on pins or beads. $Ni^{+2}$ binding PNA may be done simply by passing the entire library resulting from translation or a random oligonucleotide through commercially available Ni-NTA ("His-Tag") resin precharged with nickel. Desired molecules bind to the resin and are eluted with EDTA. Sequencing these PNAs after several cycles of selection, mutagenesis, and amplification reveals which of the initially chosen side chains can assemble together to form a $Ni^{+2}$ receptor. In addition, the isolation of a PNA $Ni^{+2}$ chelator represents the PNA equivalent of a histidine tag which may prove useful for the purification of subsequent unnatural polymers. Later efforts will involve more ambitious selections. For example, PNAs that fluoresce in the presence of specific ligands may be selected by FACS sorting of translated polymers linked through their DNA templates to beads. Those beads that fluoresce in the presence, but not in the absence, of the target ligand are isolated and characterized. Finally, the use of a biotinylated "stop" monomer as described above allows for the direct selection for the catalysis of many bond-forming or bond-breaking reactions. Two examples depicted in FIG. 28 outline a selection for a functionalized PNA that catalyzes the retroaldol cleavage of fructose 1,6-bisphosphate to glyceraldehyde 3-phosphate and dihydroxyacetone phosphate, an essential step in glycolysis, as well as a selection for PNA that catalyzes the converse aldol reaction.

Figure 29:
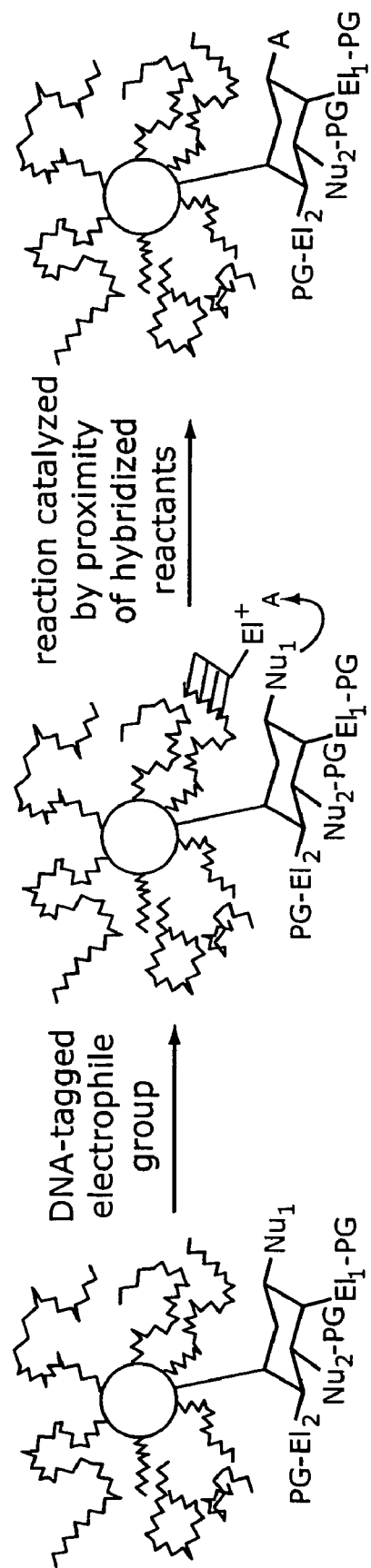
FIG. 29 depicts DNA-template-directed synthesis of a combinatorial small molecule library.

C) Evolvable Libraries of Small Molecules: In yet another embodiment of the present invention, the inventive methods are used in preparing amplifiable and evolvable unnatural nonpolymeric molecules including synthetic drug scaffolds. Nucleophilic or electrophilic groups are individually unmasked on a small molecule scaffold attached by simple covalent linkage or through a common solid support to an encoding oligonucleotide template. Electrophilic or nucleophilic reactants linked to short nucleic acid sequences are hybridized to the corresponding templates. Sequence-specific reaction with the appropriate reagent takes place by proximity catalysis (FIG. 29).

Figure 30:
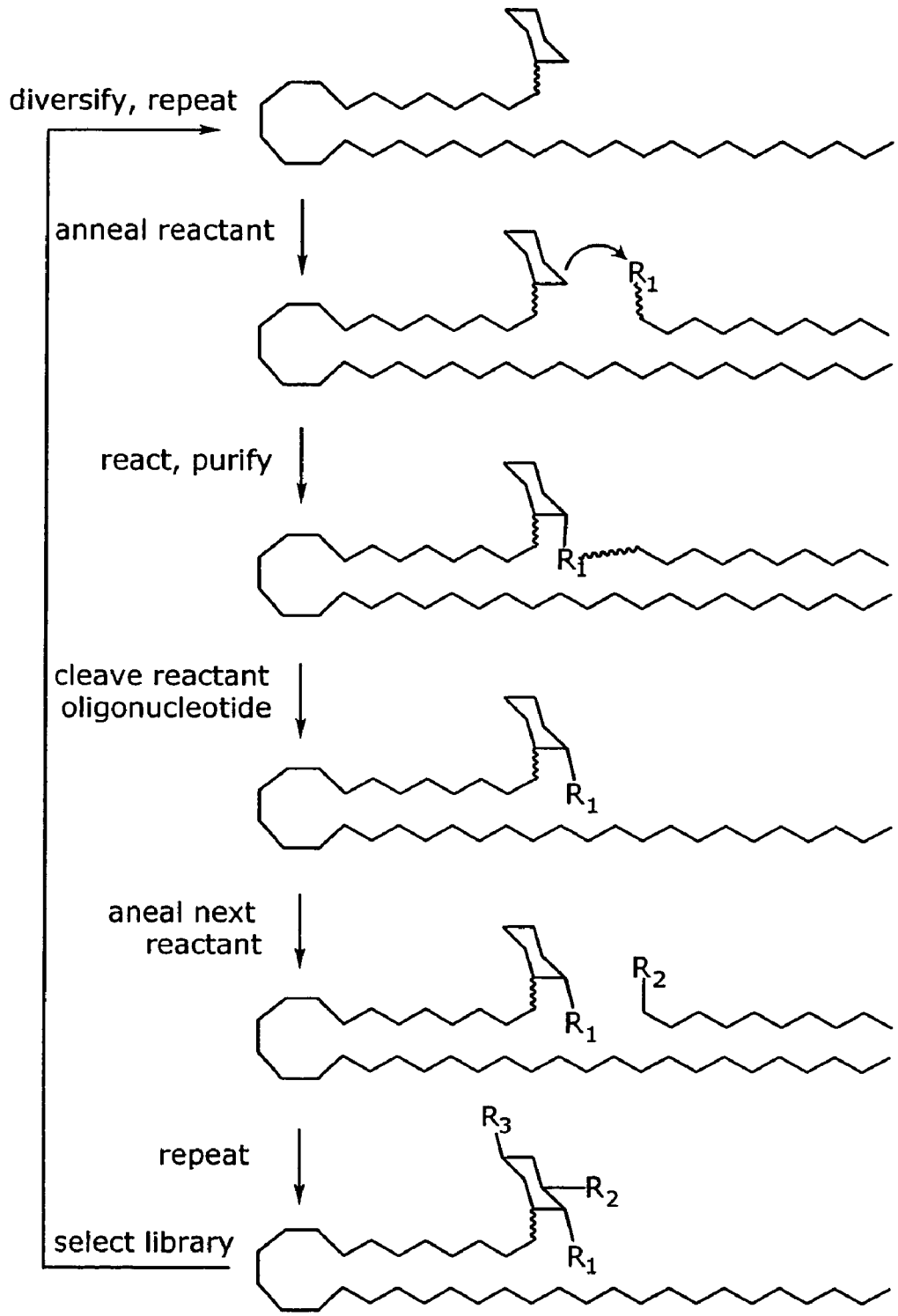
FIG. 30 shows schematically how DNA-linked small molecule scaffolds can be functionalized sequence specifically by reaction with synthetic reagents linked to complementary nucleic acid oligonucleotides, this process can be repeated to complete the synthetic transformations leading to a fully functionalized molecule.

Following synthetic functionalization of all positions in a manner determined by the sequence of the attached DNA (FIGS. 30 & 31), the resulting encoded beads may be subjected to wide range of biological screens which have been developed for assaying compounds on resin. (Gordon et al. *J. Med. Chem.* 37:1385, 1994; Gallop et al. *J. Med. Chem.* 37:1233-1251, 1994; each of which is incorporated herein by reference)

Encoding DNA is cleaved from each bead identified in the screen and subjected to PCR, mutagenesis, sequencing, or homologous recombination before reattachment to a solid support. Ultimately, this system is most flexible when the encoding DNA is directly linked to the combinatorial synthetic scaffold without an intervening bead. In this case, entire libraries of compounds may be screened or selected for desired activities, their encoding DNA liberated, amplified, mutated, and recombined, and new compounds synthesized all in a small series of one-pot, massively parallel reactions. Without a bead support, however, reactivities of hybridized reactants must be highly efficient since only one template molecule directs the synthesis of the entire small molecule.

Figure 32:
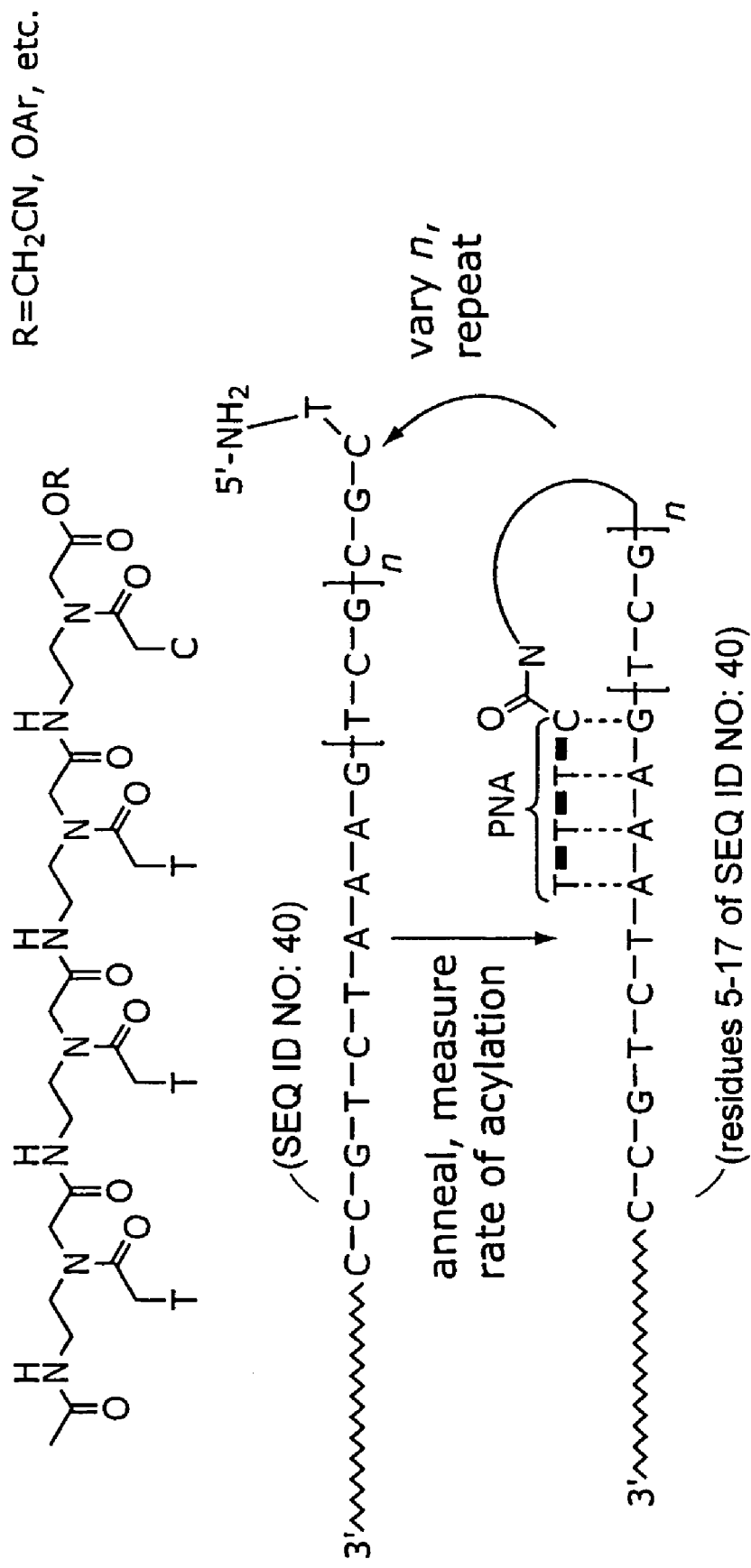
FIG. 32 depicts a way of measuring the rate of reaction between a fixed nucleophile and an electrophile hybridized at varying distances along a nucleic acid template to define an essential reaction window in which nucleic acid-templated synthesis of nonpolymeric structures can take place.

The development of evolvable synthetic small molecule libraries relies on chemical catalysis provided by the proximity of DNA hybridized reactants. It will be appreciated that acceptable distances between hybridized reactants and unmasked reactive groups must first be defined for efficient DNA-templated functionalization by hybridizing radiolabeled electrophiles (activated esters in out first attempts) attached to short oligonucleotides at varying distances from a reactive nucleophile (a primary amine) on a strand of DNA. At given timepoints, aliquots are subjected to gel electrophoresis and autoradiography to monitor the course of the reaction. Plotting the reaction as a function of the distance (in bases) between the nucleophile and electrophile will define an acceptable distance window within which proximity-based catalysis of a DNA-hybridized reaction can take place. The width of this window will determine the number of distinct reactions we can encode on a strand of DNA (a larger window allows more reactions) as well as the nature of the codons (a larger window is required for longer codons) (FIG. 32).

Once acceptable distances between functional groups on a combinatorial synthetic scaffold and hybridizes reactants is determined, the codon format is determined. The nonpolymeric nature of small molecule synthesis simplifies codon reading as frameshifting is not an issue and relatively large codons may be used to ensure that each set of reactants hybridizes only to one region of the encoding DNA strand.

Figure 31:
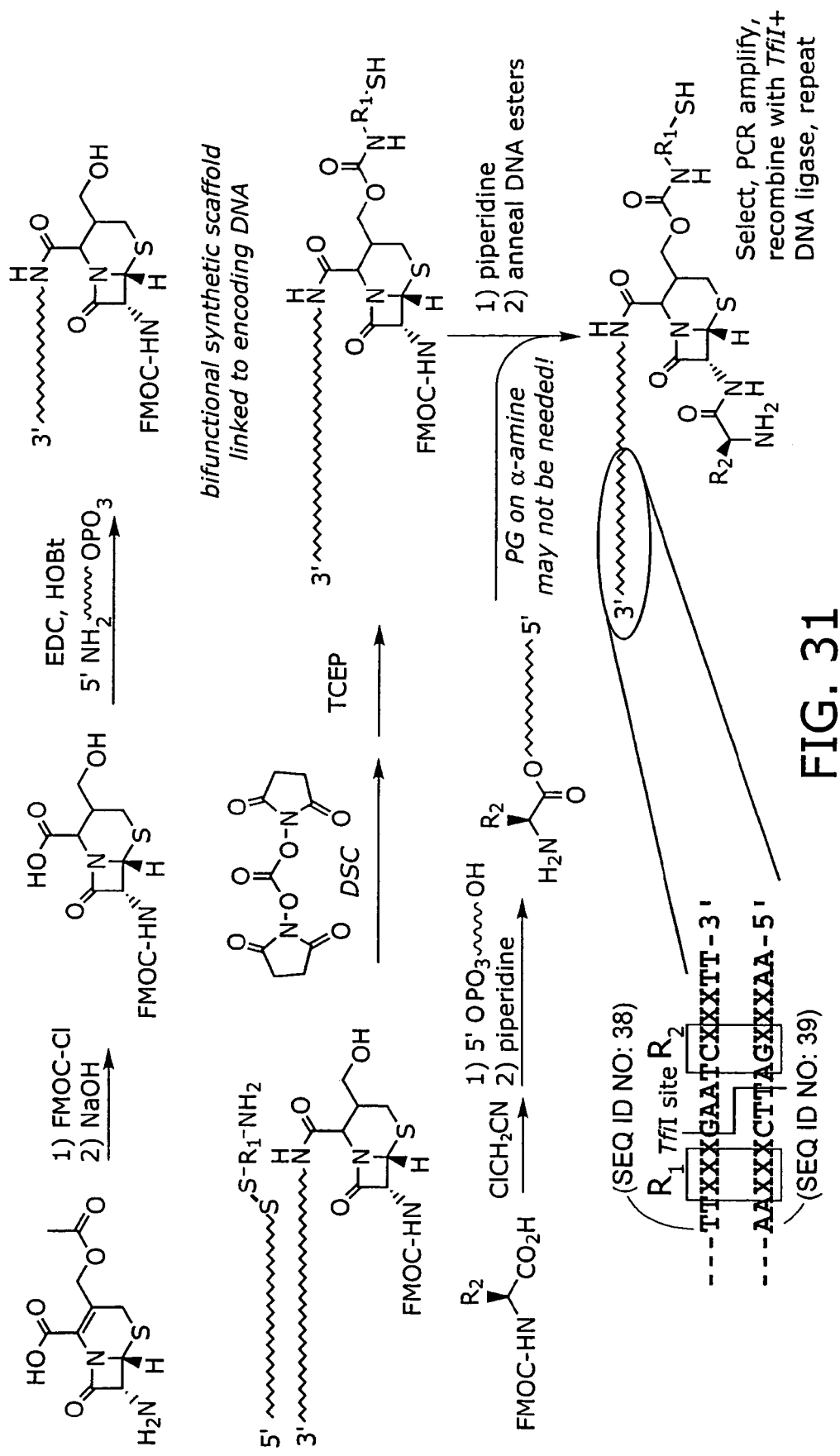
FIG. 31 shows the functionalization of a cephalosporin small molecule scaffold with various reactants.

Once the distance of the linker between the functional group and synthetic small molecule scaffold and the codon format have been determined, one can synthesize small molecules based on a small molecule scaffold such as the cephalosporin scaffold shown in FIG. 31. The primary amine of 7-aminocephalosporanic acid is first protected using FMOC-Cl, and then the acetyl group is hydrolyzed by treatment with base. The encoding DNA template is then attached through an amide linkage using EDC and HOBt to the carboxylic acid group. A transfer molecule with an anti-codon capable of hybridizing to the attached DNA template is then allowed to hybridize to the template. The transfer molcule has associated with it through a disulfide linkage a primary amine bearing $R_1$. Activation of the primary hydroxyl group on the cephalosporin scaffold with DSC following treatment with TCEP affords the amine covalently attached to the scaffold through a carbamate linkage. Further treatment with another transfer unit having an amino acid leads to functionaliztion of the deprotected primary amine of the cephalosporin scaffold. Cephalosporin-like molecules synthesized in this manner may then be selected, amplified, and/or evolved using the inventive methods and compositions. The DNA template may be diversified and evolved using DNA shuffling.

D) Multi-Step Small Molecule Synthesis Programmed by DNA Templates: Molecular evolution requires the sequence-specific translation of an amplifiable information carrier into the structures of the evolving molecules. This requirement has limited the types of molecules that have been directly evolved to two classes, proteins and nucleic acids, because only these classes of molecules can be translated from nucleic acid sequences. As described generally above, a promising approach to the evolution of molecules other than proteins and nucleic acids uses DNA-templated synthesis as a method of translating DNA sequences into synthetic small molecules. DNA-templated synthesis can direct a wide variety of powerfil chemical reactions with high sequence-specificity and without requiring structural mimicry of the DNA backbone. The application of this approach to synthetic molecules of useful complexity, however, requires the development of general methods to enable the product of a DNA-templated reaction to undergo subsequent DNA-templated transformations. The first DNA-templated multi-step small molecule syntheses is described in detail herein. Together with recent advances in the reaction scope of DNA-templated synthesis, these findings set the stage for the in vitro evolution of synthetic small molecule libraries.

Multi-step DNA-templated small molecule synthesis faces two major challenges beyond those associated with DNA-templated synthesis in general. First, the DNA used to direct reagents to appropriate templates must be removed from the product of a DNA-templated reaction prior to subsequent DNA-templated synthetic steps in order to prevent undesired hybridization to the template. Second, multi-step synthesis often requires the purification and isolation of intermediate products, yet common methods used to purify and isolate reaction products are not appropriate for multi-step synthesis on the molecular biology scale. To address these challenges, three distinct strategies were implemented in solid-phase organic synthesis, for linking chemical reagents with their decoding DNA oligonucleotides and two general approaches for product purification after any DNA-templated synthetic step were developed.

Figure 33A:
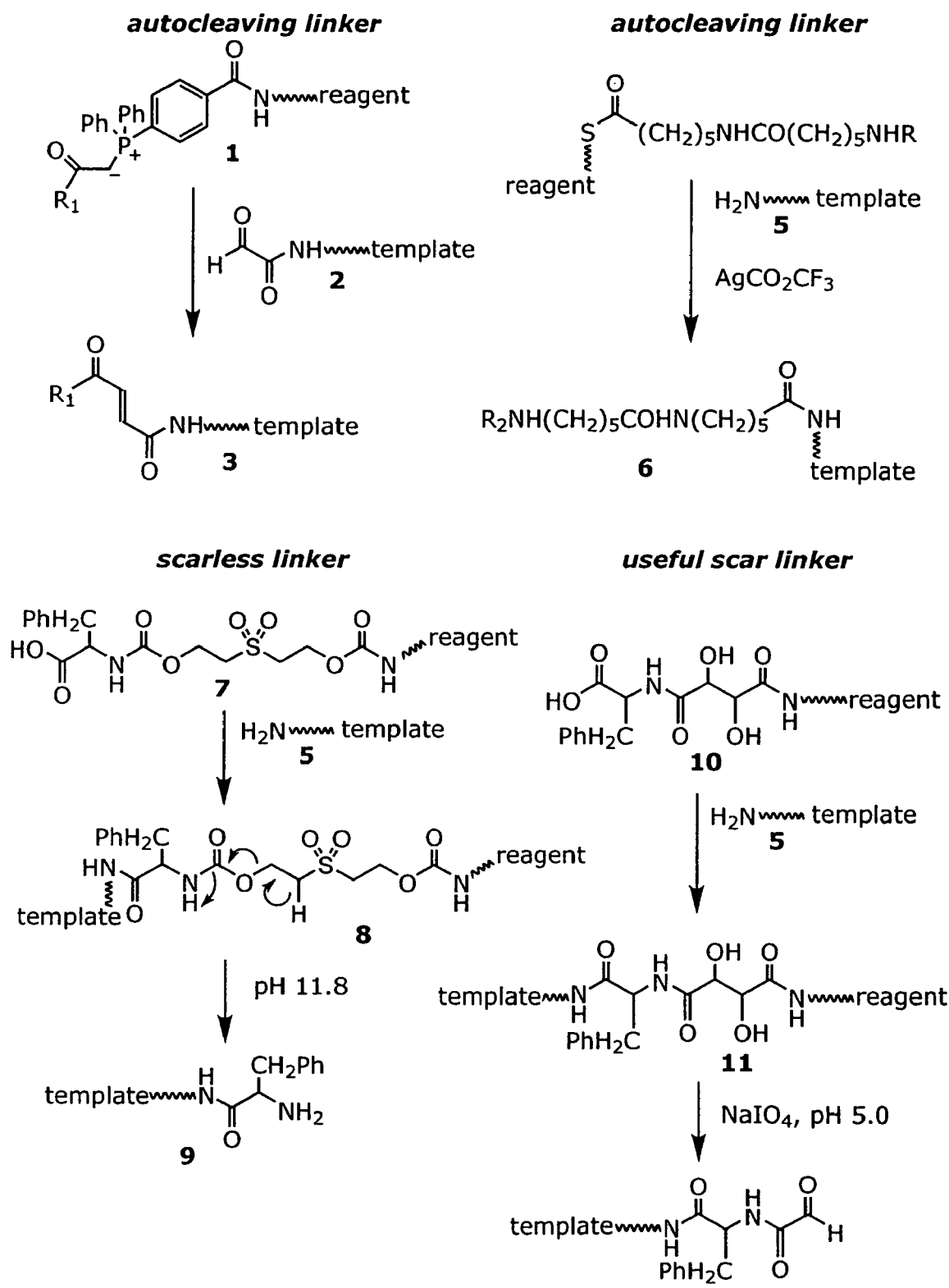
FIG. 33A depicts three linker strategies for DNA-templated synthesis. In the autocleaving linker strategy, the bond connecting the product from the reagent oligonucleotide is cleaved as a natural consequence of the reaction. In the scarless and useful scar linker strategies, this bond is cleaved following the DNA-templated reaction. The depicted reactions were analyzed by denaturing polyacrylamide gel electrophoresis shown in FIG. 33B. Lanes 1-3 were visualized using UV light without DNA staining; lanes 4-10 were visualized by staining with ethidium bromide following by UV transillumination. Conditions: 1 to 3: one equivalent each of reagent and template, 0.1 M TAPS buffer pH 8.5, 1 M NaCl, 25° C., 1.5 h; 4 to 6: three equivalents of 4, 0.1 M MES buffer pH 7.0, 1 M NaNO$_2$, 10 mM AgNO$_3$, 37° C., 8 h; 8 to 9: 0.1 M CAPS buffer pH 11.8, 60 mM BME, 37° C., 2 h; 11 to 12: 50 mM aqueous NaIO$_4$, 25° C., 2 h. R$_1$=NH(CH$_2$)$_2$NH-dansyl; R$_2$=biotin.
Figure 33B:
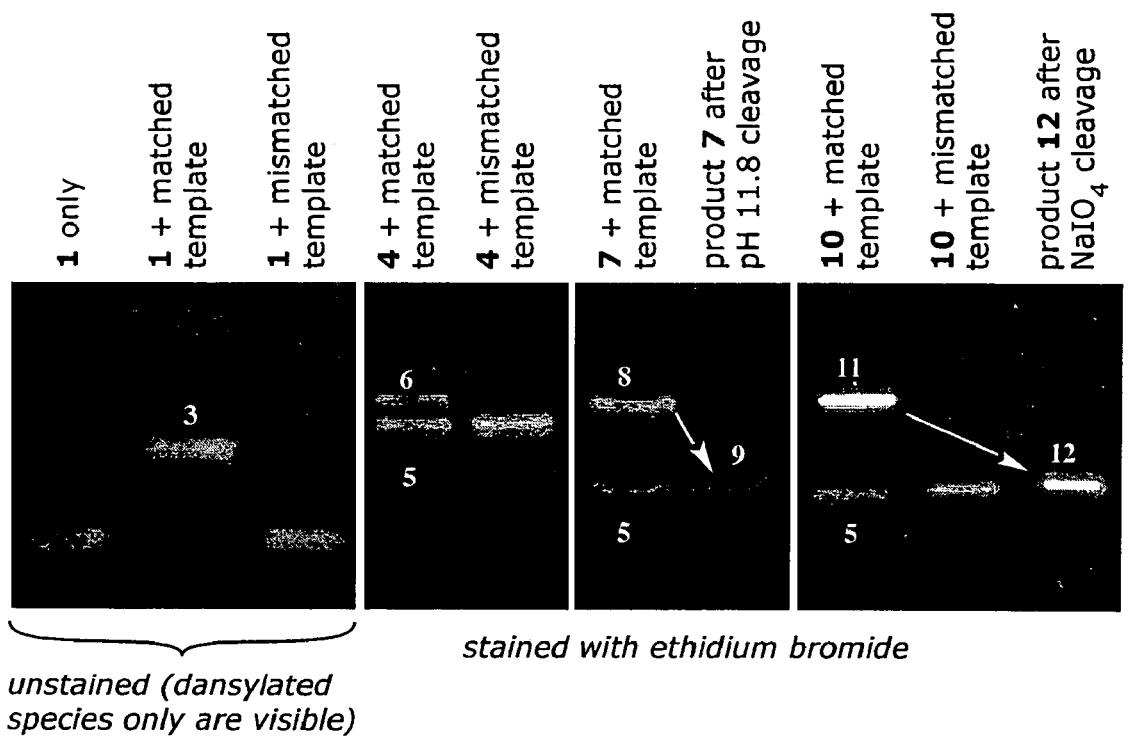

When possible, an ideal reagent-oligonucleotide linker for DNA-templated synthesis positions the oligonucleotide as a leaving group of the reagent. Under this "autocleaving" linker strategy, the oligonucleotide-reagent bond is cleaved as a natural chemical consequence of the reaction (FIG. 33). As the first example of this approach applied to DNA-templated chemistry, a dansylated Wittig phosphorane reagent (1) was synthesized in which the decoding DNA oligonucleotide was attached to one of the aryl phosphine groups (I. Hughes, Tetrahedron Lett. 1996, 37, 7595). DNA-templated Wittig olefination (as described above) with aldehyde-linked template 2 resulted in the efficient transfer of the fluorescent dansyl group from the reagent to the template to provide olefin 3 (FIG. 33). As a second example of an autocleaving linker, DNA-linked thioester 4, when activated with Ag(I) at pH 7.0 (Zhang et al. *J. Am. Chem. Soc.* 1999, 121, 3311) acylated amino-terminated template 5 to afford amide product 6 (FIG. 33). Ribosomal protein biosynthesis uses aminoacylated tRNAs in a similar autocleaving linker format to mediate RNA-templated peptide bond formation. To purify desired products away from unreacted reagents and from cleaved oligonucleotides following DNA-templated reactions using autocleaving linkers, biotinylated reagent oligonucleotides and washing crude reactions with streptavidin-linked magnetic beads (FIG. 34) were utilized. Although this approach does not separate reacted templates from unreacted templates, unreacted templates can be removed in subsequent DNA-templated reaction and purification steps (see below).

Reagents bearing more than one functional group can be linked to their decoding DNA oligonucleotides through a second and third linker strategies. In the "scarless linker" approach, one functional group of the reagent is reserved for DNA-templated bond formation, while the second functional group is used to attach a linker that can be cleaved without introducing additional unwanted chemical functionality. DNA-templated reaction is followed by cleavage of the linker attached through the second functional group to afford desired products (FIG. 33). For example, a series of aminoacylation reagents such as (D)-Phe derivative 7 were synthesized in which the a-amine is connected through a carbamoylethylsulfone linker (Zarling et al. *J Immunology* 1980, 124, 913) to its decoding DNA oligonucleotide. The product (8) of DNA-templated amide bond formation (as described herein) using this reagent and an amine-terminated template (5) was treated with aqueous base to effect the quantitative elimination and spontaneous decarboxylation of the linker, affording product 9 containing the cleanly transferred amino acid group (FIG. 33). This sulfone linker is stable in pH 7.5 or lower buffer at 25° C. for more than 24 h yet undergoes quantitative cleavage when exposed to pH 11.8 buffer for 2 h at 37 oc.

In some cases it may be advantageous to introduce new chemical groups as a consequence of linker cleavage. Under a third linker strategy, linker cleavage generates a "useful scar" that can be functionalized in subsequent steps. As an example of this class of linker, amino acid reagents such as the (L)-Phe derivative 10 were generated linked through 1,2-diols (Fruchart et al *Tetrahedron Lett.* 1999, 40, 6225) to their decoding DNA oligonucleotides. Following DNA-templated amide bond formation with amine terminated template (5), this linker was quantitatively cleaved by oxidation with 50 mM aqueous $NaIO_4$ at pH 5.0 to afford product 12 containing an aldehyde group appropriate for subsequent functionalization (for example, in a DNA-templated Wittig olefination, reductive amination, or nitrolaldol addition (FIG. 33).

Desired products generated from DNA-templated reactions using the scarless or useful scar linkers can be readily purified using biotinylated reagent oligonucleotides (FIG. 34). Reagent oligonucleotides together with desired products are first captured on streptavidin-linked magnetic beads. Any unreacted template bound to reagent by base pairing is removed by washing the beads with buffer containing 4 M guanidinium chloride. Biotinylated molecules remain bound to the streptavidin beads under these conditions. Desired product is then isolated in pure form by eluting the beads with linker cleavage buffer (in the examples above, either pH 11 or $NaIO_4$-containing buffer), while reacted and unreacted reagents remain bound to the beads.

Integrating the recently expanded repertoire of synthetic reactions compatible with DNA-templated synthesis and the linker strategies described above, multi-step DNA-templated small molecule syntheses can be conducted.

Figure 35:
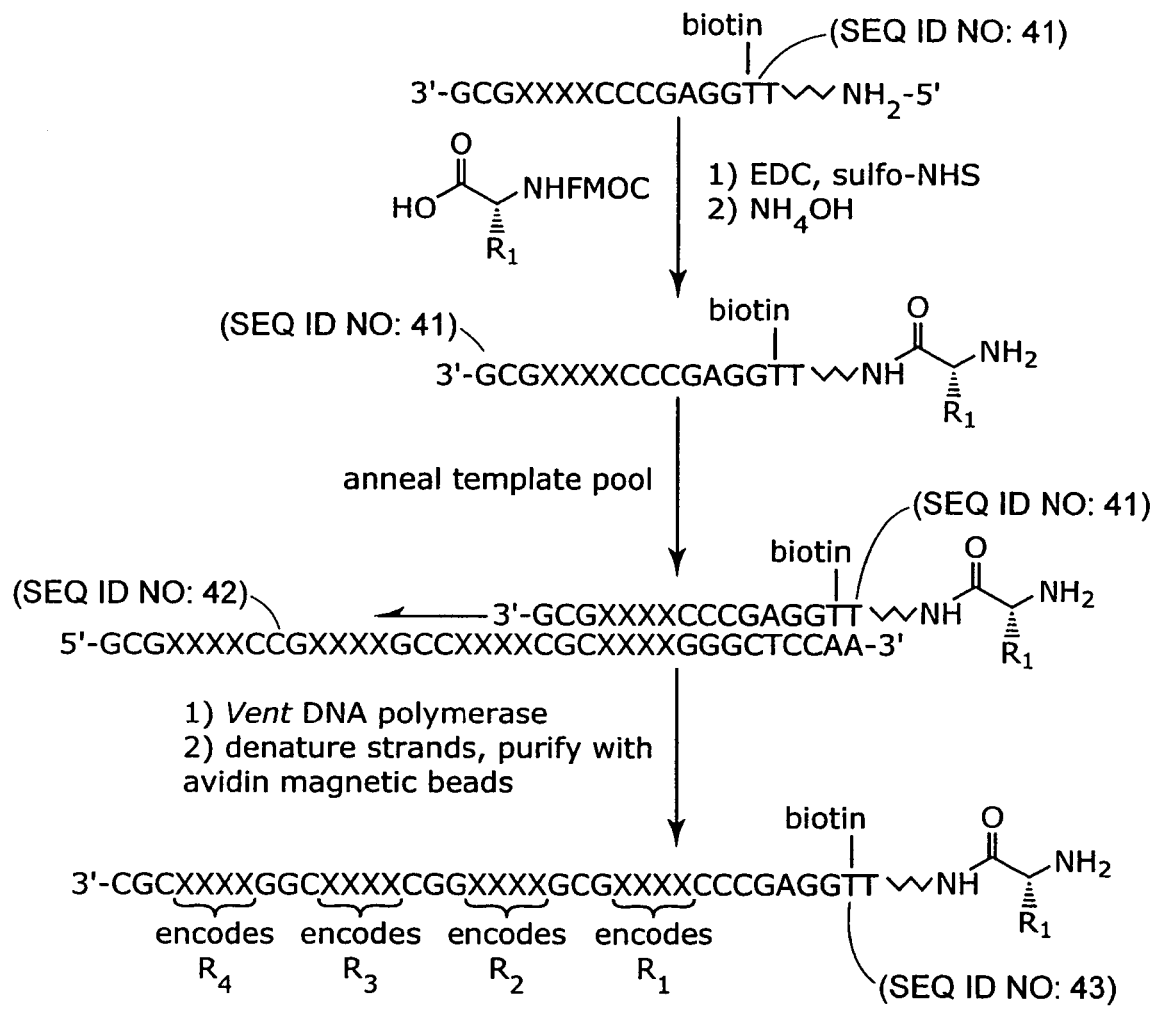
FIG. 35 depicts the generation of an initial template pool for an exemplary library synthesis.
Figure 36:
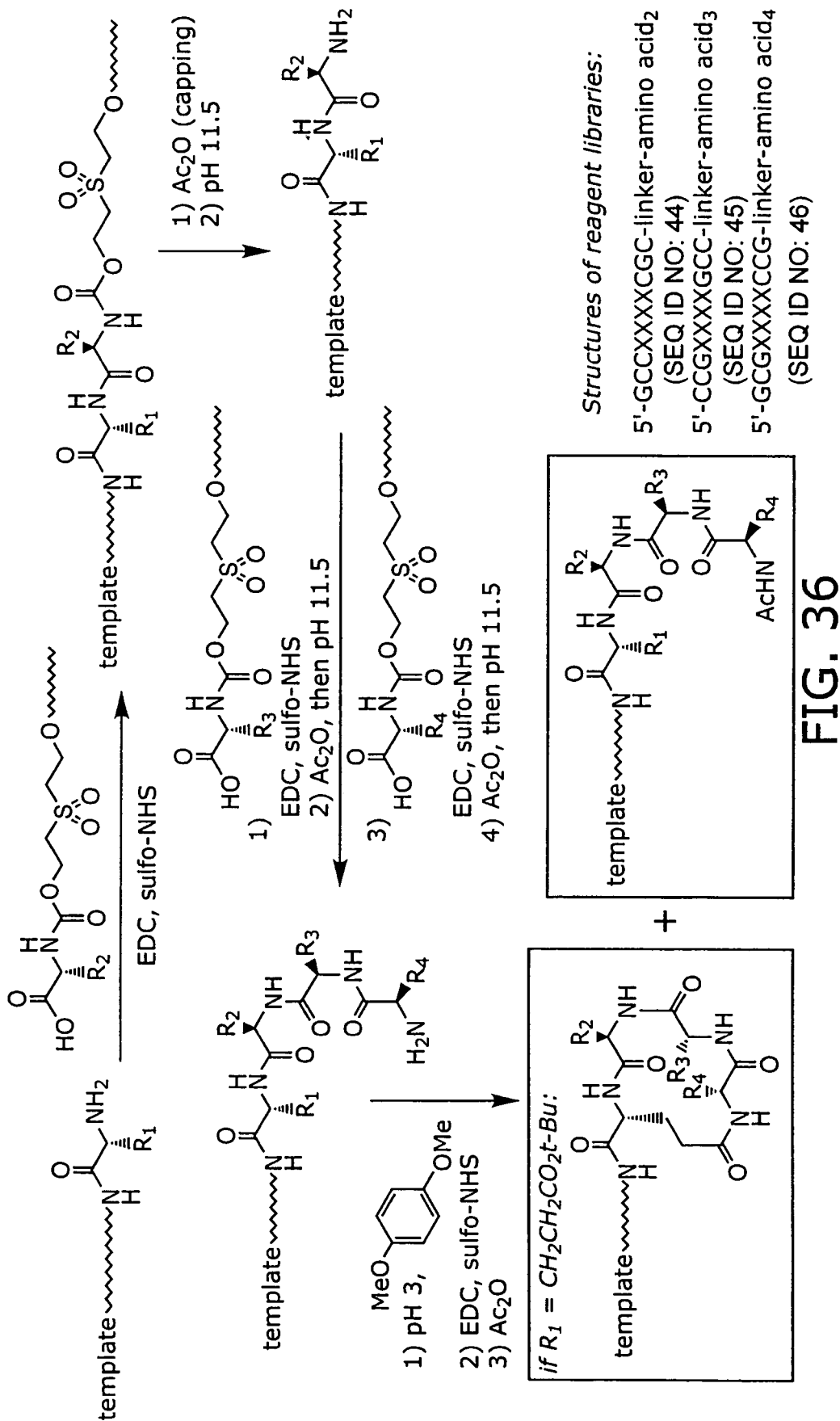
FIG. 36 depicts the DNA-templated synthesis of a non-natural peptide library.
Figure 37:
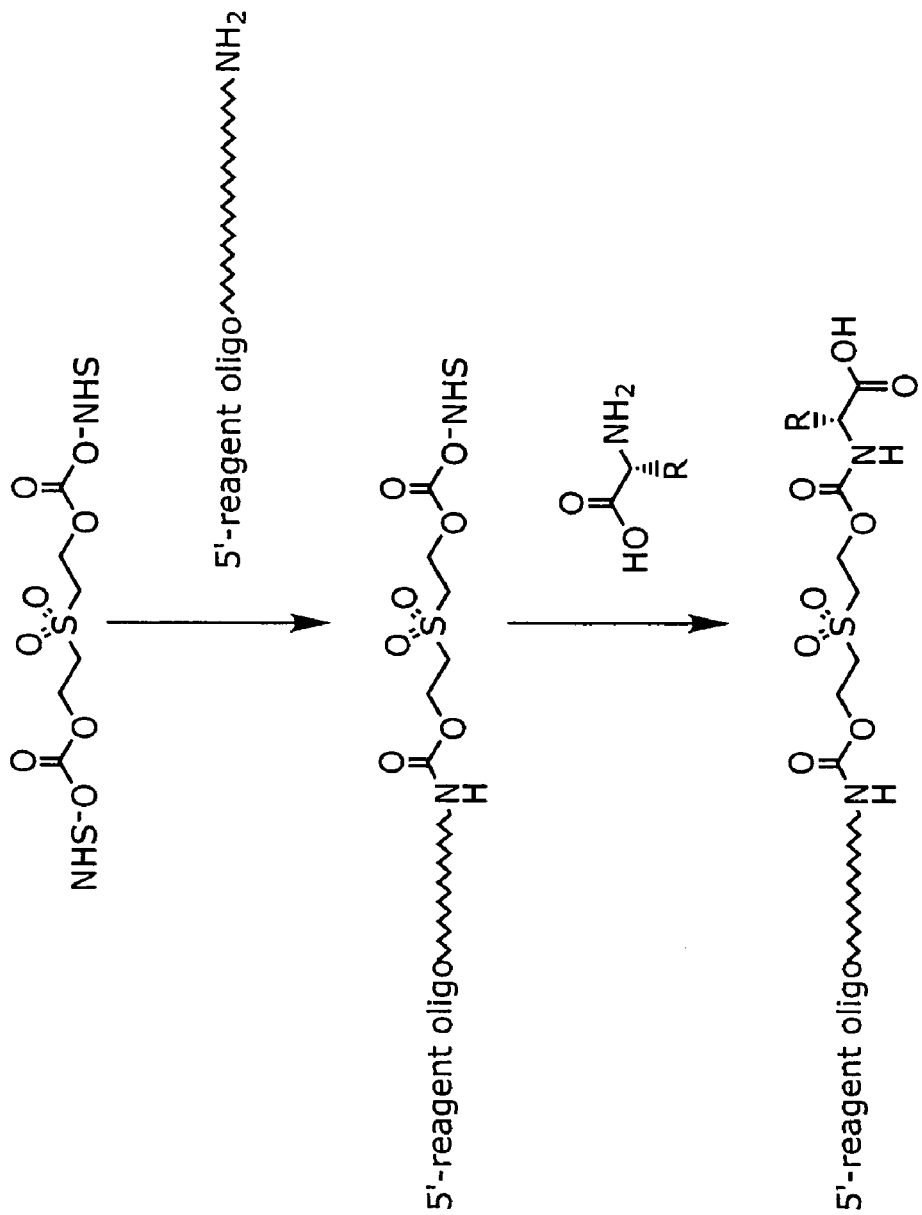
FIG. 37 depicts a 5'-reagent DNA-linker-amino acid.

In one embodiment, a solution phase DNA-templated synthesis of a non-natural peptide library is described generally below and is shown generally in FIG. 35. As shown in FIG. 35, to generate the initial template pool for the library, thirty synthetic biotinylated 5'-amino oligonucleotides of the sequence format shown in FIG. 35 are acylated with one of thirty different natural or unnatural amino acids using standard EDC coupling procedures. Four bases representing a "codon" within each amino acylated primer are designated the identity of the side chain ($R_1$). The "genetic code" for these side chains are protected with acid labile protecting groups similar to those commonly used in peptide synthesis. The resulting thirty amino acylated DNA primers are annealed to a template DNA oligonucleotide library generated by automated DNA synthesis. Primer extension with a DNA polymerase followed by strand denaturation and purification with streptavidin-linked magnetic beads yield the starting template library (see, FIG. 35). As but one general example, a solution phase DNA-templated synthesis of a non-natural peptide library is depicted in FIG. 36. The template library is subjected to three DNA-templated peptide bond formation reactions using amino acid reagents attached to 10-base decoding DNA oligonucleotides through the sulfone linker described above. Products of each step are purified by preparative denaturing polyacrylamide gel electrophoresis prior to linker cleavage if desired, although this may not be necessary. Each DNA-linked reagent can be synthesized by coupling a 3'-amino terminated DNA oligonucleotide to the encoded amino acid through the bis-NHS carbonate derivative of the sulfone linker as shown in FIG. 37. Codons are again chosen so that related codons encode chemically similar amino acids. Following each peptide bond formation reaction, acetic anhydride is used to cap unreacted starting materials and pH 11 buffer is used to effect linker cleavage to expose a new amino group for the next peptide bond formation reaction. Once the tetrapeptide is completed, those library members bearing carboxylate side chains can also be cyclized with their amino termini to form macrocyclic peptides, while linear peptide members can simply be N-acetylated (see FIG. 36).

It will be appreciated that a virtually unlimited assortment of amino acid building blocks can be incorporated into a non-natural peptide library. Unlike peptide libraries generated using the protein biosynthetic machinery such as phage displayed libraries (O'Neil et al. *Curr. Opin. Struct. Biol.* 1995, 5, 443-9), mRNA displayed libraries (Roberts et al. *Proc. Natl. Acad Sci, USA* 1997, 94, 12297-12302) ribosome displayed libraries (Roberts et al. *Curr. Opin. Chem. Biol.* 1999, 3, 268-73; Schaffitzel et al. *J Immunol Methods* 1999, 231, 119-35), or intracellular peptide libraries (Norman et al. *Science* 1999, 285, 591-5), amino acids with non-proteinogenic side chains, non-natural side chain stereochemistry, or non-peptidic backbones can all be incorporated into this library. In addition, the many commercially available di-, tri- and oligopeptides can also be used as building blocks to generate longer library members. The presence of non-natural peptides in this library may confer enhanced pharmacological properties such as protease resistance compared with peptides generated ribosomally. Similarly, the macrocyclic library members may yield higher affinity ligands since the entropy loss upon binding their targets may be less than their more flexible linear counterparts. Based on the enormous variety of commercially available amino acids fitting these descriptions, the maximum diversity of this non-natural cyclic and linear tetrapeptde library can exceed 100×100×100×100=$10^8$ members.

Figure 38:
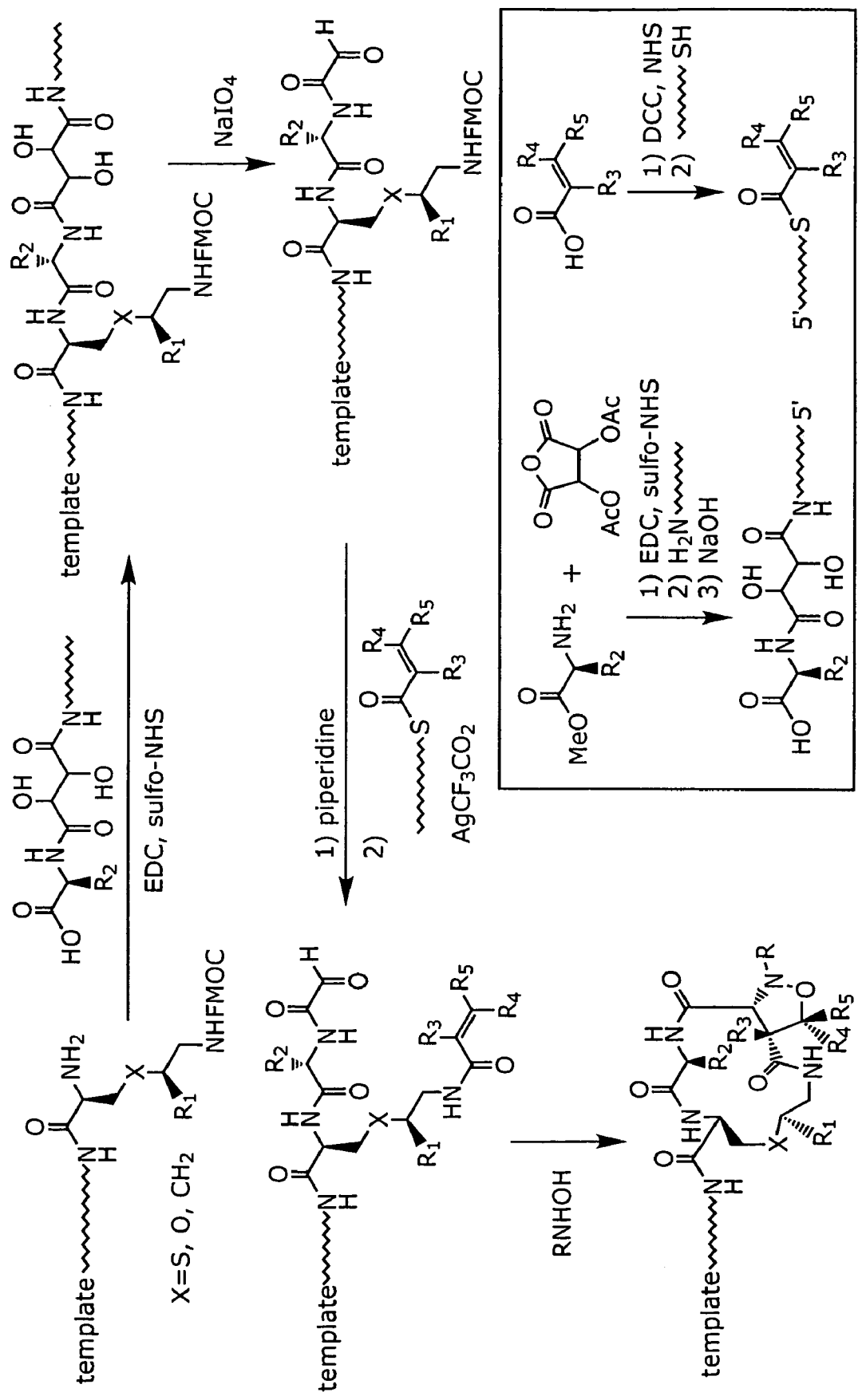
FIG. 38 depicts the DNA-templated synthesis of an evolvable diversity oriented bicyclic library.

Another example of a library using the approach described above includes the DNA-templated synthesis of a diversity-oriented macrobicyclic library containing 5- and 14-membered rings (FIG. 38). Starting material for this library consists of DNA templates aminoacylated with a variety of side-chain protected lysine derivatives and commercially available lysine analogs (including aminoethyl-cysteine, aminoethylserine, and 4-hydroxylysine). In the first step, DNA-templated amide bond formation with a variety of DNA-linked amino acids takes place as described in the non-natural peptide library, except that the vicinal diol linker 16 described above is used instead of the traceless sulfone linker. Following amide bond formation, the diol linker is oxidatively cleaved with sodium periodate. Deprotection of the lysine analog'side chain amine is followed by DNA-templated amide bond formation catalyzed by silver trifluoroacetate between the free amine and a library of acrylic derived thioesters. The resulting olefins are treated with a hydroxylamine to form nitrones, which undergo 1,3-dipolar cycloaddition to yield the bicyclic library (FIG. 38). DNA-linked reagents for this library are prepared by coupling lysine analogs to 5'-amino-terminated template primers (FIG. 35), coupling aminoacylated diol linkers to 3'-amino-terminated DNA oligonucleotides (FIG. 38), and coupling acrylic acids to 3'-thiol terminated DNA oligonucleotides (FIG. 38).

Figure 39A:
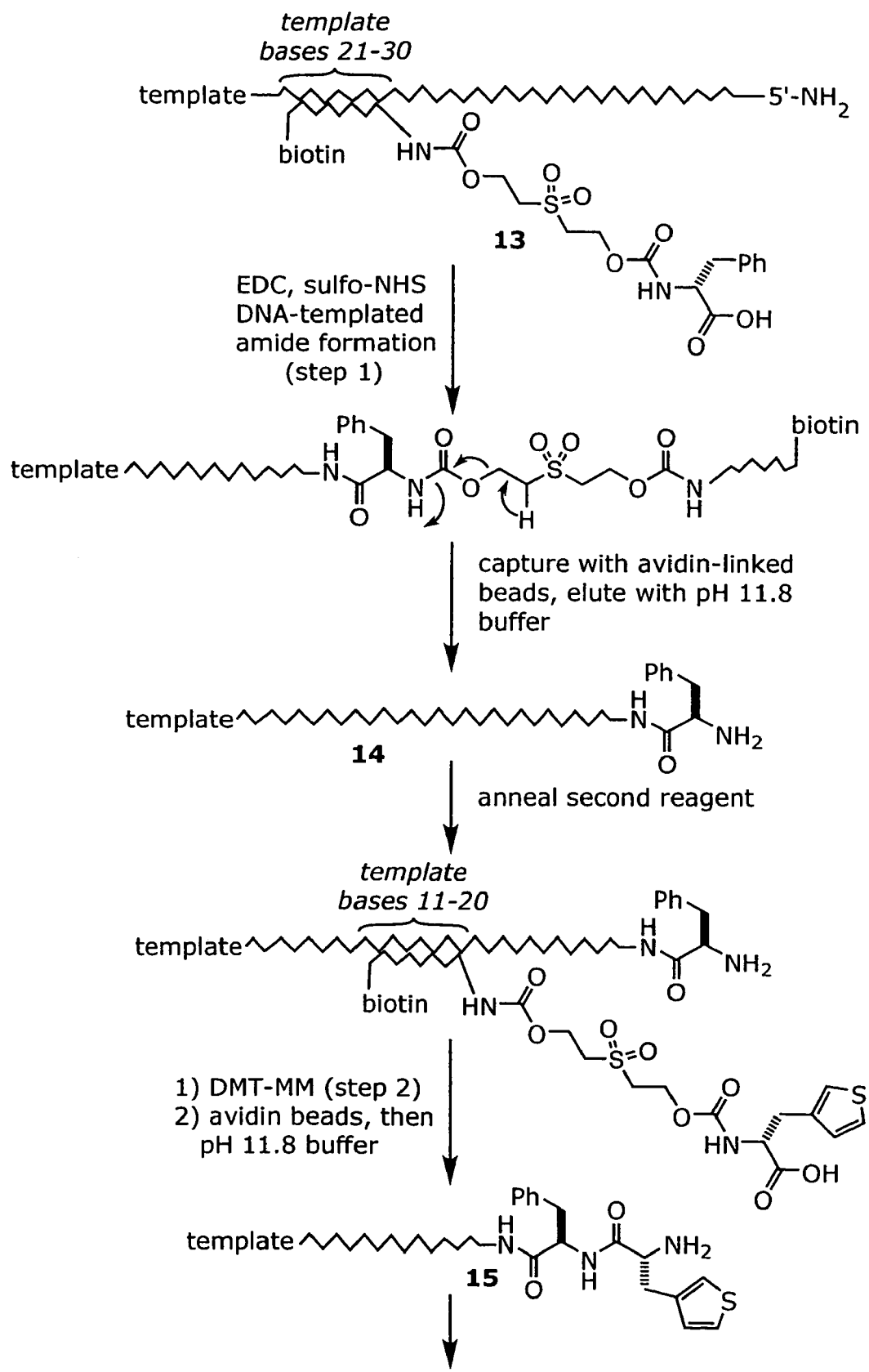

As but one example of a specific library generated from the first general approach described above, three iterated cycles of DNA-templated amide formation, traceless linker cleavage, and purification with streptavidin-linked beads were used to generate a non-natural tripeptide (FIG. 39). Each amino acid reagent was linked to a unique biotinylated 10-base DNA oligonucleotide through the sulfone linker described above. The 30-base amine-terminated template programmed to direct the tripeptide synthesis contained three consecutive 10-base regions that were complementary to the three reagents, mimicking the strategy that would be used in a multi-step DNA-templated small molecule library synthesis. The first amino acid reagent (13) was combined with the template and activator 4-(4,6-dimethoxy-1,3,5-triazin-2-yl)-4-methylmorpholinium chloride (DMT-MM) (Kunishima et al. *Tetrahedron* 2001, 57, 1551) to effect DNA-templated peptide bond formation. The desired product was purified by mixing the crude reaction with streptavidin-linked magnetic beads, washing with 4 M guanidinium chloride, and eluting with pH 11 buffer to effect sulfone linker cleavage, providing product 14. The free amine group in 14 was then elaborated in a second and third round of DNA-templated amide formation and linker cleavage to afford dipeptide 15 and tripeptide 16 (FIG. 39).

The progress of each reaction, purification, and sulfone linker cleavage step was followed by denaturing polyacrylamide gel electrophoresis. The final tripeptide linked to template (16) was digested with the restriction endonuclease EcoRI and the digestion fragment containing the tripeptide was characterized by MALDI mass spectrometry. Beginning with 2 nmol (~20 μg) of starting material, sufficient tripeptide product was generated to serve as the template for more than $10^6$ in vitro selections and PCR reactions (Kramer et al. in *Current Protocols in Molecular Biology*, Vol 3 (Ed.: F. M. Ausubel), Wiley, 1999, pp. 15.1) (assuming 1/10,000 molecules survive selection). No significant product was generated when the starting material template was capped with acetic anhydride, or when control reagents containing sequence mismatches were used instead of the complementary reagents (FIG. 39).

Figure 40A:
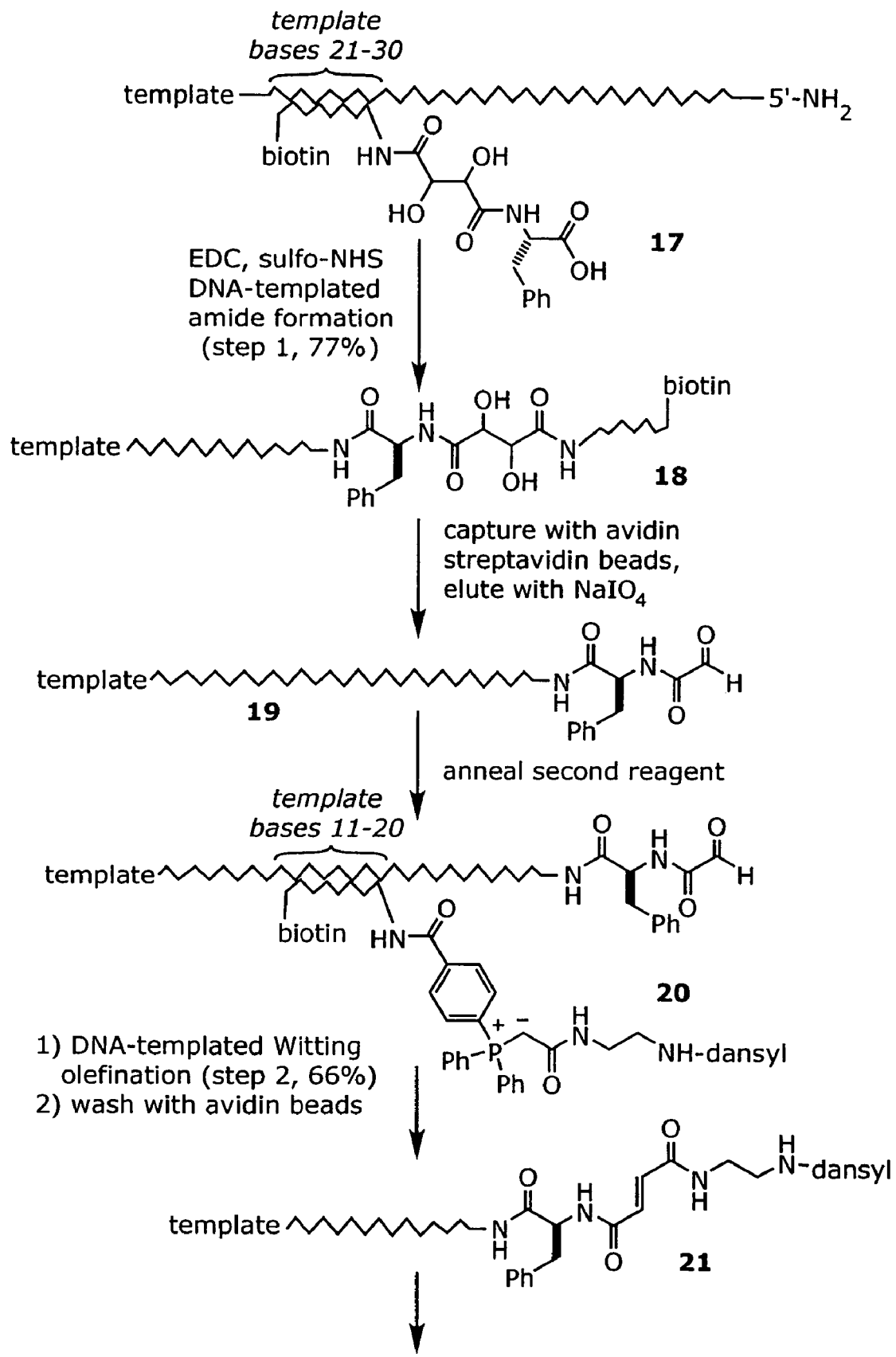
FIGS. 40A and 40B depict Non-peptidic DNA-templated multi-step synthesis. The reagent linkers used in steps 1, 2, and 3 were the diol linker, autocleaving Wittig linker, and sulfone linker, respectively; see FIG. 1 for linker cleavage conditions. Conditions: 17 to 18: activate two equivalents 17 in 20 mM EDC, 15 mM sulfo-NHS, 0.1 M MES buffer pH 5.5, 1 M NaCl, 10 min, 25° C., then add to template in 0.1 M MOPS pH 7.5, 1M NaCl, 16° C., 8 h; 19 to 21: threre equivalents 20, 0.1 M TAPS pH 9.0, 3 M NaCl, 48 h, 25° C.; 22 to 23: three equivalents 22, 0.1 M TAPS pH 8.5, 1 M NaCl, 21 h, 25° C. The progress of each reaction and purification was followed by denaturing polyacrylamide gel electrophoresis (bottom). Lanes 3, 6, and 9: control reactions using reagents containing scrambled oligonucleotide sequences.
Figure 40B:
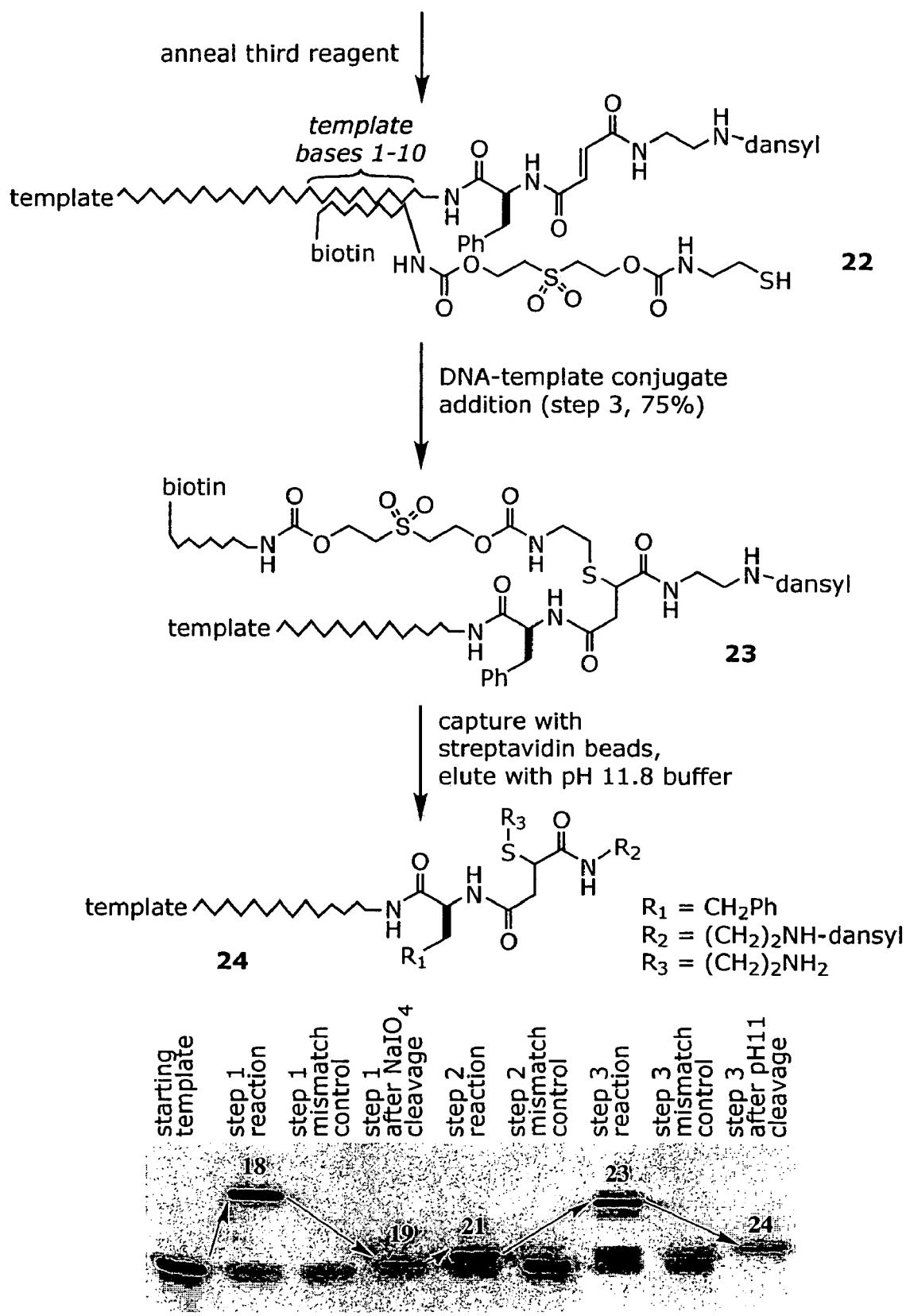

A non-peptidic multi-step DNA-templated small molecule synthesis (FIG. 40) that uses all three linker strategies developed above was also performed. An amine-terminated 30-base template was subjected to DNA-templated amide bond formation using an aminoacyl donor reagent (17) containing the diol linker and a biotinylated 10-base oligonucleotide to afford amide 18. The desired product was isolated by capturing the crude reaction on streptavidin beads followed by cleaving the linker with $NaIO_4$ to generate aldehyde 19. The DNA-templated Wittig reaction of 19 with the biotinylated autocleaving phosphorane reagent 20 afforded fumaramide 21. The products from the second DNA-templated reaction were partially purified by washing with streptavidin beads to remove reacted and unreacted reagent. In the third DNA-templated step, fumaramide 21 was subjected to a DNA-templated conjugate addition (Gartner et al. *J. Am. Chem. Soc.* 2001, 123, 6961) using thiol reagent 22 linked through the sulfone linker to a biotinylated oligonucleotide. The desired conjugate addition product (23) was purified by immobilization with streptavidin beads. Linker cleavage with pH 11 buffer afforded final product 24 in 5-10% overall isolated yield for the three bond forming reactions, two linker cleavage steps, and three purifications (FIG. 40). This final product was digested with EcoRI and the mass of the small molecule-linked template fragment was confirmed by MALDI mass spectrometry (exact mass: 2568, observed mass: 2566±5). As in the tripeptide example, each of the three reagents used during this multi-step synthesis annealed at a unique location on the DNA template, and control reactions with sequence mismatches yielded no product (FIG. 40). As expected, control reactions in which the Wittig reagent was omitted (step 2) also did not generate product following the third step. Taken together, the DNA-templated syntheses of 16 and 24 demonstrate the ability of DNA to direct the sequence-programmed multi-step synthesis of both oligomeric and non-oligomeric small molecules unrelated in structure to nucleic acids.

The commercial availability of many substrates for DNA-templated reactions including amines, carboxylic acids, α-halo carbonyl compounds, olefins, alkoxyamines, aldehydes, and nitroalkanes may allow the translation of large libraries of DNA into diverse small molecule libraries. The direct one-pot selection of these libraries for members with desired binding or catalytic activities, followed by the PCR amplification and diversification of the DNA encoding active molecules, may enable synthetic small molecules to evolve in a manner paralleling the powerful methods Nature uses to generate new molecular function. In addition, multi-step nucleic acid-templated synthesis is a requirement of previously proposed models (A. I. Scott, *Tetrahedron Lett.* 1997, 38, 4961; Li et al. *Nature* 1994, 369, 218; Tamura et al. *Proc. Natl. Acad. Sci USA* 2001, 98, 1393) for the prebiotic translation of replicable information into functional molecules. These findings demonstrate that nucleic acid templates are indeed capable of directing iterative or non-iterative multi-step small molecule synthesis even when reagents anneal at widely varying distances from the growing molecule (in the above examples, zero to twenty bases). As described in more detail below, libraries of synthetic molecules can then be evolved towards active ligand and catalysts through cycles of translation, selection, amplification and mutagenesis.

Figure 41:
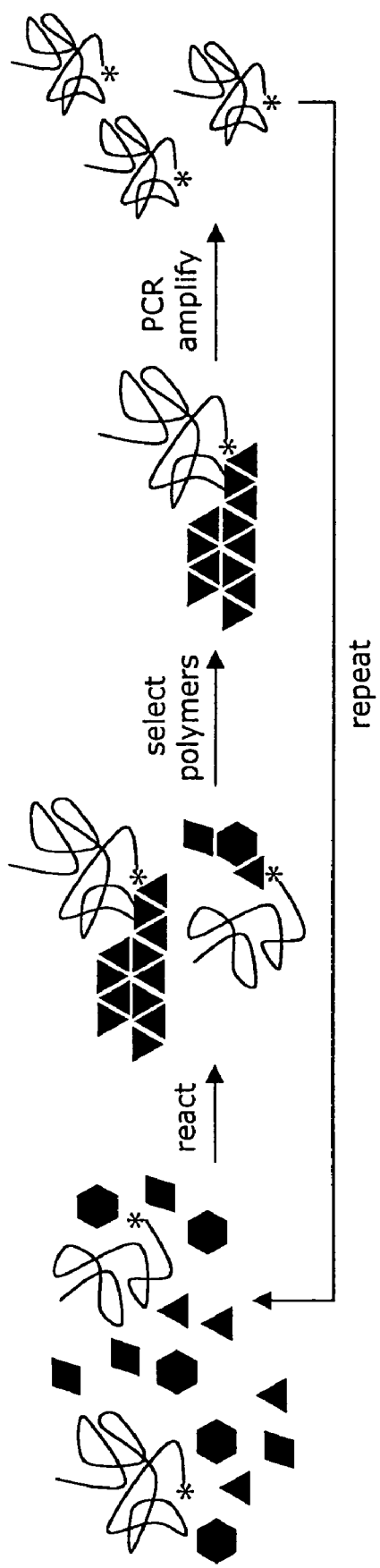
FIG. 41 depicts the use of nucleic acids to direct the synthesis of new polymers and plastics by attaching the nucleic acid to the ligand of a polymerization catalyst. The nucleic acid can fold into a complex structure which can affect the selectivity and activity of the catalyst.

E) Evolving Plastics: In yet another embodiment of the present invention, a nucleic acid (e.g., DNA, RNA, derivative thereof) is attached to a polymerization catalyst. Since nucleic acids can fold into complex structures, the nucleic acid can be used to direct and/or affect the polymerization of a growing polymer chain. For example, the nucleic acid may influence the selection of monomer units to be polymerized as well as how the polymerization reaction takes place (e.g., stereochemistry, tacticity, activity). The synthesized polymers may be selected for specific properties such molecular, weight, density, hydrophobicity, tacticity, stereoselectivity, etc., and the nucleic acid which formed an integral part of the catalyst which directed its synthesis may be amplified and evolved (FIG. 41). Iterated cycles of ligand diversification, selection, and amplification allow for the true evolution of catalysts and polymers towards desired properties.

Figure 42:
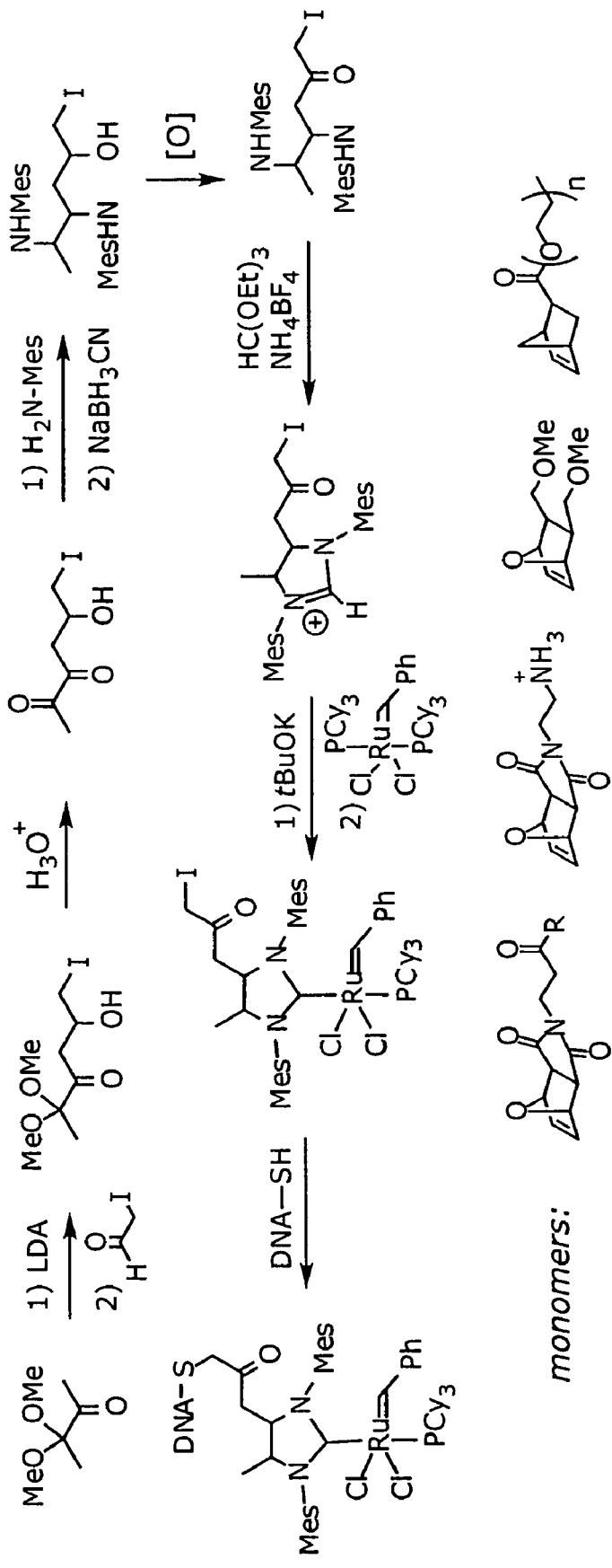
FIG. 42 depicts the use of Grubbs' ring-opening metathesis polymerization catalysis in evolving plastics. The synthetic scheme of a dihydroimidazole ligand attached to DNA is shown as well as the monomer to be used in the polymerization reaction.

To give but one example, a library of DNA molecules is attached to Grubbs' ruthenium-based ring opening metathesis polymerization (ROMP) catalyst through a dihydroimidazole ligand (Scholl et al. *Org. Lett.* 1(6):953, 1999; incorporated herein by reference) creating a large, diverse pool of potential catalytic molecules, each unique by nature of the functionalized ligand. Undoubtedly, functionalizing the catalyst with a relatively large DNA-dehydroimidazole (DNA-DHI) ligand will alter the activity of the catalyst. Each DNA molecule has the potential to fold into a unique stereoelectronic shape which potentially has different selectivities and/or activities in the polymerization reaction (FIG. 42). Therefore, the library of DNA ligands can be "translated" into a library of plastics upon the addition of various monomers. In certain embodiments, DNA-DHI ligands capable of covalently inserting themselves into the growing polymer, thus creating a polymer tagged with the DNA that encoded its creation, are used. Using the synthetic scheme shown in FIG. 42, DHI ligands are produced containing two chemical handles, one used to attach the DNA to the ligand, the other used to attach a pedant olefin to the DHI backbone. Rates of metathesis are known to vary widely based upon olefin substitution as well as the identity of the catalyst. Through alteration of these variable, the rate of pendant olefin incorporation can be modulated such that $k_{pendant\ olefin\ metathesis} \ll k_{ROMP}$, thereby, allowing polymers of moderate to high molecular weights to be formed before insertion of the DNA tag and corresponding polymer termination. Vinylic either are commonly used in ROMP to functionalize the polymer termini (Gordon et al. *Chem. Biol.* 7:9-16, 2000; incorporated herein by reference), as well as produce polymers of decreased molecular weight.

Figure 43:
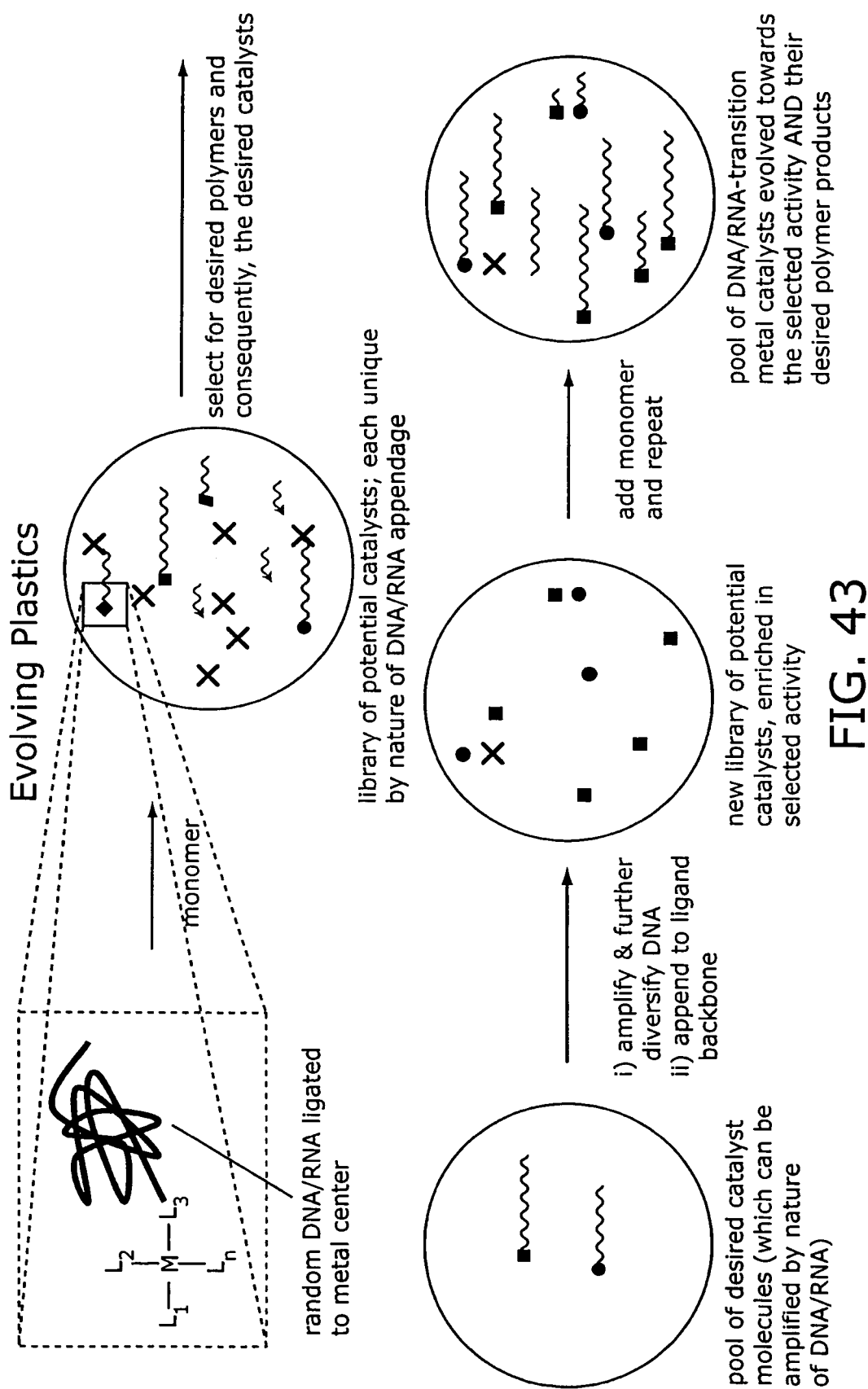
FIG. 43 depicts the evolution of plastics through iterative cycles of ligand diversification, selection and amplification to create polymers with desired properties.

Subsequent selection of a polymer from the library based on a desired property by electrophoresis, gel filtration, centrifugal sedimentation, partitioning into solvents of different hydrophobicities, etc. Amplification and diversification of the coding nucleic acid via techniques such as error-prone PCR or DNA shuffling followed by attachment to a DHI backbone will allow for production of another pool of potential ROMP catalysts enriched in the selected activity (FIG. 43). This method provides a new approach to generating polymeric materials and the catalysts that create them.

Example 6

Characterization of DNA-Templated Synthetic Small Molecule Libraries

The non-natural peptide and bicyclic libraries described above are characterized in several stages. Each candidate reagent is conjugated to its decoding DNA oligonucleotide, then subjected to model reactions with matched and mismatched templates. The products from these reactions are analyzed by denaturing polyacrylamide gel electrophoresis to assess reaction efficiency, and by mass spectrometry to verify anticipated product structures. Once a complete set of robust reagents are identified, the complete multi-step DNA-templated syntheses of representative single library members on a large scale is performed and the final products are characterized by mass spectrometry.

More specifically, the sequence fidelity of each multi-step DNA-templated library synthesis is tested by following the fate of single chemically labeled reagents through the course of one-pot library synthesis reactions. For example, products arising from building blocks bearing a ketone group are captured with commercially available hydrazide-linked resin and analyzed by DNA sequencing to verify sequence fidelity during DNA-templated synthesis. Similarly, when using non-biotinylated model templates, building blocks bearing biotin groups are purified after DNA-templated synthesis using streptavidin magnetic beads and subjected to DNA sequencing (Liu et al. *J. Am. Chem. Soc.* 2001, 123, 6961-6963) Codons that show a greater propensity to anneal with mismatched DNA are identified by screening in this manner and removed from the genetic code of these synthetic libraries.

Example 7

In Vitro Selection of Protein Ligands from Evolvable Synthetic Libraries

Because every library member generated in this approach is covalently linked to a DNA oligonucleotide that encodes and directs its synthesis, libraries can be subjected to true in vitro selections. Although direct selections for small molecule catalysts of bond-forming or bond-cleaving reactions are an exciting potential application of this approach, the simplest in vitro selection that can be used to evolve these libraries is a selection for binding to a target protein. An ideal initial target protein for the synthetic library selection both plays an important biological role and possesses known ligands of varying affinities for validating the selection methods.

One receptor of special interest for use in the present invention is the $\alpha_v\beta_3$ receptor. The $\alpha_v\beta_3$ receptor is a member of the integrin family of transmembrane heterodimeric glycoprotein receptors (Miller et al. *Drug Discov Today* 2000, 5, 397-408; Berman et al. *Membr Cell Biol.* 2000, 13, 207-44) The $\alpha_v\beta_3$ integrin receptor is expressed on the surface of many cell types such as osteoclasts, vascular smooth muscle cells, endothelial cells, and some tumor cells. This receptor mediates several important biological processes including adhesion of osteoclasts to the bone matrix (van der Pluijm et al. *J. Bone Miner. Res.* 1994, 9, 1021-8) smooth muscle cell migration (Choi et al. *J Vasc. Surg.* 1994, 19, 125-34) and tumor-induced angiogenesis (Brooks et al. *Cell* 1994, 79, 1157-64) (the outgrowth of new blood vessels). During tumor-induced angiogenesis, invasive endothelial cells bind to extracellular matrix components through their $\alpha_v\beta_3$ integrin receptors. Several studies (Brooks et al. *Cell* 1994, 79, 1157-64; Brooks et al. *Cell* 1998, 92, 391-400; Friedlander et al. *Science* 1995, 270, 1500-2; Varner et al. *Cell Adhes Commun* 1995, 3, 367-74; Brooks et al. *J Clin Invest* 1995, 96, 1815-22) have demonstrated that the inhibition of this integrin binding event with antibodies or small synthetic peptides induces apoptosis of the proliferative angiogenic vascular cells and can inhibit tumor metastasis.

A number of peptide ligands of varying affinities and selectivities for the $\alpha_v\beta_3$ integrin receptor have been reported. Two benchmark $\alpha_v\beta_3$ integrin antagonists are the linear peptide GRGDSPK [SEQ ID NO: 83] ($IC_{50}$=210 nM (Dechantsreiter et al. *J Med. Chem.* 1999, 42, 3033-40; Pfaff et al. *J. Biol. Chem.* 1994, 269, 20233-8) and the cyclic peptide cyclo-RGDfV (Pfaff et al. *J. Biol. Chem.* 1994, 269, 20233-8) (f=(D)-Phe, $IC_{50}$=10 nM). While peptides antagonists for integrins commonly contain RGD, not all RGD-containing peptides are high affinity integrin ligands. Rather, the conformational context of RGD and other peptide sequences can have a profound effect on integrin affinity and specificity (Wermuth et al. *J. Am. Chem. Soc.* 1997, 119, 1328-1335; Geyer et al. *J. Am. Chem. Soc.* 1994, 116, 7735-7743; Rai et al. *Bioorg. Med. Chem. Lett* 2001, 11, 1797-800; Rai et al. *Curr. Med. Chem.* 2001, 8, 101-19) For this reason, combinatorial approaches towards $\alpha_v\beta_3$ integrin receptor antagonist discovery are especially promising.

The biologically important and medicinally relevant role of the $\alpha_v\beta_3$ integrin receptor together with its known peptide antagonists and its commercial availability (Chemicon International, Inc., Temecula, Calif.) make the $\alpha_v\beta_3$ integrin receptor an ideal initial target for DNA-templated synthetic small molecule libraries. The $\alpha_v\beta_3$ integrin receptor can be immobilized by adsorption onto microtiter plate wells without impairing its ligand binding ability or specificity (Dechantsreiter et al. *J Med. Chem.* 1999, 42, 303340; Wermuth et al. *J. Am. Chem. Soc.* 1997, 119, 1328-1335; Haubner et al. *J. Am. Chem. Soc.* 1996, 118, 7461-7472). Alternatively, the receptor can be immobilized by conjugation with NHS ester or maleimide groups covalently linked to sepharose beads and the ability of the resulting integrin affinity resin to maintain known ligand binding properties can be verified.

Figure 44:
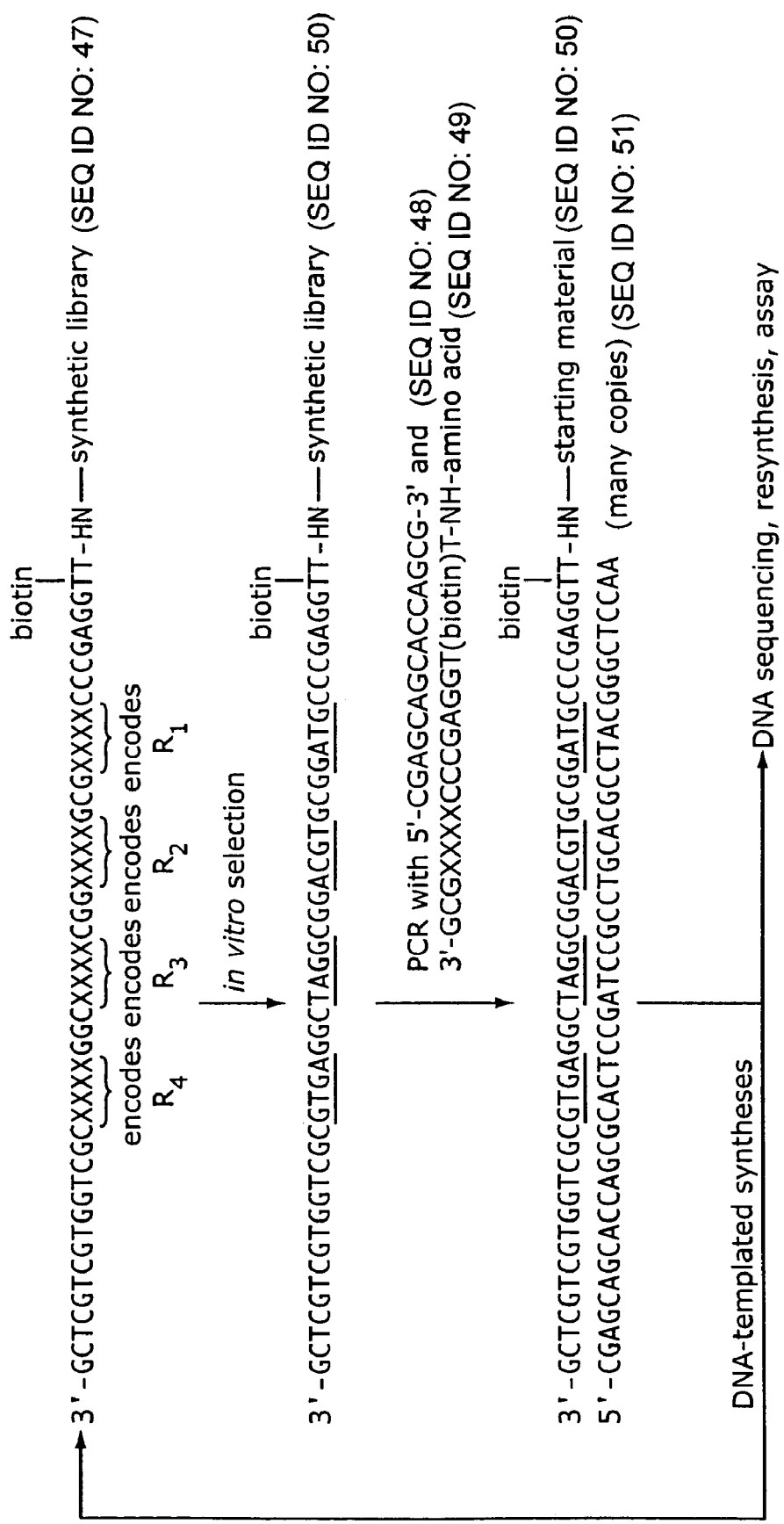
FIG. 44 depicts an exemplary scheme for the synthesis, in vitro selection and amplification of a library of compounds.

To perform the actual protein binding selections, DNA template-linked synthetic peptide or macrocyclic libraries are dissolved in aqueous binding buffer in one pot and equilibrated in the presence of immobilized $\alpha_v\beta_3$ integrin receptor. Non-binders are washed away with buffer. Those molecules that may be binding through their attached DNA templates rather than through their synthetic moieties are eliminated by washing the bound library with unfunctionalized DNA templates lacking PCR primer binding sites. Remaining ligands bound to the immobilized $\alpha_v\beta_3$ integrin receptor are eluted by denaturation or by the addition of excess high affinity RGD-containing peptide ligand. The DNA templates that encode and direct the syntheses of $\alpha_v\beta_3$ integrin binders are amplified by PCR using one primer designed to bind to a constant 3' region of the template and one pool of biotinylated primers functionalized at its 5' end with the library starting materials (FIG. 44). Purification of the biotinylated strand completes one cycle of synthetic molecule translation, selection, and amplification, yielding a sub-population of DNA templates enriched in sequences that encode synthetic $\alpha_v\beta_3$ integrin ligands.

For reasons similar to those that make the $\alpha_v\beta_3$ integrin receptor an attractive initial target for the approach to generating synthetic molecules with desired properties, the factor Xa serine protease also serves as a promising protein target. Blood coagulation involves a complex cascade of enzyme-catalyzed reactions that ultimately generate fibrin, the basis of blood clots (Rai et al. *Curr. Med. Chem.* 2001, 8, 101-109; Vacca et al. *Curr. Opin. Chem Biol.* 2000, 4, 394-400) Thrombin is the serine protease that converts fibrinogen into fibrin during blood clotting. Thrombin, in turn, is generated by the proteolytic action of factor Xa on prothrombin. Because thromboembolitic (blood clotting) diseases such as stroke remain a leading cause of death in the world (Vacca et al. *Curr. Opin. Chem. Biol.* 2000, 4, 394-400) the development of drugs that inhibit thrombin or factor Xa is a major area of pharmaceutical research. The inhibition of factor Xa is a newer approach thought to avoid the side effects associated with inhibiting thrombin, which is also involved in normal hemostasis (Maignan et al. *J. Med. Chem.* 2000, 43, 3226-32; Leadley et al. *J Cardiovasc. Pharmacol.* 1999, 34, 791-9; Becker et al. *Bioorg. Med Chem. Lett.* 1999, 9, 2753-8; Choi-Sledeski et al. *Bioorg. Med. Chem. Lett.* 1999, 9, 2539-44; Choi-Sledeski et al. *J. Med. Chem.* 1999, 42, 3572-87; Ewing et al. *J. Med. Chem.* 1999, 42, 3557-71; Bostwick et al. *Thromb Haemost* 1999, 81, 157-60). Although many agents including heparin, hirudin, and hirulog have been developed to control the production of thrombin, these agents generally have the disadvantage of requiring intravenous or subcutaneous injection several times a day in addition to possible side effects, and the search for synthetic small molecule factor Xa inhibitors remains the subject of great research effort.

Among factor Xa inhibitors with known binding affinities are a series of tripeptides ending with arginine aldehyde (Marlowe et al. *Bioorg. Med. Chem. Lett.* 2000, 10, 13-16) that are easily be included in the DNA-templated non-natural peptide library described above. Depending on the identities of the first two residues, these tripeptides exhibit $IC_{50}$ values ranging from 15 nM to 60 µM (Marlowe et al. *Bioorg Med. Chem. Lett.* 2000, 10, 13-16) and therefore provide ideal positive controls for validating and calibrating an in vitro selection for synthetic factor Xa ligands (see below). Both factor Xa and active factor Xa immobilized on resin are commercially available (Protein Engineering Technologies, Denmark). The resin-bound factor Xa is used to select members of both the DNA-templated non-natural peptide and bicyclic libraries with factor Xa affinity in a manner analogous to the integrin receptor binding selections described above.

Following PCR amplification of DNA templates encoding selected synthetic molecules, additional rounds of translation, selection, and amplification are conducted to enrich the library for the highest affinity binders. The stringency of the selection is gradually increased by increasing the salt concentration of the binding and washing buffers, decreasing the duration of binding, elevating the binding and washing temperatures, and increasing the concentration of washing additives such as template DNA or unrelated proteins. Importantly, in vitro selections can also select for specificity in addition to binding affinity. To eliminate those molecules that possess undesired binding properties, library members bound to immobilized $\alpha_v\beta_3$ integrin or factor Xa are washed with non-target proteins such as other integrins or other serine proteases, leaving only those molecules that bind the target protein but do not bind non-target proteins.

Figure 45:
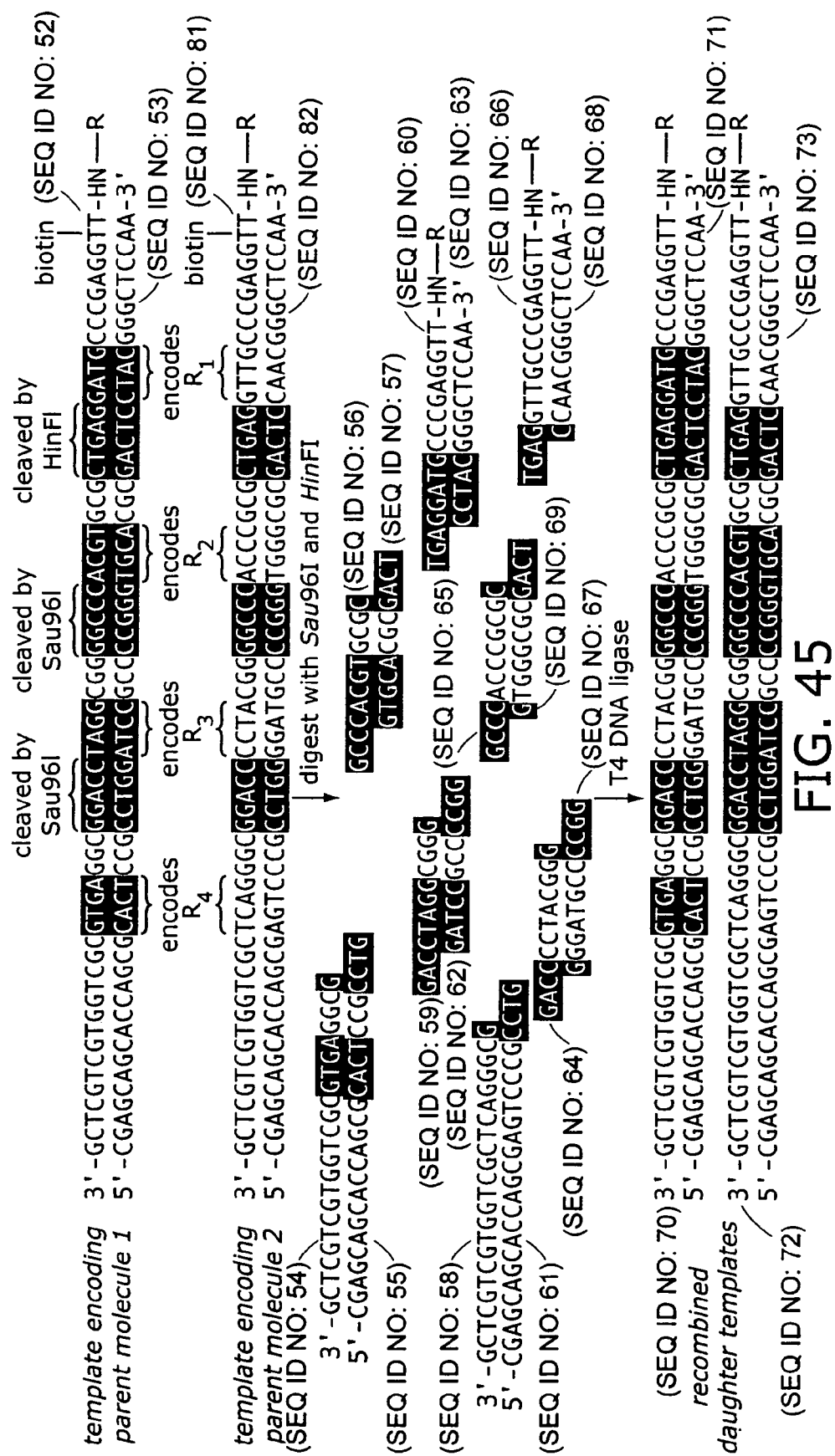
FIG. 45 depicts exemplary templates for use in recombination.

Iterated cycles of translation, selection, and amplification results in library enrichment rather than library evolution, which requires diversification between rounds of selection. Diversification of these synthetic libraries are achieved in at least two ways, both analogous to methods used by Nature to diversify proteins. Random point mutagenesis is performed by conducting the PCR amplification step under error-prone PCR (Caldwell et al. *PCR Methods Applic.* 1992, 2, 28-33) conditions. Because the genetic code of these molecules are written to assign related codons to related chemical groups, similar to the way that the natural protein genetic code is constructed, random point mutations in the templates encoding selected molecules will diversify progeny towards chemically related analogs. In addition to point mutagenesis, synthetic libraries generated in this approach are also diversified using recombination. Templates to be recombined have the structure shown in FIG. 45, in which codons are separated by five-base non-palindromic restriction endonuclease cleavage sites such as those cleaved by AvaII (G/GWCC, W=A or T), Sau96I (G/GNCC, N=A, G, T, or C), DdeI (C/TNAG), or HinFI (G/ANTC). Following selections, templates encoding desired molecules are enzymatically digested with these commercially available restriction enzymes. The digested fragments are then recombined into intact templates with T4 DNA ligase. Because the restriction sites separating codons are nonpalindromic, templates fragments can only reassemble to form intact recombined templates (FIG. 45). DNA-templated translation of recombined templates provides recombined small molecules. In this way, functional groups between synthetic small molecules with desired activities are recombined in a manner analogous to the recombination of amino acid residues between proteins in Nature. It is well appreciated that recombination explores the sequence space of a molecule much more efficiently than point mutagenesis alone (Minshull et al. *Curr. Opin. Chem. Biol.* 1999, 3, 284-90; Bogarad et al. *Proc. Natl. Acad. Sci. USA* 1999, 96, 2591-5; Stemmer, W. Nature 1994, 370, 389-391).

Small molecule evolution using mutation and recombination offers two potential advantages over simple enrichment. If the total diversity of the library is much less than the number of molecules made (typically $10^{12}$ to $10^{15}$), every possible library member is present at the start of the selection. In this case, diversification is still useful because selection conditions almost always change as rounds of evolution progress. For example, later rounds of selection will likely be conducted under higher stringencies, and may involve counter selections against binding non-target proteins. Diversification gives library members that have been discarded during earlier rounds of selection the chance to reappear in later rounds under altered selection conditions in which their fitness relative to other members may be greater. In addition, it is quite possible using this approach to generate a synthetic library that has a theoretical diversity greater than 1015 molecules. In this case, diversification allows molecules that never existed in the original library to emerge in later rounds of selections on the basis of their similarity to selected molecules, similar to the way in which protein evolution searches the vastness of protein sequence space one small subset at a time.

Example 8

Characterization of Evolved Compounds

Following multiple rounds of selection, amplification, diversification, and translation, molecules surviving the selection will be characterized for their ability to bind the target protein. To identify the DNA sequences encoding evolved synthetic molecules surviving the selection, PCR-amplified templates are cloned into vectors, transformed into cells, and sequenced as individual clones. DNA sequencing of these subcloned templates reveal the identity of the synthetic molecules surviving the selection. To gain general information about the functional groups being selected during rounds of evolution, populations of templates are sequenced in pools to reveal the distribution of A, G, T, and C at every codon position. The judicious design of each functional group's genetic code allows considerable information to be gathered from population sequencing. For example, a G at the first position of a codon may designate a charged group, while a C at this position may encode a hydrophobic substituent.

To validate the integrin binding selection and to compare selected library members with known $\alpha_v\beta_3$ integrin ligands, linear GRGDSPK [SEQ ID NO: 83] and a cyclic RGDfV analog (cyclic iso-ERGDfV) are also included in the DNA-templated cyclic peptide library. The selection conditions are adjusted until verification that libraries containing these known integrin ligands undergo enrichment of the DNA templates encoding the known ligands upon selection for integrin binding. In addition, the degree of enrichment of template sequences encoding these known $\alpha_v\beta_3$ integrin ligands is correlated with their known affinities and with the enrichment and affinity of newly discovered $\alpha_v\beta_3$ integrin ligands.

Once the enrichment of template sequences encoding known and new integrin ligands is confirmed, novel evolved ligands will be synthesized by non-DNA templated synthesis and assayed for their $\alpha_v\beta_3$ integrin receptor antagonist activity and specificity. Standard in vitro binding assays to integrin receptors (Dechantsreiter et al. *J Med. Chem.* 1999, 42, 3033-40) are performed by competing the binding of biotinylated fibrinogen (a natural integrin ligand) to immobilized integrin receptor with the ligand to be assayed. The inhibition of binding to fibrinogen is quantitated by incubation with an alkaline phosphatase-conjugated anti-biotin antibody and a chromogenic alkaline phosphate substrate. Comparison of the binding affinities of randomly chosen library members before and after selection will validate the evolution of the library towards target binding. Assays for binding non-target proteins reveal the ability of these libraries to be evolved towards binding specificity in addition to binding affinity.

Similarly, the selection for factor Xa binding is validated by including the known factor Xa tripeptide inhibitors in the library design and verifying that a round of factor Xa binding selection and PCR amplification results in the enrichment of their associated DNA templates. Synthetic library members evolved to bind factor Xa are assayed in vitro for their ability to inhibit factor Xa activity. Factor Xa inhibition can be readily assayed spectrophotometrically using the commercially available chromogenic substrate S-2765 (Chromogenix, Italy).

While the DNA sequence alone of a non-natural peptide library member is likely to reveal the exact identity of the corresponding peptide, the final step in the bicyclic library synthesis is a non-DNA-templated intramolecular 1,3-dipolar cycloaddition that may yield diastereomeric pairs of regioisomers. Although modeling strongly suggests that only the regioisomer shown in FIG. 38 can form for steric reasons, facial selectivity is less certain. Diastereomeric purity is not a requirement for the in vitro selections described above since each molecule is selected on a single molecule basis. Nevertheless, it may be useful to characterize the diastereoselectivity of the dipolar cycloaddition. To accomplish this, non-DNA-templated synthesis of selected bicyclic library members is performed, diastereomers are separated by chiral preparative HPLC, and product stereochemistry by nOe or X-ray diffraction is determined.

Example 9

Translating DNA into Non-Natural Polymers Using DNA Polymerases

An alternative approach to translating DNA into non-natural, evolvable polymers takes advantage of the ability of some DNA polymerases to accept certain modified nucleotide triphosphate substrates (D. M. Perrin et al. *J. Am. Chem. Soc.* 2001, 123, 1556; D. M. Perrin et al. *Nucleosides Nucleotides* 1999, 18, 377-91; T. Gourlain et al. *Nucleic Acids Res.* 2001, 29, 1898-1905; S. E. Lee et al. *Nucleic Acids Res.* 2001, 29, 1565-73; K. Sakthievel et al. *Angew. Chem. Int. Ed.* 1998, 37, 2872-2875). Several deoxyribonucleotides (FIG. 45) and ribonucleotides bearing modifications to groups that do not participate in Watson-Crick hydrogen bonding are known to be inserted with high sequence fidelity opposite natural DNA templates. Importantly, single-stranded DNA containing modified nucleotides can serve as efficient templates for the DNA-polymerase-catalyzed incorporation of natural or modified mononucleotides. In one of the earliest examples of modified nucleotide incorporation by DNA polymerase, Toole and co-workers reported the acceptance of 5-(1-pentynyl)-deoxyuridine 1 by Vent DNA polymerase under PCR conditions (J. A. Latham et al. *Nucleic Acids Res.* 1994, 22, 2817-22). Several additional 5-functionalized deoxyuridines (2-7) derivatives were subsequently found to be accepted by thermostable DNA polymerases suitable for PCR (K. Sakthievel et al. *Angew. Chem. Int. Ed.* 1998, 37, 2872-2875). The first functionalized purine accepted by DNA polymerase, deoxyadenosine analog 8, was incorporated into DNA by T7 DNA polymerase together with deoxyuridine analog 7 (D. M. Perrin et al. *Nucleosides Nucleotides* 1999, 18, 377-91). DNA libraries containing both 7 and 8 were successfully selected for metal-independent RNA cleaving activity (D. M. Perrin et al. *J. Am. Chem. Soc.* 2001, 123, 1556-63). Williams and co-workers recently tested several deoxyuridine derivatives for acceptance by Taq DNA polymerases and concluded that acceptance is greatest when using C5-modified uridines bearing rigid alkyne or trans-alkene groups such as 9 and 10 (S. E. Lee et al. *Nucleic Acids Res.* 2001, 29, 1565-73). A similar study (T. Gourlain et al. *Nucleic Acids Res.* 2001, 29, 1898-1905) on C7-functionalized 7-deaza-deoxyadenosines revealed acceptance by Taq DNA polymerase of 7-aminopropyl-(11), cis-7-aminopropenyl-(12), and 7-aminopropynyl-7-deazadeoxyadenosine (13).

Figure 46:
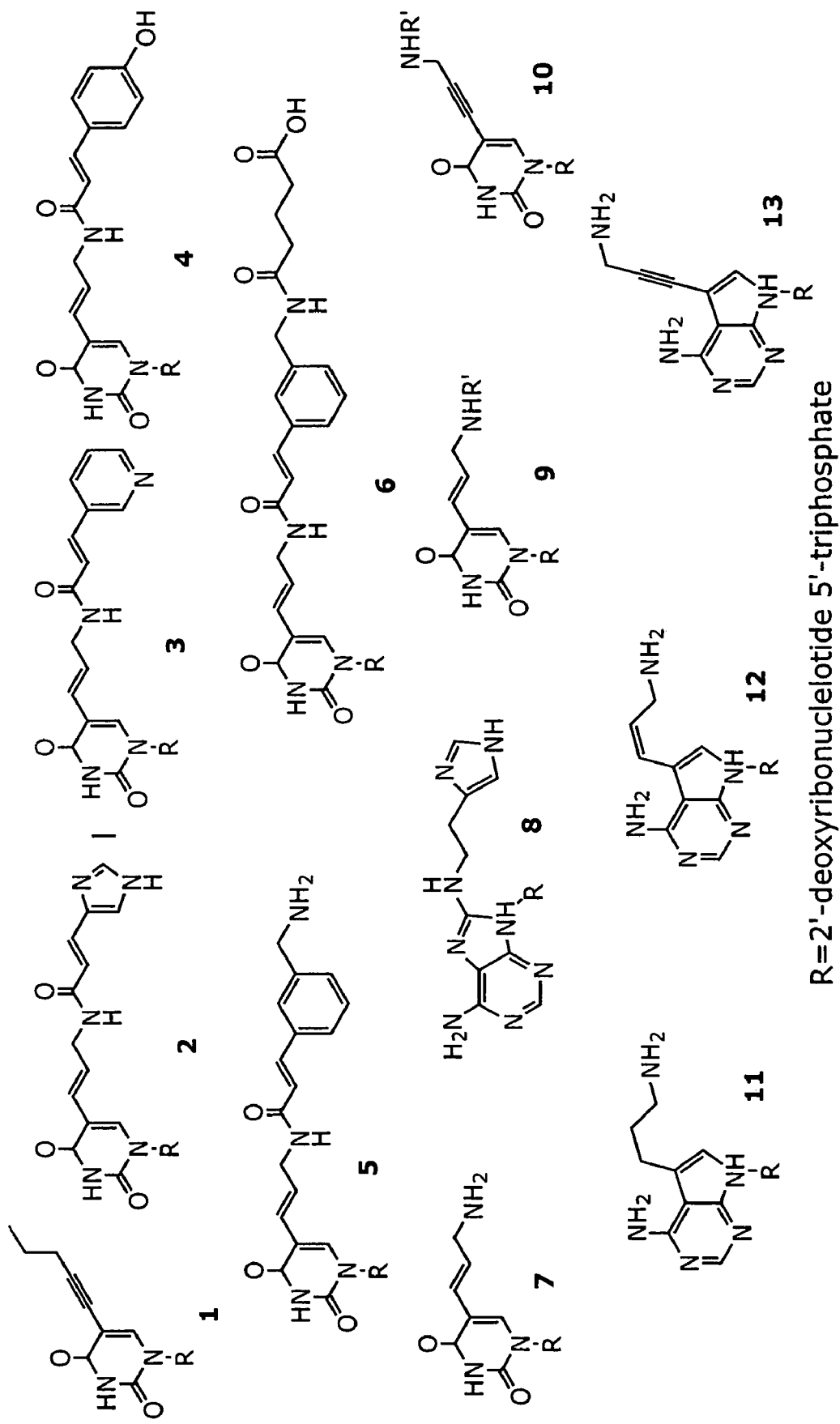
FIG. 46 depicts several exemplary deoxyribunucleotides and ribonucleotides bearing modifications to groups that do not partcipate in Watson-Crick hydrogen bonding and are known to be inserted with high sequence fidelity opposite natural DNA templates.

The functionalized nucleotides incorporated by DNA polymerases to date, shown in FIG. 46, have focused on adding "protein-like" acidic and basic functionality to DNA. While equipping nucleic acids with general acid and general base functionality such as primary amine and carboxylate groups may increase the capability of nucleic acid catalysts, the functional groups present in natural nucleic acid bases already have demonstrated the ability to serve as general acids and bases. The hepatitis delta ribozyme, for example, is thought to use the $pK_a$-modulated endocyclic amine of cytosine 75 as a general acid (S. Nakano et al. *Science* 2000, 287, 1493-7) and the peptidyl transferase activity of the ribosome may similarly rely on general base or general acid catalysis (G. W. Muth et al. *Science* 2000, 289, 947-50; P. Nissen et al. *Science* 2000, 289, 920-930; N. Ban et al. *Science* 2000, 289, 905-920) although the latter case remains the subject of ongoing debate (N. Polacek et al. *Nature* 2001, 411, 498-501). Equipping DNA bases with additional Brønsted acidic and basic groups, therefore, may not profoundly expand the scope of DNA catalysis.

In contrast with simple general acid and general base functionality, chiral metal centers would expand considerably the chemical scope of nucleic acids. Functionality aimed at binding chemically potent metal centers has yet to been incorporated into nucleic acid polymers. Natural DNA has demonstrated the ability to fold in complex three-dimensional structures capable of stereospecifically binding target molecules (C. H. Lin et al. *Chem. Biol.* 1997, 4, 817-32; C. H. Lin et al. *Chem. Biol.* 1998, 5, 555-72; P. Schultze et al. *J. Mol. Biol.* 1994, 235, 1532-47) or catalyzing phosphodiester bond manipulation (S. W. Santoro et al. *Proc. Natl. Acad. Sci. USA* 1997, 94, 4262-6; R. R. Breaker et al. *Chem. Biol.* 1995, 2, 655-60; Y. Li et al. *Biochemistry* 2000, 39, 3106-14; Y. Li et al. *Proc. Natl. Acad. Sci. USA* 1999, 96, 2746-51). DNA depurination (T. L. Sheppard et al. *Proc. Natl. Acad. Sci. USA* 2000, 97, 7802-7807) and porphyrin metallation (Y. Li et al. *Biochemistry.* 1997, 36, 5589-99; Y. Li et al. *Nat. Struct. Biol.* 1996, 3, 743-7). Non-natural nucleic acids augmented with the ability to bind chemically potent, water-compatible metals such Cu, La, Ni, Pd, Rh, Ru, or Sc may possess greatly expanded catalytic properties. For example, a Pd-binding oligonucleotide folded into a well-defined structure may possess the ability to catalyze Pd-mediated coupling reactions with a high degree of regiospecificity or stereospecificity. Similarly, non-natural nucleic acids that form chiral Sc binding sites may serve as enantioselective cycloaddition or aldol addition catalysts. The ability of DNA polymerases to translate DNA sequences into these non-natural polymers coupled with in vitro selections for catalytic activities would therefore enable the direct evolution of desired catalysts from random libraries.

Evolving catalysts in this approach addresses the difficulty of rationally designing catalytic active sites with specific chemical properties that has inspired recent combinatorial approaches (K. W. Kuntz et al. *Curr. Opin. Chem. Biol.* 1999, 3, 313-319; M. B. Francis et al. *Curr. Opin. Chem. Biol.* 1998, 2, 422-8) to organometallic catalyst discovery. For example, Hoveyda and co-workers identified Ti-based enantioselective epoxidation catalysts by serial screening of peptide ligands (K. D. Shimizu et al. *Angew. Chem. Int. Ed.* 1997, 36) Serial screening was also used by Jacobsen and co-workers to identify peptide ligands that form enantioselective epoxidation catalysts when complexed with metal cations (M. B. Francis et al. *Angew. Chem. Int. Ed. Engl.* 1999, 38, 937-941) Recently, a peptide library containing phosphine side chains was screened for the ability to catalyze malonate ester addition to cyclopentenyl acetate in the presence of Pd (S. R. Gilbertson et al. *J. Am. Chem. Soc.* 2000, 122, 6522-6523). The current approach differs fundamentally from previous combinatorial catalyst discovery efforts, however, in that it enables catalysts with desired properties to spontaneously emerge from one pot, solution-phase libraries after evolutionary cycles of diversification, amplification, translation, and selection. This strategy allows up to 1015 different catalysts to be generated and selected for desired properties in a single experiment. The compatibility of our approach with one-pot in vitro selections allows the direct selection for reaction catalysis rather than screening for a phenomenon associated with catalysis such as metal binding or heat generation. In addition, properties difficult to screen rapidly such as substrate stereospecificity or metal selectivity can be directly selected using our approach (see below).

Key intermediates for a number of C5-functionalized uridine analogs and C7-functionalized 7-deazaadenosine analogs have been synthesized for incorporation into non-natural DNA polymers. In addition, the synthesis of six C8-functionalized adenosine analogs as deoxyribonucleotide triphosphates has been completed. Because only limited information exists on the ability of DNA polymerases to accept modified nucleotides, we chose to synthesize analogs were synthesized that not only will bring metal-binding functionality to nucleic acids but that also will provide insights into the determinants of DNA polymerase acceptance.

Figure 47:
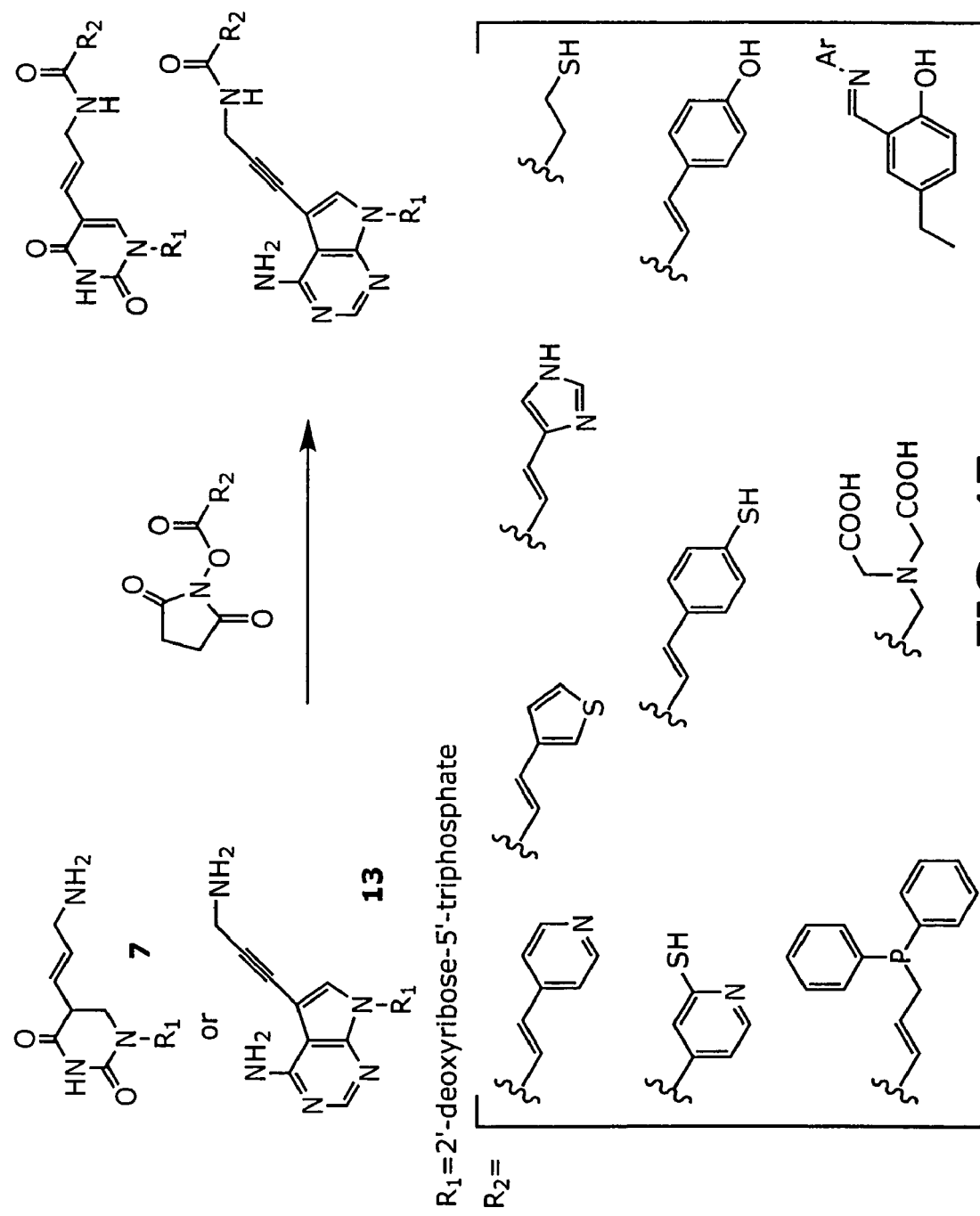
FIG. 47 depicts exemplary metal binding uridine and 7-deazaadenosine analogs.
Figure 48:
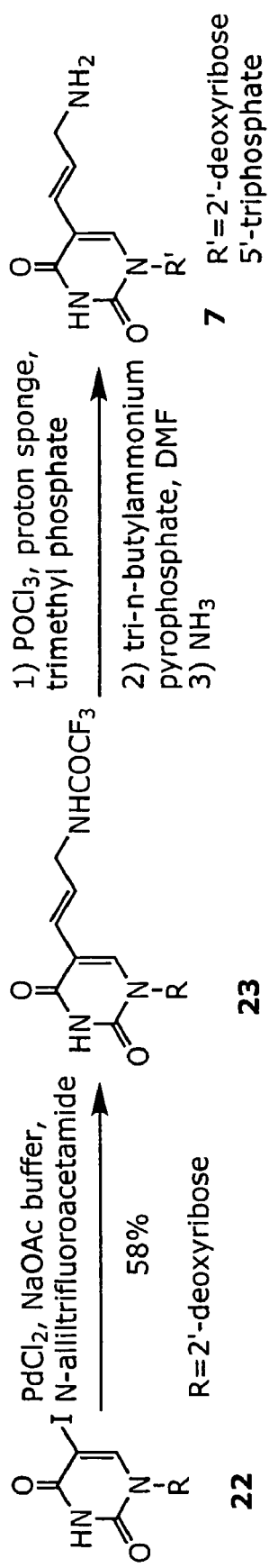
FIG. 48 depicts the synthesis of analog (7).

The strategy for the synthesis of metal-binding uridine and 7-deazaadenosine analogs is shown in FIG. 47. Both routes end with amide bond formation between NHS esters of metal-binding functional groups and amino modified deoxyribonucleotide triphosphates (7 and 13). Analogs 7 and 13 as well as acetylated derivatives of 7 have been previously shown (D. M. Perrin et al. *J. Am. Chem. Soc.* 2001, 123, 1556-63; D. M. Perrin et al. *Nucleosides Nucleotides* 1999, 18, 377-91; J. A. Latham et al. *Nucleic Acids Res.* 1994, 22, 2817-22; T. Gourlain et al. *Nucleic Acids Res.* 2001, 29, 1898-1905; S. E. Lee et al. *Nucleic Acids Res.* 2001, 29, 1565-73; K. Sakthivel et al. *Angew. Chem. Int. Ed. Engl.* 1998, 37, 2872-2875) to be tolerated by DNA polymerases, including thermostable DNA polymerases suitable for PCR. This convergent approach allows a wide variety of metal-binding ligands to be rapidly incorporated into either nucleotide analog. The synthesis of 7 has been completed following a previously reported (K. Sakthivel et al. *Angew. Chem. Int. Ed. Engl.* 1998, 37, 2872-2875) route (FIG. 48, Phillips, Chorba, Liu, unpublished results). Heck coupling of commercially available 5-iodo-2'-deoxyuridine (22) with N-allyltrifluoroacetamide provided 23. The 5'-triphosphate group was installed by treatment of 23 with trimethylphosphate, $POCl_3$, and proton sponge (1,8-bis (dimethylamino)-naphthalene) followed by tri-n-butylammonium pyrophosphate, and the trifluoroacetamide group then removed with aqueous ammonia to afford 7.

Figure 49:
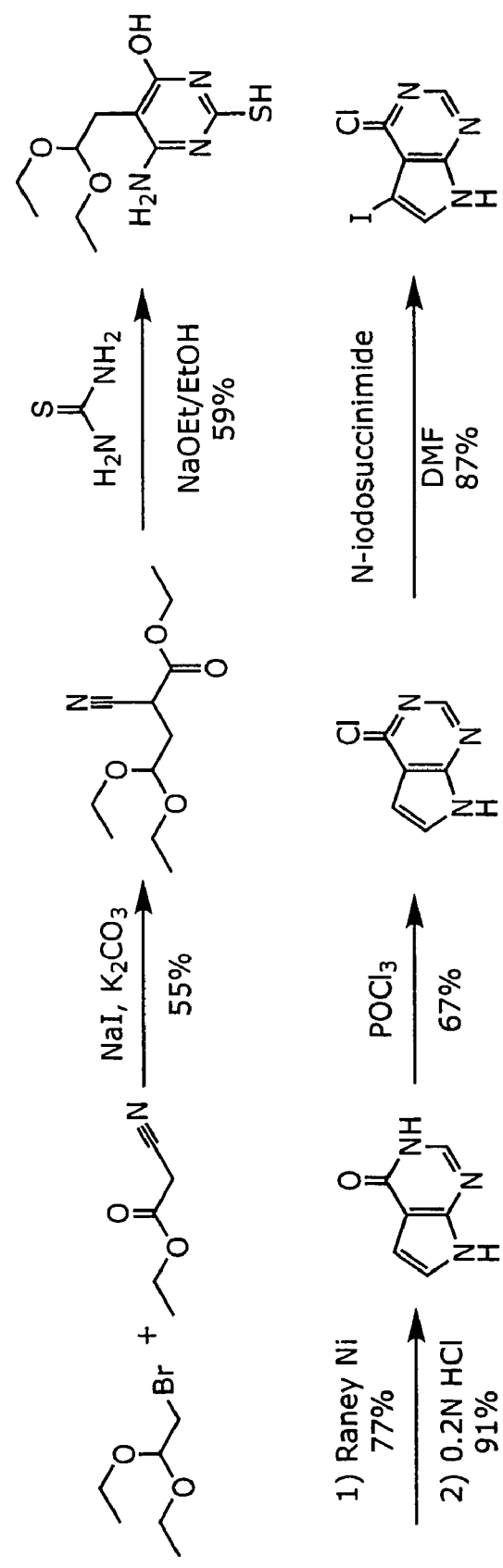
FIG. 49 depicts the synthesis of analog (30).

Several steps towards the synthesis of 13 have been completed, the key intermediate for 7-deazaadenosine analogs (FIG. 49). Following a known route (J. Davoll. *J. Am. Chem. Soc.* 1960, 82, 131-138) diethoxyethylcyanoacetate (24) was synthesized from bromoacetal 25 and ethyl cyanoacetate (26). Condensation of 24 with thiourea provided pyrimidine 27, which was desulfurized with Raney nickel and then cyclized to pyrrolopyrimidine 28 with dilute aqueous HCl. Treatment of 28 with $POCl_3$ afforded 4-chloro-7-deazaadenine (29). The aryl iodide group which will serve as a Sonogashira coupling partner for installation of the propargylic amine in 13 was installed by reacting 29 with N-iodosuccinimide to generate 4-chloro-7-iodo-7-deazaadenine (30) in 13% overall yield from bromoacetal 25.

Figure 50:
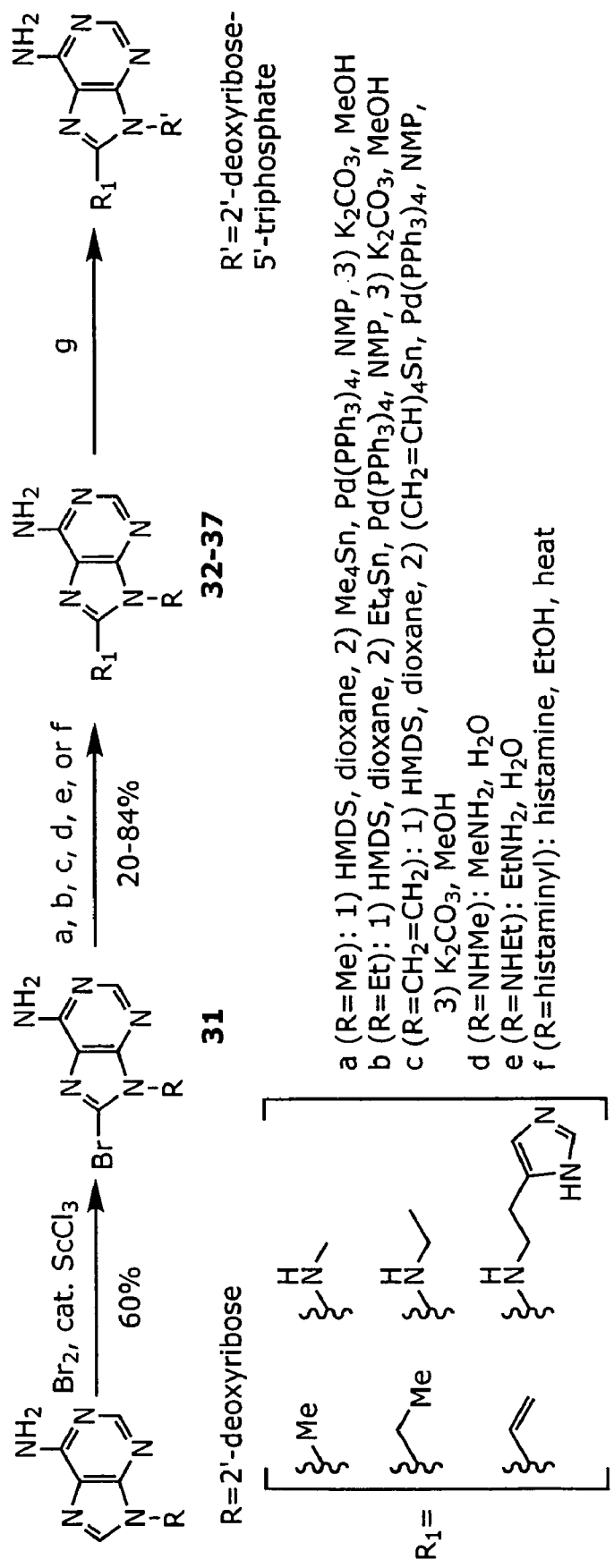
FIG. 50 depicts the synthesis of 8-modified deoxyadenosine triphosphates.

As alternative functionalized adenine analogs that will both probe the structural requirements of DNA polymerase acceptance and provide potential metal-binding functionality, six 8-modified deoxyadenosine triphosphates (FIG. 50) have been synthesized. All functional groups were installed by addition to 8-bromo-deoxyadenosine (31), which was prepared by bromination of deoxyadenosine in the presence of ScCl₃, which we found to greatly increase product yield. Methyl-(32), ethyl-(33), and vinyladenosine (34) were synthesized by Pd-mediated Stille coupling of the corresponding alkyl tin reagent and 31 (P. Mamos et al. *Tetrahedron Lett.* 1992, 33, 2413-2416). Methylamino-(35) (E. Nandanan et al. *J. Med. Chem.* 1999, 42, 1625-1638), ethylamino-(36), and histaminoadenosine (37) were prepared by treatment of 23 with the corresponding amine in water or ethanol. The 5'-nucleotide triphosphates of 32-37 were synthesized as described above.

Figure 51:
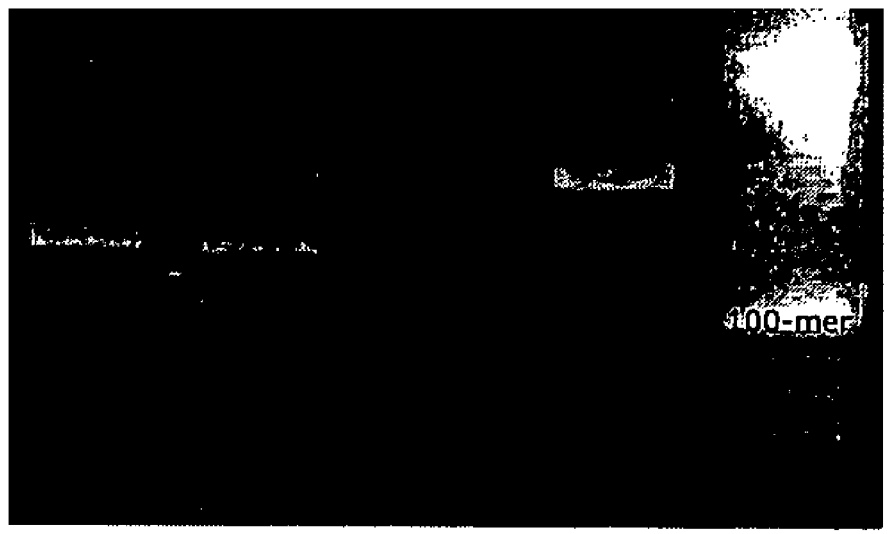
FIG. 51 depicts the results of an assay evaluating the acceptance of modified nuceotides by DNA polymerases.

The ability of thermostable DNA polymerases suitable for PCR amplification to accept these modified nucleotide triphosphates containing metal-binding functionality. Non-natural nucleotide triphosphates were purified by ion exchange HPLC and added to PCR reactions containing Taq DNA polymerase, three natural deoxynucleotide triphosphates, pUC19 template DNA, and two DNA primers. Primers were chosen to generate PCR products ranging from 50 to 200 base pairs in length. Control PCR reactions contained the four natural deoxynucleotide triphosphates and no non-natural nucleotides. PCR reactions were analyzed by agarose or denaturing acrylamide gel electrophoresis. Amino modified uridine derivative 7 was efficiently incorporated by Taq DNA polymerase over 30 PCR cycles, while the triphosphate of 23 was not an efficient polymerase substrate (FIG. 51). Previous findings on the acceptance of 7 by Taq DNA polymerase are in conflict, with both non-acceptance (K. Sakthivel et al. *Angew. Chem. Int. Ed. Engl.* 1998, 37, 2872-2875) and acceptance (S. E. Lee et al. *Nucleic Acids Res.* 2001, 29, 1565-73) reported.

Figure 52:
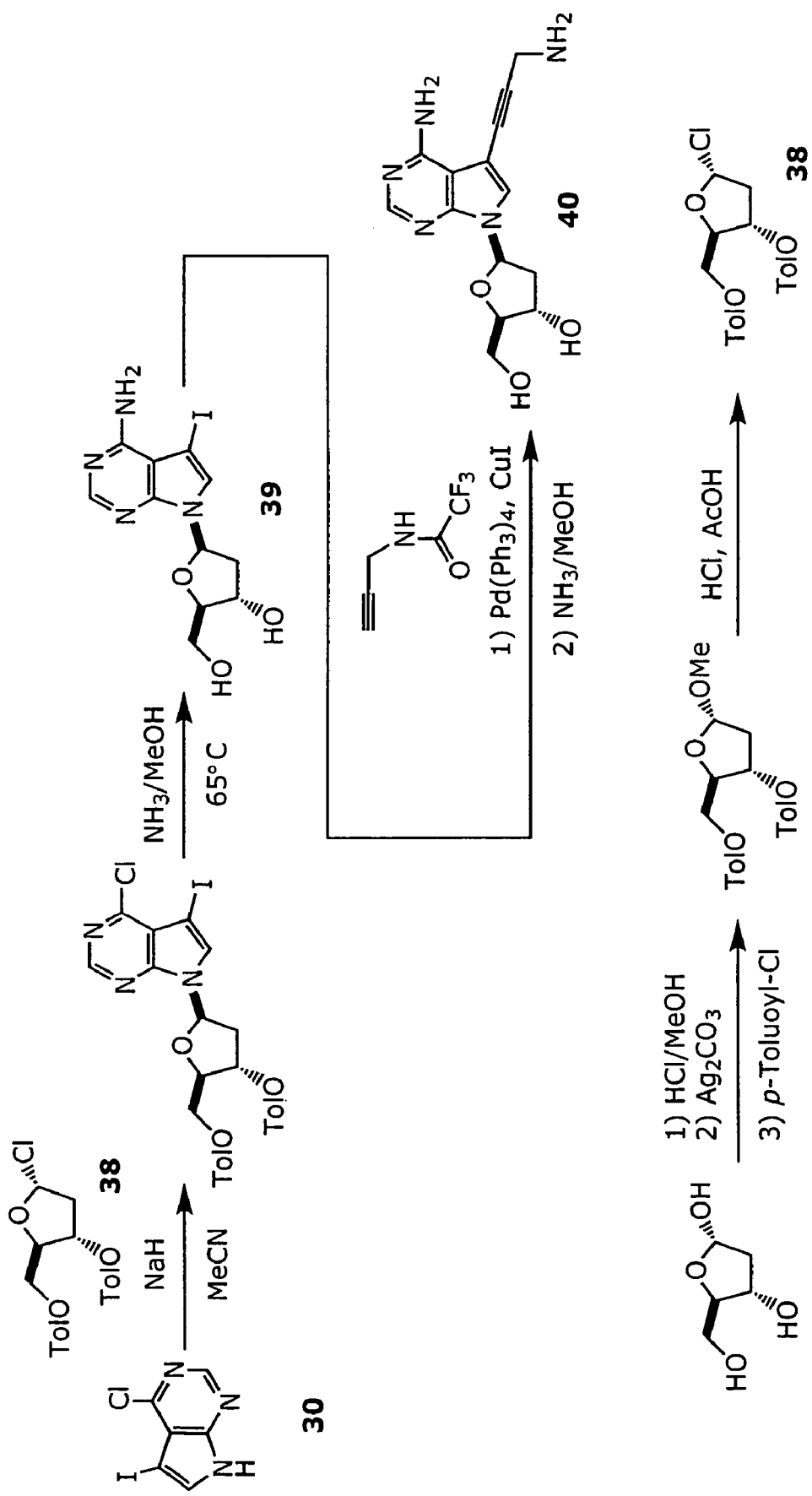
FIG. 52 depicts the synthesis of 7-deazaadenosine derivatives.

Non-Natural Metal-Binding Deoxyribonucleotide Triphosphate Synthesis: The syntheses of the C5-functionalized uridine, C7-functionalized 7-deazaadenosine, and C8-functionalized adenosine deoxynucleotide triphosphates will be completed. Synthesis of the 7-deazaadenosine derivatives from 4-chloro-7-iodo-deazaadenine (30) proceeds by glycosylation of 30 with protected deoxyribosyl chloride 38 followed by ammonolysis to afford 7-iodo-adenosine (39) (FIG. 31) (Gourlain et al. *Nucleic Acids Res.* 2001, 29, 1898-1905). Protected deoxyribosyl chloride 38 can be generated from deoxyribose as shown in FIG. 52. Pd-mediated Sonogashira coupling (Seela et al. *Helv. Chem. Acta* 1999, 82, 1878-1898) of 39 with N-propynyltrifluoroacetamide provides 40, which is then be converted to the 5' nucleotide triphosphate and deprotected with ammonia as described above to yield 13.

To generate rapidly a collection of metal-binding uridine and adenosine analogs, a variety of metal-binding groups as NHS esters will be coupled to C5-modified uridine intermediate 7 (already synthesized) and C7-modified 7-deazaadenosine intermediate 13. Metal-binding groups that will be examined initially are shown in FIG. 47 and include phosphines, thiopyridyl groups, and hemi-salen moieties. If our initial polymerase acceptance assays (see the following section) of triphosphates of 8-modified adenosines 32-37 (FIG. 50) suggest that a variety of 8-modified adenosine analogs are accepted by thermostable polymerases, alkyl- and vinyl trifluoroacetamides will be coupled to 8-bromo-deoxyadenosine (31) to generate nucleotide triphosphates such as 41 and 42 (FIG. 53). These intermediates are then coupled with the NHS esters shown in FIG. 46 to generate a variety of metal-binding 8-functionalized deoxyadenosine triphosphates.

Evaluating Non-Natural Nucleotides: Each functionalized deoxyribonucleotide triphosphate is then assayed for its suitability as a building block of an evolvable non-natural polymer library in two stages. First, simple acceptance by thermostable DNA polymerases is measured by PCR amplification of fragments of DNA plasmid pUC 19 of varying length. PCR reactions contain synthetic primers designed to bind at the ends of the fragment, a small quantity of pUC19 template DNA, a thermostable DNA polymerase (Taq, Pfu or Vent), three natural deoxyribonucleotide triphosphates, and the non-natural nucleotide triphosphate to be tested. The completely successful incorporation of the non-natural nucleotide results in the production of DNA products of any length at a rate similar to that of the control reaction. Those nucleotides that allow at least incorporation of 10 or more non-natural nucleotides in a single product molecule with at least modest efficiency are subjected to the second stage of evaluation.

Non-natural nucleotides accepted by thermostable DNA polymerases are evaluated for their possible mutagenic properties. If DNA polymerases insert a non-natural nucleotide opposite an incorrect (non-Watson-Crick) template base, or insert an incorrect natural nucleotide opposite a non-natural nucleotide in the template, the fidelity of library amplification and translation is compromised. To evaluate this possibility, PCR products generated in the above assay are subjected to DNA sequencing using each of the PCR primers. Deviations from the sequence of the pUC19 template imply that one or both of the mutagenic mechanisms are taking place. Error rates of less than 0.7% per base per 30 PCR cycles are acceptable, as error-prone PCR generates errors at approximately this rate (Caldwell et al. *PCT Methods Applic.* 1992, 2, 28-33) yet has been successfully used to evolve nucleic acid libraries.

Pairs of promising non-natural adenosine analogs and non-natural uridine analogs are also tested together for their ability to support DNA polymerization in a PCR reaction containing both modified nucleotide triphosphates together with dGTP and dCTP. Successful PCR product formation with two non-natural nucleotide triphosphates enables the incorporation of two non-natural metal-binding bases into the same polymer molecule. Functionalized nucleotides that are especially interesting yet are not compatible with Taq, Pfu, or Vent thermostable DNA polymerases can still be used in the libraries provided that they are accepted by a commercially available DNA polymerase such as the Klenow fragment of *E. coli* DNA polymerase I, T7 DNA polymerase, T4 DNA polymerase, or M-MuLV reverse transcriptase. In this case, the assays require conducting the primer extension step of the PCR reaction at 0.25-37° C., and fresh polymerase must be added at every cycle following the 94° C. denaturation step. DNA sequencing to evaluate the possible mutagenic properties of the non-natural nucleotide is still performed as described above Generating Libraries of Metal-Binding Polymers: Based on the results of the above non-natural nucleotide assays, several libraries of ~$10^{15}$ different nucleic acid sequences will be made containing one or two of the most polymerase compatible and chemically promising non-natural metal-binding nucleotides. Libraries are generated by PCR amplification of a synthetic DNA template library consisting of a random region of 20 or 40 nucleotides flanked by two 15-base constant priming regions (FIG. 54). The priming regions contain restriction endonuclease cleavage sites to allow cloning into vectors for DNA sequencing of pools or individual library members. One primer contains a chemical handle such as a primary amine group or a thiol group at its 5' terminus and becomes the coding strand of the library. The other primer contains a biotinylated T at its 5' terminus and becomes the non-coding strand. The PCR reaction includes one or two non-natural metal-binding deoxyribonucleotide triphosphates, three or two natural deoxyribonucleotide triphosphates, and a DNA polymerase compatible with the non-natural nucleotide(s). Following PCR reaction to generate the double-stranded form of the library and gel purification to remove unused primers, library member duplexes are denatured chemically. The non-coding strands are the removed by several washings with streptavidin-linked magnetic beads to ensure that no biotinylated strands remain in the library. Libraries of up to 1015 different members are generated by this method, far exceeding the combined diversity of previous combinatorial catalyst efforts.

Each library is then incubated in aqueous solution with a metal of interest from the following non-limiting list of water compatible metal salts (Fringueli et al. *Eur. J. Org. Chem.* 2001, 2001, 439455; Zaitoun et al. *J. Phys. Chem. B* 1997, 1857-1860): $ScCl_3$, $CrCl_3$, $MnCl_2$, $FeCl_2$, $FeCl_3$, $CoCl_2$, $NiCl_2$, $CuCl_2$, $ZnCl_2$, $GaCl_3$, $YCl_3$, $RuCl_3$, $RhCl_3$, $PdCl_2$, AgCl, $CdCl_2$, $InCl_3$, $SnCl_2$, $La(OTf)_3$, $Ce(OTf)_3$, $Pr(OTf)_3$, $Nd(OTf)_3$, $Sm(OTf)_3$, $Eu(OTf)_3$, $Gd(OTf)_3$, $Tb(OTf)_3$, $Dy(OTf)_3$, $Ho(OTf)_3$, $Er(OTf)_3$, $Tm(OTf)_3$, $Yb(OTf)_3$, $Lu(OTf)_3$, $IrCl_3$, $PtCl_2$, AuCl, $HgCl_2$, HgCl, $PbCl_2$, or $BiCl_3$. Metals are chosen based on the specific chemical reactions to be catalyzed. For example, libraries aimed at reactions such as aldol condensations or hetero Diels-Alder reactions that are known (Fringuelli et al. *Eur. J. Org. Chem.* 2001, 2001, 439-455) to be catalyzed by Lewis acids are incubated with $ScCl_3$ or with one of the lanthanide triflates, while those aimed at coupling electron-deficient olefins with aryl halides are incubated with $PdCl_2$. The metalated library is then purified away from unbound metal salts by gel filtration using sephadex or acrylamide cartridges, which separate DNA oligonucleotides 25 bases or longer from unbound small molecule components.

The ability of the polymer library (or of individual library members) to bind metals of interest is verified by treating the metalated library free of unbound metals with metal staining reagents such as dithiooxamide, dimethylglyoxime, KSCN (Francis et al. *Curr. Opin. Chem. Biol.* 1998, 2, 422-8) or EDTA (Zaitoun et al. *J. Phys. Chem. B* 1997, 101, 1857-1860) that become distinctly colored in the presence of different metals. The approximate level of metal binding is measured by spectrophotometric comparison with solutions of free metals of known concentration and with solutions of positive control oligonucleotides containing an EDTA group (which can be introduced using a commercially available phosphoramidite from Glen Research).

Figure 55:
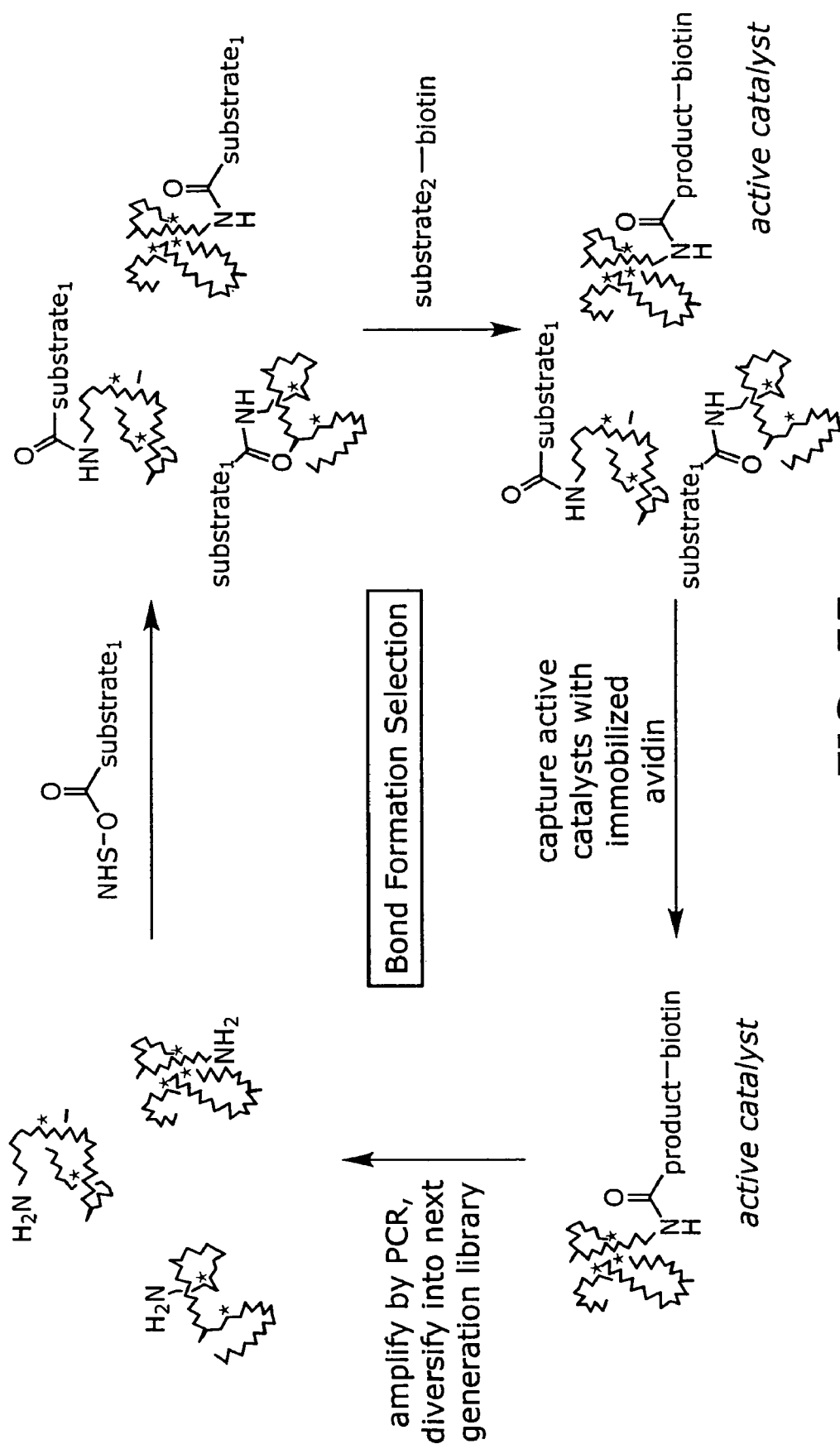
FIGS. 55 and 56 depict exemplary schemes for the in vitro selections for non-natural polymer catalysts.

In Vitro Selections for Non-Natural Polymer Catalysts: Metalated libraries of evolvable non-natural polymers containing metal-binding groups are then subjected to one-pot, solution-phase selections for catalytic activities of interest. Library members that catalyze virtually any reaction that causes bond formation between two substrate molecules or that results in bond breakage into two product molecules are selected using the schemes proposed in FIGS. 54 and 55. To select for bond forming catalysts (for example, hetero Diels-Alder, Heck coupling, aldol reaction, or olefin metathesis catalysts), library members are covalently linked to one substrate through their 5' amino or thiol termini. The other substrate of the reaction is synthesized as a derivative linked to biotin. When dilute solutions of library-substrate conjugate are reacted with the substrate-biotin conjugate, those library members that catalyze bond formation cause the biotin group to become covalently attached to themselves. Active bond forming catalysts can then be separated from inactive library members by capturing the former with immobilized streptavidin and washing away inactive polymers (FIG. 55).

Figure 56:
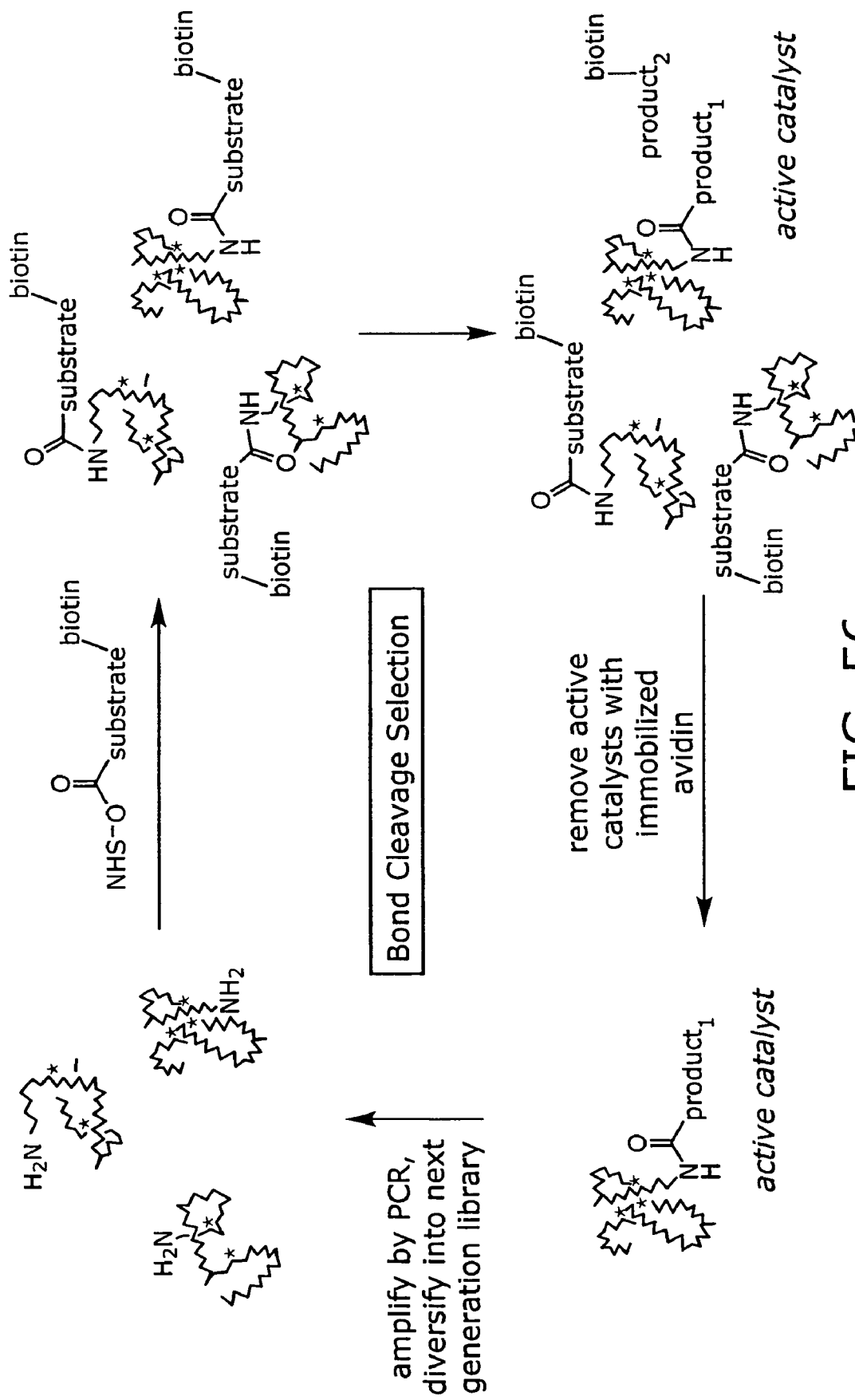

In an analogous manner, library members that catalyze bond cleavage reactions such as retro-aldol reactions, amide hydrolysis, elimination reactions, or olefin dihydroxylation followed by periodate cleavage can also be selected. In this case, metalated library members are covalently linked to biotinylated substrates such that the bond breakage reaction causes the disconnection of the biotin moiety from the library members (FIG. 56). Upon incubation under reaction conditions, active catalysts, but not inactive library members, induce the loss of their biotin groups. Streptavidin-linked beads can then be used to capture inactive polymers, while active catalysts are able to elute from the beads. Related bond formation and bond cleavage selections have been used successfully in catalytic RNA and DNA evolution (Jäschke et al. *Curr. Opin. Chem. Biol.* 2000, 4, 257-62) Although these selections do not explicitly select for multiple turnover catalysis, RNAs and DNAs selected in this manner have in general proven to be multiple turnover catalysts when separated from their substrate moieties (Jäschke et al. *Curr. Opin. Chem. Biol.* 2000, 4, 257-62; Jaeger et al. *Proc. Natl. Acad. Sci. USA* 1999, 96, 14712-7; Bartel et al. *Science,* 1993, 261, 1411-8; Sen et al. *Curr. Opin. Chem. Biol.* 1998, 2, 680-7).

Figure 57A:
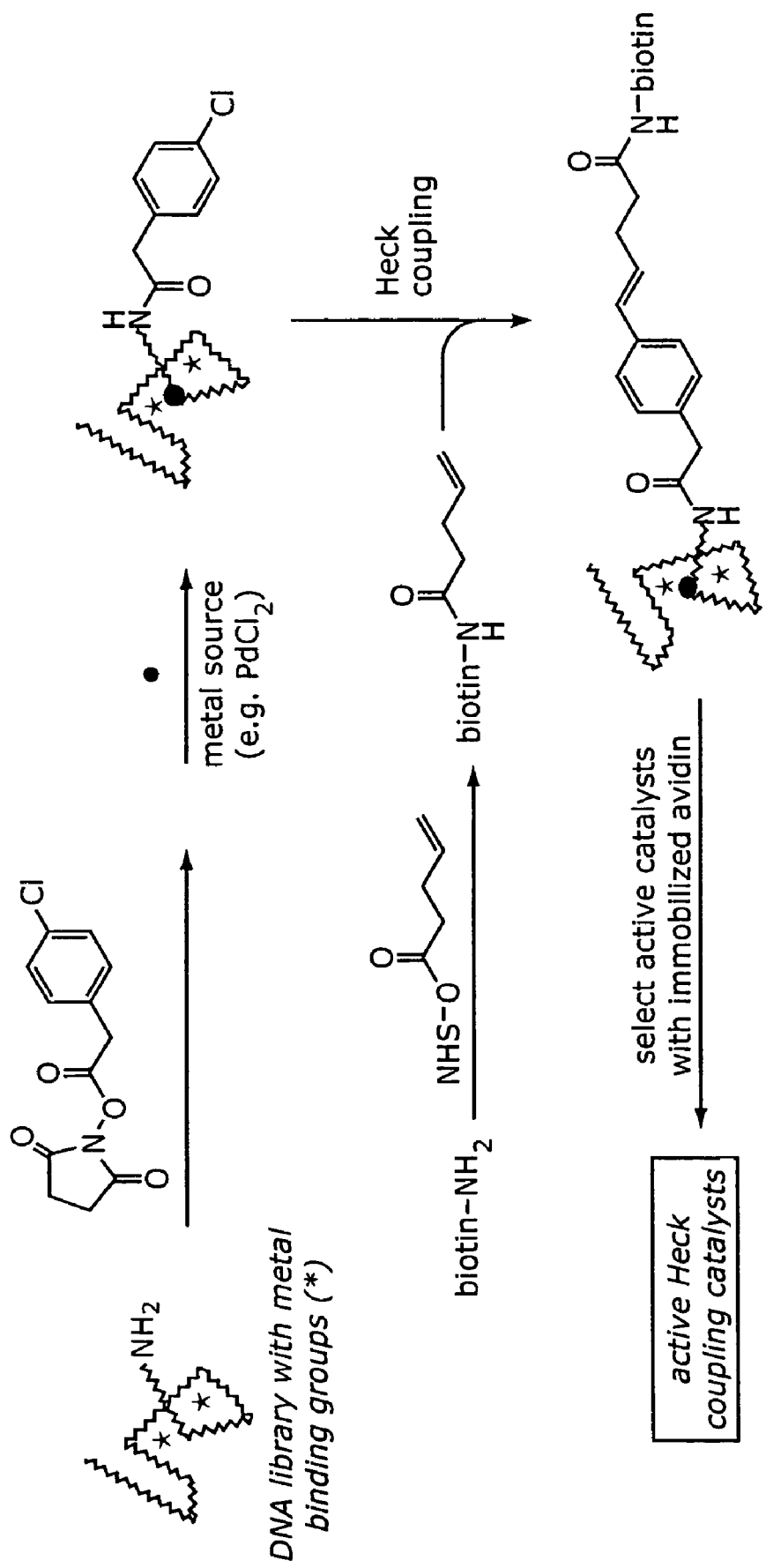
FIGS. 57A and 57C depict an exemplary scheme for the in vitro selection of catalysts for Heck reactions (FIG. 57A), hetero Diels-Alder reactions (FIG. 57B) and aldol additions (FIG. 57C).
Figure 57B:
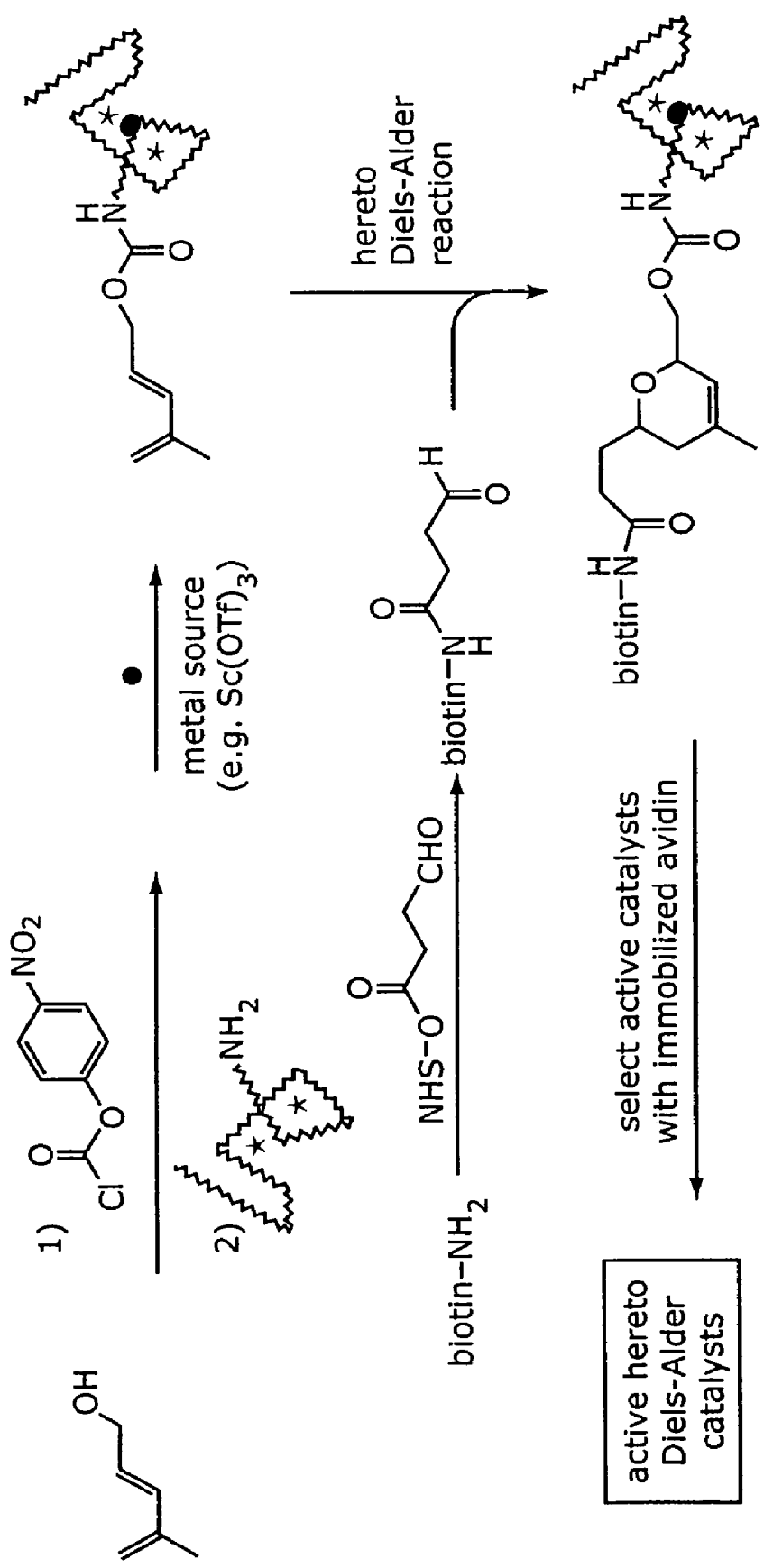
Figure 57C:
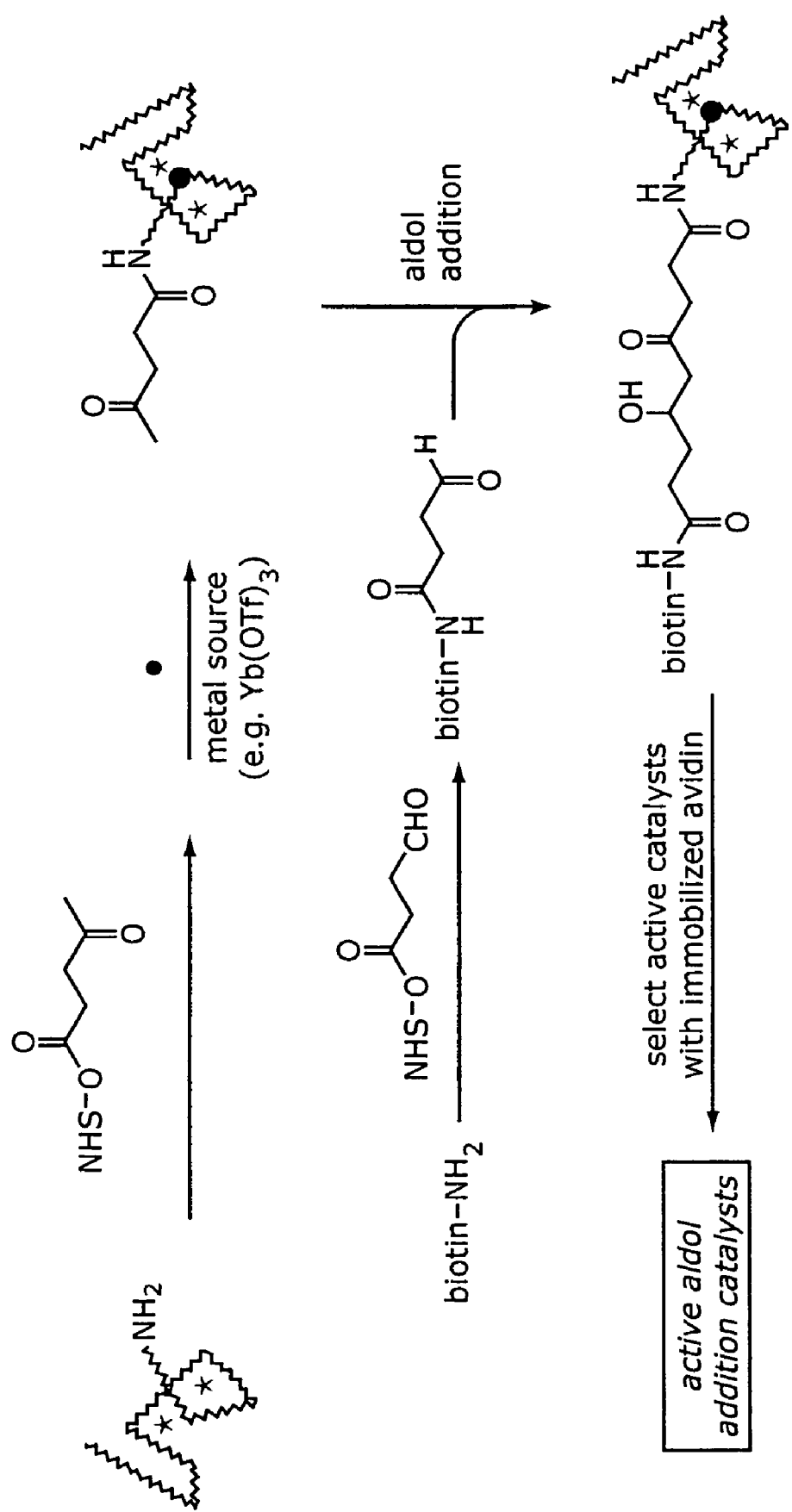

Catalysts of three important and diverse bond-forming reactions will initially be evolved: Heck coupling, hetero Diels-Alder cycloaddition, and aldol addition. All three reactions are water compatible (Kobayashi et al. *J. Am. Chem. Soc.* 1998, 120, 8287-8288; Fringuelli et al. *Eur. J. Org Chem.* 2001, 2001, 439-455; Li et al. *Organic Reactions in Aqueous Media*: Wiley and Sons: New York, 1997) and are known to be catalyzed by metals. As Heck coupling substrates both electron deficient and unactivated olefins will be used together with aryl iodides and aryl chlorides. Heck reactions with aryl chlorides in aqueous solution, as well as room temperature Heck reactions with non-activated aryl chlorides, have not yet been reported to our knowledge. Libraries for Heck coupling catalyst evolution use $PdCl_2$ as a metal source. Hetero Diels-Alder substrates include simple dienes and aldehydes, while aldol addition substrates consist of aldehydes and both silyl enol ethers as well as simple ketones. Representative selection schemes for Heck coupling, hetero Diels-Alder, and aldol addition catalysts are shown in FIG. 57. The stringency of these selections can be increased between rounds of selection by decreasing reaction times, lowering reaction temperatures, or using less activated substrates (for example, less electron poor aryl chlorides (Littke et al. *J. Am. Chem. Soc.* 2001, 123, 6989-7000) or simple ketones instead of silyl enol ethers).

Evolving Non-Natural Polymers: Diversification and Selecting for Stereospecificity Following each round of selection, active library members are amplified by PCR with the non-natural nucleotides and subjected to additional rounds of selection to enrich the library for desired catalysts. These libraries are truly evolved by introducing a diversification step before each round of selection. Libraries are diversified by random mutagenesis using error-prone PCR (Caldwell et al. *PCR Methods Applic.* 1992, 2, 28-33) or by recombination using modified DNA shuffling methods that recombine small, non-homologous nucleic acid fragments. Because error-prone PCR is inherently less efficient than normal PCR, error-prone PCR diversification will be conducted with only natural dATP, dTTP, dCTP, and dGTP and using primers that lack chemical handles or biotin groups. The resulting mutagenized products are then subjected to PCR translation into non-natural nucleic acid polymers using standard PCR reactions containing the non-natural nucleotide(s), the biotinylated primer, and the amino- or thiol-terminated primer.

In addition to simply evolving active catalysts, the in vitro selections described above are used to evolve non-natural polymer libraries in powerful directions difficult to achieve using other catalyst discovery approaches. An enabling feature of these selections is the ability to select either for library members that are biotinylated or for members that are not biotinylated. Substrate specificity among catalysts can therefore be evolved by selecting for active catalysts in the presence of the desired substrate and then selecting in the same pot for inactive catalysts in the presence of one or more undesired substrates. If the desired and undesired substrates differ by the configuration at one or more stereocenters, enantioselective or diastereoselective catalysts can emerge from rounds of selection. Similarly, metal selectivity can be evolved by selecting for active catalysts in the presence of desired metals and selecting for inactive catalysts in the presence of undesired metals. Conversely, catalysts with broad substrate tolerance can be evolved by varying substrate structures between successive rounds of selection.

Finally, the observations of sequence-specific DNA-templated synthesis in DMF and $CH_2Cl_2$ suggests that DNA-tetralkylammonium cation complexes can form base-paired structures in organic solvents. This finding raises the possibility of evolving our non-natural nucleic acid catalysts in organic solvents using slightly modified versions of the selections described above. The actual bond forming and bond cleavage selection reactions will be conducted in organic solvents, the crude reactions will be ethanol precipitated to remove the tetraalkylammonium cations, and the immobilized avidin separation of biotinylated and non-biotinylated library members in aqueous solution will be performed. PCR amplification of selected members will then take place as described above. The successful evolution of reaction catalysts that function in organic solvents would expand considerably both the scope of reactions that can be catalyzed and the utility of the resulting evolved non-natural polymer catalysts.

Characterizing Evolved Non-Natural Polymers: Libraries subjected to several rounds of evolution are characterized for their ability to catalyze the reactions of interest both as pools of mixed sequences or as individual library members. Individual members are extricated from evolved pools by ligating PCR amplified sequences into DNA vectors, transforming dilute solutions of ligated vectors into competent bacterial cells, and picking single colonies of transformants. Assays on pools or individual sequences are conducted both in the single turnover format and in a true multiple turnover catalytic format. For the single turnover assays, the rate at which substrate-linked bond formation catalysts effect their own biotinylation in the presence of free biotinylated substrate will be measured, or the rate at which biotinylated bond breakage catalysts effect the loss of their biotin groups. Multiple turnover assays are conducted by incubating evolved catalysts with small molecule versions of substrates and analyzing the rate of product formation by tlc, NMR, mass spectrometry, HPLC, or spectrophotometry.

Once multiple turnover catalysts are evolved and verified by these methods, detailed mechanistic studies can be conducted on the catalysts. The DNA sequences corresponding to the catalysts are revealed by sequencing PCR products or DNA vectors containing the templates of active catalysts. Metal preferences are evaluated by metalating catalysts with a wide variety of metal cations and measuring the resulting changes in activity. The substrate specificity and stereoselectivity of these catalysts are assessed by measuring the rates of turnover of a series of substrate analogs. Diastereoselectivities and enantioselectivities of product formation are revealed by comparing reaction products with those of known stereochemistry. Previous studies suggest that active sites buried within large chiral environments often possess high degrees of stereoselectivity. For example, peptide-based catalysts generated in combinatorial approaches have demonstrated poor to excellent stereoselectivities that correlate with the size of the peptide ligand (Jarvo et al. *J. Am. Chem. Soc.* 1999, 121, 11638-11643) while RNA-based catalysts and antibody-based catalysts frequently demonstrate excellent stereoselectivities (Jäschke et al. *Curr. Opin. Chem. Biol.* 2000, 4, 257-262; Seelig et al. *Angew. Chem. Int. Ed. Engl.* 2000, 39, 4576-4579; Hilvert, D. *Annu. Rev. Biochem.* 2000, 69, 751-93; Barbas et al. *Science* 1997, 278, 2085-92; Zhong et al. *Angew. Chem. Int. Ed. Engl.* 1999, 38, 3738-3741; Zhong et al. *J. Am. Chem. Soc.* 1997, 119, 8131-8132; List et al. *Org. Lett.* 1999, 1, 59-61) The direct selections for substrate stereoselectivity described above should further enhance this property among evolved catalysts.

Structure-function studies on evolved catalysts are greatly facilitated by the ease of automated DNA synthesis. Site-specific structural modifications are introduced by synthesizing DNA sequences corresponding to "mutated" catalysts in which bases of interest are changed to other bases. Changing the non-natural bases in a catalyst to a natural base (U* to C or A* to G) and assaying the resulting mutants may identify the chemically important metal-binding sites in each catalyst. The minimal polymer required for efficient catalysis are determined by synthesizing and assaying progressively truncated versions of active catalysts. Finally, the three-dimensional structures of the most interesting evolved catalysts complexed with metals are solved in collaboration with local macromolecular NMR spectroscopists or X-ray crystallographers.

The invention claimed is:

1. A method for selecting one or more small molecules having binding affinity to a target molecule, the method comprising:
(a) producing a library of small molecules associated with corresponding oligonucleotides by a method comprising the steps of
(i) providing a plurality of templates comprising a plurality of first reactive units associated with a corresponding plurality of first oligonucleotides, wherein each first oligonucleotide defines at least one codon sequence,
(ii) providing a plurality of transfer units comprising a plurality of second reactive units covalently attached to a corresponding plurality of second oligonucleotides, wherein each second oligonucleotide defines an anti-codon sequence complementary to a codon sequence, and
(iii) annealing oligonucleotides having complementary codon and anti-codon sequences to bring the first and second reactive units into reactive proximity thereby producing the small molecules associated with the corresponding oligonucleotides, wherein each of the corresponding oligonucleotides has a nucleotide sequence informative of the synthetic history of the small molecule associated therewith;
(b) mixing the small molecules with a target molecule under conditions to permit small molecules capable of binding the target molecule to bind thereto; and
(c) separating small molecules that bind to the target molecule from unbound small molecules thereby selecting one or more small molecules having binding affinity to the target molecule.

2. The method of claim 1 further comprising the step of determining the sequence of the oligonucleotide associated with a small molecule that binds to the target molecule.

3. The method of claim 2 wherein the oligonucleotides contain binding sites for a primer pair to permit amplification of the oligonucleotides associated with small molecules that bind to the target molecule.

4. The method of claim 3 further comprising, after step (c), the step of amplifying the oligonucleotides associated with the separated small molecules that bind to the target molecule.

5. The method of claim 1 wherein the nucleotide sequence encodes the synthesis of the small molecule associated therewith.

6. The method of claim 1 wherein the target molecule is a drug target.

7. The method of claim 1 wherein the method of producing the small molecules further comprises
(iv) providing a plurality of second transfer units comprising a plurality of third reactive units covalently attached to a corresponding plurality of third oligonucleotides, wherein each third oligonucleotide defines an anti-codon sequence complementary to a second, different codon sequence, and
(v) annealing oligonucleotides having complementary codon and anti-codon sequences to bring the reaction products of step (iii) and the third reactive units into reactive proximity thereby producing a plurality of modified small molecules.

8. A method for selecting small molecules having binding affinity to a target molecule, the method comprising:
(a) producing a library of small molecules covalently attached to corresponding oligonucleotides by annealing first oligonucleotides covalently attached to first reactive units with second oligonucleotides covalently attached to second reactive units to bring the first reactive units and the second reactive units into reactive proximity thereby to produce the small molecules, wherein each of the corresponding oligonucleotides has a nucleotide sequence informative of the synthetic history of the small molecule associated therewith:
(b) mixing a target molecule with the small molecules covalently attached to corresponding oligonucleotides under conditions to permit the small molecules capable of binding the target molecule to bind thereto;
(c) separating small molecules that bind to the target molecule from unbound small molecules;
(d) mutating the sequences of the oligonucleotides associated with the separated small molecules; and
(e) using the mutated sequences to direct synthesis of a new library of small molecules.

9. The method of claim 8 wherein, in step (d), the oligonucleotides are mutated by error-prone PCR.

10. The method of claim 8 wherein, in step (d), the oligonucleotides are mutated by in vitro homologous recombination.

11. A method for selecting one or more small molecules having binding affinity to a target molecule, the method comprising:
(a) producing a library of small molecules associated with corresponding oligonucleotides by a method comprising the steps of
(i) providing a plurality of templates comprising a plurality of first reactive units associated with a corresponding plurality of first oligonucleotides, wherein each first oligonucleotide defines at least one codon sequence,
(ii) providing a plurality of transfer units comprising a plurality of second reactive units covalently attached to a corresponding plurality of second oligonucleotides, wherein each second oligonucleotide defines an anti-codon sequence complementary to a codon sequence, and
(iii) annealing oligonucleotides having complementary codon and anti-codon sequences to bring the first and second reactive units into reactive proximity thereby producing the small molecules associated with the corresponding oligonucleotides, wherein each of the corresponding oligonucleotides has a nucleotide sequence informative of the structure of the small molecule associated therewith;

(b) mixing the small molecules with a target molecule under conditions to permit small molecules capable of binding the target molecule to bind thereto; and (c) separating small molecules that bind to the target molecule from unbound small molecules thereby selecting one or more molecules having binding affinity to the target molecule.

12. The method of claim 11 further comprising the step of determining the sequence of the oligonucleotide associated with a small molecule that binds to the target molecule.

13. The method of claim 12 wherein the oligonucleotides contain binding sites for a primer pair to permit amplification of the oligonucleotides associated with small molecules that bind to the target molecule.

14. The method of claim 13 further comprising, after step (c), the step of amplifying the oligonucleotides associated with the separated small molecules.

15. The method of claim 11 wherein the nucleotide sequence encodes the synthesis of the small molecule associated therewith.

16. The method of claim 11, wherein the method of producing the small molecules further comprises (iv) providing a plurality of second transfer units comprising a plurality of third reactive units covalently attached to a corresponding plurality of third oligonucleotides, wherein each third oligonucleotide defines an anti-codon sequence complementary to a second, different codon sequence, and (v) annealing oligonucleotides having complementary codon and anti-codon sequences to bring the reaction products of step (iii) and the third reactive units into reactive proximity thereby producing a plurality of modified small molecules.

17. A method for selecting small molecules having binding affinity to a target molecule, the method comprising:

(a) producing a library of small molecules covalently attached to corresponding oligonucleotides by annealing first oligonucleotides covalently attached to first reactive units with second oligonucleotides covalently attached to second reactive units to bring the first reactive units and the second reactive units into reactive proximity thereby to produce the small molecules, wherein each of the corresponding oligonucleotides has a nucleotide sequence informative of the structure of the small molecule associated therewith;

(b) mixing a target molecule with the small molecules covalently attached to corresponding oligonucleotides under conditions to permit the small molecules capable of binding the target molecule to bind thereto;

(c) separating small molecules that bind to the target molecule from unbound small molecules;

(d) mutating the sequences of the oligonucleotides associated with the separated small molecules; and (e) using the mutated sequences to direct synthesis of a new library of small molecules.

18. The method of claim 17 wherein, in step (d), the oligonucleotides are mutated by error-prone PCR.

19. The method of claim 17 wherein, in step (d), the oligonucleotides are mutated by in vitro homologous recombination.

20. The method of claim 17 wherein the target molecule is a drug target.

21. A method for evolving a library of small molecules, the method comprising:

(a) producing a library of small molecules covalently attached to corresponding oligonucleotides by annealing first oligonucleotides covalently attached to first reactive units with second oligonucleotides covalently attached to second reactive units to bring the first reactive units and the second reactive units into reactive proximity to produce the small molecules, wherein each of said corresponding oligonucleotide has a nucleotide sequence informative of the synthetic history of the small molecule associated therewith;

(b) selecting the oligonucleotides associated with the small molecules having a desired property;

(c) mutating the sequences of the selected oligonucleotides; and (d) synthesizing a new library of small molecules using the mutated sequences.

22. The method of claim 21 wherein the desired property is binding activity to a target molecule.

23. The method of claim 22 wherein the target molecule is a drug target.

24. The method of claim 21 wherein, in step (c), the sequence of the oligonucleotides are mutated by error-prone PCR.

25. The method of claim 21 wherein, in step (c), the sequence of the oligonucleotides are mutated by in vitro homologous recombination.

26. A method for evolving a library of small molecules, the method comprising:

(a) producing a library of small molecules covalently attached to corresponding oligonucleotides by annealing first oligonucleotides covalently attached to first reactive units with second oligonucleotides covalently attached to second reactive units to bring the first reactive units and the second reactive units into reactive proximity to produce the small molecules, wherein each of said corresponding oligonucleotide has a nucleotide sequence informative of the structure of the small molecule associated therewith;

(b) selecting the oligonucleotides associated with the small molecules having a desired property;

(c) mutating the sequences of the selected oligonucleotides; and (d) synthesizing a new library of small molecules using the mutated sequences.

27. The method of claim 26 wherein the desired property is binding activity to a target molecule.

28. The method of claim 27 wherein the target molecule is a drug target.

29. The method of claim 26 wherein, in step (c), the sequence of the oligonucleotides are mutated by error-prone PCR.

30. The method of claim 26 wherein, in step (c), the sequence of the oligonucleotides are mutated by in vitro homologous recombination.

31. A method of selecting one or more small molecules having binding affinity to a target molecule, the method comprising:

(a) producing a library of small molecules covalently attached to corresponding oligonucleotides by annealing first oligonucleotides covalently attached to first reactive units with second oligonucleotides covalently attached to second reactive units to bring the first reactive units and the second reactive units into reactive proximity thereby to produce the small molecules, wherein each said corresponding oligonucleotide attached to a small molecule has a nucleotide sequence informative of the structure or the synthetic history of the small molecule associated therewith;

(b) mixing the small molecules with a target molecule under conditions to permit small molecules capable of binding the target to bind thereto; and
(c) separating small molecules that bind to the target from unbound small molecules thereby selecting one or more small molecules having binding affinity to the target molecule.

32. The method of claim 31 further comprising the step of determining the sequence of the oligonucleotide associated with a small molecule that binds to the target molecule.

33. The method of claim 31, wherein the target molecule is a drug target.

* * * * *

SEQUENCE LISTING

<160> NUMBER OF SEQ ID NOS: 83

<210> SEQ ID NO 1
<211> LENGTH: 8
<212> TYPE: DNA
<213> ORGANISM: Artificial Sequence
<220> FEATURE:
<223> OTHER INFORMATION: Description of Artificial Sequence:Eight base
      encoding region selected for attaching a biotin
      group to template

<400> SEQUENCE: 1 tgacgggt                                                              8

```
<210> SEQ ID NO 2
<211> LENGTH: 8
<212> TYPE: DNA
<213> ORGANISM: Artificial Sequence
<220> FEATURE:
<223> OTHER INFORMATION: Description of Artificial Sequence:Anti-codon
      for a biotin group

<400> SEQUENCE: 2 acccgtca                                                                    8

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence:PCR primers
      for amplifying DNA of eluted molecules from avidin binding assay

<400> SEQUENCE: 3
tggtgcggag ccgccg                                                          16

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence:PCR primer
      for amplifying DNA of eluted molecules from avidin binding assay

<400> SEQUENCE: 4
ccactgtccg tggcgcgacc ccggctcctc ggctcgg                                   37

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer for automated DNA sequencing

<400> SEQUENCE: 5
ccactgtccg tggcgcgacc c                                                    21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:Matched
      reagent for SIAB and SBAP reactions

<400> SEQUENCE: 6
cccgagtcga agtcgtacc                                                       19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:Mismatched
      reagent in SIAB and SBAP reactions

<400> SEQUENCE: 7
gggctcagct tccccataa                                                       19
```

```
<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence:Mismatched
      reagents for other reactions in Figure 6b, 6c, 6d,
      and 8a

<400> SEQUENCE: 8
aaatcttccc                                                          10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence:Reagent
      containing one mismatch

<400> SEQUENCE: 9
aattcttacc                                                          10

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence:E template
      in Figs. 6a and 6b SMCC, GMBS, BMPS and SVSB reactions

<400> SEQUENCE: 10
cgcgagcgta cgctcgcgat ggtacgaatt cgactcggga ataccacctt cgactcgagg    60

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence:H template
      in Fig. 6b SIAB, SBAP, and SIA reactions

<400> SEQUENCE: 11
cgcgagcgta cgctcgcgat ggtacgaatt c                                  31

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence:Clamp
      oligonucleotide

<400> SEQUENCE: 12
attcgtacca                                                          10

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide templates with 1 base between reactive groups when
      template and reagent are annealed

<400> SEQUENCE: 13
tggtacgaat tcgactcggg                                               20
```

```
<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide template with 2 and 3 matched bases between
      reactive groups when template and reagent are
      annealed

<400> SEQUENCE: 14
gagtcgaatt cgtacc                                                     16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide template with 2 and 3 mismatched bases between
      reactive groups when template and reagents are
      annealed

<400> SEQUENCE: 15
gggctcagct tcccca                                                     16

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide templates with 4 and 5 number of bases between
      reactive groups when template and reagents are
      annealed.

<400> SEQUENCE: 16
ggtacgaatt cgactcggga ataccacctt                                      30

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence:
      Oligonucleotide template with 6-9 matched

<400> SEQUENCE: 17
tcccgagtcg                                                            10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence:
      Oligonucleotide template with 6 matched

<400> SEQUENCE: 18
aattcgtacc                                                            10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence:
      Oligonucleotide template with 6-9 mismatched
```

```
<400> SEQUENCE: 19
tcacctagca                                                              10

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide template

<400> SEQUENCE: 20
ggtacgaatt cgactcggga                                                   20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide template with 10, 13, 16, and 19 matched

<400> SEQUENCE: 21
tcccgagtcg aattcgtacc                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide template with 10, 13, 16, and 19 mismatched

<400> SEQUENCE: 22
gggctcagct tccccataat                                                   20

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence:
      Oligonucleotide template with 15 matched

<400> SEQUENCE: 23
aattcgtacc                                                              10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence:
      Oligonucleotide Template with 15 mismatched

<400> SEQUENCE: 24
tcgtattcca                                                              10

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide template for n=10 vs. n=0 comparison
```

<400> SEQUENCE: 25
tagcgattac ggtacgaatt cgactcggga                                              30

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide template with quadruplet non-frameshifting codon
      set
<220> FEATURE:
<221> NAME/KEY: variation
<222> LOCATION: (2)..(3)
<223> OTHER INFORMATION: N = A, T or C.
<220> FEATURE:
<221> NAME/KEY: variation
<222> LOCATION: (6)..(7)
<223> OTHER INFORMATION: N = A, T or C.
<220> FEATURE:
<221> NAME/KEY: variation
<222> LOCATION: (10)..(11)
<223> OTHER INFORMATION: N = A, T or C.
<220> FEATURE:
<221> NAME/KEY: variation
<222> LOCATION: (14)..(15)
<223> OTHER INFORMATION: N = A, T or C.

<400> SEQUENCE: 26
cnnccnnccn nccnnc                                                             16

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide template with triplet non-frameshifting condon
      set.
<220> FEATURE:
<221> NAME/KEY: variation
<222> LOCATION: (2)..(3)
<223> OTHER INFORMATION: N = A, T, or C
<220> FEATURE:
<221> NAME/KEY: variation
<222> LOCATION: (5)..(6)
<223> OTHER INFORMATION: N = A, T, or C
<220> FEATURE:
<221> NAME/KEY: variation
<222> LOCATION: (8)..(9)
<223> OTHER INFORMATION: N = A, T, or C
<220> FEATURE:
<221> NAME/KEY: variation
<222> LOCATION: (11)..(12)
<223> OTHER INFORMATION: N = A, T, or C
<220> FEATURE:
<221> NAME/KEY: variation
<222> LOCATION: (14)..(15)
<223> OTHER INFORMATION: N = A, T, or C

<400> SEQUENCE: 27
cnncnncnnc nncnn                                                              15

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence:Artificial
      anti-codon encoding thiol reagent.

<400> SEQUENCE: 28
aattcgtacc                                                               10

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence:Artificial
      anti-codon encoding thiol reagent.

<400> SEQUENCE: 29
tggtacgaat t                                                             11

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide H template.

<400> SEQUENCE: 30
tcgcgagcgt acgctcgcga tggtacgaat t                                       31

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide template.

<400> SEQUENCE: 31
tggtacgaat tcgactcggg                                                    20

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence:Artificial
      anti-codon encoding thiol reagent.

<400> SEQUENCE: 32
cccgagtcga                                                               10

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide template.

<400> SEQUENCE: 33
tggtgcggag ccgccgtgac gggtgatacc acctccgagc cgaggagccg                   50

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence:Sequence of
      mixture of 1,024; Oligonucleotide template.
<220> FEATURE:
<221> NAME/KEY: variation
<222> LOCATION: (17)
<223> OTHER INFORMATION: N = G, A, T or C

```
<220> FEATURE:
<221> NAME/KEY: variation
<222> LOCATION: (19)
<223> OTHER INFORMATION: N = G, A, T or C
<220> FEATURE:
<221> NAME/KEY: variation
<222> LOCATION: (21)
<223> OTHER INFORMATION: N = G, A, T or C
<220> FEATURE:
<221> NAME/KEY: variation
<222> LOCATION: (23)..(24)
<223> OTHER INFORMATION: N = G, A, T or C

<400> SEQUENCE: 34
tggtgcggag ccgccgncna ncnngatacc acctccgagc cgaggagccg        50

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:Non-biotin
      encoding template.
<220> FEATURE:
<221> NAME/KEY: variation
<222> LOCATION: (7)
<223> OTHER INFORMATION: N = G, A, T or C
<220> FEATURE:
<221> NAME/KEY: variation
<222> LOCATION: (9)
<223> OTHER INFORMATION: N = G, A, T or C
<220> FEATURE:
<221> NAME/KEY: variation
<222> LOCATION: (11)
<223> OTHER INFORMATION: N = G, A, T or C
<220> FEATURE:
<221> NAME/KEY: variation
<222> LOCATION: (13)..(14)
<223> OTHER INFORMATION: N = G, A, T, or C

<400> SEQUENCE: 35
ggcggcngnt ngnnctatgg        20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:Biotin-
      encoding template.

<400> SEQUENCE: 36
ggcggcactg cccactatgg        20

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence:Template
      with hairpin loop for DNA-templated PWA coupling.

<400> SEQUENCE: 37
tgcgcgatat cgcgcagaaa tctgcc        26

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence:Portion of
```

```
      sequence from encoding DNA for cephalosporin
      recombination.
<220> FEATURE:
<221> NAME/KEY: variation
<222> LOCATION: (3)

```
<220> FEATURE:
<221> NAME/KEY: variation
<222> LOCATION: (11)..(14)
<223> OTHER INFORMATION: N = G, A, T or C
<220> FEATURE:
<221> NAME/KEY: variation
<222> LOCATION: (18)..(21)
<223> OTHER INFORMATION: N = G, A, T or C
<220> FEATURE:
<221> NAME/KEY: variation
<222> LOCATION: (25)..(28)
<223> OTHER INFORMATION: N = G, A, T or C

<400> SEQUENCE: 42
gcgnnnnccg nnnngccnnn ncgcnnnngg gctccaa                              37

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence:General
      Sequence of template pool.
<220> FEATURE:
<221> NAME/KEY: variation
<222> LOCATION: (10)..(13)
<223> OTHER INFORMATION: N = G, A, T or C
<220> FEATURE:
<221> NAME/KEY: variation
<222> LOCATION: (17)..(20)
<223> OTHER INFORMATION: N = G, A, T or C
<220> FEATURE:
<221> NAME/KEY: variation
<222> LOCATION: (24)..(27)
<223> OTHER INFORMATION: N = G, A, T or C
<220> FEATURE:
<221> NAME/KEY: variation
<222> LOCATION: (31)..(34)
<223> OTHER INFORMATION: N = G, A, T  or C

<400> SEQUENCE: 43
ttggagcccn nnngcgnnnn ggcnnnncgg nnnncgc                              37

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence:Artificial
      anti-codon encoding amino acid 2.
<220> FEATURE:
<221> NAME/KEY: variation
<222> LOCATION: (4)..(7)
<223> OTHER INFORMATION: N = G, A, T or C

<400> SEQUENCE: 44 gccnnnncgc                                                            10

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence:Artificial
      anti-codon encoding amino acid 3.
<220> FEATURE:
<221> NAME/KEY: variation
<222> LOCATION: (4)..(7)
<223> OTHER INFORMATION: N = G, A, T or C

<400> SEQUENCE: 45 ccgnnnngcc                                                            10
```

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Artificial anti-codon encoding amino acid 4.
<220> FEATURE:
<221> NAME/KEY: variation
<222> LOCATION: (4)..(7)
<223> OTHER INFORMATION: N = G, A, T or C

<400> SEQUENCE: 46 gcgnnnnccg				10

<210> SEQ ID NO 47
<211> LENGTH: 49
<212> TYPE: DNA
<213> ORGANISM: Artificial Sequence
<220> FEATURE:
<223> OTHER INFORMATION: Description of Artificial Sequence:General sequence of DNA template for synthetic library.
<220> FEATURE:
<221> NAME/KEY: variation
<222> LOCATION: (10)..(13)
<223> OTHER INFORMATION: N = G, A, T or C
<220> FEATURE:
<221> NAME/KEY: variation
<222> LOCATION: (17)..(20)
<223> OTHER INFORMATION: N = G, A, T or C
<220> FEATURE:
<221> NAME/KEY: variation
<222> LOCATION: (24)..(27)
<223> OTHER INFORMATION: N = G, A, T or C
<220> FEATURE:
<221> NAME/KEY: variation
<222> LOCATION: (31)..(34)
<223> OTHER INFORMATION: N = G, A, T or C

<400> SEQUENCE: 47
ttggagcccn nngcgnnnn ggcnnnncgg nnnncgctgg tgctgctcg				49

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence:PCR Primer

<400> SEQUENCE: 48
cgagcagcac cagcg				15

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence:PCR Primer
<220> FEATURE:
<221> NAME/KEY: variation
<222> LOCATION: (9)..(12)
<223> OTHER INFORMATION: N = G, A, T or C

<400> SEQUENCE: 49
tggagcccnn nngcg				15

<210> SEQ ID NO 50
<211> LENGTH: 49
<212> TYPE: DNA

```
<213> ORGANISM: Artificial Sequence
<220> FEATURE:
<223> OTHER INFORMATION: Description of Artificial Sequence:Specific DNA
      sequence from DNA - templated library.

<400> SEQUENCE: 50
ttggagcccg taggcgtgca ggcggatcgg agtgcgctgg tgctgctcg                49

<210> SEQ ID NO 51
<211> LENGTH: 49
<212> TYPE: DNA
<213> ORGANISM: Artificial Sequence
<220> FEATURE:
<223> OTHER INFORMATION: Description of Artificial Sequence:DNA Template
      Complimentary strand of sequence above.

<400> SEQUENCE: 51
cgagcagcac cagcgcactc cgatccgcct gcacgcctac gggctccaa                 49

<210> SEQ ID NO 52
<211> LENGTH: 64
<212> TYPE: DNA
<213> ORGANISM: Artificial Sequence
<220> FEATURE:
<223> OTHER INFORMATION: Description of Artificial Sequence:Template
      encoding parent molecule 1.

<400> SEQUENCE: 52
ttggagcccg taggagtcgc gtgcacccgg ggcggatcca ggcggagtgc gctggtgctg     60
ctcg                                                                  64

<210> SEQ ID NO 53
<211> LENGTH: 64
<212> TYPE: DNA
<213> ORGANISM: Artificial Sequence
<220> FEATURE:
<223> OTHER INFORMATION: Description of Artificial Sequence:Template
      encoding parent molecule 1.

<400> SEQUENCE: 53
cgagcagcac cagcgcactc cgcctggatc cgccccgggt gcacgcgact cctacgggct     60
ccaa                                                                  64

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 54
gcggagtgcg ctggtgctgc tcg                                             23

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 55
cgagcagcac cagcgcactc cgcctg                                          26
```

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 56
cgcgtgcacc cg                                                          12

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 57
gtgcacgcga ct                                                          12

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 58
gcgggactcg ctggtgctgc tcg                                              23

<210> SEQ ID NO 59
<211> LENGTH: 12
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 59
gggcggatcc ag                                                          12

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 60
ttggagcccg taggagt                                                     17

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 61
cgagcagcac cagcgagtcc cgcctg                                           26

<210> SEQ ID NO 62

```
<211> LENGTH: 12
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 62
gatccgcccc gg                                                         12

<210> SEQ ID NO 63
<211> LENGTH: 14
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 63
cctacgggct ccaa                                                       14

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 64
gggcatcccc ag                                                         12

<210> SEQ ID NO 65
<211> LENGTH: 12
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 65
cgcgcccacc cg                                                         12

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 66
ttggagcccg ttggagt                                                    17

<210> SEQ ID NO 67
<211> LENGTH: 12
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 67
gggatgcccc gg                                                         12

<210> SEQ ID NO 68
<211> LENGTH: 14
```

```
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 68
ccaacgggct ccaa                                                            14

<210> SEQ ID NO 69
<211> LENGTH: 12
<212> TYPE: DNA
<213> ORGANISM: Artificial Sequence
<220> FEATURE:
<223> OTHER INFORMATION: Description of Artificial Sequence:Digestion
      fragment of template.

<400> SEQUENCE: 69
gtgggcgcga ct                                                              12

<210> SEQ ID NO 70
<211> LENGTH: 64
<212> TYPE: DNA
<213> ORGANISM: Artificial Sequence
<220> FEATURE:
<223> OTHER INFORMATION: Description of Artificial Sequence:Recombined
      daughter templates.

<400> SEQUENCE: 70
ttggagcccg taggagtcgc gcccacccgg ggcatcccca ggcggagtgc gctggtgctg          60
ctcg                                                                       64

<210> SEQ ID NO 71
<211> LENGTH: 64
<212> TYPE: DNA
<213> ORGANISM: Artificial Sequence
<220> FEATURE:
<223> OTHER INFORMATION: Description of Artificial Sequence:Recombined
      daughter templates.

<400> SEQUENCE: 71
cgagcagcac cagcgcactc cgcctgggga tgccccgggt gggcgcgact cctacgggct          60
ccaa                                                                       64

<210> SEQ ID NO 72
<211> LENGTH: 64
<212> TYPE: DNA
<213> ORGANISM: Artificial Sequence
<220> FEATURE:
<223> OTHER INFORMATION: Description of Artificial Sequence:Recombined
      daughter template.

<400> SEQUENCE: 72
ttggagcccg ttggagtcgc gtgcacccgg ggcggatcca ggcgggactc gctggtgctg          60
ctcg                                                                       64

<210> SEQ ID NO 73
<211> LENGTH: 64
<212> TYPE: DNA
<213> ORGANISM: Artificial Sequence
<220> FEATURE:
<223> OTHER INFORMATION: Description of Artificial Sequence:Recombined
      daughter template.
<220> FEATURE:
<221> NAME/KEY: variation
<222> LOCATION: (1)
```

```
<223> OTHER INFORMATION: N = G, A, T or C

<400> SEQUENCE: 73
cgagcagcac cagcgagtcc cgcctggatc cgccccgggt gcacgcgact ccaacgggct    60
ccaa                                                                 64

<210> SEQ ID NO 74
<211> LENGTH: 50
<212> TYPE: DNA
<213> ORGANISM: Artificial Sequence
<220> FEATURE:
<223> OTHER INFORMATION: Description of Artificial Sequence:Synthetic
      template with 20 or 40 random bases.
<220> FEATURE:
<221> NAME/KEY: variation
<222> LOCATION: (16)..(35)
<223> OTHER INFORMATION: N = G, A, T or C

<400> SEQUENCE: 74
acgtagcggc gtcgcnnnnn nnnnnnnnnn nnnnnccgtc atcgagccct               50

<210> SEQ ID NO 75
<211> LENGTH: 16
<212> TYPE: DNA
<213> ORGANISM: Artificial Sequence
<220> FEATURE:
<223> OTHER INFORMATION: Description of Artificial Sequence:PCR Primer
      with 5' amino.

<400> SEQUENCE: 75
tagggctcga tgacgg                                                    16

<210> SEQ ID NO 76
<211> LENGTH: 16
<212> TYPE: DNA
<213> ORGANISM: Artificial Sequence
<220> FEATURE:
<223> OTHER INFORMATION: Description of Artificial Sequence:PCR Primer
      with 5' biotin.

<400> SEQUENCE: 76
tacgtagcgg cgtcgc                                                    16

<210> SEQ ID NO 77
<211> LENGTH: 52
<212> TYPE: DNA
<213> ORGANISM: Artificial Sequence
<220> FEATURE:
<223> OTHER INFORMATION: Description of Artificial Sequence:Template
      w/non-natural nucleotides.
<220> FEATURE:
<221> NAME/KEY: variation
<222> LOCATION: (17)..(36)
<223> OTHER INFORMATION: N = G, A, T or C or non-natural nucleotide.

<400> SEQUENCE: 77
tagggctcga tgacggnnnn nnnnnnnnnn nnnnnngcga cgccgctacg ta            52

<210> SEQ ID NO 78
<211> LENGTH: 52
<212> TYPE: DNA
<213> ORGANISM: Artificial Sequence
<220> FEATURE:
<223> OTHER INFORMATION: Description of Artificial Sequence:Template
      with non-natural nucleotides.
<220> FEATURE:
<221> NAME/KEY: variation
<222> LOCATION: (17)..(36)
```

<223> OTHER INFORMATION: N = G, A, T or C or non-natural nucleotides.

<400> SEQUENCE: 78
tacgtagcgg cgtcgcnnnn nnnnnnnnnn nnnnnnccgt catcgagccc ta    52

<210> SEQ ID NO 79
<211> LENGTH: 52
<212> TYPE: DNA
<213> ORGANISM: Artificial Sequence
<220> FEATURE:
<223> OTHER INFORMATION: Description of Artificial Sequence:Template
      with non-natural nucleotides.
<220> FEATURE:
<221> NAME/KEY: variation
<222> LOCATION: (17)..(36)
<223> OTHER INFORMATION: N = G, A, T or C or non-natural nucleotides.

<400> SEQUENCE: 79
tagggctcga tgacggnnnn nnnnnnnnnn nnnnnngcga cgccgctacg ta    52

<210> SEQ ID NO 80
<211> LENGTH: 50
<212> TYPE: DNA
<213> ORGANISM: Artificial Sequence
<220> FEATURE:
<223> OTHER INFORMATION: Description of Artificial Sequence:Sequence of
      mixture; Oligonucleotide template.
<220> FEATURE:
<221> NAME/KEY: variation
<222> LOCATION: (17)..(24)
<223> OTHER INFORMATION: N = G, A, T or C.

<400> SEQUENCE: 80
tggtgcggag ccgccgnnnn nnnngatacc acctccgagc cgaggagccg    50

<210> SEQ ID NO 81
<211> LENGTH: 64
<212> TYPE: DNA
<213> ORGANISM: Artificial Sequence
<220> FEATURE:
<223> OTHER INFORMATION: Description of Artificial Sequence:Template
      encoding parent molecule 2.

<400> SEQUENCE: 81
ttggagcccg ttggagtcgc gcccacccgg ggcatcccca ggcgggactc gctggtgctg    60
ctcg    64

<210> SEQ ID NO 82
<211> LENGTH: 64
<212> TYPE: DNA
<213> ORGANISM: Artificial Sequence
<220> FEATURE:
<223> OTHER INFORMATION: Description of Artificial Sequence:Template
      encoding parent molecule 2.

<400> SEQUENCE: 82
cgagcagcac cagcgagtcc cgcctgggga tgccccgggt gggcgcgact ccaacgggct    60
ccaa    64

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence:linear
      peptide for validation of selection process.

-continued

```
<400> SEQUENCE: 83

Gly Arg Gly Asp Ser Pro Lys
 1               5
```